United States Patent
Hibbert et al.

(10) Patent No.: US 12,247,065 B2
(45) Date of Patent: Mar. 11, 2025

(54) METHOD FOR PRODUCING A CONTROLLED MIXTURE OF TWO OR MORE DIFFERENT ANTIBODIES

(71) Applicant: GENMAB A/S, Valby (DK)

(72) Inventors: Richard Hibbert, GN Wassenaar (NL); Rob De Jong, Utrecht (NL); Aran Frank Labrijn, Nigtevecht (NL); Arnout Gerritsen, Bunnik (NL); Janine Schuurman, Diemen (NL); Paul Parren, Odijk (NL)

(73) Assignee: GENMAB A/S, Valby (DK)

( * ) Notice: Subject to any disclaimer, the term of this patent is extended or adjusted under 35 U.S.C. 154(b) by 1055 days.

(21) Appl. No.: 17/253,286

(22) PCT Filed: Jun. 24, 2019

(86) PCT No.: PCT/EP2019/066594
§ 371 (c)(1),
(2) Date: Dec. 17, 2020

(87) PCT Pub. No.: WO2019/243626
PCT Pub. Date: Dec. 26, 2019

(65) Prior Publication Data
US 2021/0269509 A1   Sep. 2, 2021

(30) Foreign Application Priority Data

Jun. 22, 2018   (EP) .................................... 18179365

(51) Int. Cl.
*C07K 16/00* (2006.01)
*C07K 1/18* (2006.01)
*C07K 1/22* (2006.01)

(52) U.S. Cl.
CPC .............. *C07K 16/00* (2013.01); *C07K 1/18* (2013.01); *C07K 1/22* (2013.01); *C07K 2317/21* (2013.01); *C07K 2317/24* (2013.01); *C07K 2317/31* (2013.01)

(58) Field of Classification Search
CPC . C07K 16/00; C07K 1/18; C07K 1/22; C07K 2317/21; C07K 2317/24; C07K 2317/31; C07K 2317/526; C07K 2317/90; C07K 16/065; C07K 16/2803; C07K 16/2887; C07K 16/2893; C07K 16/2896
See application file for complete search history.

(56) References Cited

U.S. PATENT DOCUMENTS

| 8,586,713 B2 | 11/2013 | Davis et al. |
| 2005/0170398 A1 | 8/2005 | Van Berkel et al. |
| 2015/0239991 A1 | 8/2015 | Blein et al. |

FOREIGN PATENT DOCUMENTS

| EP | 2009101 A1 | 12/2008 |
| WO | 2004/009618 A2 | 1/2004 |
| WO | 2004/061104 A2 | 7/2004 |
| WO | 2008/145133 A2 | 12/2008 |
| WO | 2009/129814 A1 | 10/2009 |
| WO | 2010/0089387 A1 | 8/2010 |
| WO | 2011131746 A2 | 10/2011 |
| WO | 2012/068317 A2 | 5/2012 |
| WO | 2013004842 A2 | 1/2013 |
| WO | 2013088259 A2 | 6/2013 |
| WO | 2013/136186 A2 | 9/2013 |
| WO | 2014108198 A1 | 7/2014 |
| WO | 2014/209508 A1 | 12/2014 |
| WO | 2016/097300 A1 | 6/2016 |
| WO | 2017/005649 A1 | 1/2017 |
| WO | 2018/034885 A1 | 2/2018 |

OTHER PUBLICATIONS

Robak et al. (Blood, 120(18): 3670-3677, 2012).*
Coskun (North Clin. Istanbul, 3(2): 156-160, 2016).*
Rasmussen et al. (Archives of Biochemistry and Biophysics, 526: 139-145, 2012).*
De Kruif et al. "Generation of stable cell clones expressing mixtures of human antibodies," Biotechnology and Bioengineering, vol. 106(5): 741-750 (2010).
Easdale et al. "Rozrolimupab, a first-in-class recombinant monoclonal antibody product for primary immune thrombocytopenia," Expert Opinion on Biological Therapy, vol. 13(7): 1085-1092 (2013).
International Search Report and Written Opinion, PCT/EP2019/066594, dated Oct. 14, 2019, 15 pages.
Pedersen et al. "Sym004: A novel synergistic anti-epidermal growth factor receptor antibody mixture with superior anticancer efficacy," Cancer Research, vol. 70(2): 588-597 (2010).
Rasmussen et al. "Recombinant antibody mixtures: optimization of cell line generation and single-batch manufacturing processes" BMC Proceedings, vol. 5(8): 3 pages (2011).
Rasmussen et al. "Recombinant antibody mixtures: Production strategies and cost considerations," Archives of Biochemistry and Biophysics, vol. 526(2): 139-145 (2012).
Robak Tadeusz: "The emerging therapeutic role of antibody mixtures" Expert Opinion on Biological Therapy, vol. 13(7): 953-958 (2013).
Carver, T. et al., "The design of Jemboss: a graphical user interface to Emboss," Oxford University Press, vol. 19(14): 1837-1843 (2003).
Crowe, J. et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin. ex. Immunol., vol. 97(1), 105-110: (1992).

(Continued)

*Primary Examiner* — Nelson B Moseley, II
(74) *Attorney, Agent, or Firm* — Nelson Mullins Riley & Scarborough LLP; Jane E. Remillard, Esq.; Christopher L. Frank

(57) ABSTRACT

The present invention relates to a method for controlling the composition of a mixture of two or more different antibodies, such as tow or more different monoclonal antibodies, using chromatography. The mixture is for use as a drug product and the method includes a controlled downstream process for the production of a predetermined ratio of the two or more different antibodies.

36 Claims, 55 Drawing Sheets

Specification includes a Sequence Listing.

(56) References Cited

OTHER PUBLICATIONS

Dennison, C., "A Guide To Protein Isolation," Springer Netherlands, School of Molecular and Cellular Biosciences, University of Natal, Pietermaritzburg, South Africa, Chap. 4: 1-186 (2002).
Gagnon, P. et al., "Technology trends in antibody purification," Journal of Chromatography, vol. 1221: 57-70 (2012).
Graille, M, et al., "Evidence for Plasticity and Structural Mimicry at the Immunoglobulin Light Chain-Protein L Interface," The Journal of Biological Chemistry, vol. 277(49): 47500-47506 (2002).
Graille, M. et al., "Complex between Peptostreptococcus magnus Protein L and a Human Antibody Reveals Structural Convergence in the Interaction Modes of Fab Binding Proteins," Structure, vol. 9(8): 679-687 (2001).
Gramer, M.J., et al., "Production of stable bispecific IgG1 by controlled Fab-arm exchange: scalability from bench to large-scale manufacturing by application of standard approaches," MABS, vol. 5(6):962-973 (2013).
Jungbauer, A., "Chromatographic media for bioseparation," Elsevier, vol. 1065(1): 3-12 (2005).
Kallberg, K. et al., "Multimodal chromatography: An efficient tool in downstream processing of proteins," Biotechnol. J, vol. 7(12): 1485-1495 (2012).
Low, D. et al., "Future of antibody purification," Journal of Chromatography, vol. 848(1): 48-63 (2007).
Nilson, B. et al., "Protein L from Peptostreptococcus magnus binds to the kappa light chain variable domain," The Journal of Biological Chemistry, vol. 267(4): 2234-2239 (1992).

\* cited by examiner

```
              1         10         20         30         40         50         60         70
2F8HA3   (1)  VQLVQSGGG VVQPGSLRL SCAASGFTFS TYGMHWVRQA PGKGLEWVAV IWDDGSYKYY GDSVKGRFTI
2F8HA2   (1)  VQLVQSGGG VVQPGSLRL SCASGFTFS  TYGMHWVRQA PGKGLEWVAV IWDDGSYKYY GDSVKGRFTI
2F8HA1   (1)  VQLVQSGGG VVQPGSLRL SCAASGFTFS TYGMHWVRQA PGKGLEWVAV IWDDGSYKYY GDSVKGRFTI
2F8HC    (1)  VQLVQSGGG VVQPGSLRL SCAASGFTFS TYGMHWVRQA PGKGLEWVAV AAAAIKYYY  GDSVKGRFTI
2F8HP    (1)  VQLVQSGGG VVQPGSLRL SCAASGFTFS TYGMHWVRQA PGKGLEWVAV IWDDGSYKYY GDSVKGRFTI
2F8HB1   (1)  VQLVQSGGG VVQPGSLRL SCAASGFTFS TYGMHWVRQA PGKGLEWVAV IWDDGSYKYY GDSVKGRFTI
2F8HB2   (1)  VQLVQSGGG VVQPGSLRL SCAASGFTFS TYGMHWVRQA PGKGLEWVAV IWDDGSYKYY GDSVKGRFTI
2F8HB3   (1)  VQLVQSGGG VVQPGSLRL SCAASGFTFS TYGMHWVRQA PGKGLEWVAV IWDDGSYKYY GDSVKGRFTI
IMGT-NR                 17           24           40                              70

71        80        90         100        110        120        125
2F8HA3  (71)  SRDNSKNTLY LQMNSLRAED TAVYYCARDS ITMVRGVMKD YFDYWGQGTL VTVSS
2F8HA2  (71)  SRDNSKNTLY LQMNSLRAED TAVYYCARDS ITMVRGVMKD YFDYWGQGTL VTVSS
2F8HA1  (71)  SRDNSKNTLY LQMNSLRAED TAVYYCARDS ITMVRGVMKD YFDYWGQGTL VTVSS
2F8HC   (71)  SRDNSKNTLY LQMNSLRAED TAVYYCARDS ITMYRGVMKD YFDYWGQGTL VTVSS
2F8HP   (71)  SRDNSKNTLY LQMNSLRAED TAVYYCARDS ITMVRGVMKD YFDYWGQGTL VTVSS
2F8HB1  (71)  SRDNSKNTLY LQMNSLRAED TAVYYCARDG ITMVRGVMKD YFDYWGQGTL VTVSS
2F8HB2  (71)  SRDNGKNTLY LQMNSLRAED TAVYYCARDG ITMVRGVMKD YFDYWGQGTL VTVSS
2F8HB3  (71)  SRDNSKNTLY LQMNSLRAED TAVYYCARDG ITMVRGVMKD YFDYWGQGTL VTVSS
IMGT-NR                            96/97

1         10         20         30         40         50         60         70
2F8LB3   (1)  DIQMTQSPSS LSASVGDRVT ITCRASQDIS SALVWYQQKP GKAPKLLIYD ASSLQSGVPS RFSGSGSGTD
2F8LB2   (1)  DIQMTQSPSS LSASVGDRVT ITCRASQDIS SALVWYQQKP GKAPKLLIYD ASSLQSGVPS RFSGSGSGTD
2F8LB1   (1)  DIQMTQSPSS LSASVGDRVT ITCRASQDIS SALVWYQQKP GKAPKLLIYD ASSLQSGVPS RFSGSGSGTD
2F8LC    (1)  DIQMTQSPSS LSASVGDRVT ITCRASQDIS SALVWYQRS  GKAPKLLIYD ASSLQSGVPS RFSGSGSGTD
2F8LA1   (1)  DIQMTQSPSS LSASVGDRVT ITCRASQDIS SALVWYQQKP GKAPKLLIYD ASSLQSGVPS RFSGSGSGTD
2F8LA2   (1)  DIQMTQSPSS LSASVGDRVT ITCRASQDIS SALVWYQQKP GKAPKLLIYD ASSLQSGVPS RFSGSGSGTD
2F8LA3   (1)  DIQMTQSPSS LSASVGDRVT ITCRASQDIS SALVWYQQKP GKAPKLLIYD ASSLQSGVPS RFSGSGSGTD
IMGT-NR                                         26/27        40          58          70

71        80        90         100        107
2F8LB3  (71)  FTLTISSLQP EDFATYYCQQ FNSYPLTFGG GTKVEIK
2F8LB2  (71)  FTLTISSLQP EDFATYYCQQ FNSYPLTFGG GTKVEIK
2F8LB1  (71)  FTLTISSLQP EDFATYYCQQ FNSYPLTFGG GTKVEIK
2F8LC   (71)  FTLTISSLQP EDFATYYCQQ FNSYPLNFGG GTKVEIK
2F8LA1  (71)  FTLTISSLQP EDFATYYCQQ FNSYPLTFGG GTKVEIK
2F8LA2  (71)  FTLTISSLQP EDFATYYCQQ FNSYPLTFGG GTKVEIK
2F8LA3  (71)  FTLTISSLQP EDFATYYCQQ FNSYPLTFGG GTKVEIK
IMGT-NR           80       95
```

FIG. 2E

```
              1         10        20         30        40        50        60        70
1021-511HA3  (1)  EVQLLESGGG LVQPGGSLRL SCAASGFTFS SYAMNWVRQA PGKGLEWVSG ISGSGGSTYY ADSVKGRFTI
1021-511HA2  (1)  EVQLLESGGG LVQPGGSLRL SCAASGFTFS SYAMNWVRQA PGKGLEWVSG ISGSGGSTYY ADSVKGRFTI
1021-511RA1  (1)  EVQLLESGGG LVQPGGSLRL SCAASGFTFS SYAMNWVRQA PGKGLEWVSG ISGSGGSTYY ADSVKGRFTI
1021-511HC   (1)  EVQLLESGGG LVQPGGSLRL SCAASGFTFS SYAMNWVRQA PGKGLEWVSG ISGSGGSTYY ADSVKGRFTI
1021-511HP   (1)  EVQLLESGGG LVQPGGSLRL SCAASGFTFS SYAMNWVRQA PGKGLEWVSG ISGSGGSTYY ADSVKGRFTI
1021-511HB1  (1)  EVQLLESGGG LVQPGGSLRL SCAASGFTFS SYAMNWVRQA PGKGLEWVSG ISGSGGSTYY ADSVKGRFTI
1021-511HB2  (1)  EVQLLESGGG LVQPGGSLRL SCAASGFTFS SYAMNWVRQA PGKGLEWVSG ISGSGGSTYY ADSVKGRFTI
1021-511HB3  (1)  EVQLLESGGG LVQPGGSLRL SCAASGFTFS SYAMNWVRQA PGKGLEWVSG ISGSGGSTYY ADSVKGRFTI
IMGT-NR           6                    24                   48

71        80        90        100       110       120       124
1021-511HA3  (71) SRDNSKNTLY LQMNSLRAED TAVYYCAKDR YDILTGYYNL LDYWGQGTLV TVSS
1021-511HA2  (71) SRDNSKNTLY LQMNSLRAED TAVYYCAKDR YDILTGYYNL LDYWGQGTLV TVSS
1021-511RA1  (71) SRDNSKNTLY LQMNSLRAED TAVYYCAKDR YDILTGYYNL LDYWGQGTLV TVSS
1021-511HC   (71) GRDNSKNTLY LQMNSLRAED TAVYYCAKDR YDILTGYYNL LDYWGQGTLV TVSS
1021-511HP   (71) GRDNSKNTLY LQMNSLRAED TAVYYCAKDR YDILTGYYNL LDYWGQGTLV TVSS
1021-511HB1  (71) SRDNSKNTLY LQMNSLRAED TAVYYCAKDR YDILTGYYNL LDYWGQGTLV TVSS
1021-511HB2  (71) SRDNSKNTLY LQMNSLRAED TAVYYCAKDR YDILTGYYNL ALDYWGQGTL VTVSS
1021-511HB3  (71) GRDNSKNTLY LQMNSLRAED TAVYYCAKDR YDILTGYYNL LDYWGQGTLV TVSS
IMGT-NR           90        96?                                        124

1         10        20         30        40        50        60        70
1021-511LB3  (1)  DIQMTQSPSS LSASVGDRVT ITCRASQGIS SWLAWYQQKP EKAPKSLIYA ASSLQSGVP SRFSGSGSGTD
1021-511LB2  (1)  DIQMTQSPSS LSASVGDRVT ITCRASQGIS SWLAWYQQKP EKAPKSLIYA ASSLQSGVP SRFSGSGSGTD
1021-511LB1  (1)  DIQMTQSPSS LSASVGDRVT ITCRASQGIS SWLAWYQQKP EKAPKSLIYA ASSLQSGVP SRFSGSGSGTD
1021-511LC   (1)  DIQMTQSPSS LSASVGDRVT ITCRASQGIS SWLAWYQQKP EKAPKSLIYA ASSLQSGVP SRFSGSGSGTD
1021-511LA1  (1)  DIQMTQSPSS LSASVGDRVT ITCRASQGIS SWLAWYQQKP EKAPKSLIYA ASSLQSGVP SRFSGSGSGTD
1021-511LA2  (1)  DIQMTQSPSS LSASVGDRVT ITCRASQGIS SWLAWYQQKP EKAPKSLIYA ASSLQSGVP SRFSGSGSGTD
1021-511LA3  (1)  DIQMTQSPSS LSASVGDRVT ITCRASQGIS SWLAWYQQKP EKAPKSLIYA ASSLQSGVP SRFSGSGSGTD
IMGT-NR                                                    48                        74

71        80        90        100       107
1021-511LB3  (71) FTLTISSLQP EDFATYYCQQ YNSYPLTFGG GKVEIK
1021-511LB2  (71) FTLTISSLQP EDFATYYCQQ YNSYPLTFGG GKVEIK
1021-511LB1  (71) FTLTISSLQP EDFATYYCQQ YNSYPLTFGG GKVEIK
1021-511LC   (71) FTLTISSLQP EDFATYYCQQ YNSYPLTFGG GKVEIK
1021-511LA1  (71) FTLTISSLQP EDFATYYCQQ YNSYPLTFGG GKVEIK
1021-511LA2  (71) FTLTISSLQP EDFATYYCQQ YNSYPLTFGG GKVEIK
1021-511LA3  (71) FTLTISSLQP EDFATYYCQQ YNSYPLTFGG GKVEIK
IMGT-NR                     95
``` a - IgG1-1021-511-HCLC
b - IgG1-1014-153
c - IgG1-2F8-HCLC
d - IgG1-1014-005-HCLC a - IgG1-1021-511-HA3LB2
b - IgG1-1014-153
c - IgG1-2F8-HB3LC
d - IgG1-1014-005-HB3LB1 a - IgG1-1021-511-HA3LB2
b - IgG1-1014-153
c - IgG1-2F8-HB3LB3
d - IgG1-1014-005-HB3LB1 a - IgG1-1021-511-HA3LB2
b - IgG1-1014-153
c - IgG1-2F8-HB3LC
d - IgG1-1014-005-HB3LB1

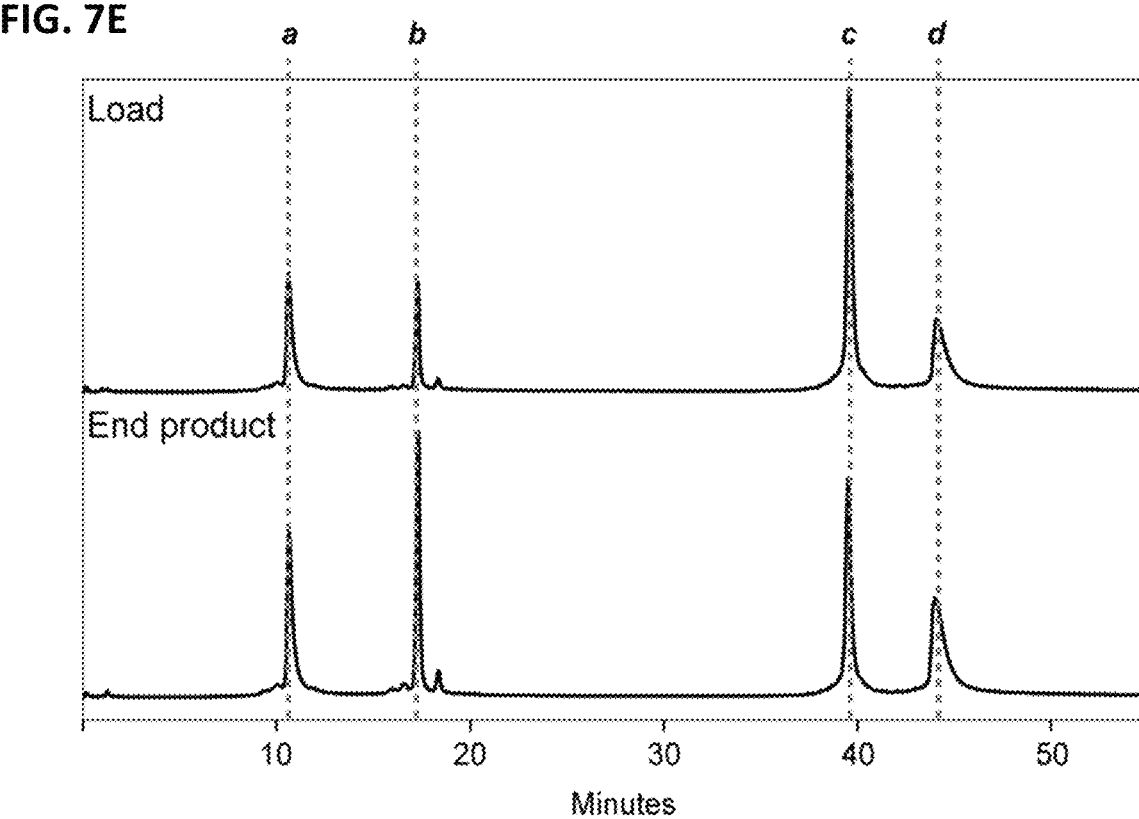

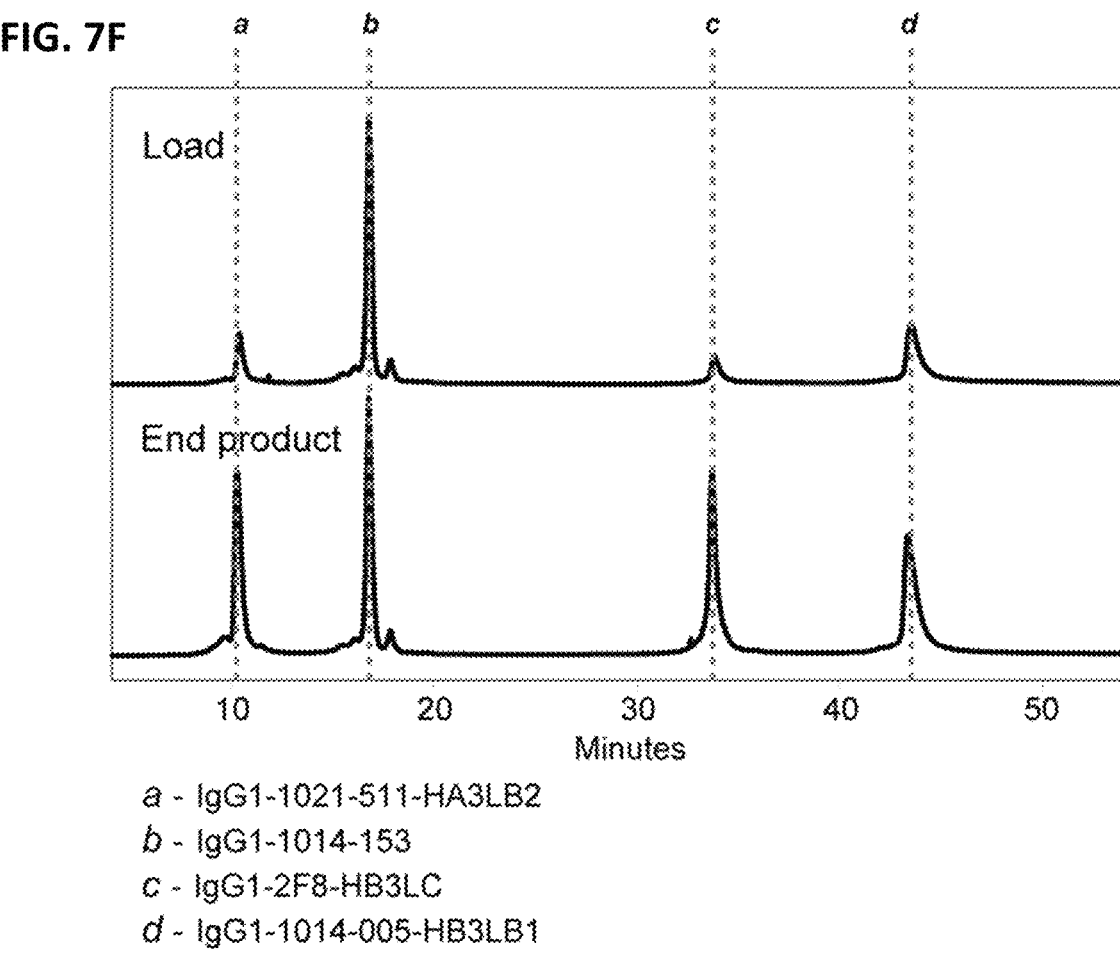

a - IgG1-7D8
b - IgG1-224
c - IgG1-CD37-37-3
d - IgG1-CD19-21D4-E345K
e - IgG1-CD52-Campath-E345K

FIG. 10

```
                                     1         1         1         1         1         1
                                     1         2         3         4         5         6
CROSS-REACTIVE                       901234567890123456789012345678901234567890123456 7890
UP|P01834|IGKC1_Homsap               TVAAPSVFIFPPSDEQLKSGTASVVCLLNNFYPREAKVQWKVDNALQSGN SQE
IMGT|M11736|IGKC2_Homsap             TVAAPSVFIFPPSDEQLKSGTASVVCLLNNFYPREAKVQWKVDNALQSGN SQE
IMGT|M11737|IGKC3_Homsap             TVAAPSVFIFPPSDEQLKSGTASVVCLLNNFYPREAKVQRKVDNALQSGN SQE
GB|AF017732|IGKC4_Homsap             TVAAPSVFIFPPSDEQLKSGTASVVCLLNNFYPREAKVQWKVDNVLQSGN SQE
GB|AF113887|IGKC5_Homsap             TVAAPSVFIFPPSDEQLKSGTASVVCLLNNFYPREAKVQWKVDNALQSGN SQE
GB|AJ619771|IGKC_Macfas              AVAAPSVFIFPPSEDQVKSGTVSVVCLLNNFYPREASVKWKVDGAVQTGN SQE
GB|FJ795855|IGKC_Macmul              AVAAPSVLIFPPSEDQVKSGTVSVVCLLNNFYPREASVKWKVDGVLKTGN SQE
CONSENSUS +                           VAAPSV IFPPS  Q KSGT SVVCLLNNFYPREA V  KVD     GN SQE NON CROSS-REACTIVE
UP|P01837|IGKC_Musmus                ADAAPTVSIFPPSSEQLTSGGASVVCFLNNFYPKDINVKWKIDGSERQNG VLN
UP|P01844|IGLC2_Musmus               PKSTPTLTVFPPSSEELKENKATLVCLISNFSPSGVTAWKANGTPITQG  VDT
UP|P01845|IGLC3_Musmus               PKSTPTLTMFPPSPEELQENKATLVCLISNFSPSGVTAWKANGTPITQG  VDT
UP|P0CG04|IGLC1_Homsap               PKANPTVTLFPPSSEELQARKATLVCLISDFYPGAVTVAWKADGSPVKAG VET
UP|P0CG05|IGLC2_Homsap               PKAAPSVTLFPPSSEELQANKATLVCLISDFYPGAVTVAWKADSSPVKAG VET
UP|P0CG06|IGLC3_Homsap               PKAAPSVTLFPPSSEELQARKATLVCLISDFYPGAVTVAWKADSSPAKAG VET
UP|P0CF74|IGLC6_Homsap               PKAAPSVTLFPPSSEELQANKATLVCLISDFYPGAVKVAWKADGSPVRTG VET
UP|A0M8Q6|IGLC7_Homsap               PKAAPSVTLFPPSSEELQARKATLVCLVSDFYPGAVTVAWKADGSPVKVG VET
IMGT|V01241|IGKC_Ratnor              ADAAPTVSIFPPSTEQLATGGASVVCLMNNFYPPDISVKWKIDGTEPRDG VLD
IMGT|K01360|IGKC1_Orycun             DPVAPTVLIFPPAADQVATGTVTIVCVANKYFPDVT VTWEVDGTTQTTG IEN
IMGT|X00232|IGKC2_Orycun             DPVAPSVLLFPPSKEELTTGTATIVCVANKFYPSDITVTWKVDGTTQQSG IEN
GB|AEM45014|IGKC_Bostau              SDAEPSVFLFKPSDEQLKTGTVSVVCLVNDFYPKDINVSWKVEGVTQSSSNFQN
CONSONSUS -                          V                          EA          GN    S E
PISA(INTERFACE)                              + ++ + ++    + +++++  +                     +
SELECTED                              *                      **          ** *        *
```

```
                                     1         1         1         2         2
                                     7         8         9         0         1
CROSS-REACTIVE                       234567890123456789012345678901234567890123456 7891234
UP|P01834|IGKC1_Homsap               SVTEQDSKDSTYSLSSTLTLSKADYEKHKVYACEVTHQGLSSPVTKSFNRGEC
IMGT|M11736|IGKC2_Homsap             SVTEQDSKDSTYSLSSTLTLSKADYEKHKVYAGEVTHQGLSSPVTKSFNRGEC
IMGT|M11737|IGKC3_Homsap             SVTEQDSKDSTYSLSSTLTLSKADYEKHKVYACEVTHQGLSSPVTKSFNRGEC
GB|AF017732|IGKC4_Homsap             SVTEQDSKDSTYSLSSTLTLSKADYEKHKLYACEVTHQGLSSPVTKSFNRGEC
GB|AF113887|IGKC5_Homsap             SVTEQDSKDSTYSLSNTLTLSKADYEKHKVYACEVTHQGLSSPVTKSFNRGEC
GB|AJ619771|IGKC_Macfas              SVTEQDSKDNTYSLSSTLTLSSTDYQSHNVYACEVTHQGLSSPVTKSFNRGEC
GB|FJ795855|IGKC_Macmul              SVTEQDSKDNTYSLSSTLTLSSTDYQSHNVYACEVTHQGLSSPVTKSFNRGEC
CONSENSUS +                          SVTE  SKD TYSLS TLTLS  DY  H  YA EVTHQGLSSPVTKSFNRGEC NON CROSS-REACTIVE
UP|P01837|IGKC_Musmus                SWTDQDSKDSTYSMSSTLTLTKDEYERHNSYTCEATHKTSTSPIVKSFNRNEC
UP|P01844|IGLC2_Musmus               SNPTKEGN  KFMASSFLHLTSDQWRSHNSFTCQVTHEGDT  VEKSLSPAECL
UP|P01845|IGLC3_Musmus               SNPTKEDN  KYMASSFLHLTSDQWRSHNSFTCQVTHEGDT  VEKSLSPAECL
UP|P0CG04|IGLC1_Homsap               TKPSKQSN  NKYAASSYLSLTPEQWKSHRSYSCQVTHEGST  VEKTVAPTECS
UP|P0CG05|IGLC2_Homsap               TTPSKQSN  NKYAASSYLSLTPEQWKSHRSYSCQVTHEGST  VEKTVAPTECS
UP|P0CG06|IGLC3_Homsap               TTPSKQSN  NKYAASSYLSLTPEQWKSHKSYSCQVTHEGST  VEKTVAPTECS
UP|P0CF74|IGLC6_Homsap               TTPSKQSN  NKYAASSYLSLTPEQWKSHRSYSCRVTHEGST  VEKTVAPAECS
UP|A0M8Q6|IGLC7_Homsap               TKPSKQSN  NKYAASSYLSLTPEQWKSHRSYSCRVTHEGST  VEKTVAPAECS
IMGT|V01241|IGKC_Ratnor              SVTDQDSKDSTYSMSSTLSLEKADYESHNLYTCEVVHKTSSSPVVKSFNRNEC
IMGT|K01360|IGKC1_Orycun             SKTPQNSADCTYNLSSTLTLTSTQYNSHEKYTCKVT QTTS  VVQSFNRGLC
IMGT|X00232|IGKC2_Orycun             SRTPQSPEDNTYSLSSTLSLTSAQYNSHSVYTCEVV  QGSASPIVQSFNRGDC
GB|AEM45014|IGKC_Bostau              SFTDQDSKSTYSLSSILTLPSSEYQSHNAYTCEVSHKSLTTALVKSFSRNEC
CONSENSUS -                                 E        S      A        T                +
PISA(INTERFACE)                      + +      +++              + +                    +
SELECTED                              *         *
```

FIG. 11

```
                   1         2         3         4         5         6
          123456789012345678901234567890123456789012345678901234567890 1234
PDB|1MHH_A    DIVMSQSPSSLAVSAGEKVTMSCKSSQSLLNSRTRKNYLAWYQQKPGQSPKVLIYWA----
PDB|1HEZ_A    DIQMTQSPSSLSASVGDRVTITCRTSQSI-------SSYLNWYQQKPGKAPKLLIYAA----
2F8_VL        AIQLTQSPSSLSASVGDRVTITCRASQDI-------SSALVWYQQKPGKAPKLLIYDA----
SP|P01617|KV204 DIVMTQSPLSLPVTPGEPASISCRSSQSLLHS-DGFDYLNWYLQKPGQSPZLLIYAL----
SP|P01699|LV101 QSVLTQPP SASGTPGQRVTISCSGGNFDI----GRNSVNWYQVHPGTAPRLLIYSS----
PISA(INTERFACE)    +++++++++         ++++                     ++
SELECTED           *  *  *         *  *                       *

7         8         9         10        11        12
          567890123456789012345678901234567890123456789012345678901234567
PDB|1MHH_A    STRESGVP-DRFTGKG--SGTDFTLTISSVQAEDQAVYYCKQAYI----PPLTFGAGTKLELK
PDB|1HEZ_A    SSLQSGVP-SRFSGSG--SGTDFTLTISSLQPEDFATYYCQQSYS----TPRTFGQGTKVEIK
2F8_VL        SSLESGVP-SRFSGSE--SGTDFTLTISSLQPEDFATYYCQQFNS-----YPLTFGGGTKVEIK
SP|P01617|KV204 SNRASGVP-DRFSGSG--SGTDFTLKISRVEAEDVGVYYCMZALQ----APITFGQGTRLEIK
SP|P01699|LV101 DQRSSGVP-DRFSGSK--SGTSASLAISGLQSENEADYFCATWDDS---LDGPVFGGGTKVTVL
PISA(INTERFACE)                                                +
SELECTED                                                       *
```

FIG. 20K
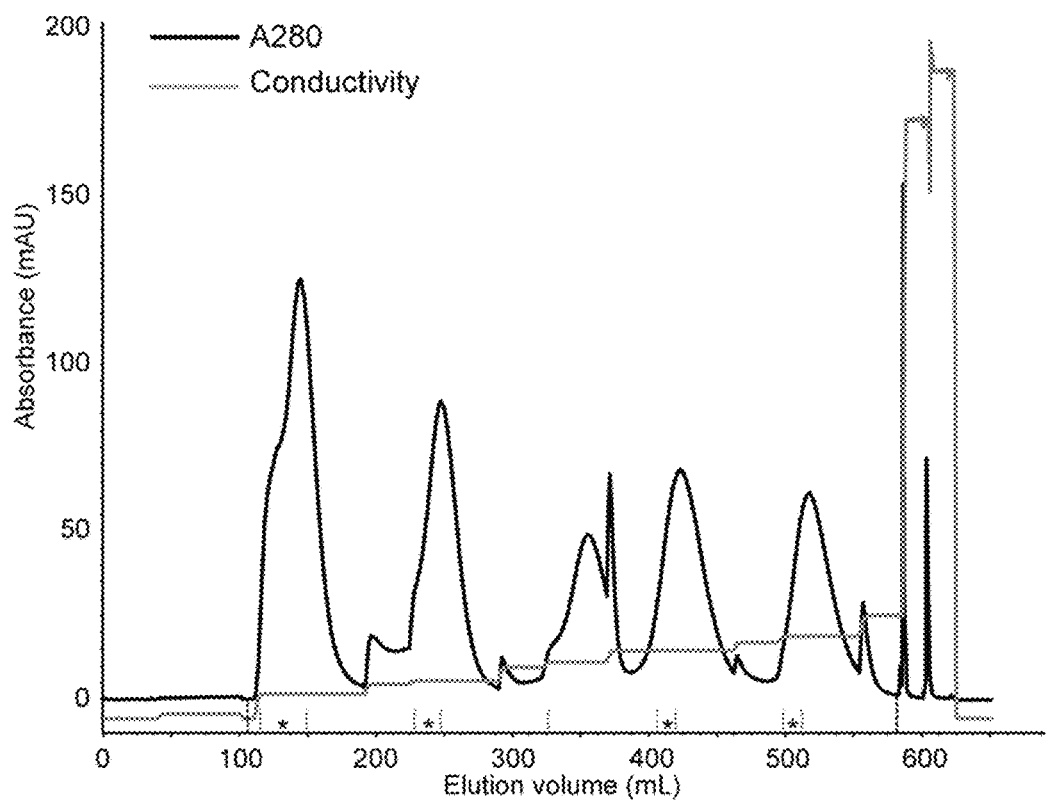
FIG. 20L
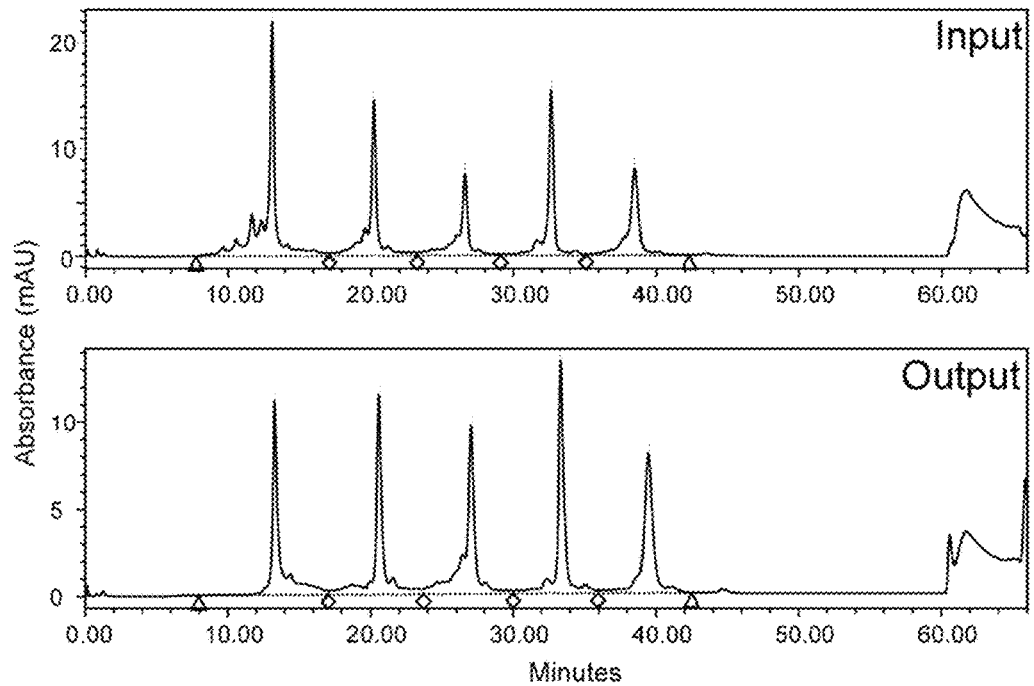
Figure 20 (continued)

METHOD FOR PRODUCING A CONTROLLED MIXTURE OF TWO OR MORE DIFFERENT ANTIBODIES

CROSS-REFERENCE TO RELATED APPLICATIONS

This application is a 35 U.S.C. 371 national stage filing of International Application No. PCT/EP2019/066594, filed Jun. 24, 2019, which claims priority to European Patent Application No. 18179365.4, filed Jun. 22, 2018. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Dec. 17, 2020, is named GMI_203US_Sequence_Listing.txt and is 81,761 bytes in size.

FIELD OF THE INVENTION

The present invention relates to a method for controlling the composition of a mixture of two or more different antibodies using chromatography. The mixture is for use as a drug product and the method includes a controlled downstream process for the production of a predetermined ratio of the two or more different antibodies.

BACKGROUND OF THE INVENTION

A number of human diseases are today treated with therapeutic monoclonal antibodies. However, some diseases are not treated sufficiently effectively by a monoclonal antibody or the treatment loses effect over time with application of monoclonal antibodies, for example due to down-regulation of the target or a switch to a distinct pathogenic pathway. Therefore, an alternative could be treatment with polyclonal antibodies or mixtures of antibodies such as a mixture of different monoclonal antibodies. Such mixtures of antibodies could comprise two or more antibodies directed against different epitopes on the same target, or alternatively a mixture of antibodies directed against different targets, or a combination thereof.

To produce such mixtures of antibodies, two or more monoclonal antibodies can be produced and characterized separately and subsequently mixed into one drug product. This would require controlled manufacturing and analysis of each of the separately produced monoclonal antibodies as well analysis of the final mixture for consistency in composition and potency. However, producing mixtures of antibodies using parallel production and purification trains can have higher manufacturing or development costs compared with co-producing mixtures of antibodies in a single bioreactor.

A mixture of antibodies can be produced from a single cell line expressing two or more monoclonal antibodies. WO 2004/009618 describes a method to transfect a single cell with genes that encode antibodies that all use a single, identical light chain. This allows for at least three binding-specificities to be produced by a single cell line. A disadvantage of this approach is that it is limited to the production of antibodies that all use an identical light chain, which precludes the use of many available antibody sequences and common antibody identification platforms. Furthermore, co-expression of the single light chain with multiple heavy chains in the absence of further engineering will lead to the formation of both mono- and bispecific antibodies that may not both be desired components, at a composition specific to the expression ratios of the multiple heavy chains during cell culture. Another approach, described in WO 2010/0089387, is to produce at least two antibodies in a single cell, wherein each of the genes encoding the antibodies is under the control of a distinct eukaryotic promotor. The cell line is cultured under conditions that allow the sequential expression of the genes of each of the antibodies. This approach can be expected to be highly sensitive to large scale culture process parameters such as scale or feeding differences would require strict control over the timing of promoter switching and harvesting which may compromise yield, and would only allow for the manufacturing of products of limited complexity. Both co-expression approaches essentially do not provide control over the composition of the product if the expression levels of individual antibody chains are differentially sensitive to changes in culture conditions.

Alternatively, a mixture of antibodies can be produced by co-culture of cell lines, each expressing one antibody. The recombinant antibody mixture can be manufactured by an adapted mammalian expression technology, which is based on site-specific integration of one antibody expression plasmid into the same genomic site of each cell as described in WO 2004/061104. WO2008/145133 describes a method for manufacturing a recombinant antibody mixture by means of random integration, wherein host cells are separately transfected with a set of expression vectors under conditions that avoid site-specific integration of the expression vectors into the genome of the host cells. Various approaches for production of a recombinant antibody mixture in multiple bioreactors, where the cell lines or antibody preparations are combined at a later point upstream or prior to or during downstream processing are described in WO 2009/129814. WO 2012/068317 describes a method to express mixtures of antibodies using non-viral AAV-based preferential integration into multiple, stable sites in the genome and the use of stable pools of cells instead of clonal cell lines. Although the composition of the mixture of antibodies can be controlled to a certain extent during production, this control is not sufficient to produce recombinant antibody mixtures for clinical trials or for drug products.

Therapeutic antibodies are purified by distinct chromatography steps to reduce contaminants such as DNA, host cell proteins or product related impurities to below pre-defined specifications. In general, antibody purification methods involve (1) fractionation based on physico-chemical characteristics such as size and charge, (2) fractionation based on class-specific affinity using solid-phase binding of particular antibody classes by immobilized biological ligands that have specific affinity to immunoglobulins or (3) fractionation based on antigen-specific affinity, as generally described in Current Protocols in Immunology, John Wiley & Sons, Coligan et al (eds).

In the context of bispecific antibodies, purification steps are used to separate the bispecific antibodies from product-related impurities. EP2009101 describes a method for purifying antibodies using chromatography based on the difference in isoelectric points between the heavy chains of two types of antibodies, wherein the difference is introduced by modifying the amino acids present in the antibody variable regions of the antibodies that constitute the bispecific antibody.

Another approach for isolating bispecific antibodies based on differential Protein A binding has been described in U.S. Pat. No. 8,586,713. In this method the Fc-region of one of the heavy chains is engineered to have reduced affinity for Protein A, allowing isolation of the bispecific antibody by differential binding of the IgG regions to Protein A. Another approach described in US2015239991 is based upon engineered antibodies with reduced affinity for Protein G and isolation using Protein G affinity chromatography.

Various resins have been described that specifically bind to Kappa light chains of antibodies, such as Protein L (GE Healthcare), KappaSelect (GE Healthcare), and KappaXL (ThermoFisher). Uses of these have been described in the context of bispecific antibodies. A method has been described in which bispecific monoclonal antibodies composed of a single heavy chain and two different light chains (LC), one containing Kappa constant domain and the other a Lambda constant domain, were purified using light chain specific resins (WO2013/088259). A method has also been described to purify bispecific antibodies based upon mutations of the CH1 domain (WO2013/136186). PCT/EP2016/065576 describes a method of purifying heterodimeric binding proteins such as bispecific and multispecific antibodies that contain two or more Kappa light chains using resins that bind to Kappa light chains, combined with mutations that prevent or reduce binding of one or more of the kappa light chains to the resins.

For recombinant antibody mixtures, a method for removing contaminating multimers using multi-modal chromatography, apatite chromatography and hydrophobic interaction chromatography is described in WO 2014/209508.

There is a need for methods to control the composition of mixtures of antibodies downstream of production. This can allow co-production of mixtures of antibodies while achieving the necessary control in the composition of the mixture. It is an object of the present invention to provide methods to control the composition of recombinant antibody mixtures using chromatography. These methods include using fractionation based upon the physio-chemical properties of the antibodies in the mixture to control the composition of the mixture. The methods also include protein engineering to alter the physio-chemical properties of the antibodies in the mixture to improve the separation. These methods also include the introduction of mutations into antibodies in the mixture that prevent or reduce binding of the antibodies to affinity resins, and control the composition of the mixture of antibodies by purification using resins that bind to the antibodies.

SUMMARY OF THE INVENTION

In a first aspect the invention relates to method for producing an output mixture of two or more different antibodies having a difference in their amino acid sequences, which difference enables separation of the antibodies by chromatography, wherein
 the two or more different antibodies are present in said output mixture at a desired or predetermined concentration ratio or within a tolerated deviation thereof; and
 the method comprises the steps of:
  1. providing an input mixture wherein the two or more different antibodies are not present at, or essentially at, the desired or predetermined concentration ratio;
  2. separating the two or more antibodies by chromatography;
  3. recovering the two or more antibodies in the amounts required to provide the output mixture.

In a second aspect the invention relates to a mixture of two or more different antibodies, said mixture being obtainable by the method of the invention.

In a third aspect the invention relates to a pharmaceutical composition comprising the mixture of the invention.

In a fourth aspect the invention relates to an antibody mixture for use in a method of treatment of a disease.

BRIEF DESCRIPTION OF THE FIGURES

(FIG. 1A) The process comprises an upstream co-production process wherein the production levels of the antibodies cannot be controlled to consistently comply with the release specifications. The antibodies are purified during the downstream processing steps that additionally control the composition of the antibody mixture. The chromatography can comprise affinity chromatography based upon differences in the binding properties of the antibodies for affinity resin(s), where (FIG. 1B) the resin(s) are saturated with the antibody mixture at the correct ratio; (FIG. 1C) the resin(s) bind excess antibodies to yield an antibody mixture at the correct ratio, following pre-determination of the antibody ratio using an analytical assay. The chromatography can also comprise chromatography based on differences in the physiochemical properties of the antibodies, where (FIG. 1D) the design space of the chromatography experiment has been pre-explored such that excess antibodies are removed from the mixture to yield an antibody mixture at the correct ratio, following pre-determination of the antibody ratio using an analytical assay; (FIG. 1E) fractionation and pooling of fractions based upon the chromatogram or concentration measurements of the fractions.

FIGS. 2A-2E: (FIG. 2A) Sequence alignment of heavy chain variable regions of human germlines and antibodies IgG1-1014-005, IgG1-2F8, and IgG1-1021-511. Amino acids are numbered according to IMGT numbering. Asterisks indicate positions at which point mutations were introduced in either of the antibodies. (FIG. 2B) Sequence alignment of light chain variable regions of human germlines and antibodies IgG1-1014-005, IgG1-2F8, and IgG1-1021-511. Amino acids are numbered according to IMGT numbering. Asterisks indicate positions at which point mutations were introduced in either of the antibodies. (FIGS. 2C-2E) Alignment of charge modulated variable domain variants of antibodies IgG1-2F8 (FIG. 2C), IgG1-1014-005 (FIG. 2D), and IgG1-1021-511 (FIG. 2E). Amino acids are numbered consecutively (above the alignment), or according to IMGT numbering of human variable regions (below the alignment); positions tested by mutation are indicated by highlighting.

HA1, HA2, and HA3 (more negative), and HB1, HB2, and HB3 (more positive) indicate heavy chain variable domains with stepwise increasing charge difference relative to variant HC, indicating the reference heavy chain variable domain sequence that was expressed as a fusion to a constant domain sequence without C-terminal lysine. HP indicates the sequence of the un-mutated heavy chain variable domain of the parental antibody expressed as a sequence containing C-terminal lysine, and N-terminal pyroglutamate where applicable. In analogous fashion, LA1, LA2, LA3 (more negative) and LB1, LB2, and LB3 (more positive) indicate the sequences of light chain variable domains.

Figure 3:
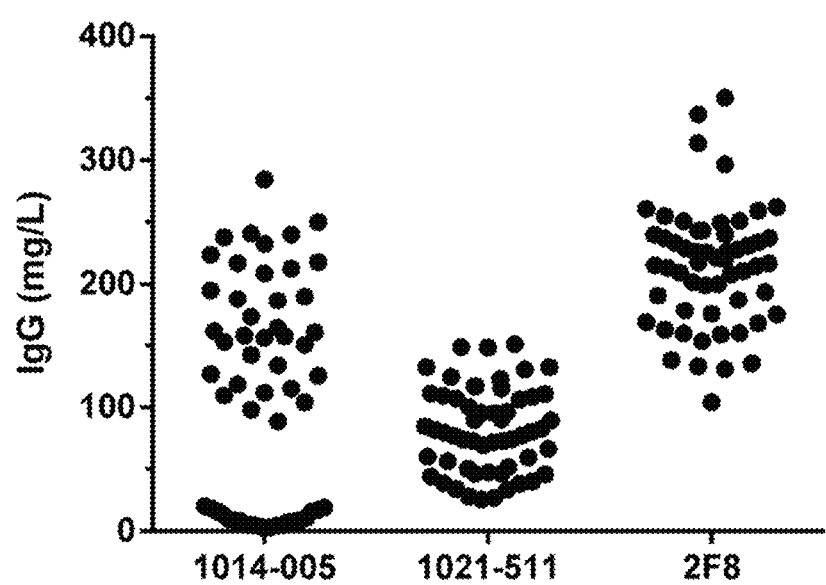

FIG. 3: IgG titer determinations of charge-modulated antibody variants. A scatter plot showing the antibody expression levels of each variant of IgG1-1014-005, IgG1-

1021-511 and IgG1-2F8 as a single data point. The expression levels are sufficiently tightly clustered to show that the point mutations do not have a major effect on protein expression with the exception of IgG1-1014-005 heavy chain mutation Q6E, which had a detrimental effect on the antibody titer of all variants containing this mutation.

FIGS. 4A-4E: Analysis of the charge properties of the charge-modulated antibody variants. (FIG. 4A) A scatter plot showing the theoretical isoelectric points (pI) of each variant of IgG1-1014-005, IgG1-1021-511 and IgG1-2F8. (FIG. 4B) A scatter plot showing the retention times that were sampled by the antibody variants in an analytical HPLC cation exchange (CEX) experiment. Control antibody variants are shown by open grey symbols, whereas antibody variants that elute in the flow-through and show no significant interaction with the column resin under these conditions are excluded from the figure. Correlation of analytical cation exchange retention times with pI for (FIG. 4C) IgG1-1014-005 charge variants, (FIG. 4D) IgG1-1021-511 charge variants and (FIG. 4E) IgG1-2F8 charge variants. These data show that the charge-modulating point mutations have a significant effect on the charge properties of the antibodies.

FIGS. 5A-5E: Exemplary Protein A separations of mixtures of antibody variants from cell culture supernatants containing (FIG. 5A) IgG1-1014-005-HCLC, IgG1-2F8-HCLC, IgG1-1021-511-HCLC and IgG1-1014-153; (FIG. 5B) IgG1-2F8-HB3LC, IgG1-1014-005-HB3LB1, IgG1-1021-511-HA3LB2 and IgG1-1014-153; (FIG. 5C) IgG1-2F8-HB3LB3, IgG1-1014-005-HB3LB1, IgG1-1021-511-HA3LB2 and IgG1-1014-153; (FIG. 5D) IgG1-2F8-V110D, IgG1-7D8-S12P and IgG1-HepC, (FIG. 5E) IgG1-2F8-HB3LC, IgG1-1014-005-HB3LB1, IgG1-1021-511-HA3LB2 and IgG1-1014-153. The absorption at 280 nm (solid line) and conductivity or pH (dashed grey line) were monitored. All purifications show an elevated absorption during column loading from non-bound material from the cell culture supernatants in the flow-through. Specifically bound antibody variants were eluted at pH 3.0 and detected by peaks in the absorption at 280 nm. Minor peaks at 280 nm during the wash step are indicative of less tightly bound material.

FIGS. 6A-6E: Exemplary preparative cation exchange chromatography separations of purified (FIG. 6A) IgG1-1014-005-HCLC, IgG1-2F8-HCLC, IgG1-1021-511-HCLC and IgG1-1014-153 of similar concentrations; (FIG. 6B) IgG1-2F8-HB3LC, IgG1-1014-005-HB3LB1, IgG1-1021-511-HA3LB2 and IgG1-1014-153 of similar concentrations, (FIG. 6C) IgG1-2F8-HB3LB3, IgG1-1014-005-HB3LB1, IgG1-1021-511-HA3LB2 and IgG1-1014-153 purified from supernatant containing the antibody variants in an approximate ratio of 5:3:2:1, and (FIG. 6D) IgG1-2F8-HB3LC, IgG1-1014-005-HB3LB1, IgG1-1021-511-HA3LB2 and IgG1-1014-153 purified from supernatant containing the antibody variants in an approximate ratio of 1:3:2:5. The absorption at 280 nm (solid line) and conductivity (dashed grey line) were monitored. The non-charge modulated variants in (FIG. 6A) show a defined peak of IgG1-1021-511-HCLC at ~120 mL but the other three species are poorly resolved. The charge-modulated variants (FIGS. 6B and 6C) are resolved since four defined peaks can be observed at each of the antibody ratios. The pooling schemes in each experiment are indicated by the vertical markers and numerals (1-4). The chromatograms from the 3 antibody mixtures are quantified in Table 1. (FIG. 6E) schematic showing the calculation of resolution (Rs) according to the equation Rs=2 (t2−t1)/(W1+W2) where t1=retention time of a given antibody, t2=retention time of the sequentially-eluting antibody, and W1 and W2 are the corresponding peak widths of the antibodies in units of time at the bases of the peaks, obtained by extrapolating the relatively straight sides of the main peaks to the baseline.

FIGS. 7A-7F: Analytical cation exchange chromatograms from load antibody mixtures and pooled fractions collected from the preparative cation exchange chromatography separations shown in FIG. 6. (FIG. 7A) IgG1-1014-005-HCLC, IgG1-2F8-HCLC, IgG1-1021-511-HCLC and IgG1-1014-153 of similar concentration. Dashed lines are used to identify main peaks (a-d). The antibodies are not fully resolved on the high resolution analytical column and several of the pooled fractions contain mixtures of antibodies. (FIG. 7B) IgG1-2F8-HB3LC, IgG1-1014-005-HB3LB1, IgG1-1021-511-HA3LB2 and IgG1-1014-153 of similar concentration. Dashed lines are used to identify main peaks (a-d). The antibodies are well resolved on the high resolution analytical column and the pooled fractions contain >99% pure antibody, as inferred by integration of the analytical cation exchange profiles. (FIG. 7C) IgG1-2F8-HB3LB3, IgG1-1014-005-HB3LB1, IgG1-1021-511-HA3LB2 and IgG1-1014-153. Dashed lines are used to identify main peaks (a-d). The antibodies are well resolved on the high resolution analytical column and the pooled fractions contain >99% pure antibody, as inferred by integration of the analytical cation exchange profiles. (FIG. 7D) IgG1-2F8-HB3LC, IgG1-1014-005-HB3LB1, IgG1-1021-511-HA3LB2 and IgG1-1014-153 of different concentrations. Dashed lines are used to identify main peaks (a-d). The antibodies are well resolved on the high resolution analytical column and the pooled fractions contain >99% pure antibody, as inferred by integration of the analytical cation exchange profiles. (FIG. 7E) The non-equimolar mixture of IgG1-2F8-HB3LB3, IgG1-1014-005-HB3LB1, IgG1-1021-511-HA3LB2 and IgG1-1014-153 before preparative cation exchange chromatography (top panel), and the end product following preparative chromatography and re-pooling (lower panel). The chromatograms are quantified in Table 2. (FIG. 7F) The non-equimolar mixture of IgG1-2F8-HB3LC IgG1-1014-005-HB3LB1, IgG1-1021-511-HA3LB2 and IgG1-1014-153 before preparative cation exchange chromatography (top panel), and the end product following preparative chromatography and re-pooling (lower panel). The chromatograms are quantified in Table 2.

FIGS. 8A-8E: (FIG. 8A) Preparative cation exchange chromatogram of an equimolar mixture of IgG1-7D8, IgG1-224, IgG1-CD37-37-3, IgG1-CD19-21D4-K409R and IgG1-CD52-Campath at a load of 2 g/L resin, using material produced by transient production in FreeStyle™ 293-F cells. Three distinct peaks can be identified in the chromatogram from the separation of the 5 antibodies, showing that the 5 antibodies are not sufficiently different in their charge properties to achieve separation in this experiment. The K409R mutation does not significantly affect the elution behavior of the IgG1-CD19-21D4 antibody since it is not on the surface of the antibody and does result in a change in net charge. (FIG. 8B) Preparative cation exchange chromatogram of an equimolar mixture of IgG1-7D8, IgG1-224, IgG1-CD37-37-3, IgG1-CD19-21D4-E345K and IgG1-CD52-Campath-E345K at a load of 2 g/L resin, using material produced by transient production in FreeStyle™ 293-F cells. Introduction of the E345K mutation into IgG1-CD19-21D4-E345K and IgG1-CD52-Campath-E345K alters the retention time of these antibodies and gives rise to five resolved peaks in the chromatogram under these chromatography conditions. (FIG. 8C) Preparative cation exchange chromatogram of an equimolar mixture of IgG1-7D8, IgG1-224, IgG1-CD37-37-

3, IgG1-CD19-21D4-E345K and IgG1-CD52-Campath-E345K at a load of 0.2 g/L resin, using material produced by transient production in FreeStyle™ 293-F cells. The eluted peaks were fractionated and pooled as indicated by the vertical markers and numerals (1-5). In each experiment the absorption at 280 nm (solid line) and conductivity (dashed grey line) were monitored. (FIG. 8D) The peaks were individually collected (labelled 1-5) and analyzed by cation exchange chromatography. The retention time allows assignment of peaks 1-5 as IgG1-7D8, IgG1-224, IgG1-CD37-37-3, IgG1-CD19-21D4-E345K and IgG1-CD52-Campath-E345K, respectively. (FIG. 8E) Loading study showing the elution portion of stacked chromatograms of individual separations in which an equimolar mixture of IgG1-7D8, IgG1-224, IgG1-CD37-37-3, IgG1-CD19-21D4-E345K and IgG1-CD52-Campath-E345K was separated at a total load of 0.2, 0.5, 1.0, 2.0, 5.0, 10, 20, or 50 g antibody mixture per L resin, using material produced from CHO cell lines. Five resolved peaks are observed at all loads, detected by absorption at 280 nm, with some degree of peak broadening detected at the highest loads, as quantified in Table 3. The chromatograms are similar when using transiently-produced material or materials from CHO cell lines.

FIGS. 9A-9E: (FIG. 9A) Preparative cation exchange chromatogram showing the separation of mixtures of IgG1-7D8, IgG1-224, IgG1-CD37-37-3, IgG1-CD19-21D4-E345K and IgG1-CD52-Campath-E345K using sequential step elutions. The respective load ratios of IgG1-7D8, IgG1-224, IgG1-CD37-37-3, IgG1-CD19-21D4-E345K and IgG1-CD52-Campath-E345K are indicated in each panel, based upon calculation of the relative mass amounts of the antibodies in the mixture. Each separation was fractionated and pooled as indicated by the vertical markers and numerals (1-5). The absorption at 280 nm (solid line) and conductivity (dashed grey line) were monitored. The chromatograms are quantified in Table 4. (FIGS. 9B-9E) Each of the five fractions from the 4 fractionation experiments were individually analyzed by analytical cation exchange chromatography, alongside a sample of the load material from the preparative chromatography experiments. The retention time allows assignment of peaks a-e as IgG1-7D8, IgG1-224, IgG1-CD37-37-3, IgG1-CD19-21D4-E345K and IgG1-CD52-Campath-E345K, respectively. The ratios on each panel indicate the input ratio of IgG1-7D8, IgG1-224, IgG1-CD37-37-3, IgG1-CD19-21D4-E345K and IgG1-CD52-Campath-E345K prior to the preparative chromatography experiments.

FIG. 10: Sequence alignment of kappa light chain CL domains. (allo) indicates allotypic variations; CONSENSUS+indicates conserved residues present in all cross-reactive species; CONSENSUS-indicates "CONSENSUS+" residues that are present in one of the non-cross-reactive species (and human lambda CL); PISA (INTERFACE) indicates residues (+) that are located at the CL-VL and CL-CH1 interfaces with <50% exposed surface area in the PDB 1HZH structure as determined by the PDBePISA tool (pdbe.org/pisa/) (Krissinel, E. and Henrick, K.; J Mol Biol (372): 774-97, 2007); Selected residues (*) were mutated in this study to the mouse equivalent. EU-numbering convention is used to annotate amino acid residues (Kabat et al., Sequences of Proteins of Immunological Interest, 5th Ed. Public Health Service, National Institutes of Health, Bethesda, MD. (1991)).

FIG. 11: Sequence alignment of kappa light chain VL domains. PBD structures 1HEZ and 1MHH were analyzed using the PDBePISA tool (pdbe.org/pisa/) (Krissinel, E. and Henrick, K.; J Mol Biol (372): 774-97, 2007). Residues identified as being at the interface with Protein L in all models are marked (+). Selected residues (marked *) were mutated in this study to the equivalent residue found in the kappa subtype V-II (P01617) or Lambda subtype V-1 (P01699) sequences. IMGT numbering is used to annotate amino acid residues (Lefranc, M.-P. et al., Dev. Comp. Immunol., 2003, 27, 55-77).

FIGS. 12A-12F: Exemplary KappaSelect purifications of modified IgG1-2F8-F405L variants using purified protein (FIG. 12A) IgG1-2F8-F405L, or cell culture supernatants containing produced (FIG. 12B) IgG1-2F8-F405L-mmF135L, (FIG. 12C) IgG1-2F8-F405L-V110D, (FIG. 12D) IgG1-2F8-F405L-E143D and (FIG. 12E) IgG1-2F8-F405L-E165D. The absorption at 280 nm (solid line) and pH (dashed grey line) were monitored. The purifications from cell culture supernatant show an elevated absorption during column loading from non-bound material in the flow-through. Specifically bound IgG1-2F8-F405L variants were eluted at pH 3.0 and pH 2.0 and detected by peaks in the absorption at 280 nm. (FIG. 12F) Analysis of flow-through fractions from KappaSelect purifications of modified IgG1-2F8 variants using SDS-PAGE. Non-reducing SDS-PAGE gels shows a band of intact IgG1 variants in the flow-through of IgG1-2F8-F405L-mmF135L (lane 1) and IgG1-2F8-F405L-V110D (lane 2) but not the other IgG1-2F8-F405L variants (lanes 3-10). The other major bands are assigned as antibody fragments.

FIGS. 13A-13F: Exemplary CaptureSelect® KappaXL separations of Modified IgG1-7D8-K409R variants from cell culture supernatants containing produced (FIG. 13A) IgG1-7D8-K409R, (FIG. 13B) IgG1-7D8-K409R-V110R, (FIG. 13C) IgG1-7D8-K409R-V110K, (FIG. 13D) IgG1-7D8-K409R-V110D, (FIG. 13E) IgG1-7D8-K409R-V110E, (FIG. 13F) IgG1-7D8-K409R-V110T. The absorption at 280 nm (solid line) and pH (dashed grey line) were monitored. All purifications show an elevated absorption during column loading from non-bound material from the cell culture supernatants in the flow-through. Specifically bound IgG1-7D8-K409R variants were eluted at pH 3.5 and detected by peaks in the absorption at 280 nm. Peaks at 280 nm during the pH 5.0 wash are indicative of less tightly bound material, whereas peaks at 280 nm during the guanidine-HCl wash at approximately 30 mL are caused by an incomplete elution of antibodies during the wash and elution phases.

Figure 14A:
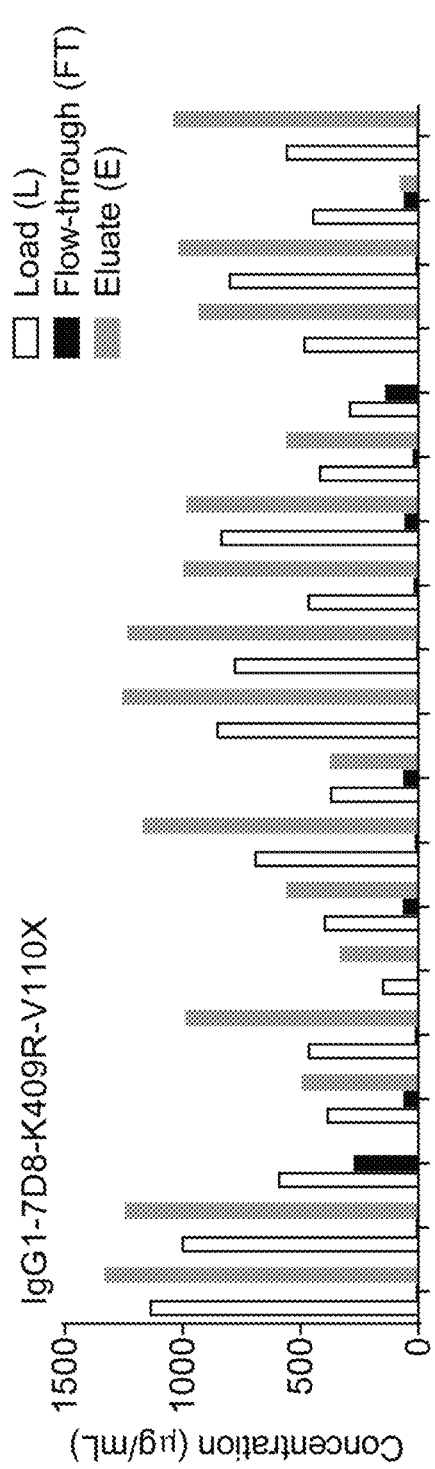
Figure 14B:
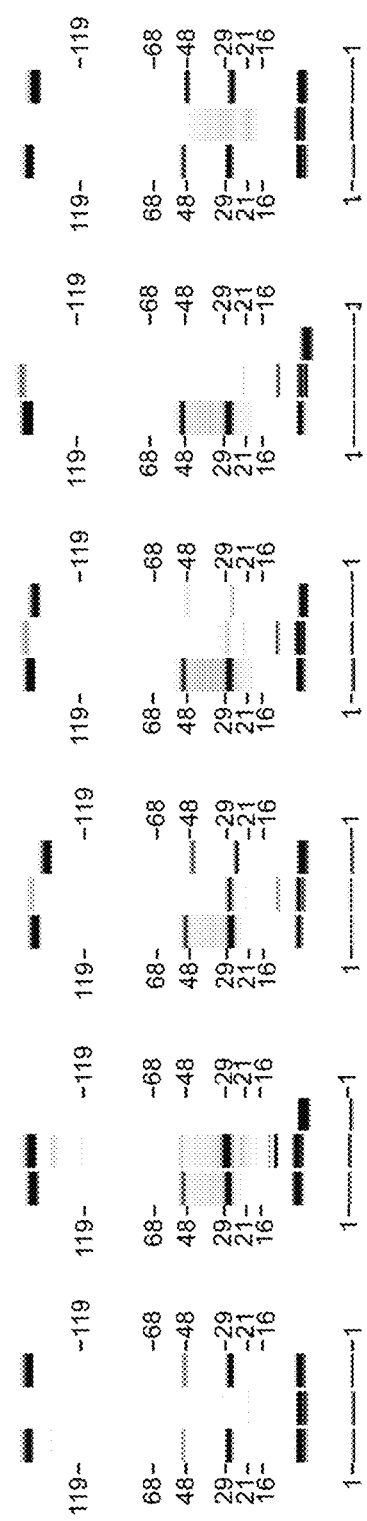

FIGS. 14A and 14B: Analysis of fractions from CaptureSelect® KappaXL separations of modified IgG1-7D8-K409R variants using Bio-Layer Interferometry and CE-SDS. (FIG. 14A) The concentration of IgG1-7D8-K409R variants in load samples, pooled flow-through samples and pooled eluate samples were inferred from bio-layer interferometry measurements. The data from the IgG1-7D8-K409R variants, with a different amino acid at position 110 (EU-numbering convention) of the kappa light chain, are grouped and labeled using the single amino acid code for the amino acid at this position. The measured protein concentrations in the flow-through are lower than in the load samples for variants that show no detectable binding to the resin as a result of the dilution of the flow-through samples during the purification experiments. (FIG. 14B) Analysis of fractions from CaptureSelect® KappaXL separations of modified IgG1-7D8-K409R variants using CE-SDS. Exemplary non-reducing CE-SDS electropherograms that have been calibrated according to a molecular weight standard, show a band of intact IgG1 variants at a molecular weight of approximately 150 kDa in the load samples of IgG1-7D8-K409R, IgG1-7D8-K409R-V110D, IgG1-7D8-K409R-V110E, IgG1-7D8-K409R-V110K, IgG1-7D8-K409R-

V110R and IgG1-7D8-K409R-V110T. Intact IgG1 variants may be detected in flow-through and/or the eluate depending on the relative binding of the IgG1-7D8-K409R variants to the CaptureSelect® KappaXL resin. The other major bands of lower molecular weights are assigned as antibody fragments, system calibration peaks or other material from the transient production experiments.

Figure 15A:
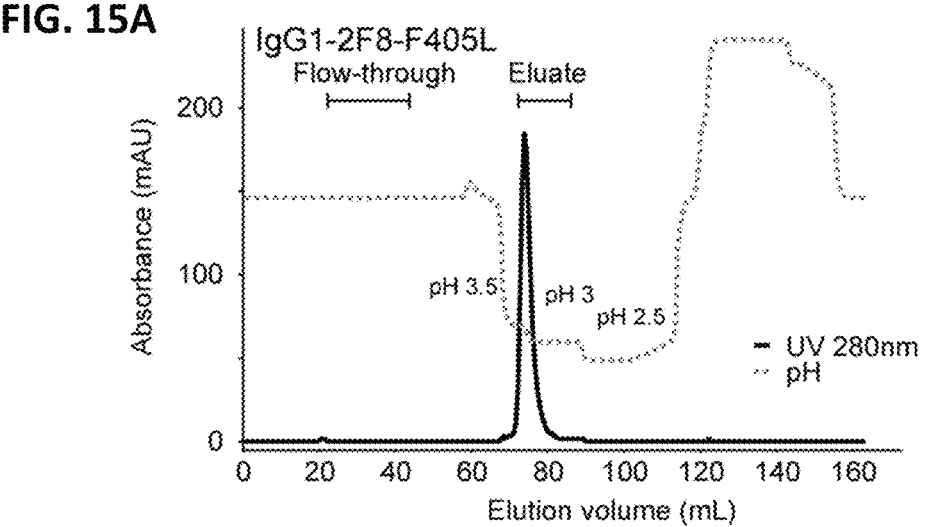
Figure 15B:
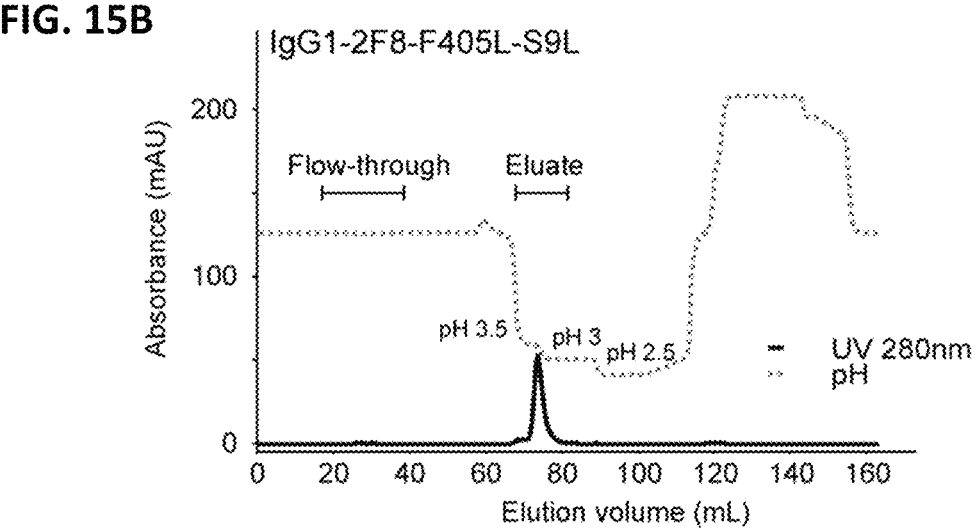
Figure 15C:
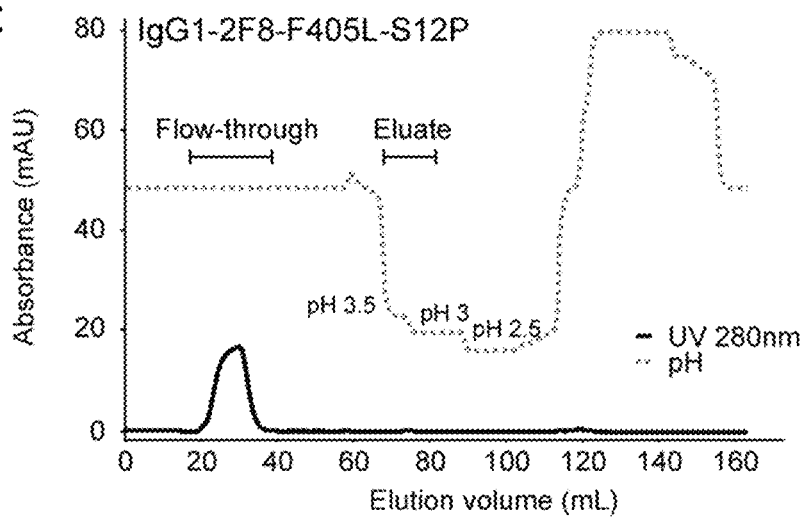
Figure 16A:
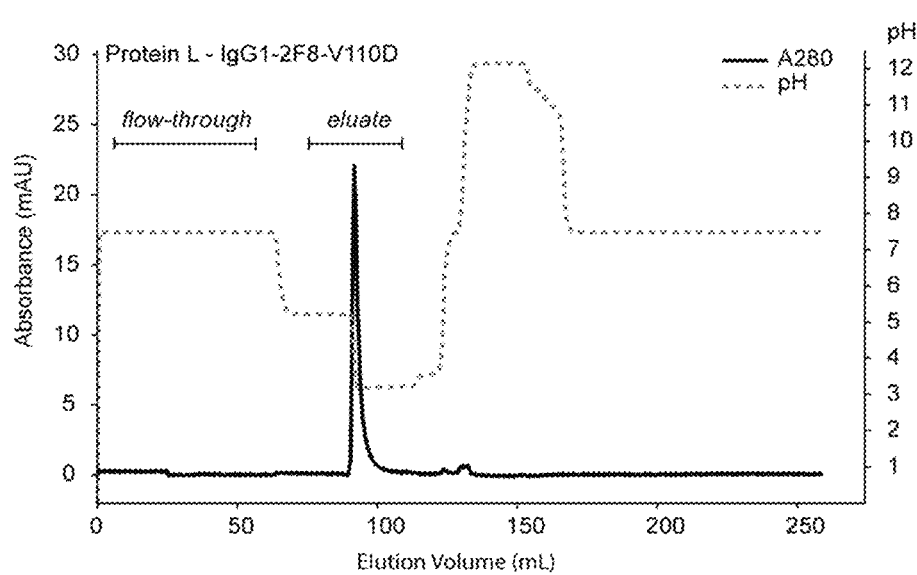
Figure 16B:
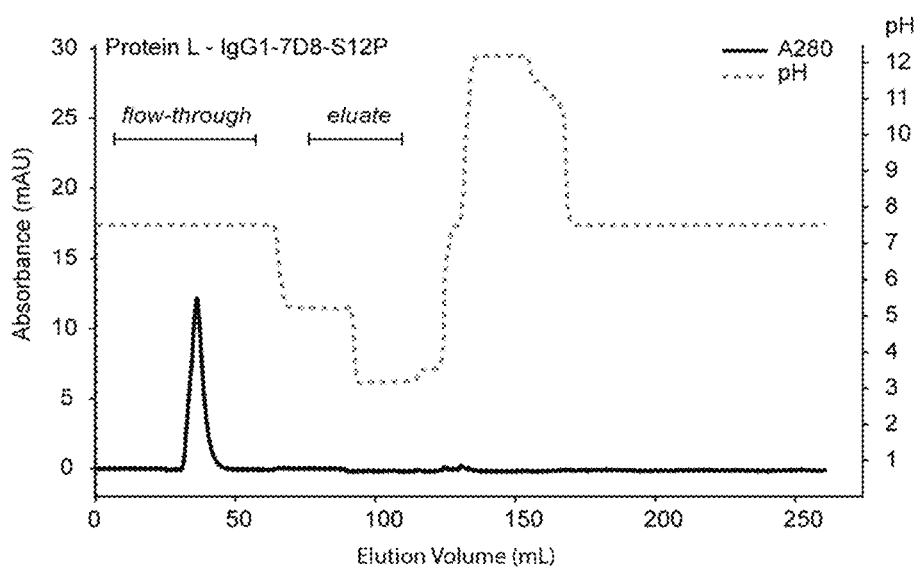
Figure 16C:
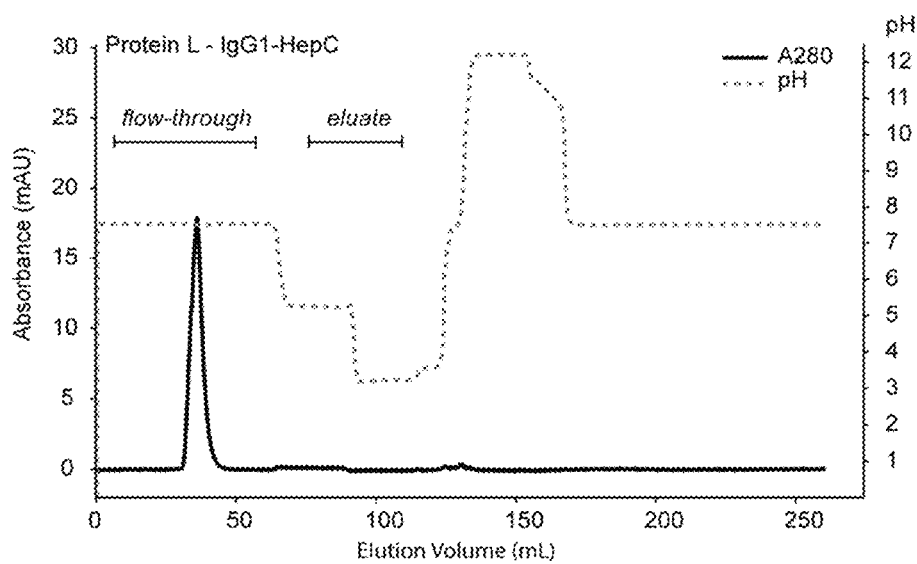
Figure 16D:
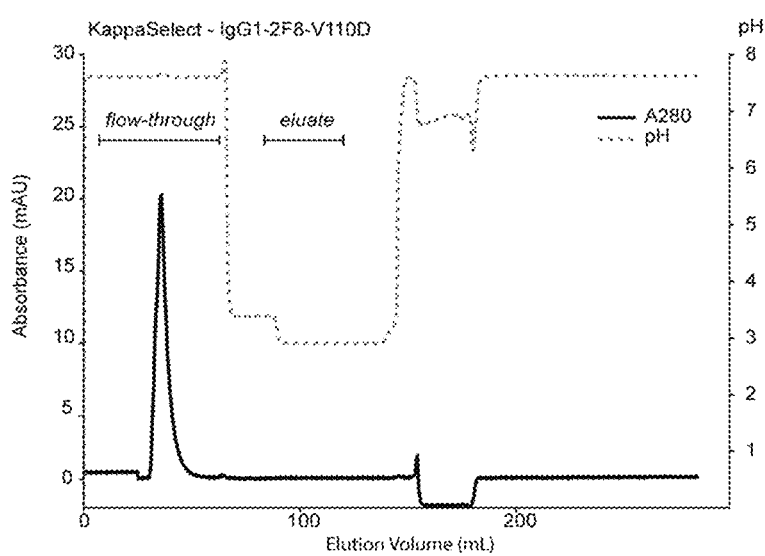
Figure 16E:
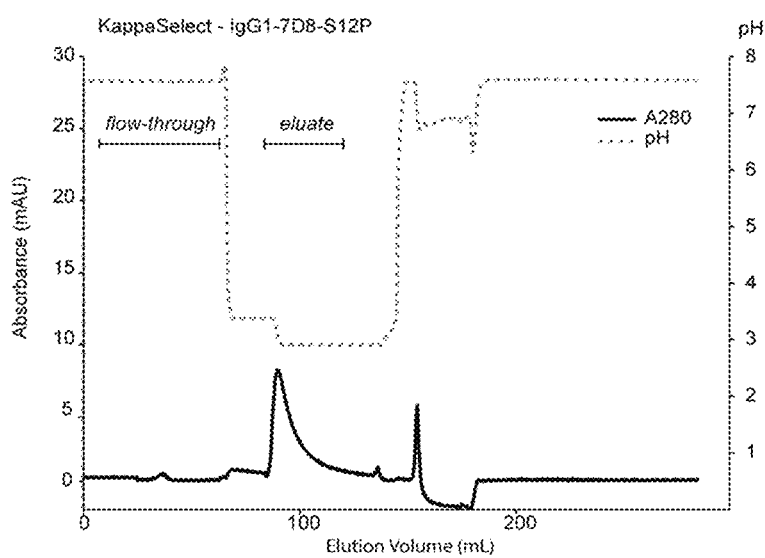
Figure 16F:
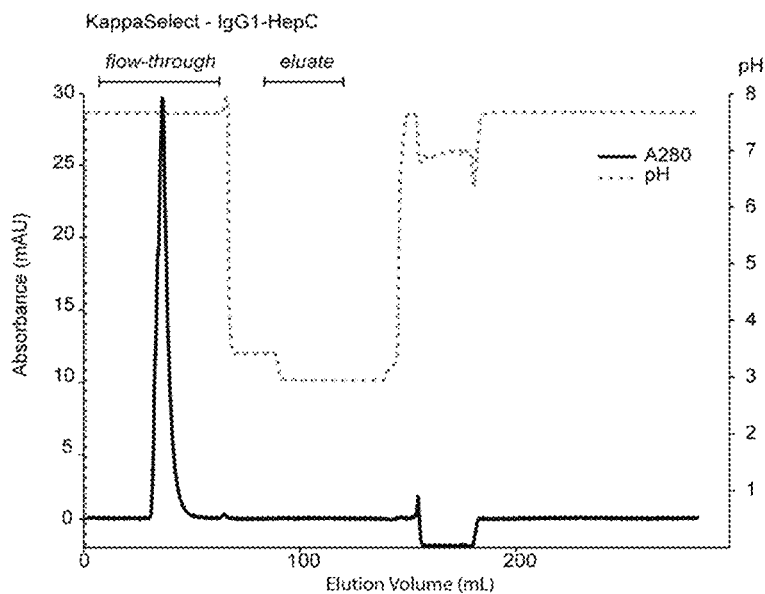
Figure 16G:
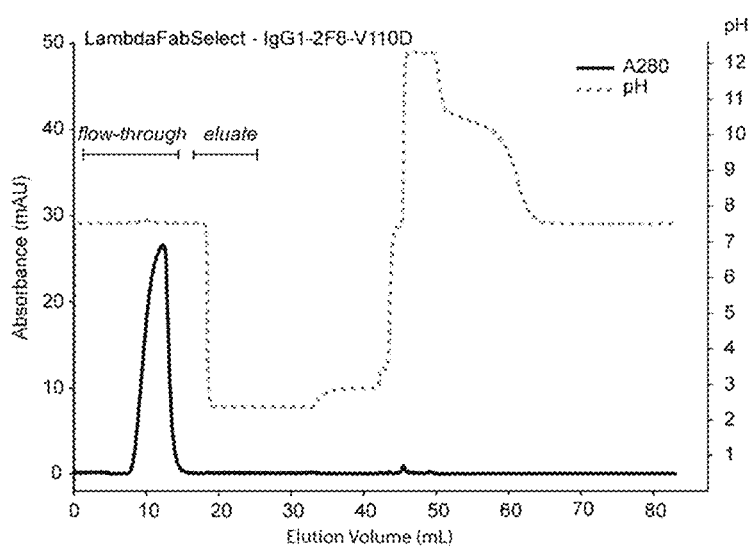
Figure 16H:
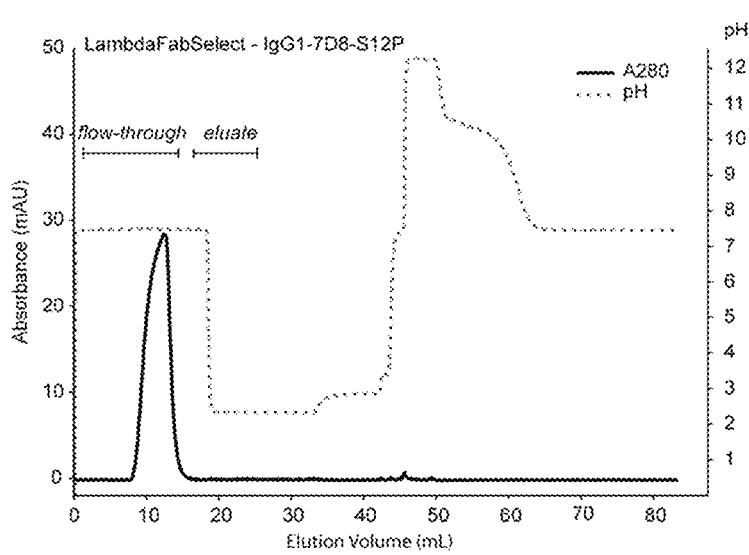
Figure 16I:
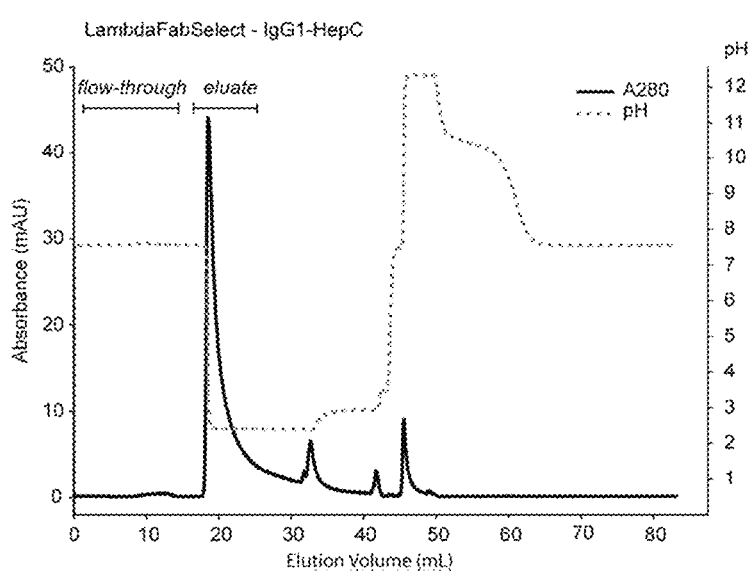

FIGS. 15A-15C: HiTrap Protein L purifications of purified IgG-2F8-F405L variants. Chromatograms showing the absorption at 280 nm (solid line) and the pH profile (dashed grey line) during the separations of purified (FIG. 15A) IgG1-2F8-F405L, (FIG. 15B) IgG1-2F8-F405L-S9L and (FIG. 15C) IgG1-2F8-F405L-S12P.

FIGS. 16A-16I: Chromatography experiments showing the specificity of antibody variants for three affinity chromatography resins. HiTrap Protein L separations of purified (FIG. 16A) IgG1-2F8-V110D, (FIG. 16B) IgG1-7D8-S12P, (FIG. 16C) IgG1-HepC. HiTrap KappaSelect separations of purified (FIG. 16D) IgG1-2F8-V110D, (FIG. 16E) IgG1-7D8-S12P, (FIG. 16F) IgG1-HepC. HiTrap LambdaFabSelect separations of (FIG. 16G) IgG1-2F8-V110D, (FIG. 16H) IgG1-7D8-S12P, (FIG. 16I) IgG1-HepC. The chromatograms show the absorption at 280 nm (solid line) and the pH profile (dashed grey line) during the separations.

Figure 17A:
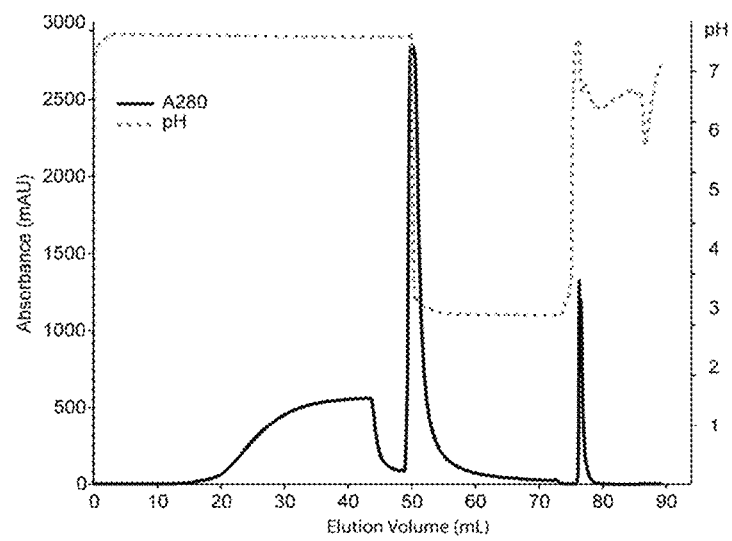
Figure 17B:
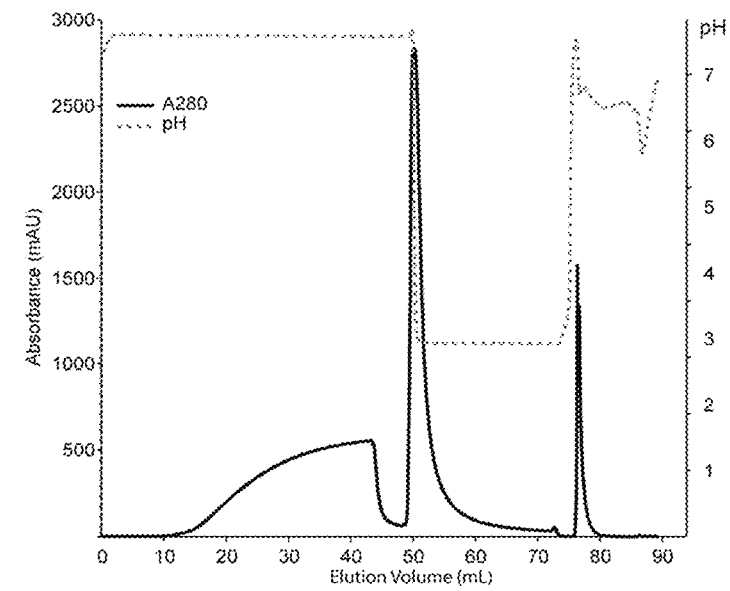
Figure 17C:
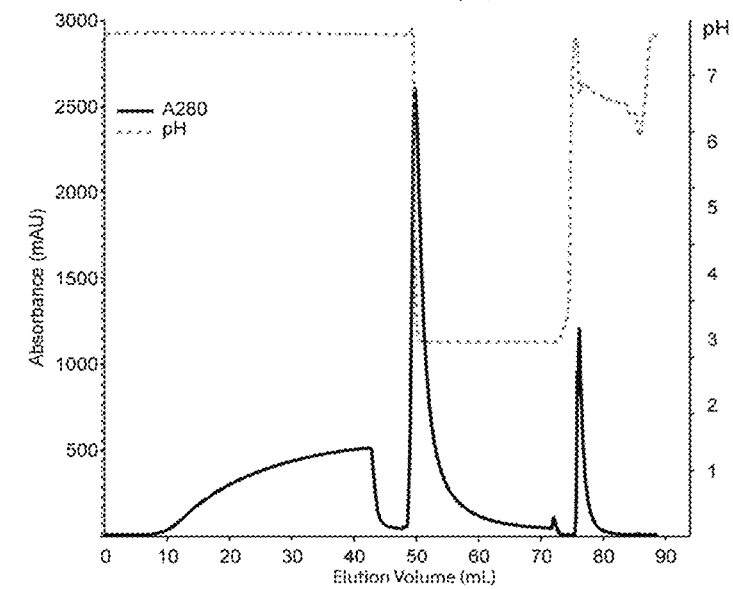

FIGS. 17A-17C: Loading studies of purified IgG1-7D8-K409R into a HiTrap KappaSelect column at a residence time of (FIG. 17A) 4 minutes, (FIG. 17B) 2 minutes, (FIG. 17C) 1 minute. The chromatograms show the absorption at 280 nm (solid line) and the pH profile (dashed grey line) during the separations. The increase in absorption at 280 nm during the loading phase indicates that the column load approached the binding capacity as the column became saturated.

Figure 18:
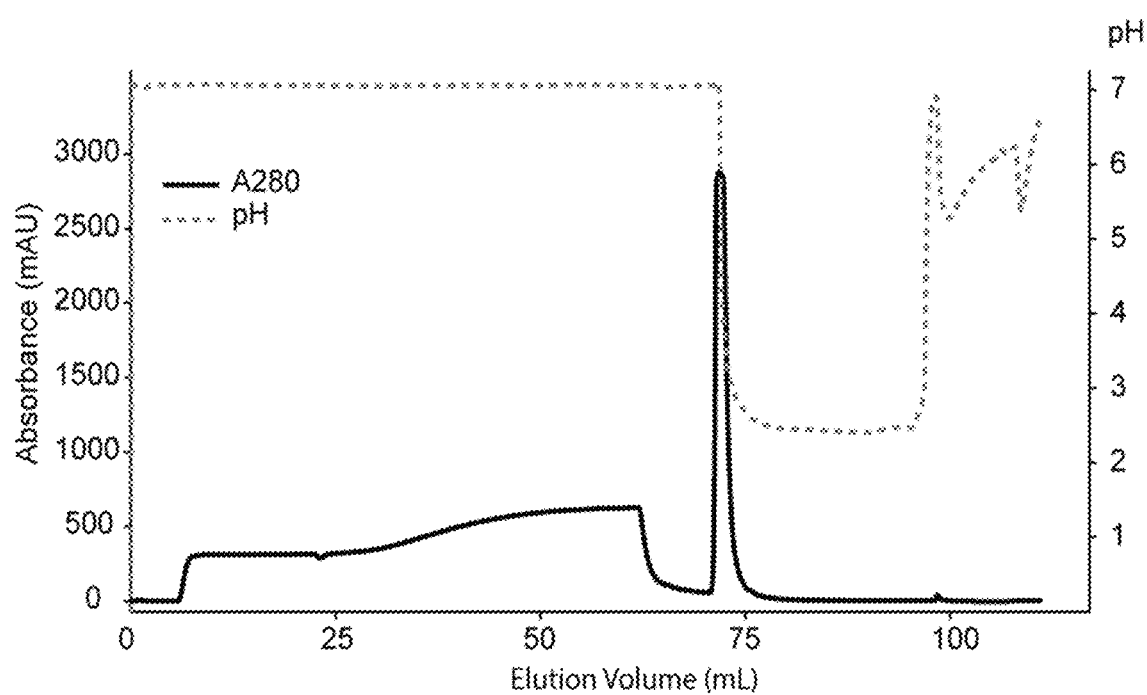

FIG. 18: Chromatogram from the KappaSelect purification of a mixture IgG1-2F8-V110D, IgG1-7D8-S12P and IgG1-HepC, under saturating conditions. The chromatogram was monitored for absorption at 280 nm (solid line) and pH (dashed grey line) during the separation. The increase in absorption at 280 nm during the loading phase indicates that the column load approached the binding capacity as the column became saturated.

Figure 19A:
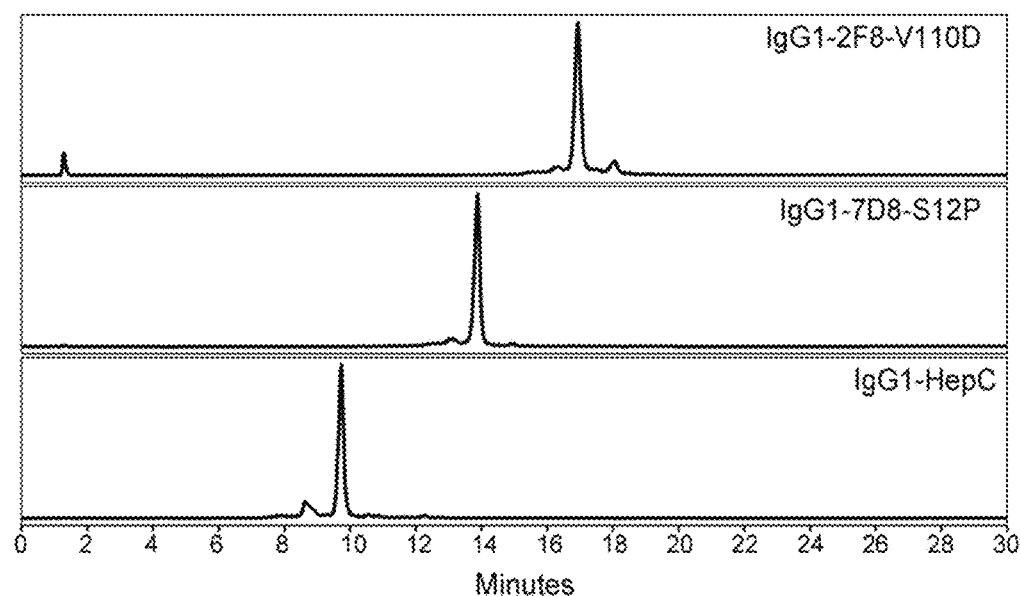
Figure 19B:
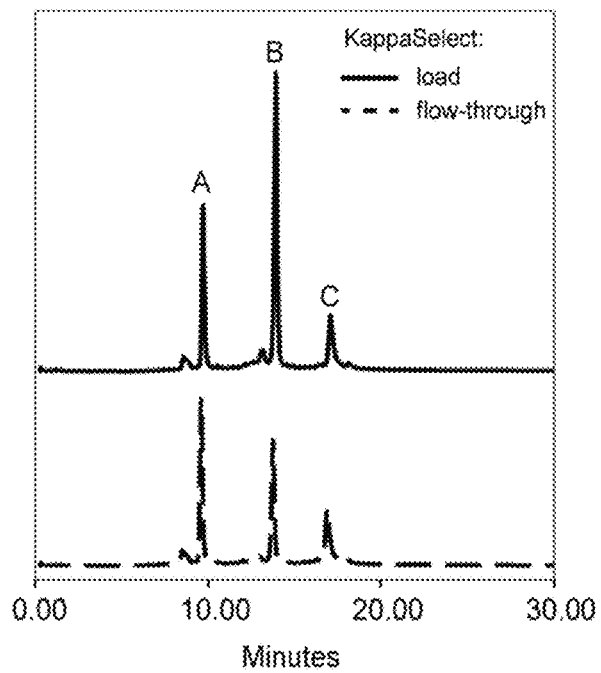

FIGS. 19A and 19B: (FIG. 19A) Stacked analytical cation exchange chromatograms of purified IgG1-2F8-V110D, IgG1-7D8-S12P and IgG1-HepC. (FIG. 19B) Stacked analytical cation exchange chromatograms of mixtures of IgG1-HepC (annotated A), IgG1-7D8-S12P (annotated B) and IgG1-2F8-V110D (annotated C), and before and after the KappaSelect separation. The chromatograms are quantified in Table 10.

Figure 20A:
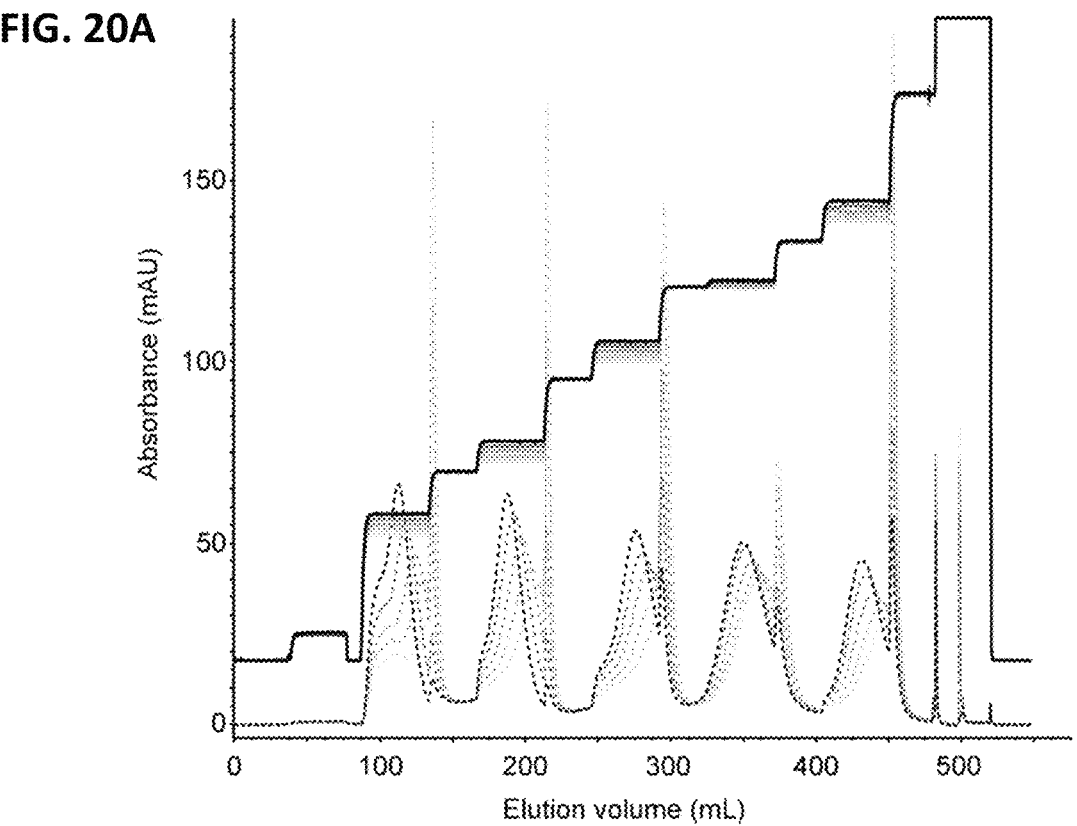
Figure 20B:
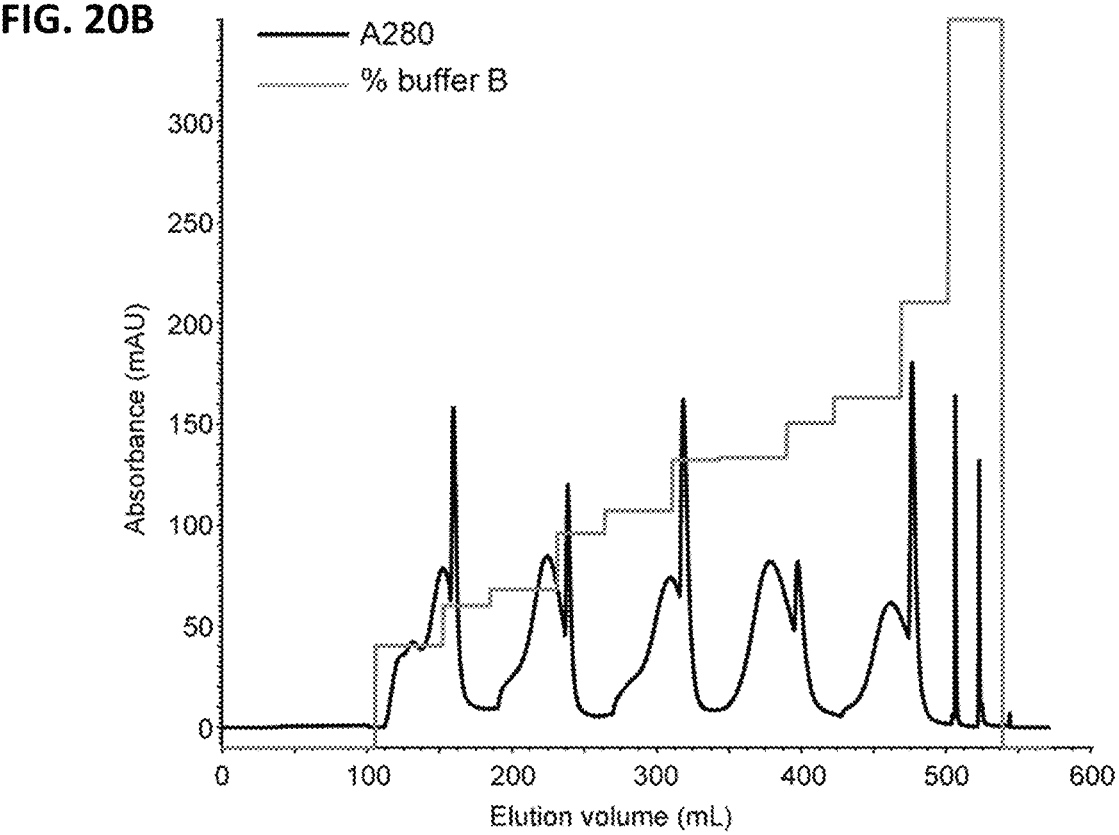
Figure 20C:
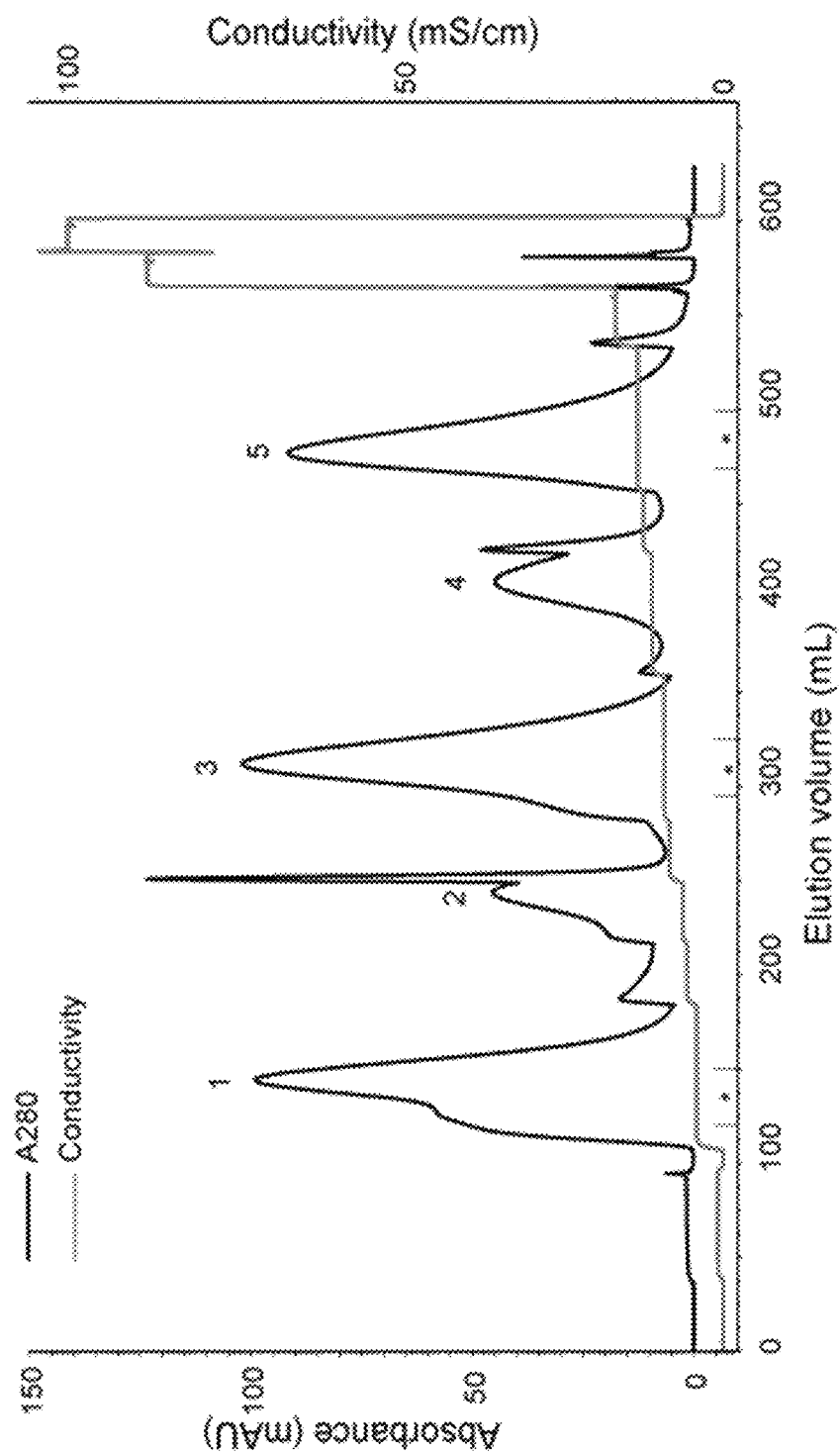
Figure 20D:
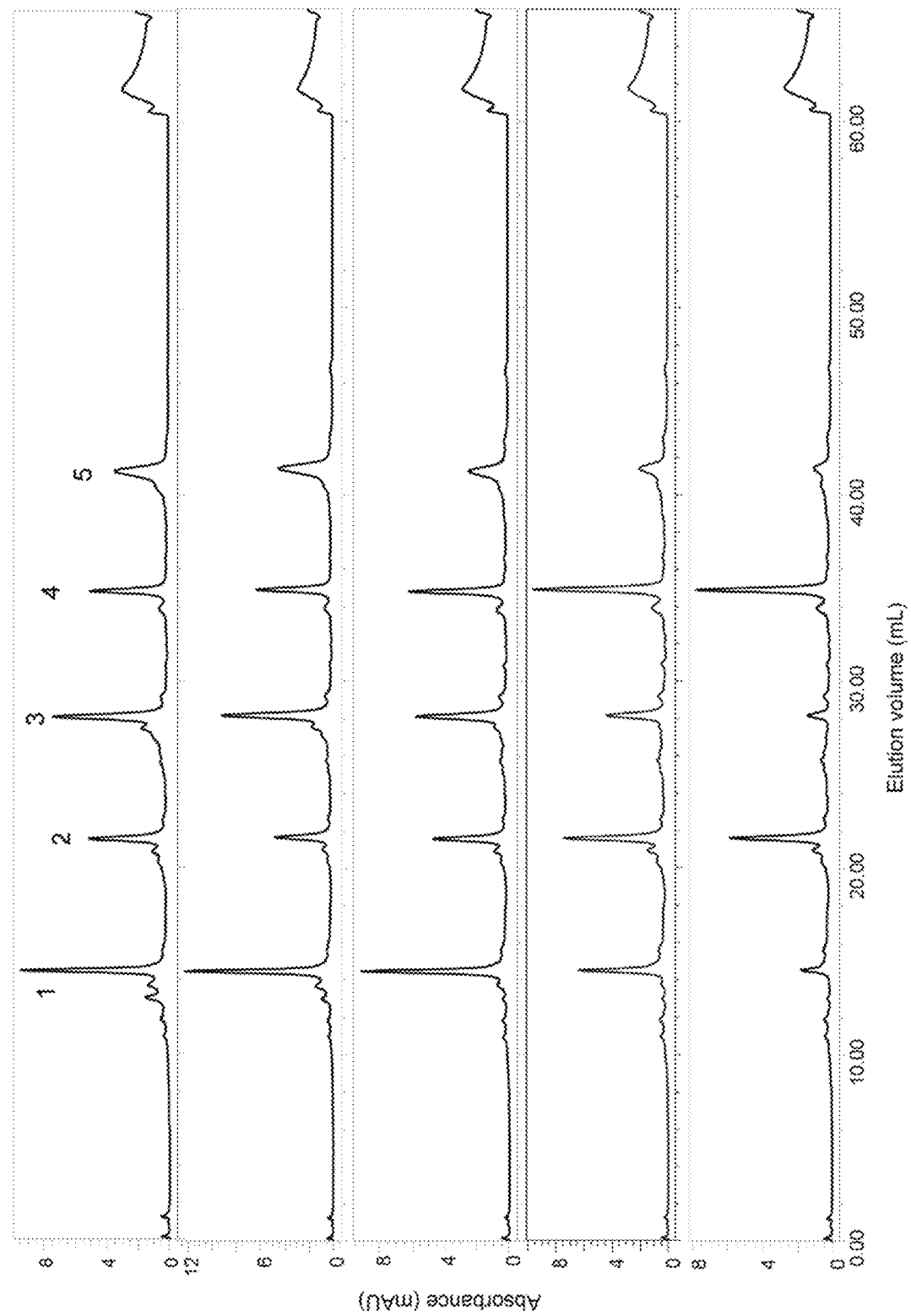
Figure 20E:
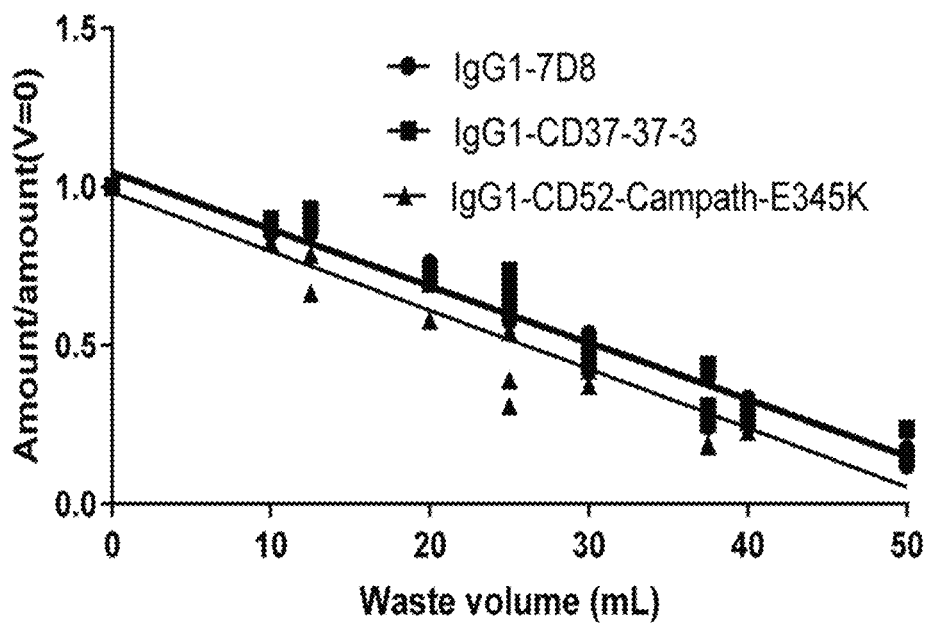
Figure 20F:
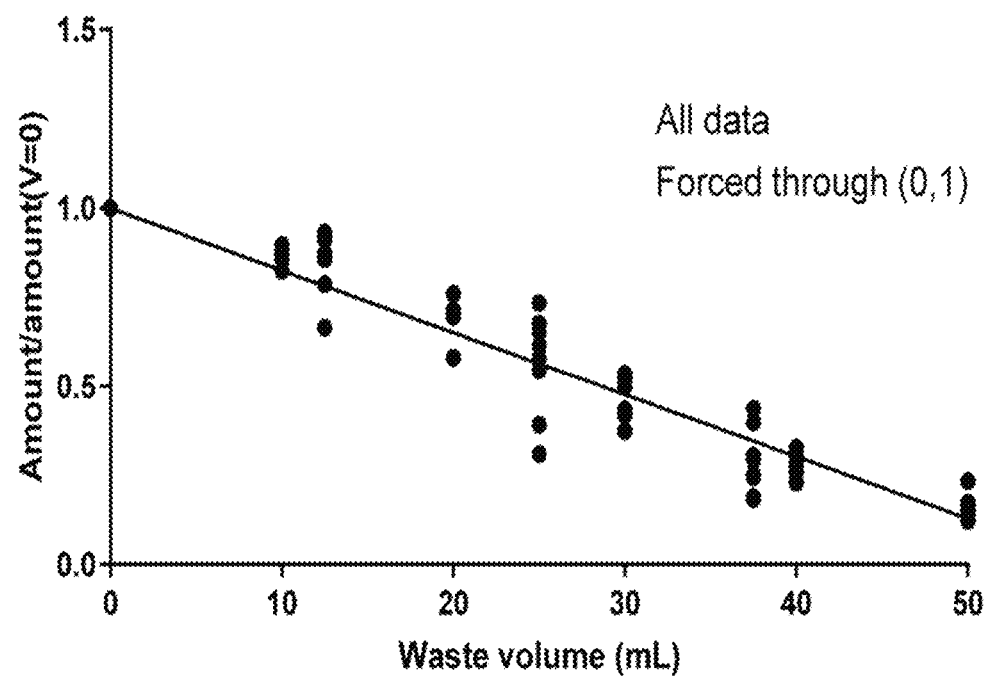
Figure 20G:
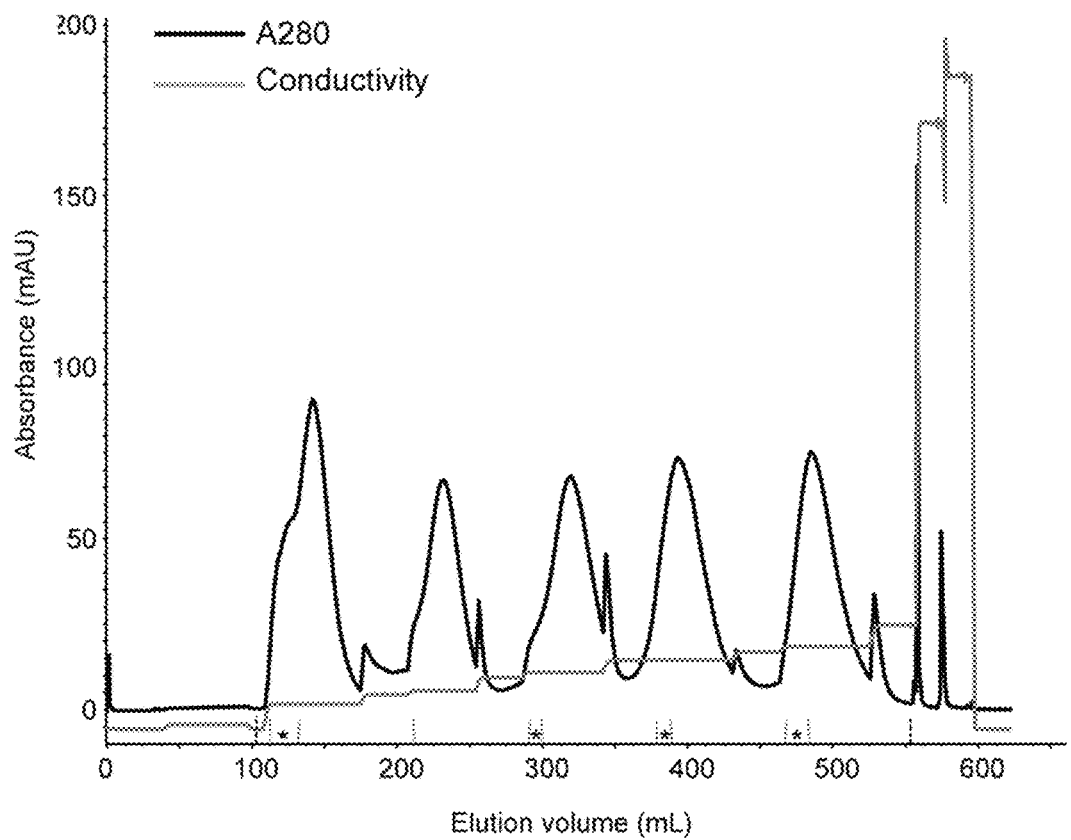
Figure 20H:
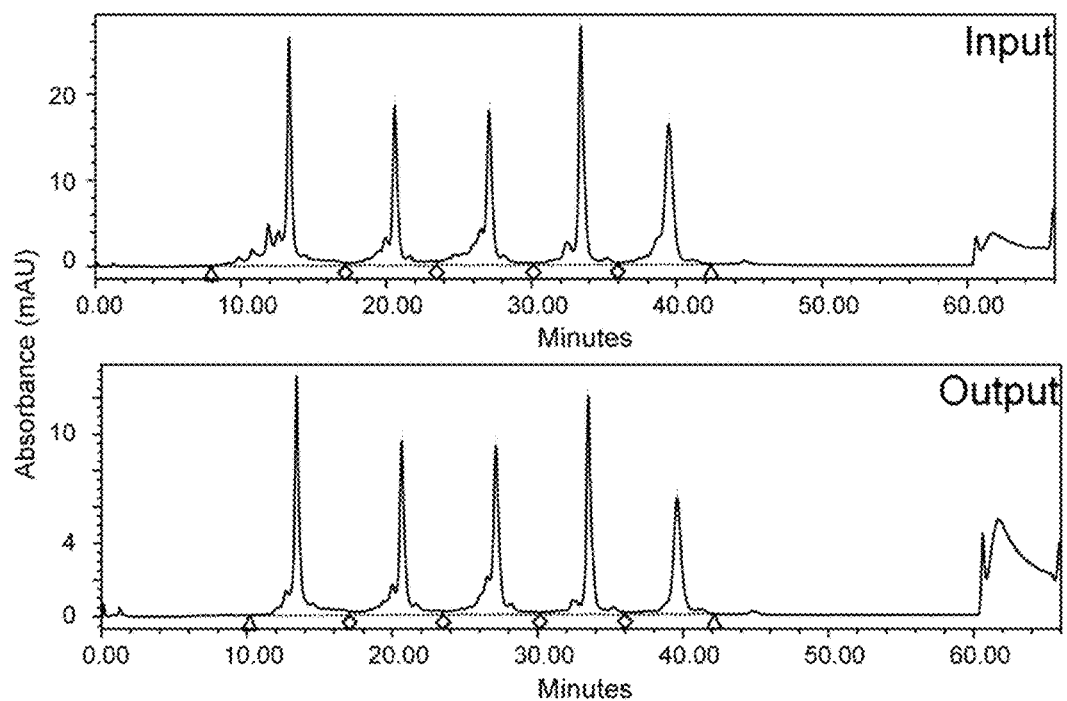
Figure 20I:
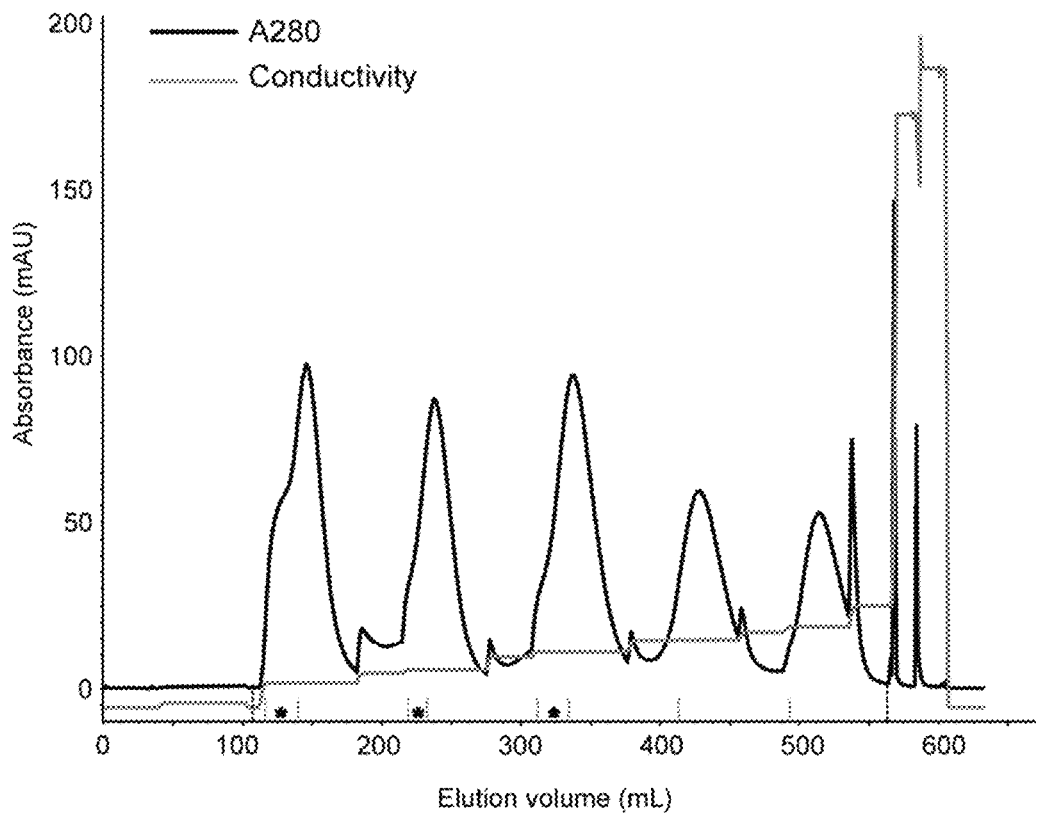
Figure 20J:
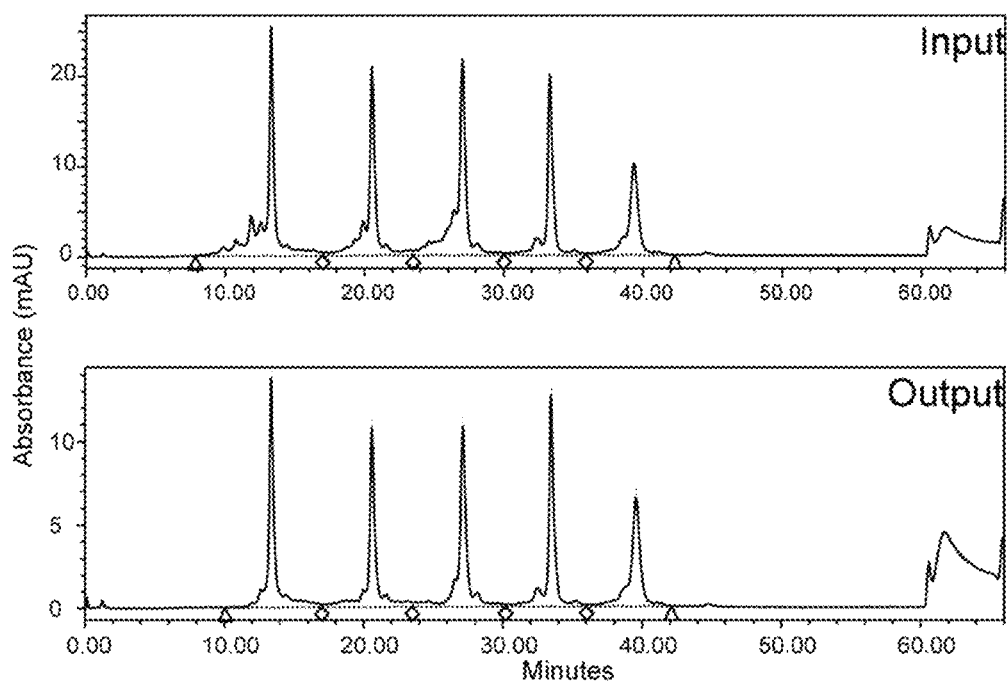
Figure 20M:
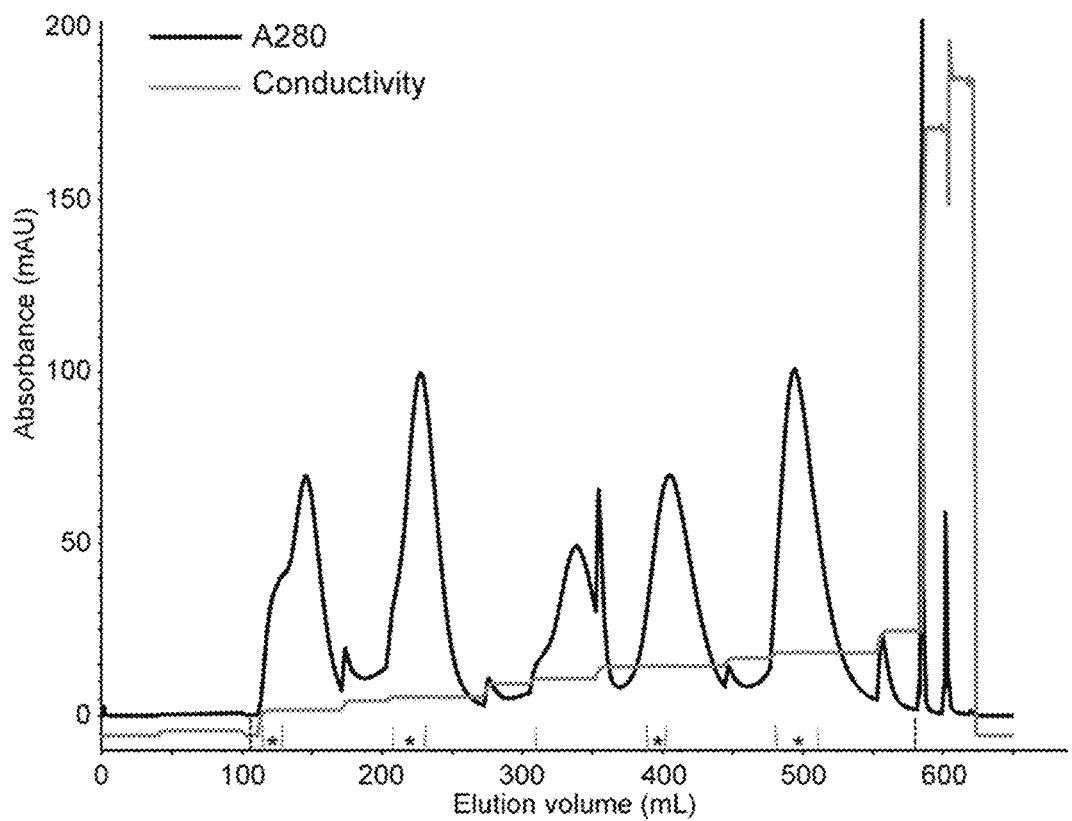
Figure 20N:
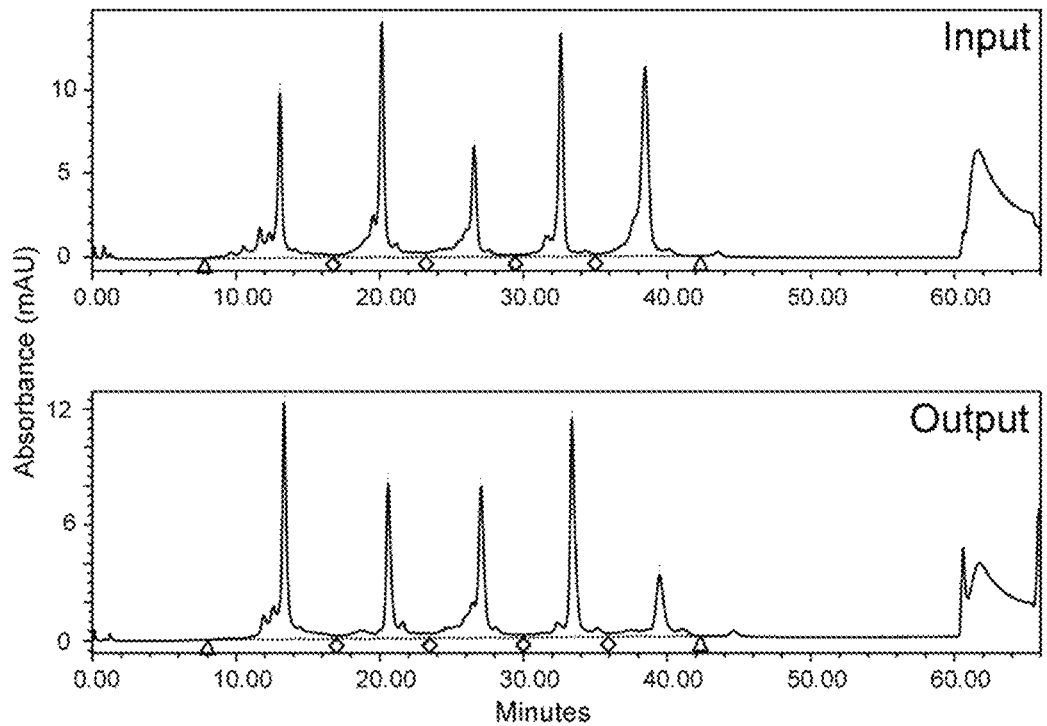

FIGS. 20A-20N: (FIG. 20A) Overlays of preparative cation exchange chromatograms showing the variation of the peak shapes with different salt concentrations during the elution of IgG1-7D8, IgG1-224, IgG1-CD37-37-3, IgG1-CD19-21D4-E345K and IgG1-CD52-Campath-E345K using sequential step elutions. The absorption at 280 nm (dashed line) and % buffer B (solid line) were monitored. The higher peaks in the absorption at 280 nm correspond with the conditions with higher ionic strength. (FIG. 20B) Preparative cation exchange chromatogram showing the separation of mixtures of IgG1-7D8, IgG1-224, IgG1-CD37-37-3, IgG1-CD19-21D4-E345K and IgG1-CD52-Campath-E345K using sequential step elutions. The five baseline separated peaks in the A280 absorption profile (black line) correspond with the elution of IgG1-7D8, IgG1-224, IgG1-CD37-37-3, IgG1-CD19-21D4-E345K and IgG1-CD52-Campath-E345K, respectively. The % buffer B (grey line) were monitored. (FIG. 20C) Exemplary preparative chromatogram collected during the design space experiment, with a 2.5:1:2.5:1:2.5 load ratio of IgG1-7D8, IgG1-224, IgG1-CD37-37-3, IgG1-CD19-21D4-E345K and IgG1-CD52-Campath-E345K. The volume indicated (*) within the $1^{st}$, $3^{rd}$ and $5^{th}$ major peaks in the A280 absorption profile (solid line; numbered) is a predefined variable volume of 30 ml that was removed from the pool during the elution of IgG1-7D8, IgG1-CD37-37-3 and IgG1-CD52-Campath-E345K. The % buffer B (grey line) were monitored. (FIG. 20D) Stacked analytical cation exchange chromatograms of IgG1-7D8, IgG1-224, IgG1-CD37-37-3, IgG1-CD19-21D4-E345K and IgG1-CD52-Campath-E345K during the set of design space experiments 2.5:1:2.5:1:2.5 load ratio of IgG1-7D8, IgG1-224, IgG1-CD37-37-3, IgG1-CD19-21D4-E345K and IgG1-CD52-Campath-E345K. Increasing the waste volumes (0 mL, 10 mL, 20 mL, 30 mL, 40 mL top to bottom) of IgG1-7D8, IgG1-CD37-37-3 and IgG1-CD52-Campath-E345K causes depletion of these proteins (peaks labeled 1, 3, 5, respectively) from the mixture. (FIGS. 20E and 20F) Correlation plots showing the relationship of the amount of protein in the pool and the size of the waste fractions for IgG1-7D8, IgG1-CD37-37-3 and IgG1-CD52-Campath-E345K. (V=0)=analytical cation exchange chromatography derived mass of protein from purification in which waste volume=0. FIGS. 20G-20N Analytical cation exchange chromatograms of the input material and end products and preparative cation exchange chromatograms of four mixtures of IgG1-7D8, IgG1-224, IgG1-CD37-37-3, IgG1-CD19-21D4-E345K and IgG1-CD52-Campath-E345K. Preparative cation exchange chromatogram showing the separation of the mixtures using sequential step elutions are shown in FIG. 20G, FIG. 20I, FIG. 20K, FIG. 20M. The waste volumes in each chromatography experiment are indicated (*). The absorption at 280 nm (black line) and conductivity (grey line) were monitored. The corresponding analytical cation exchange chromatograms of the input material and end products are in FIG. 20H, FIG. 20J, FIG. 20L, FIG. 20N, respectively, with peak integration boundaries indicated. The chromatograms are quantified in Table 12.

FIGS. 21A-21G: (FIGS. 21A and 21B) Preparative chromatogram showing the loading of the tandem KappaSelect, LambdaFabSelect and Protein L columns loaded with 1:1:1 (FIG. 21A) or 1:1.5:2 (FIG. 21B) mixtures of IgG1-2F8-V110D, IgG1-7D8-S12P and IgG1-HepC. The absorption at 280 nm was monitored and is indicated by a solid line in the chromatogram. The absorption at 280 nm reaches a plateau during the loading step, indicating that the columns are saturated. (FIGS. 21C-21E): Exemplary elution of the 1:1:1 mixture of IgG1-2F8-V110D, IgG1-7D8-S12P and IgG1-HepC from KappaSelect (FIG. 21C), Protein L (FIG. 21D) and LambdaFabSelect (FIG. 21E) columns. The absorption at 280 nm, pH and conductivity were monitored. Specifically bound proteins were eluted at low pH and detected by peaks in the absorption at 280 nm. (FIG. 21F) Exemplary Protein A separations of mixtures of antibody variants from cell culture supernatants containing 1:1:1 mixtures of IgG1-2F8-V110D, IgG1-7D8-S12P and IgG1-HepC. The absorption at 280 nm (solid line) and conductivity or pH (dashed grey line) were monitored. The purification shows an elevated absorption during column loading from non-bound material from the cell culture supernatants in the flow-through. Specifically bound antibody variants were eluted at pH 3.0 and detected by peaks in the absorption at 280 nm. (FIG. 21G) Segments of analytical cation exchange chromatograms of 1:1:1 or 1:1.5:2 mixtures of IgG1-2F8-V110D, IgG1-7D8-S12P and IgG1-HepC supernatants, or antibody mixtures following purification by protein A affinity chromatography or tandem chromatography using KappaSelect, Protein L and LambdaFabSelect columns. The peaks were identified and are indicated by dotted lines to be IgG1-HepC (1), IgG1-7D8-S12P (2) and IgG1-2F8-V110D (3) by reference to individually-purified reference proteins.

DETAILED DISCLOSURE OF THE INVENTION

Definitions

The term "immunoglobulin" refers to a class of structurally related glycoproteins consisting of two pairs of polypeptide chains, one pair of light chains (LC) and one pair of heavy chains (HC), all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region (CH). The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The CL can be of κ (kappa) or λ (lambda) isotype. Herein, constant domain and constant region are used interchangeably.

If not stated otherwise the numbering of amino acid residues in the constant region is according to the EU-index as described in Kabat et al., Sequences of Proteins of Immunological Interest, 5th Ed. Public Health Service, National Institutes of Health, Bethesda, MD. (1991). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Numbering of amino acid residues in the variable region is according to the IMGT numbering as described in Lefranc, M.-P. et al., Dev. Comp. Immunol., 2003, 27, 55-77, unless contradicted by the context.

In the context of the present invention, substitutions which may alter the interaction of an antibody with a chromatography resin may be substitutions from changing the amino acid to one of a different class of amino acids reflected in the following table:

Amino Acid Residue Classes for Substitutions:

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

The imidazolium group of histidine has pKa of approximately 6.0, so can be neutral or basic depending upon the pH of the solution and the local chemical environment of the histidine residue.

In the context of the present invention the following notations are, unless otherwise indicated, used to describe an amino acid modification; name of amino acid which is modified, followed by the position number which is modified, followed by what the modification encompasses. Thus if the modification is a substitution, the name of the amino acid which replaces the prior amino acid is included, if the amino acid is deleted a * is included, if the modification is an addition the amino acid being added is included after. Amino acid names may be one or three-letter codes. Thus for example, substitution of a Lysine in position 409 with an Arginine is K409R, substitution of Lysine in position 409 with any amino acid is K409X, deletion of Lysine in position 409 is indicated by K409* and addition of P after Lysine at position K409 is indicated by K409KP. It is well known to a person skilled in the art how to introduce modifications.

When used herein, the terms "Fc region" and "Fc domain" are used interchangeably and refer to an antibody region comprising at least the hinge region, a CH2 domain and a CH3 domain (see e.g. Kabat E A, in US Department of Health and Human Services, NIH publication no 91-3242, Edn. 5th edition 662, 680, 689 (1991). The Fc region may be generated by digestion of an antibody with papain, where the Fc region is the fragment obtained thereby, which includes the two CH2-CH3 regions of an immunoglobulin and a hinge region. The constant domain of an antibody heavy chain defines the antibody isotype, e.g. IgG1, IgG2, IgG3, IgG4, IgA1, IgA2, IgE. The Fc-domain mediates the effector functions of antibodies with cell surface receptors called Fc receptors and proteins of the complement system.

The term "CH1 region" or "CH1 domain" are used interchangeably and as used herein is intended to refer to the CH1 region of an immunoglobulin. Thus for example the CH1 region of a human IgG1 antibody corresponds to amino acids 118-215 according to the EU numbering system. However, the CH1 region may also be any of the other antibody isotypes as described herein.

The term "CH2 region" or "CH2 domain" are used interchangeably and as used herein is intended to refer to the CH2 region of an immunoglobulin. Thus for example the CH2 region of a human IgG1 antibody corresponds to amino acids 228-340 according to the EU numbering system. However, the CH2 region may also be any of the other antibody isotypes as described herein.

The term "CH3 region" or "CH3 domain" are used interchangeably and as used herein is intended to refer to the CH3 region of an immunoglobulin. Thus for example the CH3 region of a human IgG1 antibody corresponds to amino acids 341-447 according to the EU numbering system. However, the CH3 region may also be any of the other antibody isotypes as described herein.

The term "antibody" comprises immunoglobulin molecules, fragments of immunoglobulin molecules, or a derivatives of either thereof, which have the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, inhibit and/or modulate a physiological response associated with antibody binding to the antigen and/or time sufficient for the antibody to recruit an effector activity). The variable regions of the heavy and light chains of the immunoglobulin molecules contain a binding domain that interacts with an antigen. The constant regions of the antibodies (Abs) may mediate the binding of the immunoglobulin molecules to host tissues or factors, including various cells of the immune system (such as effector cells) and components of the complement system such as Clq, the first component in the classical pathway of complement activation. Alternatively, the constant regions may be inert or non-activating, such that they are at least not able to bind any Fc gamma receptors (FcgR), induce Fc-mediated cross-linking of FcgRs, or induce FcgR-mediated cross-linking of target antigens via two Fc regions of individual antibodies, or is not able to bind Clq. An antibody may also be a bispecific antibody, diabody, multispecific antibody or similar molecule. Antibodies can have monospecific affinity, in that they bind to/have specificity to only one epitope. Alternatively, antibodies may have multispecific affinity in the sense that one antibody molecule is capable of binding to/has specificity for epitopes on multiple antigens and/or multiple epitopes on the same antigen. The term "antibody" includes recombinant antibodies, diabody molecules and "multispecific antibodies", "bispecific antibodies", "humanized antibodies", "human antibodies", "chimeric antibodies", "full length antibodies", and heavy-chain antibodies or similar molecules as defined in the following.

The term "monoclonal antibody" as used herein refers to a preparation of antibody molecules that are recombinantly produced with a single primary amino acid sequence. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York:

Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "bispecific antibody" refers to an antibody having specificities for at least two different epitopes, typically non-overlapping epitopes or an antibody that contains two distinct antigen-binding sites. A bispecific antibody may be described as a heterodimeric protein whereas a monospecific antibody may be described as a homodimeric protein. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. Fab or F (ab') 2 fragments. It also should be understood that the term antibody, unless specified otherwise, also includes monoclonal antibodies (mAbs), antibody-like polypeptides, such as chimeric antibodies and humanized antibodies. An antibody as generated can possess any isotype.

The term "multispecific antibody" refers to an antibody having specificities for more than two different epitopes, typically non-overlapping epitopes or an antibody that contains more than two distinct antigen-binding sites. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. Fab or F (ab') 2 fragments. It also should be understood that the term antibody, unless specified otherwise, also includes monoclonal antibodies (mAbs), antibody-like polypeptides, such as chimeric antibodies and humanized antibodies. An antibody as generated can possess any isotype.

The term "full-length antibody" when used herein, refers to an antibody which contains all heavy and light chain constant and variable domains that are normally found in an antibody of that isotype.

As used herein, "isotype" refers to the immunoglobulin class (for instance IgG1, IgG2, IgG3, IgG4, IgD, IgA, IgE, or IgM) that is encoded by heavy chain constant region genes.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked by the antigen binding peptide (in other words, the amino acid residue is within the footprint of the antigen binding peptide).

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific). The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

When used herein the term "heterodimeric interaction between the first and second CH3 regions" refers to the interaction between the first CH3 region and the second CH3 region in a first-CH3/second-CH3 heterodimeric protein.

When used herein, the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

An "isolated antibody", as used herein, denotes that the material has been removed from its original environment (e.g., the natural environment if it is naturally occurring or from the host cell, culture of host cells or supernatant thereof if it is recombinantly expressed). It is also advantageous that the antibodies are in purified form. The term "purified" does not require absolute purity; rather, it is intended as a relative definition, indicating an increase of the antibody concentration relative to the concentration of contaminants in a composition as compared to the starting material.

The terms "antibody mixture", "polyclonal mixture", and "polyclonal antibody mixture", are used interchangeably to describe a mixture of two or more different recombinant antibodies of predetermined molecular composition. A mixture of two or more different antibodies of predetermined molecular composition is intended to refer to a mixture of antibodies of which the molecular identities are, or can be, known prior to production of the mixture. The molecular identity of an antibody can be defined by determining the amino acid sequence of the antibody. A mixture of predetermined molecular composition can be collected from different expression or production systems, for example from recombinantly modified host cells, from hybridoma's, or using cellular extracts supporting the in vitro transcription and/or translation of nucleic acid sequences. A polyclonal antibody mixture isolated from the blood, plasma, or serum of a human, an animal, or a transgenic animal, such as in response to immunization with a foreign antigen or combination of antigens, is in the context of the present application considered not to be a mixture of predetermined molecular composition. An "antibody mixture" may be referred to as a "recombinant antibody mixture" if one or more antibodies in the mixture is/are produced using a recombinantly modified host cell. A "recombinantly modified host cell", as used herein, is intended to refer to a cell into which an expression vector has been introduced, e.g. an expression vector encoding an antibody. Recombinant host cells include, for example, transfectomas, such as CHO cells, HEK293 cells, NS/0 cells, and lymphocytic cells.

The term "output mixture", as used herein, is intended to refer to an antibody mixture, wherein the two or more different antibodies are present at a desired or predetermined concentration ratio. As the skilled person will understand however, some deviation from the desired or predetermined ratio in the output mixture may be tolerated. This may especially be the case if the deviation has no measurable effect, or essentially no measurable effect, on the functionality of the output mixture or a drug substance or drug product produced from the output mixture. In particular, this is the case if no effect of the deviation can be determined in relevant preclinical or clinical trials performed in order to determine the pharmaceutical effect and safety profile of the output mixture, drug substance or drug product. Hence, the desired or predetermined concentration ratio of any two antibodies can be defined along with a specification of the tolerated deviation from the desired or predetermined concentration ratio, and the acceptable upper and lower limits of the concentration ratio of the antibodies.

Hence, it is also within the scope of the present invention to provide a process that produces an output mixture wherein the two or more different antibodies are present in said output mixture essentially at a desired or predetermined concentration ratio. In particular, any two antibodies may be considered to be present essentially at the desired or predetermined concentration ratio if the ratio between the respective concentrations is within a tolerated deviation from the desired or predetermined concentration ratio. For any two of the two or more different antibodies, the maximum tolerated deviation from the desired or predetermined concentration ratio may for instance be 75%, 70%, 65%, 60%, 55%, 50%, 45%, 40%, 35%, 30%, 25%, 20%, 15%, 10%, 5%, or 2.5%.

In one example, an output mixture is provided according to the invention, wherein two antibodies are present at a desired or predetermined concentration ratio which is 1 (1:1). With a 10% tolerated deviation from the desired or predetermined concentration ratio, output mixtures wherein the concentration ratio between the two antibodies is from 0.9 to 1.1 would be considered output mixtures in which the two antibodies are present essentially at the desired or predetermined concentration ratio. Similarly, for an output mixture, wherein two antibodies are present at a desired or predetermined concentration ratio which is 0.5 (1:2), output mixtures wherein the concentration ratio between the two antibodies is from 0.45 to 0.55, would be considered output mixtures in which the two antibodies are present essentially at the desired or predetermined concentration ratio, if the tolerated deviation from the desired or predetermined concentration ratio is 10%.

The term "input mixture", as used herein, is intended to refer to an antibody mixture, wherein at least two of the two or more different antibodies referred to in the context of the "output mixture" are present at a concentration ratio, which is not the desired or predetermined concentration ratio and/or is not within the tolerated deviation from the desired or predetermined concentration ratio.

When the term "purity" is applied to fractions collected in the process according to the present invention, "purity" is preferably a measure of the amount of a particular antibody, such as monoclonal antibody, relative to the amount of other protein or proteinaceous matter, including an antibody or antibodies having amino acid sequence(s) different from that of the particular antibody. As an example, when the present disclosure teaches to collect a fraction containing a particular antibody at a purity of at least 80%, or teaches to pool a multitude of such fractions, it is required that the amount of the said particular antibody in each fraction is at least 80% of the total amount of other protein or proteinaceous matter in the fraction, including other antibodies, such as monoclonal antibodies. For the determination of "purity" all relative amounts of an antibody are determined or calculated on a weight/weight (w/w) basis].

The term "host cell", as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

When used herein, the term "co-expression" of two or more nucleic acid constructs, refers to expression of the two constructs in a single host cell.

When used herein, the term "co-production" of two or more antibodies refers to the recombinant production of two or more antibodies in a single vessel such as a bioreactor.

When used herein, "antibody ratio" refers to the ratio of different antibodies in a mixture. This can be the mass ratio or the molar ratio of the antibodies in the mixture. The antibody ratio can be inferred from an analytical method such as analytical chromatography, mass spectrometry or a bioanalytical method.

The term "predetermined ratio", "predetermined concentration ratio" and "predetermined antibody ratio" are used interchangeably to describe the required antibody ratio of antibodies in a mixture for a given application. The predetermined ratio can be defined with specifications that define the acceptable upper and lower limits of the relative ratio of each antibody.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells, including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell. In some embodiments, an effector cell may phagocytose a target antigen or target cell.

The term "reducing conditions" or "reducing environment" refers to conditions sufficient to allow reduction of the inter-chain disulfide bonds in the hinge region of an antibody.

The terms "resin" refers to a matrix that is modified with ligands such as chemical groups or biomolecules to provide the matrix with binding properties for use in chromatography applications. Chromatography matrices include beads, monolithic supports, filters, membranes and gels.

The term "affinity reagent" when used herein refers to a resin that contains a ligand that is immobilized on a matrix and specifically binds to surface groupings of molecules such as amino acids or sugar side chains and usually have specific three dimensional structural characteristics, as well as specific charge characteristics. Affinity reagents are tools in affinity chromatography, where purification is enabled by the specific interaction between the ligand and the product.

The term "Protein L" when used herein refers to recombinant protein L that is immobilized onto a matrix to form an affinity ligand that has affinity for a subset of the variable domain of immunoglobulin kappa light chains. For example, Protein L affinity reagents can be marketed as HiTrap™ Protein L and Capto™ L by GE Healthcare.

The term "LambdaFabSelect" when used herein refers to a recombinant 13 kDa camelid-derived single chain antibody that is immobilized onto a matrix to form an affinity ligand that has affinity for the constant domain of human immunoglobulin lambda light chains. For example, LambdaFabSelect affinity reagents can be marketed as LambdaFabSelect™ by GE Healthcare.

The term "KappaSelect" when used herein refers to a recombinant 13 kDa camelid-derived single chain antibody that is immobilized onto a matrix to form an affinity ligand that has affinity for the constant domain of human immunoglobulin kappa light chains. For example, KappaSelect affinity reagents can be marketed as KappaSelect™ by GE Healthcare.

The term "KappaXL" when used herein refers to a recombinant 13 kDa camelid-derived single chain antibody that is immobilized onto a matrix to form an affinity ligand that has affinity for the constant domain of human immunoglobulin kappa light chains. For example, KappaXL affinity reagents can be marketed as CaptureSelect® KappaXL by Thermo Fisher.

The term "IgG-CH1" when used herein refers to a recombinant 13 kDa camelid-derived single chain antibody that is immobilized onto a matrix to form an affinity ligand that has affinity for the human CH1® domain. For example, IgG1-CH1 affinity reagents can be marketed as CaptureSelect® IgG-CH1 by Thermo Fisher.

The term "treatment" refers to the administration of an effective amount of a therapeutically active mixture of different antibodies, such as monoclonal antibodies, of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of a therapeutically active mixture of different antibodies, such as monoclonal antibodies, of the present invention, may vary according to factors such as the disease state, age, sex, and weight of the individual, and the ability of the binding agent to elicit a desired response in the individual. A therapeutically effective amount is also one in which any toxic or detrimental effects of the mixture of different antibodies, such as monoclonal antibodies, of the present invention are outweighed by the therapeutically beneficial effects.

In the context of the present invention, the term "Active Pharmaceutical Ingredient" is defined as any substance or mixture of substances intended to be used in the manufacture of a drug (medicinal) product and, when used in the production of a drug, becomes an active ingredient of the drug product. Such substances are intended to furnish pharmacological activity or other direct effect in the diagnosis, cure, mitigation, treatment, or prevention of disease or to affect the structure and function of the body. This definition is consistent with the definition of "Active Pharmacutical Ingredient" adopted by the International Conference on Harmonisation of Technical Requirements for Registration of Pharmaceuticals for Human Use (ICH) (see "ICH HARMONISED TRIPARTITE GUIDELINE, GOOD MANUFACTURING PRACTICE GUIDE FOR ACTIVE PHARMACEUTICAL INGREDIENTS, Q7; Current Step 4 version, dated 10 Nov. 2000; available at www.ich.org/fileadmin/Public_Web_Site/ICH_Products/Guidelines/Quality/Q7/Step4/Q7_Guideline.pdf) and by the US Food and Drug Administration (FDA) (see Guidance for Industry CGMP for Phase 1 Investigational Drugs, U.S. Department of Health and Human Services Food and Drug Administration Center for Drug Evaluation and Research (CDER) Center for Biologics Evaluation and Research (CBER) Office of Regulatory Affairs July 2008, available at (ORA) www.fda.gov/downloads/Drugs/GuidanceCompliance-Regulatoryinformation/Guidances/UCM070273.pdf).

For purposes of the present invention, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1).

Further Aspects and Embodiments of the Invention

The present invention relates in one embodiment to a method for producing an output mixture of two or more different antibodies having a difference in their amino acid sequences, which difference enables separation of the antibodies by chromatography, wherein the two or more different antibodies are present in said output mixture at, or substantially at, a desired or predetermined concentration ratio; and the method comprises the steps of:

a. providing an input mixture wherein the two or more different antibodies are not present at, or essentially at, the desired or predetermined concentration ratio;

b. separating the two or more antibodies by chromatography;

c. recovering the two or more antibodies in the amounts required to provide the output mixture.

Hereby, a novel method for producing a controlled mixture of two or more different antibodies is provided. The method has the advantage that the same relative amount of each of the different antibodies can be obtained in the output mixture independently of the concentration of the different antibodies which are provided in the input mixture. Thus, variability in production yield of each of the different antibodies can be compensated for or corrected through this method so that the output mixture is normalized to obtain the desired predetermined ratio of antibodies.

The process according to the present invention is intended in particular for application in the manufacture of a drug product or medicinal product, which is an antibody mixture comprising two or more different antibodies. In that context, the process of the invention may be used to produce a drug substance in which the amounts or concentrations of the two or more antibodies and the ratio between the concentrations of the two or more antibodies are such that the drug substance can be formulated, without any additional means or measures for changing or substantially changing the ratio between the concentrations of the antibodies, to a composition that complies with the requirements of an applicable Drug Product Specification.

A drug product specification sets forth various criteria, which a batch of the drug product must meet in order to be released. For a drug product, which is a controlled mixture of several antibodies, the Drug Product Specification sets forth, for each individual antibody, the range within which the concentration ratio or the relative amount of each antibody must be. Generally, in early clinical development, such ranges set forth by the drug product specification are based on preclinical data obtained from ex vivo and in vivo studies. The ranges set forth at this stage in the development process are generally relatively broad. As the clinical development process progresses, the ranges may be revised based on data from the clinical trials and from the manufacturing process. As the skilled person will know, the drug product specification is dynamic throughout development and must be accepted by the authorities before the drug can be marketed: the regulatory authorities may for instance require that the range of acceptable ratios set forth in the drug product specification be narrowed upon a showing by the manufacturer that in multiple successive batches of the drug product the relative amount of the one or more of the antibodies is well within the respective range or ranges set forth in the pending drug product specification.

In the context of the present invention, the desired or predetermined concentration ratio at which the two or more different antibodies are present in the output mixture and the tolerated deviation from the desired or predetermined concentration ratio may therefore correspond to the requirements of the drug product specification. Alternatively, the predetermined concentration ratio may correspond to that of the drug product specification, with the allowed deviation from the ratio being less than that allowed for in the drug product specification as this will ensure that the relative amount of each antibody in the output mixture never approaches the limits of the ranges set forth in the Drug Product Specification. It also follows that, if a regulatory authority requires that the accepted range of concentration ratios be changed, the predetermined concentration ratio established for the process of the invention and/or the allowed deviation therefrom may be changed accordingly.

In addition to the relative amount of each antibody, the Drug Product specification may specify the total amount of antibody or the total protein concentration of the drug product. Further criteria being specified by the Drug Product Specification may include the pH, e.g. as defined by a target value and the accepted deviation therefrom, the osmolality e.g. as defined by an acceptable range, the content of host cell proteins, e.g. as defined by an upper limit, the color and clarity of the product and the content of visible and sub-visible particles. Any of these criteria may apply to the output mixture or drug substance provided according to the present invention and/or to a medicinal product obtained by formulating the output mixture or drug substance.

In the method according to the invention, the output mixture may be a drug substance.

In some embodiments, the process of the invention further comprises processing said output mixture to produce a drug substance, wherein the two or more different antibodies are present at, or essentially at, a concentration ratio, which is the same as the desired or predetermined concentration ratio specified above. In further embodiments, the process of the invention further comprises processing said output mixture to produce a drug product, wherein the two or more different antibodies are present at, or essentially at, a concentration ratio, which is the same as the desired or predetermined concentration ratio specified above.

In other embodiments, the output mixture is processed without any additional means or measures for changing or substantially changing the ratio between the concentrations of the antibodies, to produce a drug substance or drug product in which the relative amounts of the two or more antibodies and the ratio between the concentrations of the two or more antibodies are in accordance with an applicable drug product specification. It is another advantage of the present invention that the two or more different antibodies of the mixture may be produced, purified and recovered in parallel without having to produce and purify each antibody separately. This simplifies the manufacturing process and thus may save costs in the production of the mixture compared to purifying each of the antibodies separately and subsequently mixing them at a correct ratio.

Thus, the inventive method provides for an efficient new way of producing a controlled output mixture of two or more different antibodies having a predetermined ratio of the concentration of the various different antibodies by downstream process control and where the concentration of the different antibodies provided in an input mixture from the upstream process is not sufficiently controlled or regulated.

In one embodiment of the present invention, the different antibodies for the mixture are produced by separate host cells and subsequently initially purified by known methods such as e.g. by use of Protein A or Protein G, which capture the antibodies based upon their affinity for the constant regions of the antibodies and thus separate the antibodies from cellular material. Thus, the antibodies provided for the present method may in one embodiment initially have been purified without normalization of the ratio between the different antibodies. This normalization is obtained in the method by one or more steps of chromatography where all the different antibodies of the mixture are recovered in the predetermined ratio. It is an important feature of the present method that the different antibodies of the mixture are separable by the given chromatography method as all the different antibodies will be recovered and normalized in the chromatography step. The different antibodies can be separated using chromatography and the antibodies that are present in excess of the required composition may be depleted from the product to yield the required composition. Alternatively, the different antibodies can be separated using chromatography and fractionated and re-pooled at the desired composition. Thus, in cases where the antibodies are initially found to be inseparable by chromatography then one or more of the antibodies will have to be modified to enable separation. In a preferred embodiment the method uses a single chromatography resin preferably in one step. In step c) the two or more antibodies may be recovered by collecting part(s) of the eluate or flow-through produced in step b), containing the two or more different antibodies.

In the method according to the invention, it is preferred that each binding specificity and/or each antibody charge variant in the input mixture is also found in the output mixture.

In the method according to the invention, step (c) may comprise recovering the two or more antibodies in the same pool or fraction, thereby obtaining the output mixture. Alternatively, step (c) may comprise recovering the two or more antibodies in multiple pools or fractions, and combining said multiple pools or fractions or parts of said multiple pools or fractions, thereby obtaining the output mixture.

In the method according to the invention, the chromatography in step (b) preferably produces an eluate and a flow-through and the output mixture may be produced by:
 i) Collecting the eluate and discarding the flow-through; or
 ii) Discarding the eluate and collecting the flow-through.

Figure 1A:
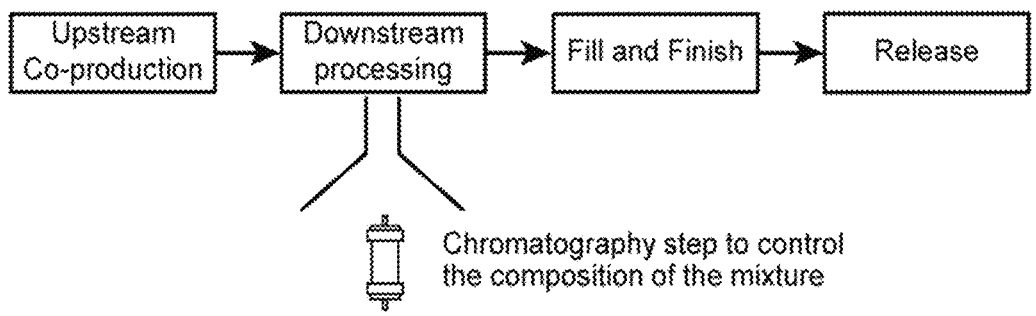
FIGS. 1A-1E: Schematic illustration of a production and purification process of the invention.
Figure 1B:
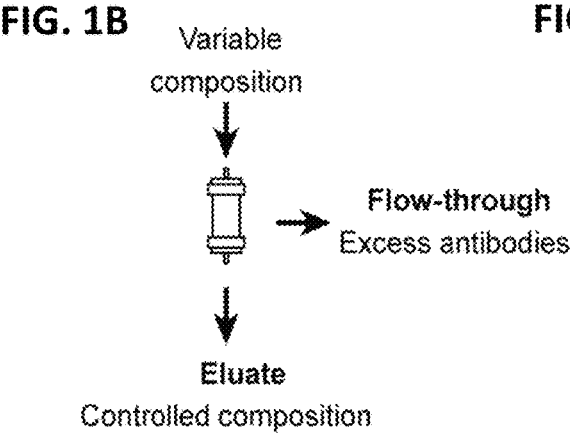

In a particular embodiment of the invention, which is illustrated in FIG. 1B, step (b) comprises adjusting the conditions of the chromatography step so that the total binding capacity for a given antibody under these conditions is adequate to retain the amount of that antibody which is required in order to provide the output mixture.

Figure 1C:
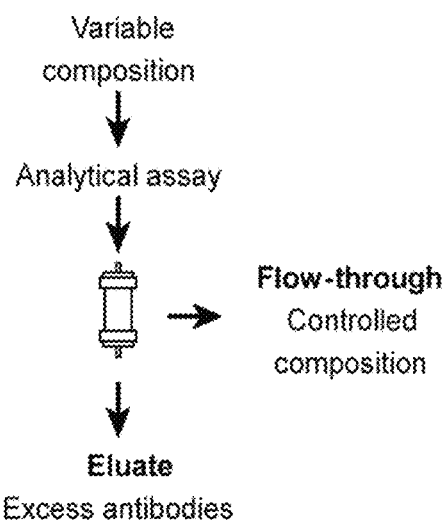
Figure 1D:
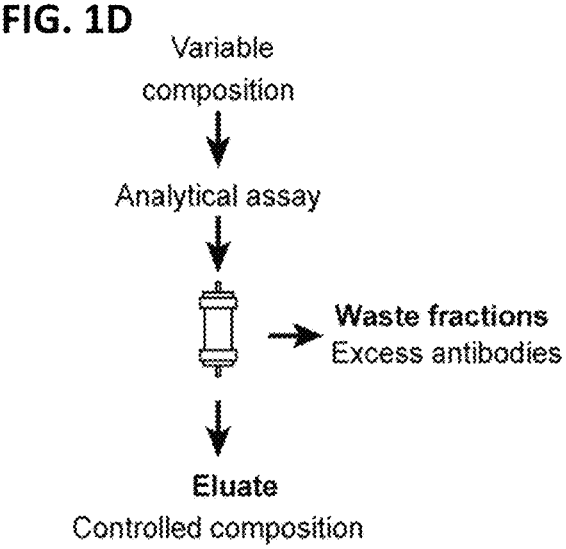

In a particular embodiment of the invention, which is illustrated in FIG. 1D, step (b) comprises adjusting the conditions of the chromatography step so that the total binding capacity for a given antibody under these conditions is adequate to retain the amount of each antibody that is in excess to the amount needed to provide the output mixture.

In one embodiment of the invention, the method comprises the separation of the two or more antibodies and depletion of excess of one or more of the antibodies to recover the predetermined ratio of the two or more different antibodies. The desired fractions of a chromatography eluate are customarily collected by controlling a valve that directs the eluate flow to either the waste vessel or the collection vessel. To deplete the excess of one of more antibodies, the excess of protein pre-determined using an analytical assay can be directed to the waste vessel. Each antibody commonly elutes as a collection of charge variants, the distribution of which is maintained between manufacturing batches by proper process control to ensure batch-to-batch consistency. When excess protein is syphoned off by redirecting specific charge-separated antibody fractions into the waste vessel during the elution of an ion-exchange or mixed mode resin, this may impact the charge distribution of the collected antibody fraction. In one embodiment of the invention, the charge distribution of each individual antibody in the input mixture is recovered in the output mixture.

In one embodiment of the invention, the charge distribution of each individual antibody in the input mixture is recovered in the output mixture by alternating the elution switch valve between the waste position and the collection position, over the full duration of the eluted antibody peak. The time delay assigned to the waste position relative to the time delay assigned to the elution position enables control of the relative amount depleted over the full duration of the peak. The frequency of subsequent waste/collection cycles will define the resolution with which the charge distribution is maintained.

In another embodiment of the invention, the charge distribution of each individual antibody in the input mixture is recovered in the output mixture by using an adjustable flow divider or adjustable flow splitter that enables the dynamic distribution of the eluate flow between waste and collection vessels. The adjustable flow divider or adjustable flow splitter can be used to direct a predetermined fraction of the eluate flow into the waste vessel simultaneously with directing the remainder of the eluate flow into the collection vessel. The relative fractions to be directed to waste or collection vessels according to the predetermined ratio of the two or more different antibodies in the output mixture can be inferred from the composition of the input mixture measured using an analytical assay in-line with or prior to step b). In one embodiment, the adjustable flow divider or adjustable flow splitter can be controlled electronically.

In one embodiment of the invention, the dynamic control of the waste and collection liquid flows is achieved by separate diaphragm valves applied to both liquid flows. In one embodiment of the invention the dynamic control of waste and collection liquid flows is achieved by separate diaphragm valves combined with a pressure release valve and feed-back pressure control of the liquid flow. The diaphragm valves enable the restriction of the flow through the eluate or waste lines to achieve the predetermined ratio of the two or more different antibodies in the output mixture. In one embodiment, the diaphragm valves of the preceding embodiments are replaced by pinching valves, butterfly valves, or other valves suitable for application in bioprocess liquid flow control.

In the method according to the invention, each of said two or more different antibodies is preferably present in the output mixture in a therapeutically effective amount.

In particular embodiments of the invention, the least abundant of said two or more different antibodies is present in an amount which is at least 1% (w/w), 2% (w/w), 3% (w/w), 4% (w/w), 5% (w/w), 6% (w/w), 7% (w/w), 8% (w/w), 9% (w/w) or 10% (w/w) of the amount of the most abundant of the said two or more different antibodies. In particular, the two or more antibodies may be present in such amounts that the ratio (w/w) between the amounts of any two antibodies is between 1:5 and 5:1, such as between 1:4 and 5:1, 1:3 and 5:1, 1:2 and 5:1, 1:1 and 5:1, 2:1 and 5:1, 3:1 and 5:1, 3:4 and 5:1, 1:5 and 4:1, 1:5 and 3:1, 1:5 and 2:1, 1:5 and 1:1, 1:5 and 1:2, 1:5 and 1:3, 1:5 and 1:4, 1:4 and 4:1, 1:4 and 3:1, 1:4 and 2:1, 1:4 and 1:1, 1:4 and 1:2, 1:4 and 1:3, 1:3 and 4:1, 1:3 and 3:1, 1:3 and 2:1, 1:3 and 1:1, 1:3 and 1:2, 1:2 and 4:1, 1:2 and 3:1, 1:2 and 2:1, 1:2 and 1:1, 1:1 and 4:1, 1:1 and 3:1, or such as between 1:1 and 2:1. Each of said two or more different antibodies may be an active pharmaceutical ingredient.

In addition to the requirement for the antibodies to be present at a certain concentration ratio in the output mixture produced according to the invention, there may also be a minimum requirement for the absolute amount of each antibody present in the output mixture. In most commercial product, whether intended for therapeutic or other uses, the amount of antibody is substantially above 1 g/L. Hence, the process according to the invention may comprise recovering the two or more antibodies in the amounts required to provide an output mixture wherein the total amount of antibody (i.e. the combined amounts of all antibodies present in the output mixture) is 0.5 g/L or more, such as 1 g/L or more, 1.5 g/L or more, 2 g/L or more, 3 g/L or more, 4 g/L or more, 5 g/L or more, 7 g/l or more, 8 g/L or more, 9 g/L or more or such as 10 g/L or more.

Further, the process according to the invention may comprise recovering the two or more antibodies in the amounts required to provide an output mixture wherein the total amount of antibody (i.e. the combined amounts of all antibodies present in the output mixture) is 0.5-20 g/L, such as 1-20 g/L, 1.5-20 g/L, 2-20 g/L, 3-20 g/L, 4-20 g/L, 5-20 g/L, 7-20 g/l, 8-20 g/L, 9-20 g/L, or such as 10-20 g/L.

The process according to the present invention is applicable to production of high antibody titers and accordingly the output mixture may be a drug product for an indication where there is a high product demand, such as a drug product for application in cancer therapy.

In some embodiments of the invention, at least one of said two or more antibodies is an antibody binding an antigen expressed on the surface of a tumor, such as on a solid tumor, such as a metastasic, solid tumor or such as a metastasic, locally advanced tumor, or such as a hematologic tumor. The solid tumor may in particular be selected from the group consisting of: colorectal cancer, including colorectal carcinoma and colorectal adenocarcinoma, bladder cancer, osteosarcoma, chondrosarcoma, breast cancer, including triple-negative breast cancer, cancers of the central nervous system, including glioblastoma, astrocytoma, neuroblastoma, neural fibrosarcoma, neuroendocrine tumors, cervical cancer, endometrium cancer, gastric cancer, including gastric adenocarcinoma, head and neck cancer, kidney cancer, liver cancer, including hepatocellular carcinoma, lung cancer, including NSCLC and SCLC, ovarian cancer, pancreatic cancer, including pancreatic ductal carcinoma and pancreatic adenocarcinoma, sarcoma or skin cancer, including malignant melanoma and non-melanoma skin cancers.

In other embodiments, at least one of said two or more antibodies is an antibody binding an antigen expressed in a hematological tumor, such as a hematological tumor selected from the group consisting of: leukemia, including chronic lymphocytic leukemia and myeloid leukemia, including acute myeloid leukemia and chronic myeloid leukemia, lymphoma, including Non-Hodgkin lymphoma or multiple myeloma, including Hodgkin Lymphoma, and including myelodysplastic syndromes.

According to other embodiments of the invention, at least one of said two or more antibodies is an antibody binding an antigen associated with or expressed during an immune or autoimmune disease, an inflammatory disease, a cardiovascular disease, a disease in the central nervous system (CNS) or a musculo-skeletal disease.

In one embodiment of the inventive method, the mixture of different antibodies is a mixture of two different antibodies. In another embodiment of the invention the mixture of different antibodies is a mixture of three or more different antibodies, such as a mixture of four or more, or of five or more, or of six or more, or of seven or more, or of eight or more, or of nine or more, or even a mixture of ten or more different antibodies. In one embodiment of the invention the mixture of two or more different antibodies is a mixture of three different I antibodies. In another embodiment it is a mixture of four different antibodies. In another embodiment it is a mixture of five different antibodies. In another embodiment it is a mixture of six different antibodies. In another embodiment it is a mixture of seven different antibodies. In another embodiment it is a mixture of eight different antibodies. In another embodiment it is a mixture of nine different antibodies. In another embodiment it is a mixture of ten different antibodies. In one embodiment of the invention the different antibodies of the mixture bind the same target but different epitopes of the target. In one embodiment of the invention two or more of the different antibodies of the mixture bind the same target but different epitopes of the target. In one embodiment of the invention three or more of the different antibodies of the mixture bind the same target but different epitopes of the target.

In particular, the mixture of different antibodies may comprise 2-10 different antibodies, such as 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-7, 7-10, 7-9, 7-8, 8-10, 8-9, or 9-10 different antibodies.

In one embodiment of the invention, all the antibodies of the mixture bind the same target but different epitopes of the target. The different epitopes may be overlapping epitopes. In one embodiment of the invention the mixture of different antibodies is a mixture of antibodies where two or more antibodies bind the same target but different epitopes and one or more antibodies bind different targets. In another embodiment the different antibodies of the mixture bind different targets.

In particular embodiments of the invention, at least one of said two or more different antibodies is a monoclonal antibody. In further embodiments all of said two or more different antibodies are monoclonal antibodies. In one embodiment of the invention, the input mixture of the two or more different antibodies in step a) is produced by co-expression from a clonal cell population. In one embodiment of the invention, the input mixture of the two or more different antibodies in step a) is produced by co-culturing in a single bioreactor of different cells each expressing a single antibody species. In one embodiment of the invention, the input mixture of the two or more different antibodies in step a) is produced by co-culturing of different cells in a single bioreactor each expressing one or more antibody species. In one embodiment of the invention, the input mixture of the two or more different antibodies in step a) is produced in more than one bioreactor, after which the cell culture supernatants are mixed before downstream processing. In one embodiment of the invention, the input mixture of the two or more different antibodies in step a) is produced by the culturing of different cells each expressing a single antibody species in separate bioreactors, after which the cell culture supernatants are mixed before downstream processing.

In one embodiment of the invention, the two or more different antibodies of the mixture have a difference in their amino acid sequences which results in a difference in the charge properties of the two or more antibodies so that the two or more antibodies interact differently with a chromatography resin such as an ion exchange resin. Hereby the two or more different antibodies may be separated by use of an ion exchange resin such as a cation exchange resin or an anion exchange resin or a mixed mode resin with an ionic component to the interaction. In another embodiment of the invention, the two or more different antibodies of the mixture have a difference in their amino acid sequences which results in a difference in the hydrophobic properties of the two or more antibodies so that the two or more monoclonal antibodies interact differently with a chromatography resin. Hereby the two or more different antibodies may be separated by e.g. use of a hydrophobic interaction resin or a mixed mode resin with a hydrophobic component to the interaction. In another embodiment of the invention the two or more different antibodies of the mixture have a difference in their amino acid sequences which results in a difference in affinity for a chromatography resin of the two or more antibodies. Hereby the two or more different antibodies may be separated by use of an affinity resin.

The skilled person will be well aware of the various different methods, which can be used to separate biomolecules from impurities, including precipitation, liquid: liquid extraction and high performance tangential flow filtration (Gagnon, P. J Chromatography A 1221 (2012) 57-70). Chromatography as applied in the context of the present invention is the dominant method for the preparative separation of biomolecules, such as antibodies, and it will be within the capacity of the skilled person to select the type of chromatography suited for the particular purpose.

The application format of the chromatography matrix can be either a fluidized bed or fixed bed chromatography, with fixed bed formats being dominant (Gagnon, 2012). Gagnon also classified the stationary phase architecture of the chromatography as comprising diffusive microparticles, perfusive microparticles, adsorptive microfiltration membranes or monoliths. Hence, following the classification of Gagnon, the stationary phase architecture of the chromatography applied in the process of the invention, including in step b) in the process defined above, may comprise material selected from the group consisting of diffusive microparticles, perfusive microparticles, adsorptive microfiltration membranes and monoliths In the process of the present invention, e.g. in step b) in the process as defined above, the material from which the chromatography matrix is composed may be selected from the group consisting of natural polymers such as cellulose, agarose, dextran and chitosan; synthetic polymers such as hydrophobic vinyl polymers, polyacrylamide polymers and polyvinylstyrene; inorganic media such as hydroxyapatite, silica or porous glass, or composite materials (Jungbauer, A. J Chromatography A, 1065 (2005) 3-12). The chromatography matrix used in the process of the invention, e.g. in step b) in the process defined above may be modified with a ligand so as to give rise to a resin that can separate a biomolecule using different action principles, depending on the properties of the ligand. These action principles include adsorption, ion exchange, size exclusion, affinity, hydrophobic interaction, metal chelate, normal phase, reversed phased chromatography, or mixed mode chromatography that utilizes more than one action principle (Jungbauer, 2005; Gagnon, 2012). The resulting resins can separate mixtures of biomolecules based upon their physical properties. The most important classes of such resins for antibody separations are anion exchange resins, cation exchange resins, hydrophobic interaction resins or mixed mode resins (Gagnon, 2012).

Hence, in particular embodiments of the invention the chromatography resin used in the process, such as in step b) in the process as defined above may be selected from the group consisting of anion exchange resins, cation exchange resins, hydrophobic interaction resins or mixed mode resins. The resin may be chosen based on the antibodies to be separated and how these differ in their charge, size, hydrophobicity or the like. That can be tested in a standard assay which will be well known to the person skilled in the art.

Some common ligands that are used in single or mixed mode chromatography of proteins have been reviewed (e.g. Kallberg, K et al. Biotechnol. J. 2012, 7, 1-11), as have potential considerations when selecting the appropriate purification strategy (e.g. Low, D et al. J Chromatography B; 848 (2007) 48-63; Clive Dennison. A Guide to Protein Isolation, Chromatography (Book Chapter), Chapter 4; p: 71-114; 2002; Springer Netherlands). The physical properties of the antibodies in the mixture may not be sufficiently different on these resins to allow separation, and hence control of the composition of an antibody mixture. In such cases the physical properties one or more of the antibodies can be modulated by introducing one or more substitutions or point mutations to improve the separation, such as the substitutions disclosed in the following.

Affinity reagents are another important class of resins for separation of biomolecules, such as antibodies. Here a biomolecule is immobilized on the matrix to form a resin that specifically binds to antibodies. The immobilized biomolecule can be selected from immunoglobulin ligands, such as naturally occurring immunoglobulin ligands, including Protein A, Protein G and Protein L, often with modifications to increase their stability or another property (Gagnon, 2012). Information on such biomolecules is provided in the following table:

Biomolecule ligands/affinity reagents

| Sequence identifier | Name | Sequence |
| --- | --- | --- |
| SEQ ID NO: 62 | Staphylococcus aureus Protein A (Uniprot Q70AB8) | AAQHDEAQQNAFYQVLNMPNLNADQRNGFIQSLKDDPSQSAN VLGEAKKLNESQAPKADNNFNKEQQNAFYEILNMPNLNEEQRN GFIQSLKDDPSQSANLLSEAKKLNESQAPKADNKFNKEQQNAFEI LHLPNLNEEQRNGFIQSLKDDPSQSANLLAEAKKLNDAQAPKAD NKFNKEQQNAFYEILHLPNLTEEQRNGFIQSLKDDPSVSKEILAEA KKLNDAQAPKEEDNNKPGKEDGNKPGKEDGN |
| SEQ ID NO: 63 | Streptococcus sp. group G Protein G (UniProtKB - P06654 amino acids 34-417) | VDSPIEDTPIIRNGGELTNLLGNSETTLALRNEESATADLTAAAVA DTVAAAAAENAGAAAWEAAAAADALAKAKADALKEFNKYGVS DYYKNLINNAKTVEGIKDLQAQVVESAKKARISEATDGLSDFLKSQ TPAEDTVKSIELAEAKVLANRELDKYGVSDYHKNLINNAKTVEGV KELIDEILAALPKTDTYKLILNGKTLKGETTTEAVDAATAEKVFKQY ANDNGVDGEWTYDDATKTFTVTEKPEVIDASELTPAVTTYKLVIN GKTLKGETTTKAVDAETAEKAFKQYANDNGVDGVWTYDDATKT FTVTEMVTEVPGDAPTEPEKPEASIPLVPLTPATPIAKDDAKKDDT KKEDPEAKKDDAKKAETLPTTGEG |
| SEQ ID NO: 64 | Finegoldia magna Protein L (UniProtKB - Q51918) amino acids 17-992) | AEEDNTDNNLSMDEISDAYFDYHGDVSDSVDPVEEEIDEALAKA LAEAKETAKKHIDSLNHLSETAKKLAKNDIDSATTINAINDIVARAD VMERKTAEKEEAEKLAAAKETAKKHIDELKHLADKTKELAKRDIDS ATTINAINDIVARADVMERKTAEKEEAEKLAAAKETAKKHIDELKH LADKTKELAKRDIDSATTIDAINDIVARADVMERKLSEKETPEPEEE VTIKANLIFADGSTQNAEFKGTFAKAVSDAYAYADALKKDNGEYT VDVADKGLTLNIKFAGKKEKPEEPKEEVTIKVNLIFADGKTQTAEF KGTFEEATAKAYAYADLLAKENGEYTADLEDGGNTINIKFAGKET PETPEEPKEEVTIKVNLIFADGKIQTAEFKGTFEEATAKAYAYANLL AKENGEYTADLEDGGNTINIKFAGKETPETPEEPKEEVTIKVNLIFA DGKTQTAEFKGTFEEATAEAYRYADLLAKVNGEYTADLEDGGYTI NIKFAGKEQPGENPGITIDEWLLKNAKEEAIKELKEAGITSDLYFSLI NKAKTVEGVEALKNEILKAHAGEETPELKDGYATYEEAEAAAKEA LKNDDVNNAYEIVQGADGRYYYVLKIEVADEEEPGEDTPEVQEG YATYEEAEAAAKEALKEDKVNNAYEVVQGADGRYYYVLKIEDKED EQPGEEPGENPGITIDEWLLKNAKEDAIKELKEAGISSDIYFDAINK AKTVEGVEALKNEILKAHAEKPGENPGITIDEWLLKNAKEAAIKEL KEAGITAEYLFNLINKAKTVEGVESLKNEILKAHAEKPGENPGITID EWLLKNAKEDAIKELKEAGITSDIYFDAINKAKTIEGVEALKNEILKA HKKDEEPGKKPGEDKKPEDKKPGEDKKPEDKKPGDKKPEDKKPG KTDKDSPNKKKKAKLPKAG |

The chromatography in step b) of the present invention may hence use an affinity reagent comprising a biomolecule immobilized on a matrix, the immobilized biomolecule comprise an amino acid sequence selected from the group consisting of:
- a) an amino acid sequence set forth in any one of SEQ ID NOs: 62, 63 and 64;
- b) a subsequence of any one of the sequences in a) comprising at least 200, such as at least 300, at least 400, at least 500, at least 600, at least 700 or at 800 consecutive amino acid residues;
- c) an amino acid having at least 80%, such as 85%, 90%, 95%, 98% or 99% sequence identity to any one of the amino acid sequences defined in a) and b).

Alternatively, the biomolecule can be an affinity reagent such as a camelid VHH IgG analog ligand (Gagnon, 2012). In order to gain full control of the composition of an antibody mixture using affinity reagents, a sufficient number of specific affinity reagents need to be selected to provide specificity and control of all the components in the mixture. Again, the specificity of an antibody for an affinity reagent can be engineered into the antibody by introducing substitutions and/or designing point mutants in the antibody that reduce or prevent binding of the antibody to a specific affinity resin.

Other affinity resins, which may be useful in the method according to the invention are resins that bind to tags, including Immobilized metal affinity chromatography (IMAC) resins, which recognize a His tag, Strep-Tactin® which binds to Strep-tag II and C-tag. Other affinity resins of potential use include resins that bind to carbohydrates: Lentil lectin resins and Con A resins. Still further resins that may be used according to the invention include CaptureSelect® FcXL.

If two or more of the antibodies are initially found to be inseparable in the chromatogram then at least one of the antibodies may be modified in the amino acid sequence to obtain a difference which enables the separation. In one embodiment the modification may introduce one or more amino acids having a different charge than the wildtype amino acid which is substituted so as to introduce separability in the chromatogram. In one embodiment two or more of the antibodies of the mixture are modified to obtain separability. In another embodiment three or more of the antibodies of the mixture are modified to obtain separability. It is an advantage of the present invention that two or more antibodies may be produced at unknown concentration ratio in the input mixture and may be separated by chromatography and can be recovered in correct predetermined concentration ratio. This means that each antibody of the input is recovered in the chromatography method and excess of one or more of the antibodies is depleted from the mixture to obtain the correct ratio or the different antibodies are fractionated in the chromatography experiment and re-pooled at the desired composition. This may be obtained by analysis of the different peaks in the chromatogram and thus by in-line analysis of the concentration of the different antibodies. Hereby, the correct ratio of the different antibodies can be recovered and any excess of one or more different antibodies can be discarded. Accordingly, in one embodiment of the invention the two or more different I antibodies of the output mixture may be recovered in a single pool in step c). This may be obtained by an in-line analysis of the concentrations of the different antibodies so that each pool of antibodies is recovered in the correct ratio to each other and excess antibody is discarded in a waste pool. Hereby the output mixture is recovered and collected in a single pool.

Thus, in one embodiment of the invention the method comprises the separation of the two or more antibodies and depletion of excess of one or more of the antibodies to recover the predetermined ratio of the two or more different antibodies.

In another embodiment of the present invention, the two or more antibodies in step b) are separated into different fractions and the fractions which contain one of the antibodies at a purity of at least 80% are subsequently pooled at the predetermined concentration ratio of the different antibodies to recover the output mixture. Hereby a method is provided where the different antibodies are recovered in separate fractions by a chromatography step. This is possible because the different antibodies are separable by chromatography. The different fractions collected will contain the different antibodies in varying purity. It is to be understood that only fractions containing one of the antibodies at a purity of at least about 80% will be used and pooled with other fractions containing the other antibodies at a purity of at least about 80%.

The various pure fractions of each different antibody will be pooled at the predetermined ratio to obtain the output mixture. Hence, the method according to the invention may comprise:
i) separating in step (b) the two or more antibodies into different fractions, and selecting for each antibody one or more fractions containing that antibody at a purity of at least 80%; and
ii) Providing said output mixture by pooling volumes of the selected fractions, the size of the volumes being adjusted to provide the predetermined concentration ratio of said two or more antibodies.

In one embodiment, the method comprises a further step of determining the concentration of the antibodies in each fraction prior to the pooling of the antibodies. This may be done by analytics on the fractions or in-line analytics. In other embodiments only fractions containing one of the antibodies at a purity of at least about 85% will be used. In other embodiments where a higher purity of the antibodies in the fractions is required only fractions containing the antibodies at a purity of at least about 90% or at least about 95% or even at least about 97% or 98% will be used.

In yet another embodiment of the invention, separation of the two or more antibodies is done by a single chromatography step using a single chromatography resin. In one embodiment the single chromatography resin is a preparative chromatography resin.

In yet another embodiment of the invention, the separation of the two or more antibodies is done by use of a mixture of chromatography resins at a predetermined ratio or by multiple resins in series. This may be an advantage in cases where the resin has a specific and known binding capacity so that it is known how much antibody it will bind. Either the excess antibodies will be depleted by binding to and saturating the resins so that the unbound fraction is collected to recover the output mixture at the predetermined concentration ratio, or the bound antibodies are subsequently eluted at the predetermined ratio.

In yet another embodiment of the invention, the composition of the input mixture is measured using an analytical assay prior to step b). Hereby the concentration of each antibody in the pool is known prior to the separation in step b) and this knowledge can be used to recover each antibody in the predetermined ratio.

In another embodiment of the invention, the composition of the input mixture is measured by an analytical assay in-line with the chromatography step in step b. Hereby the measurement of the composition of the input mixture is used to adjust the elution conditions of the chromatography such that the antibodies that are present in excess are depleted to yield a mixture of the desired ratio.

As discussed above in one embodiment of the invention the method comprises an initial step of determining the separability of the two or more antibodies by chromatography and where the different antibodies are inseparable then modifying the amino acid sequence of one or more of the antibodies to obtain separability by chromatography.

In one embodiment of the invention, the modification of the amino acid sequence of one or more of the antibodies is selected from: amino acid substitutions, additions or deletions in one or more of the antibodies or a combination hereof. Thus, it may be that one or more of the antibodies of the mixture are modified by one or more substitutions and other antibodies of the mix are modified by deletion of one or more amino acids and/or by addition of one or more amino acids. In other embodiments the only kind of modifications of antibodies is by substitutions.

In one embodiment of the invention, the one or more modifications comprises a modification in the constant domain of one or more of the antibodies.

In another embodiment of the invention, the one or more modifications comprises a modification in the variable domain of one or more of the antibodies. In a preferred embodiment the modifications are in the framework regions and not in the CDR regions. Hereby the specific affinities of the antibodies are not altered, or are altered by less than 2-fold, or less than 3-fold or less than 4-fold. It is preferred that the modifications are silent with respect to the antibody functionalities.

In another embodiment of the invention, the modification comprises a modification in the framework sequence of the light chain variable region and/or of the heavy chain variable region.

In another embodiment of the invention, the modification comprises a modification one or more amino acid substitutions in one or more of the different antibodies.

In another embodiment of the invention, the modification is a single amino acid substitution in one or more of the antibodies. In another embodiment of the invention, the modification is a single amino acid substitution in only one of the antibodies. In another embodiment of the invention, the modification is a single amino acid substitution in two of the antibodies. In another embodiment of the invention, the modification is a single amino acid substitution in three different monoclonal antibodies of the mixture. In another embodiment of the invention, the modification is a single amino acid substitution in four different antibodies of the mixture. In another embodiment of the invention, the modification is a single amino acid substitution in five different antibodies of the mixture.

In yet another embodiment of the invention, the modification is two amino acid substitutions in one or more of the antibodies. It may also be in some embodiments that three, four, five, six or more substitutions are made in one or more of the antibodies to obtain separability.

In another embodiment of the invention, the modifications do not alter the functional characteristics of the one or more modified antibodies. The main purpose of introducing modifications to the antibodies is to make the antibodies separable by chromatography so that the antibodies can be separated and recovered by chromatography in the selected ratio.

In another embodiment of the invention, the functional characteristics which are unaltered are selected from the group comprising: the antibody binding affinity, effector functions such as CDC or ADCC, avidity and clustering.

In yet another embodiment of the invention, the one or more amino acid substitutions comprises a modification in the heavy chain variable region and/or in the light chain variable region of one or more of the antibodies wherein the substitution is at one or more positions selected from the group comprising: 1, 6, 17, 24, 48, 75, 90, 93, 96, 97 in the heavy chain variable region and/or from the group comprising: 1, 4, 47, 48, 51, 68, 74, 80, 90, 93, and 95 in the light chain variable region, wherein the numbering is according to the IMGT numbering of IgG1 variable regions.

In another embodiment of the invention, the one or more amino acid substitutions comprises a modification in the heavy chain variable region and/or in the light chain variable region of one or more of the antibodies wherein the substitution is at one or more positions selected from the group consisting of: 1, 6, 17, 24, 48, 75, 90, 93, 96, 97 in the heavy chain variable region and/or from the group consisting of: 1, 4, 47, 48, 51, 68, 74, 80, 90, 93, and 95 in the light chain variable region, wherein the numbering is according to the IMGT numbering of IgG variable regions.

Hereby, amino acid positions are provided which may be amended by substitution if e.g. two or more different antibodies are not separated in the chromatogram. These amino acid positions have been found by the inventors to be suitable for substitution to enable separation of the antibodies by chromatography. These amino acids have been found to affect resin binding so that a change in e.g. the charge of the substituted amino acid compared to the wild type or in the size or in the hydrophobic interactions will cause the antibody to interact differently with the chromatography resin. Thereby, separability may be obtained. It is to be understood that the amino acid substitution should preferably not alter the functional characteristics of the antibodies. Accordingly, the variant antibodies may be screened in standard assays for functionality and variants which have unaltered functionality are preferred.

In another embodiment, the mutation is a substitution to an amino acid present in the repertoire of human antibody germlines and is not significantly immunogenic since the mutation in the intact antibody or processed peptides is not recognized as non-self by the human immune system. Accordingly, the one or more substitutions may be selected based on naturally occurring germline variations so that a substitution can be made which is not immunogenic but which introduces separability in the chromatogram.

In one embodiment of the invention, the one or more substitutions introduce an amino acid which has a different charge than the wild type amino acid at the corresponding position.

In a particular embodiment, the two or more different antibodies comprise a first and a second antibody, which are mutated in the CH3 region of the heavy chain to allow for Fab-arm exchange as described in WO 11/131746.

In one embodiment, the conditions allowing for formation of a bispecific antibody is described in WO 11/131746. Preferably, these conditions are reducing conditions allowing for reduction of the inter chain disulfide bonds in the hinge region. In one embodiment the first and the second antibody comprises one or more mutations in the CH3 regions which mutations are different and are such that the heterodimeric interaction between said first and second CH3 regions is stronger than each of the homodimeric interactions of said first and second CH3 regions. In one embodiment, the first antibody has an amino acid substitution at a position selected from the group consisting of: 366, 368, 370, 399, 405, 407 and 409, and said second antibody has an amino acid substitution at a position selected from the group consisting of: 366, 368, 370, 399, 405, 407 and 409, and the first and second antibody is not substituted in the same positions. In one embodiment, the first antibody is substituted in position 405 and the second antibody is substituted in position 409. In a particular embodiment the first antibody has an F405L substitution. In another embodiment the second antibody has a K409R substitution. In a preferred embodiment, the first antibody has a F405L substitution and the second antibody has a K409R mutation in the CH3 region.

In further embodiments, the two or more different antibodies comprise a bispecific antibody produced by Fab-arm exchange as described in WO 11/131746, from monoclonal antibodies having mutations in the CH3 region of the heavy chain as disclosed above.

In one embodiment, one or more of the antibodies comprise an Fc region of a human immunoglobulin IgG wherein the Fc region comprises a mutation at an amino acid position corresponding to position E430, E345 or S440 in human IgG1 according to EU numbering. The positions corresponding to E430, E345 and S440 in human IgG1 according to EU numbering are located in the CH3 domain of the Fc region. In the context of the present invention, these mutations are considered to be "hexamerization enhancing mutations."

The rationale for introducing mutations at these positions is based on the finding that a combination of two antibodies binding to a first and a second epitope on a cell surface antigen may form heterohexamers when each antibody has a mutation at position E430, E345 or S440. The formation of such heterohexamers greatly enhances the effect of antibody binding, compared to a combination of the two antibodies without the mutation in the Fc region. Hence, the hexamerization enhancing mutations strengthen the Fc-Fc interactions between antibodies comprising the mutation when bound to the corresponding target on a cell surface, while the antibody molecules remain monomeric in solution (WO2013/004842; WO2014/108198).

In one embodiment of the present invention, the Fc region in one or more of the antibodies comprises a mutation corresponding to E430G, E430S, E430F, E430T, E345K, E345Q, E345R, E345Y, S440Y or S440W in human IgG1, EU numbering. More specifically, the said one or more antibodies each comprises an Fc region comprising a first heavy chain and a second heavy chain, wherein one of the above mentioned hexamerization enhancing mutations may be present in the first and/or the second heavy chain.

In one embodiment of the present invention, the one or more of the antibodies comprise a mutation at an amino acid positon corresponding to E430 in human IgG1 according to EU numbering, wherein the mutation is selected form the group consisting of: E430G, E430S, E430F and E430T. In one embodiment of the present invention one or more of the antibodies comprises a mutation corresponding to E430G.

One or more of the antibodies may comprise a mutation at an amino acid positon corresponding to E345 in human IgG1 according to EU numbering, wherein the mutation is selected form the group consisting of: E345K, E345Q, E345R and E345Y. Preferably, the mutation corresponds to E345K In a specific embodiment of the invention, the one or more amino acid substitutions comprise an E345K substitution in the heavy chain constant region using the EU numbering system.

In one embodiment of the present invention, one or more of the antibodies may comprise a "hexamerization-inhibiting mutation" in the Fc region, such as K439E or S440K in human IgG1, EU numbering. The hexamerization-inhibiting mutation such as K439E or S440K prevents Fc-Fc interaction with antibodies comprising the same hexamerization inhibiting mutation, but by combining antibodies with a K439E mutation and antibodies with a S440K mutation the inhibiting effect is neutralized and Fc-Fc interactions is restored. In one embodiment of the present invention the antibody comprises a further mutation at an amino acid position corresponding to one of the following positions S440 or K439 in human IgG1, EU numbering, provided the mutation at position S440 is not S440Y or S440W. In one embodiment of the invention the Fc region comprises a further mutation in a position corresponding to S440 or K439, with the proviso that the further mutation is not in position S440 if the hexamerization enhancing mutation is in S440. Antibodies comprising a mutation in a position corresponding to E430, E345 or S440 according to the present invention and a further mutation at an amino acid position corresponding to K439 such as a K439E mutation do not form oligomers with antibodies comprising a further mutation at an amino acid position corresponding to K439 such as a K439E mutation. However, antibodies comprising hexamerization enhancing mutation in E430, E345 or S440 and a further mutation in K439 such a K439E do form oligomers with antibodies comprising a hexamerization enhancing mutation in E430 or E345 and a further mutation in S440 such as S440K. Antibodies comprising a mutation in a position corresponding to E430 or E345 according to the present invention and a further mutation at an amino acid position corresponding to S440 such as an S440K mutation do not form oligomers with antibodies comprising a further mutation at an amino acid position corresponding to S440 such as an S440K mutation. However, antibodies comprising hexamerization enhancing mutation in E430 or E345 and a further mutation in S440 such as S440K do form oligomers with antibodies comprising a hexamerization enhancing mutation in E430 or E345 and a further mutation in K439 such as K439. In one embodiment of the present invention the Fc region comprises a hexamerization enhancing mutation such as E430G and a hexamerization inhibiting mutation such as K439E. In one embodiment of the present invention the Fc region comprises a hexamerization enhancing mutation such as E345K and a hexamerization inhibiting mutation such as K439E. In another embodiment of the present invention the Fc region comprises a hexamerization enhancing mutation such as E430G and a hexamerization inhibiting mutation such as S440K. In one embodiment of the present invention the Fc region comprises a hexamerization enhancing mutation such as E345K and a hexamerization inhibiting mutation such as S440K. In one embodiment of the present invention the Fc region comprises a hexamerization enhancing mutation such as S440Y and a hexamerization inhibiting mutation such as K439E Hereby embodiments are provided that allow for exclusive hexamerization between combinations of antibodies comprising a K439E mutation and antibodies comprising a S440K mutation.

In one embodiment of the present invention, the Fc-region comprises a mutation at an amino acid positon corresponding to S440 in human IgG1 according to EU numbering, wherein the mutation is selected form the group consisting of: S440W and S440Y.

In yet another embodiment of the invention, the modifying the one or more antibodies comprises introducing at least one amino acid substitutions in the light chain of one or more of the antibodies wherein the substitution introduces a proline (P) at position 12 in the light chain variable region using the IMGT numbering system. Preferably the substitution eliminates binding to an affinity resin and the chromatography uses the affinity resin for which the substitution eliminates binding. Hereby modified antibodies will have a different affinity to an affinity resin which resin may then be used to separate the two or more antibodies. In one embodiment the affinity reagent is Protein L which has affinity for kappa light chains. HiTrap™ Protein L and Capto™ L may be obtained from GE Healthcare.

In yet another embodiment of the invention, the modifying the one or more antibodies comprises introducing at least one amino acid substitutions in the light chain of one or more of the antibodies wherein the substitution eliminates binding to an affinity resin and wherein the substitution is selected from the group comprising V110D, V110R, V110E, V110H, V110K, V110N, V110P, V110Q, V110W and E143D using the EU numbering system, wherein the chromatography uses the affinity resin for which the substitution eliminates binding. Hereby modified antibodies will have a different affinity to an affinity resin which resin may then be used to separate the two or more antibodies. In one embodiment the affinity reagent is CaptureSelect® or KappaXL which has affinity for the kappa light chain constant region. CaptureSelect® and KappaXL may be obtained from ThermoFisher. In another embodiment the affinity reagent is KappaSelect™ which has affinity for kappa light chain constant region. KappaSelect™ may be obtained from GE Healthcare.

In another embodiment of the invention, the modifying the one or more antibodies comprises introducing at least one amino acid substitution in said one or more of the antibodies wherein the substitution is in the CH1 domain wherein the substitution eliminates binding to an affinity resin and the substitution comprises an S157T and/or a T164S mutation using the EU numbering system and wherein the chromatography uses the affinity resin for which the substitution eliminates binding. Hereby modified antibodies will have a different affinity to an affinity resin which resin may then be used to separate the two or more antibodies.

In one embodiment, the affinity reagent is an IgG-CH1 affinity reagent such as e.g. CaptureSelect® IgG-CH1 which may be obtained from ThermoFisher.

In another embodiment of the invention, modifying the one or more antibodies comprises introducing at least one amino acid substitution in the heavy chain constant region of said one or more antibodies wherein the substitution is selected from the group comprising M252A, S254M, E380A, E380M, E382A, E382L, S426M, M428G, M428T, M428V, H433D, N434A, N434G, N434S, M428A using the EU numbering system and wherein the substitution eliminates binding to an affinity resin and wherein the chromatography uses the affinity resin for which the substitution eliminates binding. Hereby modified antibodies will have a different affinity to an affinity resin which resin may then be used to separate the two or more antibodies. In one embodiment the affinity reagent is Protein G.

In yet another embodiment of the invention, the two or more antibodies are determined to be separable if the resolution (Rs) is Rs≥0.3 as determined in a cation exchange chromatography assay; using an ionic strength gradient with Rs≥0.3 according to the equation $Rs=2(t2-t1)/(W1+W2)$ where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline. Hereby, the separability of the different antibodies of the mixture can be determined. Such determination may be performed as an initial step prior to step a) of the method disclosed herein. Should two or more of the different antibodies be inseparable in such a chromatography assay one or more of the different antibodies may be modified as described above so that the antibodies become separable by chromatography. It may however be that the antibodies of the mixture are separable in a different chromatography assay using a different resin or different elution conditions. Accordingly, in another embodiment the two or more antibodies are determined to be separable if the resolution (Rs) is Rs≥0.3 as determined in a hydrophobic interaction chromatography assay; using an ionic strength gradient with Rs≥0.3 according to the equation $Rs=2(t2-t1)/(W1+W2)$ where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline. In yet another embodiment the two or more antibodies are determined to be separable if the resolution (Rs) is Rs≥0.3 as determined in a mixed mode chromatography assay; using an ionic strength gradient with Rs≥0.3 according to the equation $Rs=2(t2-t1)/(W1+W2)$ where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline. In another embodiment the two or more antibodies are determined to be separable as determined in an affinity chromatography assay if baseline separation is achieved between antibodies in the unbound fractions that do not bind to the column and fractions eluting from the column, or if the resolution (Rs) is Rs≥0.3 as determined in an affinity chromatography assay using a pH gradient with Rs≥0.3 according to the equation $Rs=2(t2-t1)/(W1+W2)$ where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline.

Hereby different tests are given which are suitable for determining whether the different antibodies will be separable by chromatography and it may be determined which chromatography resin will be most suitable for separating the different antibodies. As mentioned above, in cases where the antibodies are initially found to be inseparable by chromatography it may be desired to modify one or more of the antibodies of the mixture in the amino acid sequence(s) so that the antibodies become separable when tested as above. When the antibodies are separable by chromatography it is possible to recover the different antibodies in the desired and predetermined ratio from a single chromatography step.

In one embodiment, the two or more different antibodies of the input mixture are expressed in and provided from different production host cells. In another embodiment the two or more different antibodies are expressed in and provided from different production host cells co-cultured in a single vessel. In yet another embodiment the two or more different antibodies are co-expressed in a single production host cell. Hereby, the present invention is versatile with regards to the production of the different antibodies of the mixture. It is an important element of the present invention that the concentration of the different antibodies in the input mixture does not need to be completely controlled to within the required specifications for the output mixture and thus the upstream process does not need to be completely controlled with regards to relative concentration of each antibody of the mixture. Complete control and normalization of the ratio of the different antibodies is obtained through the downstream process through the use of chromatography.

It is further to be understood that the process according to the invention may be used downstream of a production process in which measures have been taken to achieve normalization of the ratio of the different antibodies, but where such normalization has failed. In that situation, absent a suitable downstream process, the only option would be to discard the entire production batch.

In one embodiment of the invention, the two or more different antibodies are selected from the group comprising IgG1, IgG2, IgG3 or IgG4 antibodies or a combination hereof. In one embodiment all the different antibodies of the mixture are from the same isotype. Accordingly, in one embodiment all the different antibodies of the mixture are IgG1 antibodies. In another embodiment all the different antibodies of the mixture are IgG2 antibodies. In another embodiment all the different antibodies of the mixture are IgG3 antibodies. In another embodiment all the different antibodies of the mixture are IgG4 antibodies. In another embodiment the different antibodies of the mixture are a combination of IgG1, IgG2, IgG3 and IgG4 antibodies. In another embodiment the different antibodies of the mixture are a combination of IgG1 and IgG4 antibodies. In another embodiment the different antibodies of the mixture includes bispecific antibodies.

In one aspect, the method of the invention is for the production of a drug product which drug is the mixture of different antibodies. In one aspect the method of the invention is for the manufacture of a medicament for the treatment of a disease, for clinical trials, for toxicology studies or for determining batch-to-batch consistency.

It is an important element of the invention that the process leads to reproducible results between different batches of the output mixture, such that the two or more different antibodies are present at, or essentially at, the desired or predetermined concentration ratio.

In another aspect, the invention relates to a mixture of two or more different antibodies, wherein the mixture is obtainable by the method of the invention. In the mixture according to the invention, the two or more different antibodies are present at, or essentially at, a desired or predetermined concentration ratio.

In yet another aspect, the invention relates to a mixture of two or more different antibodies having a predetermined ratio of two or more different antibodies which antibodies have a difference in size, charge, hydrophobicity or affinity for a chromatography resin.

In one embodiment of the invention, the mixture of different antibodies is a mixture of 3 different antibodies. In another embodiment it is a mixture of 4 different antibodies. In another embodiment it is a mixture of 5 different antibodies. In another embodiment it is a mixture of 6 different antibodies. In another embodiment it is a mixture of 7 different antibodies. In another embodiment it is a mixture of 8 different antibodies. In another embodiment it is a mixture of 9 different antibodies. In another embodiment it is a mixture of 10 different antibodies.

An antibody mixture of the invention may be used in the treatment of a disease. It may be an advantage to use a mixture of different antibodies in the treatment of various diseases where regular monoclonal antibodies as monotherapy is not sufficient to treat the disease. This may be due to down-regulation of the target or a switch to a distinct pathogenic pathway. By use of a mixture of different antibodies it may be possible to target multiple cell surface receptor antigens which may prevent down-regulation of the target or a switch to a distinct pathogenic pathway. It may further be an advantage to target multiple epitopes on a single target using a mixture of antibodies as the different antibodies may have distinct mechanisms of action or have different potencies to treat the disease.

In one aspect, the mixture of two or more different antibodies according to the invention comprise at least one modified antibody which comprise at least one amino acid substitution in the heavy chain variable region and/or in the light chain variable region wherein the substitutions is at one or more positions selected from the group comprising: 1, 6, 17, 24, 48, 75, 90, 93, 96, 97 in the heavy chain variable region and/or from the group comprising: 1, 4, 47, 48, 51, 68, 74, 80, 90, 93, and 95 in the light chain variable region, wherein the numbering is according to the IMGT numbering of IgG variable regions.

In yet another aspect, the mixture of two or more different antibodies according to the invention comprise at least one modified antibody which comprise at least an E345K substitution of in the heavy chain constant region using the EU numbering system. Hereby the antibody is modified to have a different charge which may aid the separation of the antibodies by e.g. ion exchange chromatography.

In yet another aspect, the mixture of two or more different antibodies according to the invention comprise at least one modified antibody which comprise at least one amino acid substitution in the kappa light chain constant region of one or more of the antibodies wherein the substitution is selected from the group comprising V110D, V110R, V110E, V110H, V110K, V110N, V110P, V110Q, V110W, and E143D using the EU numbering system. Hereby modified antibodies will have a different affinity to an affinity resin which resin may then be used to separate the two or more antibodies. In one embodiment the affinity resin is a KappaSelect or KappaXL resin.

In yet another aspect, the mixture of two or more different antibodies according to the invention comprise at least one modified antibody which comprise a substitution of S157T and/or a T164S in the CH1 domain using the EU numbering system. Antibodies having such a substitution may have an amended affinity to an IgG-CH1 affinity resin such as CaptureSelect® affinity resin. In yet another aspect the mixture of the two or more different antibodies according to the invention comprise at least one modified antibody which comprise one or more substitutions in the heavy chain constant region selected from the group comprising M252A, S254M, E380A, E380M, E382A, E382L, S426M, M428G, M428T, M428V, H433D, N434A, N434G, N434S, M428A using the EU numbering system. Such modified antibodies may have a reduced binding to an affinity resin such as e.g. a Protein G resin.

In another embodiment, the invention provides a pharmaceutical composition comprising the mixture of different antibodies as described above as an active ingredient.

The pharmaceutical composition of the invention may in particular be a composition, which is sterile and has one or more of the following characteristics:

I. A physiologically acceptable pH, such as a pH, which is between 5 and 8, such as a pH which is between 6 and 8;
II. An osmolality, which is 600 mOsm/kg or lower, such as between 600 and 100 mOsm/kg, or such as between 600 and 200 mOsm/kg; and
III. A level of aggregates, which is such that 10% by weight or less of the antibodies in the composition are present in the form of aggregates, such as 9%, 8%, 7%, 6%, 5%, 4%, 3% or 2% by weight or less.

The pharmaceutical composition may in particular be isotonic or substantially isotonic, such as having an osmolality, which is from 290-300 mOsm/kg, such as 295 mOsm/kg.

In yet another embodiment, the invention relates to the mixture of two or more different antibodies as described above for use as a medicament. In a preferred embodiment the mixture is for use in a method for treating and/or preventing a disease. In one embodiment the disease is cancer. In another embodiment the disease is an infectious disease. The pharmaceutical compositions may be formulated with pharmaceutically acceptable carriers or diluents as well as any other known adjuvants and excipients in accordance with conventional techniques. A pharmaceutical composition of the present invention may include diluents, fillers, salts, buffers, detergents (e. g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, the pharmaceutical composition of the present invention is administered parenterally.

The terms "parenteral administration" and "administered parenterally" as used herein refers to modes of administration other than enteral and topical administration, usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion. In one embodiment, the pharmaceutical composition of the present invention is administered by intravenous or subcutaneous injection or infusion.

As the skilled person will realize utility of the present invention is not limited to antibodies agains any particular target or antigen. Exemplary target for antibodies processed according to the invention includes antigens selected from the group consisting of 5T4; ADAM-10; ADAM-12; ADAM17; AFP; AXL; ANGPT2 anthrax antigen; BSG; CAIX; CAXII; CA72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNMB; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM1; IFNA1; IFNA1; IFNB1; IgE Fc; IGF1R; IGHE connecting region; IL12B; IL13; IL15; IL17A; IL1A; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolyaccharide LPS; LTA; MET; MMP14; MMp15; MST1R; MSTN; MUC1; MUC4; MUC16; MUC5AC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS 011; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; TF; TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; and Vimentin.

In certain embodiments, at least one of the two or more different antibodies processed according to the invention may be specific for a target on a tumor cells, such as a target selected from the group consisting of erbB1 (EGFR), erbB2 (HER2), erbB3, erbB4, MUC-I, CD19, CD20, CD4, CD38, CD138, CXCR5, c-Met, HERV-envelop protein, periostin, Bigh3, SPARC, BCR, CD79, CD37, EGFrvIII, U-CAM, AXL, Tissue Factor (TF), CD74, EpCAM and MRP3.

Alternatively, at least one of the two or more different antibodies is specific for a target on an effector cell, such as, CD1, CD3, CD4, CD8, FcgammaRIII (CDI6), CD25, CD89, CD32, CD32a, FCεRI, CD40, or FcgammaRI (CD64). In other embodiments, at least one of the two or more different antibodies is specific for a death receptor, such as a death receptor selected from the group consisting of FAS, DR1, DR2, DR3, DR4, DR5, DR6, TNFR1, EDAR or NGFR.

In still further embodiments, at least one of the two or more different antibodies is specific for an immune checkpoint target, such as an immune checkpoint target selected from the group consisting of CTLA4, PD-1, PD-L1, LAG-3, TIM-3, OX40, Nectin-2, Nectin-3, PVR, HVEM, CD80, PD-L2, CD86, ICOSL, 4-1BBL, GITRL, CD27L, CD30L, CD40, OX40L, LIGHT, TL1A, CD3, TIGIT, BTLA, CD160, CD28, ICOS, 4-1BB, GITR, CD27, CD30, CD40L, OX40, DR3, GAL9, TNF-R3, RANK, TACI, BAFFR, BCM, RELT, CD120b, TWEAKR, TAJ-alpha, EDA2R, KIR2DL1, KIR2DL2, KIR2DL3, LY49, CD94, NKG2D, NKG2A, VISTA, CD96.

In other embodiments, at least one of the two or more different antibodies is specific for a blood brain barrier protein, such as a blood brain barrier protein selected from the group consisting of TfR, insulin receptor, MTfR, LfR, ApoER2, LRP1, LRP2, RAGE, DTR (=HB-EGF) or gp190.

In yet a different aspect, the invention relates to a mixture of two or more different monoclonal as described above for use in a method of targeting a tumor in a subject, the method comprising administering to the subject the mixture.

Preferably, each of said two or more different antibodies is present in the mixture in a therapeutically effective amount; i.e. each of the two or more different antibodies is present in an amount or in a concentration which allows the mixture to be processed into a drug product without additional steps to increase the amount or concentration of each of the two or more different antibodies relative to that of the other antibodies, wherein each of said two or more different antibodies is included in the drug product as an active pharmaceutical ingredient. In the context of the present invention the term "drug product" means a finished dosage form (e.g., tablet, capsule, solution) that contains an active drug ingredient or active pharmaceutical ingredient generally, but not necessarily, in association with inactive ingredients.

In the mixture provided according to the invention, the least abundant of said two or more different antibodies is preferably present in an amount which is at least 1% (w/w), 2% (w/w), 3% (w/w), 4% (w/w), 5% (w/w), 6% (w/w), 7% (w/w), 8% (w/w), 9% (w/w) or 10% (w/w) of the amount of the most abundant of the said two or more different antibodies.

The two or more antibodies are preferably present in the mixture in such amounts that the ratio (w/w) between the amounts of any two antibodies is between 1:5 and 5:1, such as between 1:4 and 5:1, 1:3 and 5:1, 1:2 and 5:1, 1:1 and 5:1, 2:1 and 5:1, 3:1 and 5:1, 3:4 and 5:1, 1:5 and 4:1, 1:5 and 3:1, 1:5 and 2:1, 1:5 and 1:1, 1:5 and 1:2, 1:5 and 1:3, 1:5 and 1:4, 1:4 and 4:1, 1:4 and 3:1, 1:4 and 2:1, 1:4 and 1:1, 1:4 and 1:2, 1:4 and 1:3, 1:3 and 4:1, 1:3 and 3:1, 1:3 and 2:1, 1:3 and 1:1, 1:3 and 1:2, 1:2 and 4:1, 1:2 and 3:1, 1:2 and 2:1, 1:2 and 1:1, 1:1 and 4:1, 1:1 and 3:1, or such as between 1:1 and 2:1.

In preferred embodiments, the mixture provided according to the invention is a mixture, wherein each of said two or more different antibodies is an active pharmaceutical ingredient.

The mixture provided according to the invention may comprise 2-10 different antibodies, such as 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-7, 7-10, 7-9, 7-8, 8-10, 8-9, or 9-10 different antibodies.

In the mixture according to the invention, at least one of said two or more different antibodies may be a monoclonal antibody. Further, in the mixture according to the invention all of said two or more different antibodies may be monoclonal antibodies.

In other embodiments, at least one of said one or more antibodies is a bispecific or multispecific antibody.

In the mixture according to the invention, the resolution of said two or more different antibodies (Rs) is preferably Rs≥0.3 as determined in one or more chromatography assays selected from the group comprising: hydrophobic interaction chromatography assay, cation exchange chromatography assay and/or a mixed mode chromatography assay; using an ionic strength gradient, pH gradient or salt gradient with Rs≥0.3 according to the equation Rs=2 (t2−t1)/(W1+W2) where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline.

In the mixture according to the invention, the said two or more antibodies are preferably separable as determined in an affinity chromatography assay, the antibodies being separable if baseline separation is achieved between antibodies in the unbound fractions that do not bind to the column and fractions eluting from the column, or if the resolution (Rs) is Rs≥0.3 as determined in an affinity chromatography assay using a pH gradient with Rs≥0.3 according to the equation Rs=2 (t2−t1)/(W1+W2) where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline.

In yet a different aspect, the invention relates a method of treatment of a disease comprising administering the mixture of two or more different antibodies as described above or the pharmaceutical composition as described above to a subject in need thereof.

In yet a different aspect, the invention relates use of a mixture of two or more different antibodies as described above for the manufacture of a medicament for the treatment of a disease.

The disease to be treated may be a cancer, a tumor, an immune or autoimmune disease, an inflammatory disease, a cardiovascular disease, a disease in the central nervous system (CNS), a musculo-skeletal diseases or an infectious disease.

The treatment may in particular be treatment of a solid tumor, such as a solid tumor selected from the group consisting of colorectal cancer, including colorectal carcinoma and colorectal adenocarcinoma, bladder cancer, osteosarcoma, chondrosarcoma, breast cancer, including triple-negative breast cancer, cancers of the central nervous system, including glioblastoma, astrocytoma, neuroblastoma, neural fibrosarcoma, neuroendocrine tumors, cervical cancer, endometrium cancer, gastric cancer, including gastric adenocarcinoma, head and neck cancer, kidney cancer, liver cancer, including hepatocellular carcinoma, lung cancer, including NSCLC and SCLC, ovarian cancer, pancreatic cancer, including pancreatic ductal carcinoma and pancreatic adenocarcinoma, sarcoma or skin cancer, including malignant melanoma and non-melanoma skin cancers.

The treatment may in particular be treatment of a hematological tumor, such as a hematological tumor selected from the group consisting of leukemia, including chronic lymphocytic leukemia and myeloid leukemia, including acute myeloid leukemia and chronic myeloid leukemia, lymphoma, including Non-Hodgkin lymphoma or multiple myeloma, including Hodgkin Lymphoma, and including myelodysplastic syndromes.

EXAMPLES

Example 1: Expression Vectors for the Expression of Human IgG1-2F8, Human IgG1-7D8, Human IgG1-1014-005, IgG1-1021-511 or Human IgG1-HepC and Variants For antibody expression of isolated immunoglobulin proteins, variable heavy (VH) chain and variable light (VL) chain sequences were prepared by gene synthesis (GeneArt Gene Synthesis; ThermoFisher Scientific, Germany) and cloned in pcDNA3.3 expression vectors (ThermoFisher Scientific, US) containing IgG1m (f) allotype heavy chain (HC) and light chain (LC) constant regions. The heavy chain constant region amino acid sequences as used are identified in the below sequence reference table.

Desired mutations were introduced either by gene synthesis or site directed mutagenesis. Antibodies mentioned in this application have VH and VL sequences derived from previously described IgG1-1014-005 (WO11/147982), IgG1-2F8 (WO 02/100348), and IgG1-1021-511 (WO16/005593), IgG1-7D8 (WO 04/035607), IgG1-1014-153 (WO2012/143523), IgG1-CD37-37-3 (WO11/112978), IgG1-CD19-21D4 (WO/2009/054863), Campath (Crowe et al., Immunology 87 (1): 105-110 (1992)), IgG1-HepC (WO 00/05266), and IgG1-224. The sequences are also provided herein.

| Sequence references: | |
|---|---|
| Heavy chain variable region of IgG1-1014-005 | SEQ ID NO: 7 |
| Light chain variable region of IgG1-1014-005 | SEQ ID NO: 15 |
| Heavy chain variable region of IgG1-2F8 | SEQ ID NO: 38 |
| Light chain variable region of IgG1-2F8 | SEQ ID NO: 45 |
| Heavy chain variable region of IgG1-1021-511 | SEQ ID NO: 22 |
| Light chain variable region of IgG1-1021-511 | SEQ ID NO: 30 |
| Heavy chain variable region of IgG1-7D8 | SEQ ID NO: 49 |
| Light chain variable region of IgG1-7D8 | SEQ ID NO: 50 |
| Heavy chain variable region of IgG1-1014-153 | SEQ ID NO: 51 |
| Light chain variable region of IgG1-1014-153 | SEQ ID NO: 52 |
| Heavy chain variable region of IgG1-CD37-37-3 | SEQ ID NO: 53 |
| Light chain variable region of IgG1-CD37-37-3 | SEQ ID NO: 54 |
| Heavy chain variable region of IgG1-CD19-21D4 | SEQ ID NO: 55 |
| Light chain variable region of IgG1-CD19-21D4 | SEQ ID NO: 56 |
| Heavy chain variable region of IgG1-CD52-Campath | SEQ ID NO: 57 |
| Light chain variable region of IgG1-CD52-CAMPATH | SEQ ID NO: 58 |
| Heavy chain variable region of IgG1-HepC | SEQ ID NO: 59 |
| Light chain variable region of IgG1-HepC | SEQ ID NO: 60 |
| Human IgG1 heavy chain constant region | SEQ ID NO: 46 |
| Human kappa light chain constant region | SEQ ID NO: 47 |
| Human lambda light chain constant region | SEQ ID NO: 48 |

Example 2: Introduction of Largely Non-Immunogenic Charge-Modulating Mutations into IgG1-1014-005, IgG1-1021-511 and IgG1-2F8

Figure 2A:
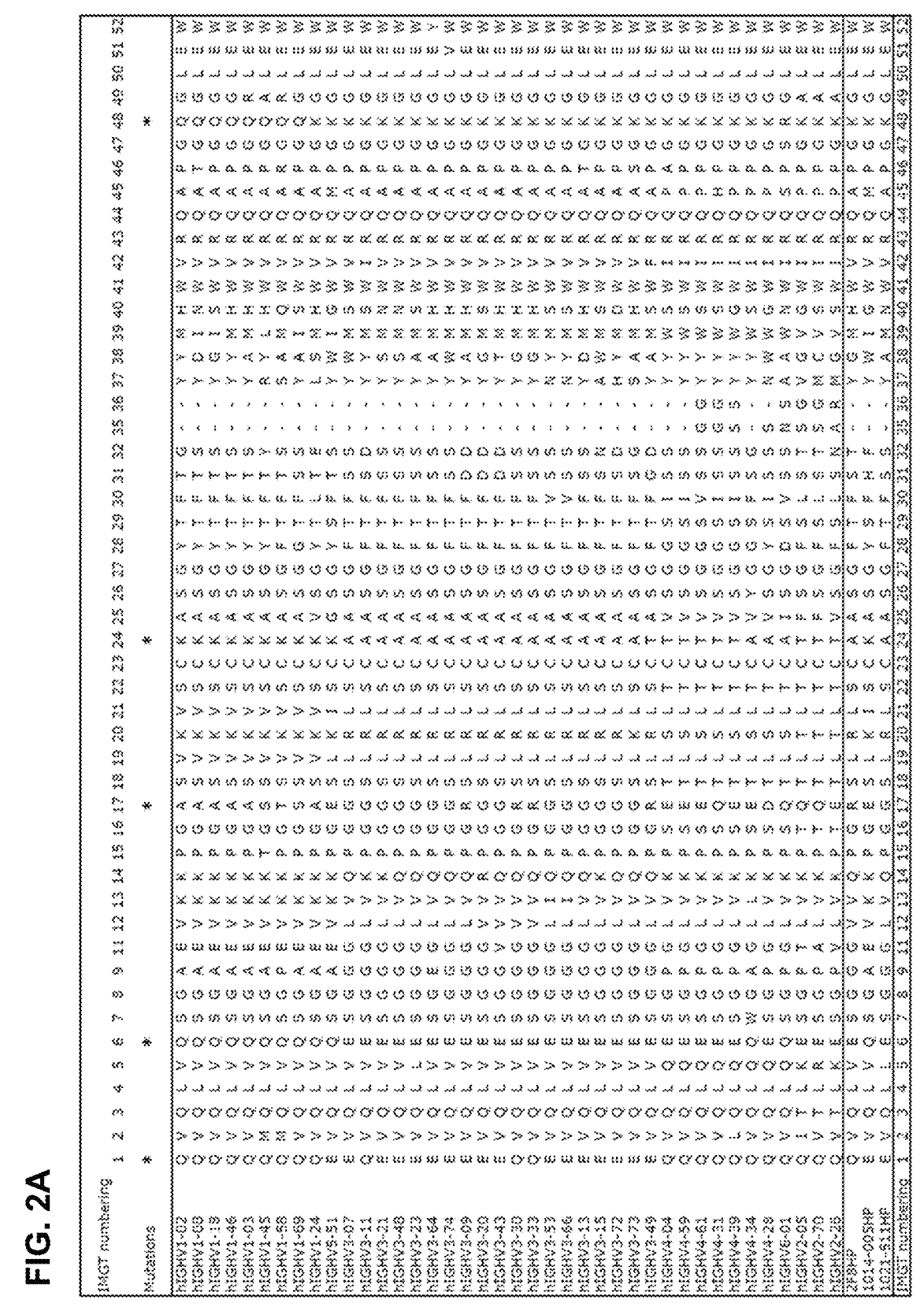
Figure 2A:
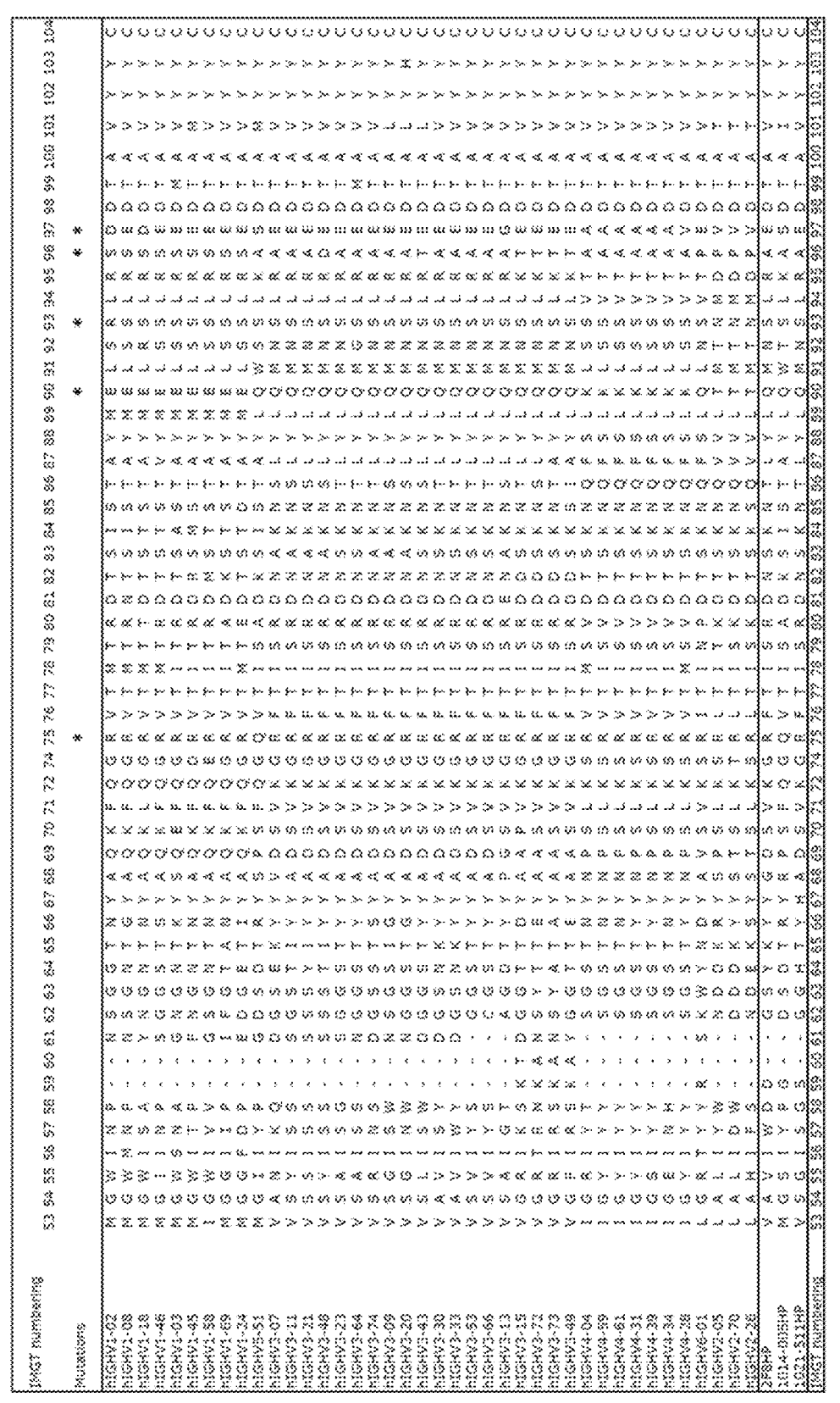
Figure 2B:
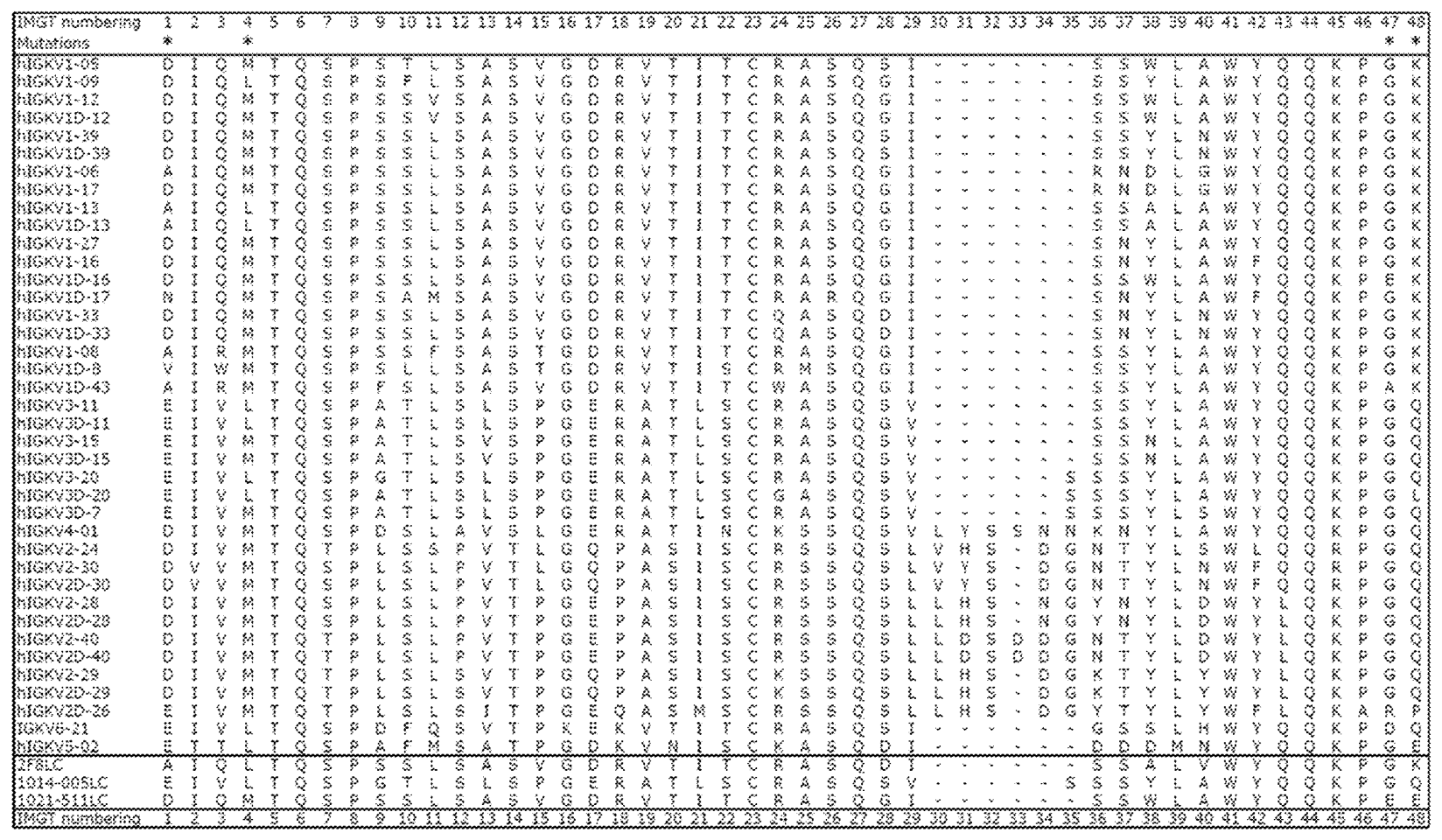
Figure 2B:
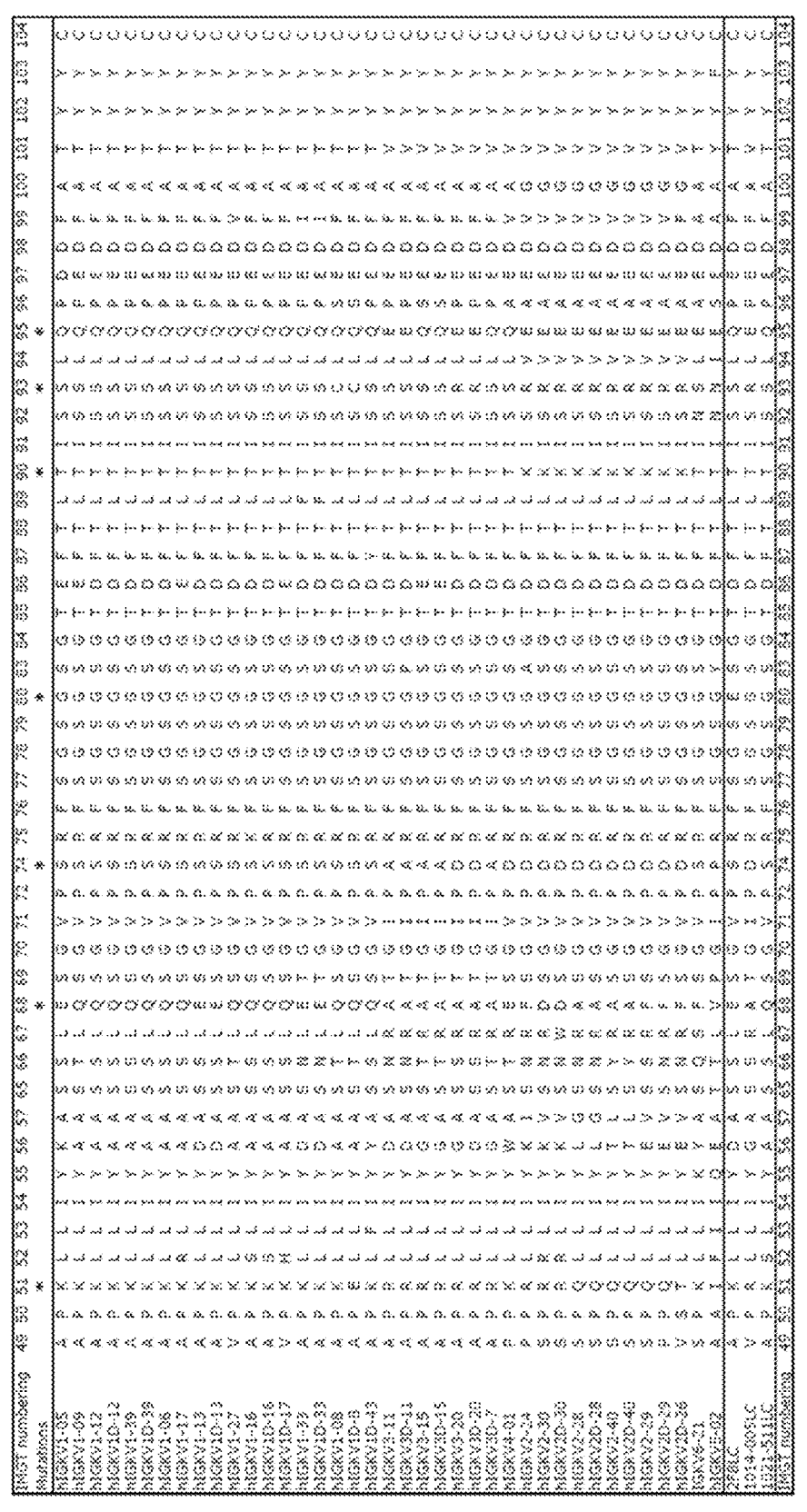
Figure 2D:
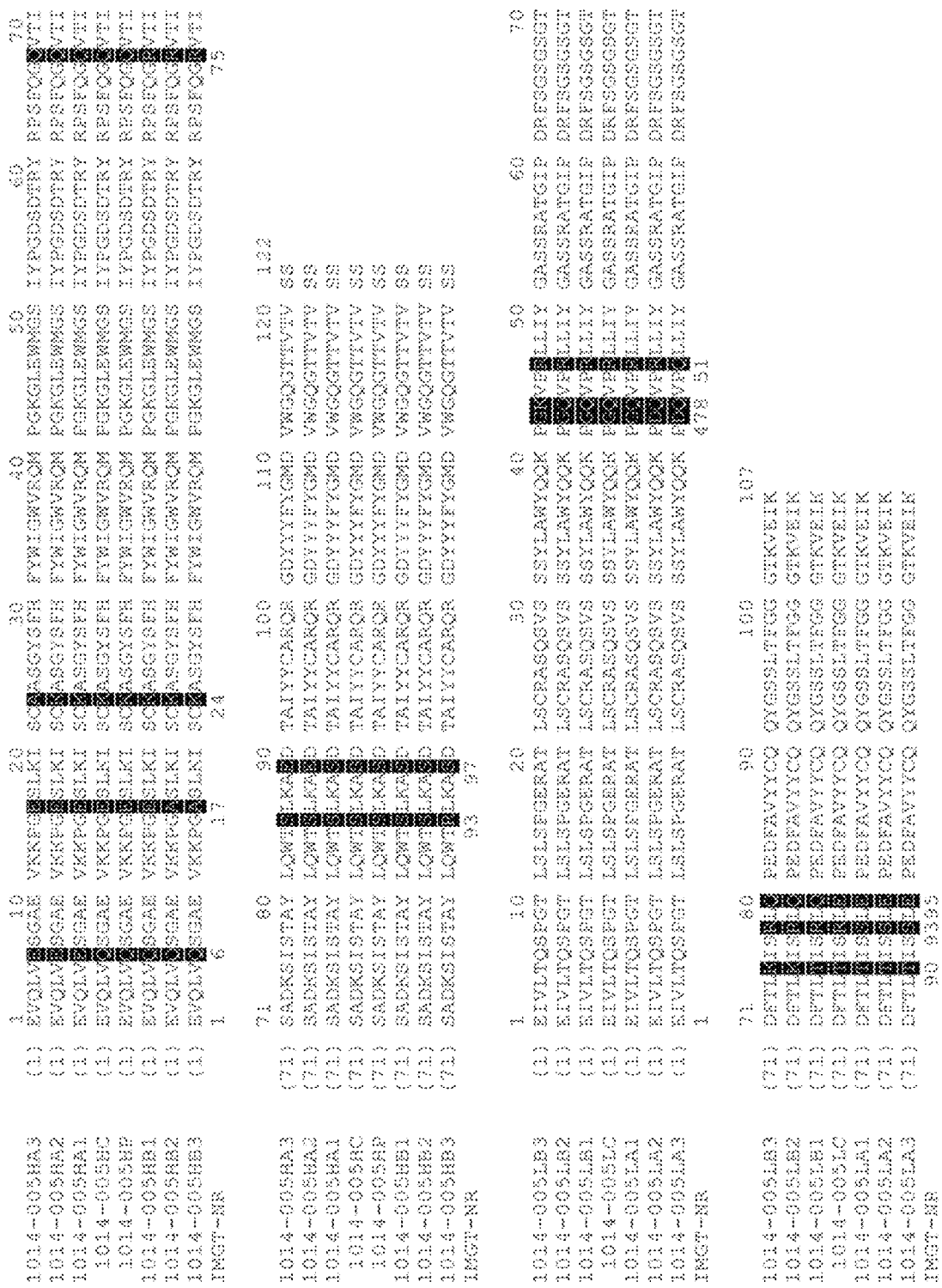

The heavy chain and light chain DNA sequences of IgG1-1014-005, IgG1-2F8, and IgG1-1021-511, selected for co-production and purification as a mixture, were aligned to a collection of human germline sequences. FIG. 2A shows an alignment of human germline heavy chain variable regions, and FIG. 2B an alignment of human germline kappa light chain variable regions, respectively, numbered according to the IMGT numbering scheme of human variable domains. To modulate the pI of the parental antibodies IgG1-1014-005, IgG1-2F8, and IgG1-1021-511 while minimizing a potential increase of immunogenicity, charge modulating mutations were introduced at amino acid positions where charge variation was observed in the natural human germline repertoire, or observed in the parental antibody sequence compared to the human germline variable domains. For each parental light or heavy chain sequence, seven variant variable domains were designed: a reference sequence lacking pyroglutamic acid at the N-terminus when present in the parental antibody, three sequence variants stepwise decreasing the pI and three sequence variants stepwise increasing the pI. Each of these seven heavy chain variable domains were expressed as intact heavy chains by fusing the sequences with a human IgG1 heavy chain constant domain lacking the C-terminal lysine (SEQ ID: 61). Each of the seven light chain variable domains were expressed as intact kappa light chains by fusing the sequences with a human kappa constant domain (SEQ ID: 47). For comparison, parental antibodies were expressed with sequences that encoded N-terminal pyroglutamic acids if present in the parental sequences, and encoding C-terminal lysines.

FIG. 2C shows an alignment of the antibody chain sequence variable domain variants designed for antibodies IgG1-1014-005, IgG1-2F8, and IgG1-1021-511. The sequence variants were named as follows: HA1 indicates a more acidic heavy chain variant with one extra negative charge when compared to the reference sequence HC, while variants HA2 and HA3 contain two and three extra negative charges when compared to the reference sequence HC. Analogously, the more basic charge variants HB1, HB2 and HB3 contain one, two, and three extra positive charges when compared to the reference sequence HC. HP indicates the sequence of the unmutated parental heavy chain variable domain that was expressed as a fusion to a constant domain encoding a C-terminal lysine. The light chain variants were named analogously so that LA1 indicates a more acidic light chain variant with one extra negative charge when compared to the reference sequence LC and so forth.

Antibody chain DNA sequence variants were produced by gene synthesis as described in Example 1. Antibodies were generated by co-transfection of a vector encoding a heavy chain variant and a vector encoding a light chain variant as described in Example 3, and were named as follows: IgG1-1014-005-HA1LA1 comprises a heavy chain with variable domain sequence 1014-005HA1 (SEQ ID 1: Heavy chain variable domain 1014-005HA1) and a light chain with variable domain 1014-005LA1 (SEQ ID 9: Light chain variable domain 1014-005LA1). Table A summarizes the composition of the antibodies produced by co-transfection of heavy and light chain charge variants.

TABLE A

| Antibody | Heavy chain | HC SEQ ID | Light Chain | LC SEQ ID |
|---|---|---|---|---|
| IgG1-1014-005-HA1LA1 | 1014-005HA1 | SEQ ID 1 | 1014-005LA1 | SEQ ID 9 |
| IgG1-1014-005-HA2LA1 | 1014-005HA2 | SEQ ID 2 | 1014-005LA1 | SEQ ID 9 |
| IgG1-1014-005-HA3LA1 | 1014-005HA3 | SEQ ID 3 | 1014-005LA1 | SEQ ID 9 |
| IgG1-1014-005-HB1LA1 | 1014-005HB1 | SEQ ID 4 | 1014-005LA1 | SEQ ID 9 |
| IgG1-1014-005-HB2LA1 | 1014-005HB2 | SEQ ID 5 | 1014-005LA1 | SEQ ID 9 |
| IgG1-1014-005-HB3LA1 | 1014-005HB3 | SEQ ID 6 | 1014-005LA1 | SEQ ID 9 |
| IgG1-1014-005-HCLA1 | 1014-005HC | SEQ ID 7 | 1014-005LA1 | SEQ ID 9 |
| IgG1-1014-005-LA1 | 1014-005HP | SEQ ID 8 | 1014-005LA1 | SEQ ID 9 |
| IgG1-1014-005-HA1LA2 | 1014-005HA1 | SEQ ID 1 | 1014-005LA2 | SEQ ID 10 |
| IgG1-1014-005-HA2LA2 | 1014-005HA2 | SEQ ID 2 | 1014-005LA2 | SEQ ID 10 |
| IgG1-1014-005-HA3LA2 | 1014-005HA3 | SEQ ID 3 | 1014-005LA2 | SEQ ID 10 |
| IgG1-1014-005-HB1LA2 | 1014-005HB1 | SEQ ID 4 | 1014-005LA2 | SEQ ID 10 |
| IgG1-1014-005-HB2LA2 | 1014-005HB2 | SEQ ID 5 | 1014-005LA2 | SEQ ID 10 |
| IgG1-1014-005-HB3LA2 | 1014-005HB3 | SEQ ID 6 | 1014-005LA2 | SEQ ID 10 |
| IgG1-1014-005-HCLA2 | 1014-005HC | SEQ ID 7 | 1014-005LA2 | SEQ ID 10 |
| IgG1-1014-005-LA2 | 1014-005HP | SEQ ID 8 | 1014-005LA2 | SEQ ID 10 |
| IgG1-1014-005-HA1LA3 | 1014-005HA1 | SEQ ID 1 | 1014-005LA3 | SEQ ID 11 |
| IgG1-1014-005-HA2LA3 | 1014-005HA2 | SEQ ID 2 | 1014-005LA3 | SEQ ID 11 |
| IgG1-1014-005-HA3LA3 | 1014-005HA3 | SEQ ID 3 | 1014-005LA3 | SEQ ID 11 |
| IgG1-1014-005-HB1LA3 | 1014-005HB1 | SEQ ID 4 | 1014-005LA3 | SEQ ID 11 |
| IgG1-1014-005-HB2LA3 | 1014-005HB2 | SEQ ID 5 | 1014-005LA3 | SEQ ID 11 |
| IgG1-1014-005-HB3LA3 | 1014-005HB3 | SEQ ID 6 | 1014-005LA3 | SEQ ID 11 |
| IgG1-1014-005-HCLA3 | 1014-005HC | SEQ ID 7 | 1014-005LA3 | SEQ ID 11 |

TABLE A-continued

| Antibody | Heavy chain | HC SEQ ID | Light Chain | LC SEQ ID |
|---|---|---|---|---|
| IgG1-1014-005-LA3 | 1014-005HP | SEQ ID 8 | 1014-005LA3 | SEQ ID 11 |
| IgG1-1014-005-HA1LB1 | 1014-005HA1 | SEQ ID 1 | 1014-005LB1 | SEQ ID 12 |
| IgG1-1014-005-HA2LB1 | 1014-005HA2 | SEQ ID 2 | 1014-005LB1 | SEQ ID 12 |
| IgG1-1014-005-HA3LB1 | 1014-005HA3 | SEQ ID 3 | 1014-005LB1 | SEQ ID 12 |
| IgG1-1014-005-HB1LB1 | 1014-005HB1 | SEQ ID 4 | 1014-005LB1 | SEQ ID 12 |
| IgG1-1014-005-HB2LB1 | 1014-005HB2 | SEQ ID 5 | 1014-005LB1 | SEQ ID 12 |
| IgG1-1014-005-HB3LB1 | 1014-005HB3 | SEQ ID 6 | 1014-005LB1 | SEQ ID 12 |
| IgG1-1014-005-HCLB1 | 1014-005HC | SEQ ID 7 | 1014-005LB1 | SEQ ID 12 |
| IgG1-1014-005-LB1 | 1014-005HP | SEQ ID 8 | 1014-005LB1 | SEQ ID 12 |
| IgG1-1014-005-HA1LB2 | 1014-005HA1 | SEQ ID 1 | 1014-005LB2 | SEQ ID 13 |
| IgG1-1014-005-HA2LB2 | 1014-005HA2 | SEQ ID 2 | 1014-005LB2 | SEQ ID 13 |
| IgG1-1014-005-HA3LB2 | 1014-005HA3 | SEQ ID 3 | 1014-005LB2 | SEQ ID 13 |
| IgG1-1014-005-HB1LB2 | 1014-005HB1 | SEQ ID 4 | 1014-005LB2 | SEQ ID 13 |
| IgG1-1014-005-HB2LB2 | 1014-005HB2 | SEQ ID 5 | 1014-005LB2 | SEQ ID 13 |
| IgG1-1014-005-HB3LB2 | 1014-005HB3 | SEQ ID 6 | 1014-005LB2 | SEQ ID 13 |
| IgG1-1014-005-HCLB2 | 1014-005HC | SEQ ID 7 | 1014-005LB2 | SEQ ID 13 |
| IgG1-1014-005-LB2 | 1014-005HP | SEQ ID 8 | 1014-005LB2 | SEQ ID 13 |
| IgG1-1014-005-HA1LB3 | 1014-005HA1 | SEQ ID 1 | 1014-005LB3 | SEQ ID 14 |
| IgG1-1014-005-HA2LB3 | 1014-005HA2 | SEQ ID 2 | 1014-005LB3 | SEQ ID 14 |
| IgG1-1014-005-HA3LB3 | 1014-005HA3 | SEQ ID 3 | 1014-005LB3 | SEQ ID 14 |
| IgG1-1014-005-HB1LB3 | 1014-005HB1 | SEQ ID 4 | 1014-005LB3 | SEQ ID 14 |
| IgG1-1014-005-HB2LB3 | 1014-005HB2 | SEQ ID 5 | 1014-005LB3 | SEQ ID 14 |
| IgG1-1014-005-HB3LB3 | 1014-005HB3 | SEQ ID 6 | 1014-005LB3 | SEQ ID 14 |
| IgG1-1014-005-HCLB3 | 1014-005HC | SEQ ID 7 | 1014-005LB3 | SEQ ID 14 |
| IgG1-1014-005-LB3 | 1014-005HP | SEQ ID 8 | 1014-005LB3 | SEQ ID 14 |
| IgG1-1014-005-HA1LC | 1014-005HA1 | SEQ ID 1 | 1014-005LC | SEQ ID 15 |
| IgG1-1014-005-HA2LC | 1014-005HA2 | SEQ ID 2 | 1014-005LC | SEQ ID 15 |
| IgG1-1014-005-HA3LC | 1014-005HA3 | SEQ ID 3 | 1014-005LC | SEQ ID 15 |
| IgG1-1014-005-HB1LC | 1014-005HB1 | SEQ ID 4 | 1014-005LC | SEQ ID 15 |
| IgG1-1014-005-HB2LC | 1014-005HB2 | SEQ ID 5 | 1014-005LC | SEQ ID 15 |
| IgG1-1014-005-HB3LC | 1014-005HB3 | SEQ ID 6 | 1014-005LC | SEQ ID 15 |
| IgG1-1014-005-HCLC | 1014-005HC | SEQ ID 7 | 1014-005LC | SEQ ID 15 |
| IgG1-1014-005-LC | 1014-005HP | SEQ ID 8 | 1014-005LC | SEQ ID 15 |
| IgG1-1021-511-HA1LA1 | 1021-511HA1 | SEQ ID 16 | 1021-511LA1 | SEQ ID 24 |
| IgG1-1021-511-HA2LA1 | 1021-511HA2 | SEQ ID 17 | 1021-511LA1 | SEQ ID 24 |
| IgG1-1021-511-HA3LA1 | 1021-511HA3 | SEQ ID 18 | 1021-511LA1 | SEQ ID 24 |
| IgG1-1021-511-HB1LA1 | 1021-511HB1 | SEQ ID 19 | 1021-511LA1 | SEQ ID 24 |
| IgG1-1021-511-HB2LA1 | 1021-511HB2 | SEQ ID 20 | 1021-511LA1 | SEQ ID 24 |
| IgG1-1021-511-HB3LA1 | 1021-511HB3 | SEQ ID 21 | 1021-511LA1 | SEQ ID 24 |
| IgG1-1021-511-HCLA1 | 1021-511HC | SEQ ID 22 | 1021-511LA1 | SEQ ID 24 |
| IgG1-1021-511-LA1 | 1021-511HP | SEQ ID 23 | 1021-511LA1 | SEQ ID 24 |
| IgG1-1021-511-HA1LA2 | 1021-511HA1 | SEQ ID 16 | 1021-511LA2 | SEQ ID 25 |
| IgG1-1021-511-HA2LA2 | 1021-511HA2 | SEQ ID 17 | 1021-511LA2 | SEQ ID 25 |
| IgG1-1021-511-HA3LA2 | 1021-511HA3 | SEQ ID 18 | 1021-511LA2 | SEQ ID 25 |
| IgG1-1021-511-HB1LA2 | 1021-511HB1 | SEQ ID 19 | 1021-511LA2 | SEQ ID 25 |
| IgG1-1021-511-HB2LA2 | 1021-511HB2 | SEQ ID 20 | 1021-511LA2 | SEQ ID 25 |
| IgG1-1021-511-HB3LA2 | 1021-511HB3 | SEQ ID 21 | 1021-511LA2 | SEQ ID 25 |
| IgG1-1021-511-HCLA2 | 1021-511HC | SEQ ID 22 | 1021-511LA2 | SEQ ID 25 |
| IgG1-1021-511-LA2 | 1021-511HP | SEQ ID 23 | 1021-511LA2 | SEQ ID 25 |
| IgG1-1021-511-HA1LA3 | 1021-511HA1 | SEQ ID 16 | 1021-511LA3 | SEQ ID 26 |
| IgG1-1021-511-HA2LA3 | 1021-511HA2 | SEQ ID 17 | 1021-511LA3 | SEQ ID 26 |
| IgG1-1021-511-HA3LA3 | 1021-511HA3 | SEQ ID 18 | 1021-511LA3 | SEQ ID 26 |
| IgG1-1021-511-HB1LA3 | 1021-511HB1 | SEQ ID 19 | 1021-511LA3 | SEQ ID 26 |
| IgG1-1021-511-HB2LA3 | 1021-511HB2 | SEQ ID 20 | 1021-511LA3 | SEQ ID 26 |
| IgG1-1021-511-HB3LA3 | 1021-511HB3 | SEQ ID 21 | 1021-511LA3 | SEQ ID 26 |
| IgG1-1021-511-HCLA3 | 1021-511HC | SEQ ID 22 | 1021-511LA3 | SEQ ID 26 |
| IgG1-1021-511-LA3 | 1021-511HP | SEQ ID 23 | 1021-511LA3 | SEQ ID 26 |
| IgG1-1021-511-HA1LB1 | 1021-511HA1 | SEQ ID 16 | 1021-511LB1 | SEQ ID 27 |
| IgG1-1021-511-HA2LB1 | 1021-511HA2 | SEQ ID 17 | 1021-511LB1 | SEQ ID 27 |
| IgG1-1021-511-HA3LB1 | 1021-511HA3 | SEQ ID 18 | 1021-511LB1 | SEQ ID 27 |
| IgG1-1021-511-HB1LB1 | 1021-511HB1 | SEQ ID 19 | 1021-511LB1 | SEQ ID 27 |
| IgG1-1021-511-HB2LB1 | 1021-511HB2 | SEQ ID 20 | 1021-511LB1 | SEQ ID 27 |
| IgG1-1021-511-HB3LB1 | 1021-511HB3 | SEQ ID 21 | 1021-511LB1 | SEQ ID 27 |
| IgG1-1021-511-HCLB1 | 1021-511HC | SEQ ID 22 | 1021-511LB1 | SEQ ID 27 |
| IgG1-1021-511-LB1 | 1021-511HP | SEQ ID 23 | 1021-511LB1 | SEQ ID 27 |
| IgG1-1021-511-HA1LB2 | 1021-511HA1 | SEQ ID 16 | 1021-511LB2 | SEQ ID 28 |
| IgG1-1021-511-HA2LB2 | 1021-511HA2 | SEQ ID 17 | 1021-511LB2 | SEQ ID 28 |
| IgG1-1021-511-HA3LB2 | 1021-511HA3 | SEQ ID 18 | 1021-511LB2 | SEQ ID 28 |
| IgG1-1021-511-HB1LB2 | 1021-511HB1 | SEQ ID 19 | 1021-511LB2 | SEQ ID 28 |
| IgG1-1021-511-HB2LB2 | 1021-511HB2 | SEQ ID 20 | 1021-511LB2 | SEQ ID 28 |
| IgG1-1021-511-HB3LB2 | 1021-511HB3 | SEQ ID 21 | 1021-511LB2 | SEQ ID 28 |
| IgG1-1021-511-HCLB2 | 1021-511HC | SEQ ID 22 | 1021-511LB2 | SEQ ID 28 |
| IgG1-1021-511-LB2 | 1021-511HP | SEQ ID 23 | 1021-511LB2 | SEQ ID 28 |
| IgG1-1021-511-HA1LB3 | 1021-511HA1 | SEQ ID 16 | 1021-511LB3 | SEQ ID 29 |
| IgG1-1021-511-HA2LB3 | 1021-511HA2 | SEQ ID 17 | 1021-511LB3 | SEQ ID 29 |
| IgG1-1021-511-HA3LB3 | 1021-511HA3 | SEQ ID 18 | 1021-511LB3 | SEQ ID 29 |
| IgG1-1021-511-HB1LB3 | 1021-511HB1 | SEQ ID 19 | 1021-511LB3 | SEQ ID 29 |
| IgG1-1021-511-HB2LB3 | 1021-511HB2 | SEQ ID 20 | 1021-511LB3 | SEQ ID 29 |

TABLE A-continued

| Antibody | Heavy chain | HC SEQ ID | Light Chain | LC SEQ ID |
|---|---|---|---|---|
| IgG1-1021-511-HB3LB3 | 1021-511HB3 | SEQ ID 21 | 1021-511LB3 | SEQ ID 29 |
| IgG1-1021-511-HCLB3 | 1021-511HC | SEQ ID 22 | 1021-511LB3 | SEQ ID 29 |
| IgG1-1021-511-LB3 | 1021-511HP | SEQ ID 23 | 1021-511LB3 | SEQ ID 29 |
| IgG1-1021-511-HA1LC | 1021-511HA1 | SEQ ID 16 | 1021-511LC | SEQ ID 30 |
| IgG1-1021-511-HA2LC | 1021-511HA2 | SEQ ID 17 | 1021-511LC | SEQ ID 30 |
| IgG1-1021-511-HA3LC | 1021-511HA3 | SEQ ID 18 | 1021-511LC | SEQ ID 30 |
| IgG1-1021-511-HB1LC | 1021-511HB1 | SEQ ID 19 | 1021-511LC | SEQ ID 30 |
| IgG1-1021-511-HB2LC | 1021-511HB2 | SEQ ID 20 | 1021-511LC | SEQ ID 30 |
| IgG1-1021-511-HB3LC | 1021-511HB3 | SEQ ID 21 | 1021-511LC | SEQ ID 30 |
| IgG1-1021-511-HCLC | 1021-511HC | SEQ ID 22 | 1021-511LC | SEQ ID 30 |
| IgG1-1021-511-LC | 1021-511HP | SEQ ID 23 | 1021-511LC | SEQ ID 30 |
| IgG1-2F8-HA1LA1 | 2F8HA1 | SEQ ID 31 | 2F8LA1 | SEQ ID 39 |
| IgG1-2F8-HA2LA1 | 2F8HA2 | SEQ ID 32 | 2F8LA1 | SEQ ID 39 |
| IgG1-2F8-HA3LA1 | 2F8HA3 | SEQ ID 33 | 2F8LA1 | SEQ ID 39 |
| IgG1-2F8-HB1LA1 | 2F8HB1 | SEQ ID 34 | 2F8LA1 | SEQ ID 39 |
| IgG1-2F8-HB2LA1 | 2F8HB2 | SEQ ID 35 | 2F8LA1 | SEQ ID 39 |
| IgG1-2F8-HB3LA1 | 2F8HB3 | SEQ ID 36 | 2F8LA1 | SEQ ID 39 |
| IgG1-2F8-HCLA1 | 2F8HC | SEQ ID 37 | 2F8LA1 | SEQ ID 39 |
| IgG1-2F8-LA1 | 2F8HP | SEQ ID 38 | 2F8LA1 | SEQ ID 39 |
| IgG1-2F8-HA1LA2 | 2F8HA1 | SEQ ID 31 | 2F8LA2 | SEQ ID 40 |
| IgG1-2F8-HA2LA2 | 2F8HA2 | SEQ ID 32 | 2F8LA2 | SEQ ID 40 |
| IgG1-2F8-HA3LA2 | 2F8HA3 | SEQ ID 33 | 2F8LA2 | SEQ ID 40 |
| IgG1-2F8-HB1LA2 | 2F8HB1 | SEQ ID 34 | 2F8LA2 | SEQ ID 40 |
| IgG1-2F8-HB2LA2 | 2F8HB2 | SEQ ID 35 | 2F8LA2 | SEQ ID 40 |
| IgG1-2F8-HB3LA2 | 2F8HB3 | SEQ ID 36 | 2F8LA2 | SEQ ID 40 |
| IgG1-2F8-HCLA2 | 2F8HC | SEQ ID 37 | 2F8LA2 | SEQ ID 40 |
| IgG1-2F8-LA2 | 2F8HP | SEQ ID 38 | 2F8LA2 | SEQ ID 40 |
| IgG1-2F8-HA1LA3 | 2F8HA1 | SEQ ID 31 | 2F8LA3 | SEQ ID 41 |
| IgG1-2F8-HA2LA3 | 2F8HA2 | SEQ ID 32 | 2F8LA3 | SEQ ID 41 |
| IgG1-2F8-HA3LA3 | 2F8HA3 | SEQ ID 33 | 2F8LA3 | SEQ ID 41 |
| IgG1-2F8-HB1LA3 | 2F8HB1 | SEQ ID 34 | 2F8LA3 | SEQ ID 41 |
| IgG1-2F8-HB2LA3 | 2F8HB2 | SEQ ID 35 | 2F8LA3 | SEQ ID 41 |
| IgG1-2F8-HB3LA3 | 2F8HB3 | SEQ ID 36 | 2F8LA3 | SEQ ID 41 |
| IgG1-2F8-HCLA3 | 2F8HC | SEQ ID 37 | 2F8LA3 | SEQ ID 41 |
| IgG1-2F8-LA3 | 2F8HP | SEQ ID 38 | 2F8LA3 | SEQ ID 41 |
| IgG1-2F8-HA1LB1 | 2F8HA1 | SEQ ID 31 | 2F8LB1 | SEQ ID 42 |
| IgG1-2F8-HA2LB1 | 2F8HA2 | SEQ ID 32 | 2F8LB1 | SEQ ID 42 |
| IgG1-2F8-HA3LB1 | 2F8HA3 | SEQ ID 33 | 2F8LB1 | SEQ ID 42 |
| IgG1-2F8-HB1LB1 | 2F8HB1 | SEQ ID 34 | 2F8LB1 | SEQ ID 42 |
| IgG1-2F8-HB2LB1 | 2F8HB2 | SEQ ID 35 | 2F8LB1 | SEQ ID 42 |
| IgG1-2F8-HB3LB1 | 2F8HB3 | SEQ ID 36 | 2F8LB1 | SEQ ID 42 |
| IgG1-2F8-HCLB1 | 2F8HC | SEQ ID 37 | 2F8LB1 | SEQ ID 42 |
| IgG1-2F8-LB1 | 2F8HP | SEQ ID 38 | 2F8LB1 | SEQ ID 42 |
| IgG1-2F8-HA1LB2 | 2F8HA1 | SEQ ID 31 | 2F8LB2 | SEQ ID 43 |
| IgG1-2F8-HA2LB2 | 2F8HA2 | SEQ ID 32 | 2F8LB2 | SEQ ID 43 |
| IgG1-2F8-HA3LB2 | 2F8HA3 | SEQ ID 33 | 2F8LB2 | SEQ ID 43 |
| IgG1-2F8-HB1LB2 | 2F8HB1 | SEQ ID 34 | 2F8LB2 | SEQ ID 43 |
| IgG1-2F8-HB2LB2 | 2F8HB2 | SEQ ID 35 | 2F8LB2 | SEQ ID 43 |
| IgG1-2F8-HB3LB2 | 2F8HB3 | SEQ ID 36 | 2F8LB2 | SEQ ID 43 |
| IgG1-2F8-HCLB2 | 2F8HC | SEQ ID 37 | 2F8LB2 | SEQ ID 43 |
| IgG1-2F8-LB2 | 2F8HP | SEQ ID 38 | 2F8LB2 | SEQ ID 43 |
| IgG1-2F8-HA1LB3 | 2F8HA1 | SEQ ID 31 | 2F8LB3 | SEQ ID 44 |
| IgG1-2F8-HA2LB3 | 2F8HA2 | SEQ ID 32 | 2F8LB3 | SEQ ID 44 |
| IgG1-2F8-HA3LB3 | 2F8HA3 | SEQ ID 33 | 2F8LB3 | SEQ ID 44 |
| IgG1-2F8-HB1LB3 | 2F8HB1 | SEQ ID 34 | 2F8LB3 | SEQ ID 44 |
| IgG1-2F8-HB2LB3 | 2F8HB2 | SEQ ID 35 | 2F8LB3 | SEQ ID 44 |
| IgG1-2F8-HB3LB3 | 2F8HB3 | SEQ ID 36 | 2F8LB3 | SEQ ID 44 |
| IgG1-2F8-HCLB3 | 2F8HC | SEQ ID 37 | 2F8LB3 | SEQ ID 44 |
| IgG1-2F8-LB3 | 2F8HP | SEQ ID 38 | 2F8LB3 | SEQ ID 44 |
| IgG1-2F8-HA1LC | 2F8HA1 | SEQ ID 31 | 2F8LC | SEQ ID 45 |
| IgG1-2F8-HA2LC | 2F8HA2 | SEQ ID 32 | 2F8LC | SEQ ID 45 |
| IgG1-2F8-HA3LC | 2F8HA3 | SEQ ID 33 | 2F8LC | SEQ ID 45 |
| IgG1-2F8-HB1LC | 2F8HB1 | SEQ ID 34 | 2F8LC | SEQ ID 45 |
| IgG1-2F8-HB2LC | 2F8HB2 | SEQ ID 35 | 2F8LC | SEQ ID 45 |
| IgG1-2F8-HB3LC | 2F8HB3 | SEQ ID 36 | 2F8LC | SEQ ID 45 |
| IgG1-2F8-HCLC | 2F8HC | SEQ ID 37 | 2F8LC | SEQ ID 45 |
| IgG1-2F8-LC | 2F8HP | SEQ ID 38 | 2F8LC | SEQ ID 45 |

Example 3: Antibody Production

Antibodies were produced, under serum-free conditions, by co-transfecting relevant heavy and light chain expression vectors in FreeStyle™ 293-F cells (LifeTechnologies), using 293fectin™ (LifeTechnologies), according to the manufacturer's instructions. Alternatively, antibodies were produced, under serum-free conditions, by co-transfecting relevant heavy and light chain expression vectors in Expi293F™ cells (LifeTechnologies), using ExpiFectamine™ 293 (LifeTechnologies), according to the manufacturer's instructions. Culture supernatants were filtered over 0.2 μm dead-end filters before analysis and purification.

Alternatively, DNA sequences encoding full length heavy chain and light chain open reading frames (ORF) of IgG1-7D8, IgG1-224, IgG1-CD37-37-3, IgG1-CD19-21D4-E345K and IgG1-CD52-Campath-E345K were prepared in Example 1. The sequences were subcloned from pcDNA 3.3 expression vectors into the in-house developed expression vector pGENpr6DGV, expressing both ORF's from the same vector. The expression vector contained both antibody open reading frames regulated by an upstream CMV promoter and downstream TK poly-A transcription termination signal, and a glutamine synthetase selection marker expressed under the control of an SV40 promoter fragment and a SV40 poly-A transcription termination signal. Vectors were transferred into cells of a CHO-K1 cell line (ECACC cat. nr. 85051005), in house adapted to suspension growth on chemically defined media, at 1 µg/1.0E+06 cells, by nucleofection (Lonza Nucleofector 2b) using Amaxa Solution V kit essentially according to the instructions of the manufacturer. Cells containing expression vectors were grown in 96-well plates in CD-CHO medium (Life Technologies/Thermo Scientific) containing GS EM supplement (Sigma) under MSX selection (Sigma) for 4 weeks, after which a panel of parental cultures displaying growth and IgG expression was expanded to larger volumes. Top producing clones were tested for IgG expression in an ambr15 platform (TAP Biosystems), after which the best producing parentals were selected for inoculation of 500 mL up to 3L bioreactors to supply IgG material. Cell cultures were harvested after 10-12 days and IgG containing supernatants were collected by filtration. Alternatively, IgG1-7D8-K409R was produced as described in Gramer et al., MAbs 2013, 5:962-973.

Example 4: Antibody Quantitation in Cell Culture Samples or Chromatography Fractions Using Bio-Layer Interferometry The IgG concentration of cell culture samples was quantified using Bio-Layer Interferometry using Protein A biosensors with the Octet QK (ForteBio). Samples were diluted 4-fold and 20-fold in Sample Diluent (ForteBio). The initial binding rate of each sample was measured using a read time of 60 seconds and a shaking speed 200 rpm, and the concentration was inferred by reference to a standard curve. 10 mM glycine pH 1.0 was used as a regeneration solution.

Example 5: Purification of Antibodies from Cell Culture Supernatant Using Protein a Chromatography Protein A purifications were used to purify antibodies or antibody mixtures from cellular materials for use in biochemical experiments or subsequent chromatography experiments. Isolated antibodies were bulk purified by protein A affinity chromatography. In short, culture supernatant were loaded on 5 mL MabSelect SuRe columns (GE Healthcare), washed and eluted with 0.02 M sodium citrate-NaOH, pH 3. The eluate was loaded on a HiPrep Desalting column (GE Healthcare) immediately after purification and the antibody was exchanged into 12.6 mM $NaH_2PO_4$, 140 mM NaCl, pH 7.4 buffer (PBS, B.Braun or Thermo Fisher). Alternatively, eluted fractions were pooled and dialyzed into PBS using 10 kDa molecular-weight cutoff Slide-A-Lyzer carriages (ThermoFisher) of the appropriate size. After buffer exchange, samples were sterile filtered over 0.2 µm dead-end filters. Purity was determined by SDS-PAGE/CE-SDS and concentration was measured by absorbance at 280 nm. Purified antibodies were stored at 2-8° C. Alternatively, mixtures of antibodies were bulk purified from cellular material by the same protocol. This was intended to generate pure mixtures of antibodies, but not to control the ratios of the antibodies.

Alternatively, small-scale purifications were performed to purify isolated antibodies for biochemical experiments. The purifications were performed in a 96-well format using PreDictor MabSelect SuRe plates (GE-Healthcare) pre-filled with 50 µL MabSelect SuRe resin, essentially according to the product manual. The plate was mounted on Multi Screen HTS Vacuum manifold connected to pressure vacuum station. The storage solution was removed and the resin washed with PBS (12.6 mM $NaH_2PO_4$, 140 mM NaCl, pH 7.4; B.Braun or Thermo Fisher). The resin was incubated with 0.33 mL cell culture supernatant with orbital agitation for 5 minutes at 900 rpm and supernatant was removed using the vacuum manifold. This was repeated until 2 ml of supernatant was loaded. The resin was washed with PBS. Bound antibodies were eluted using 150 uL of elution buffer (20 mM citric Acid pH 3.0) per well and collected by centrifugation. Each well of eluate was neutralized to approximately pH 6.0 by addition of neutralization buffer (2 M Tris-HCl pH 9.0). The protein concentration of the eluate was determined in each well by measuring absorbance at 280 nm.

Example 6: Preparative Cation Exchange Chromatography of Monoclonal Antibody Mixtures Using a HiScreen Capto S ImpAct Column with an Ionic Strength Gradient Preparative cation exchange chromatography was used to resolve Protein A purified mixtures of antibodies in order to study if the antibody sequences contain differences in their charge properties which enables separation of the monoclonal antibodies by chromatography, and ultimately control their composition. Capto S ImpAct (GE Healthcare) was selected as a high resolution cation exchange column that is applicable for manufacturing applications. The HiScreen column format (GE Healthcare) has a 10 cm a bed height that is suitable for such screening applications as a model for manufacturing scale purifications.

Input mixtures of protein-A purified antibodies were buffer exchanged into Loading buffer (20 mM $NaHPO_4$, pH 6.75 or 20 mM $NaHPO_4$, pH 6.5) to lower the ionic strength such that they bound to the column. This was achieved either by dialysis using 10 kDa molecular-weight cutoff Slide-A-Lyzer carriages (ThermoFisher) of the appropriate size or by 20-fold dilution into the Loading Buffer. The antibody mixtures were loaded onto a 5 mL Capto S ImpAct columns (GE Healthcare) at 2.3 mL/minute and washed using 5 column volumes of Loading Buffer. The antibody mixtures were separated using a linear gradient from Loading Buffer to Elution Buffer. The loading and elution buffers and the elution gradient were selected based upon the properties of the mixtures of antibodies and are stated in Examples 7, 9, 23, 25, 26 for different mixtures of antibodies. The column was washed with sequentially 1 M tris(hydroxymethyl)aminomethane buffer pH 9.0 or 20 mM tris(hydroxymethyl)aminomethane, 1000 mM NaCl pH 8.5 or 20 mM tris(hydroxymethyl)aminomethane, 50 mM NaCl pH 8.0; and 0.2 or 0.5 M NaOH, and re-equilibrated using Loading Buffer.

Figure 6A:
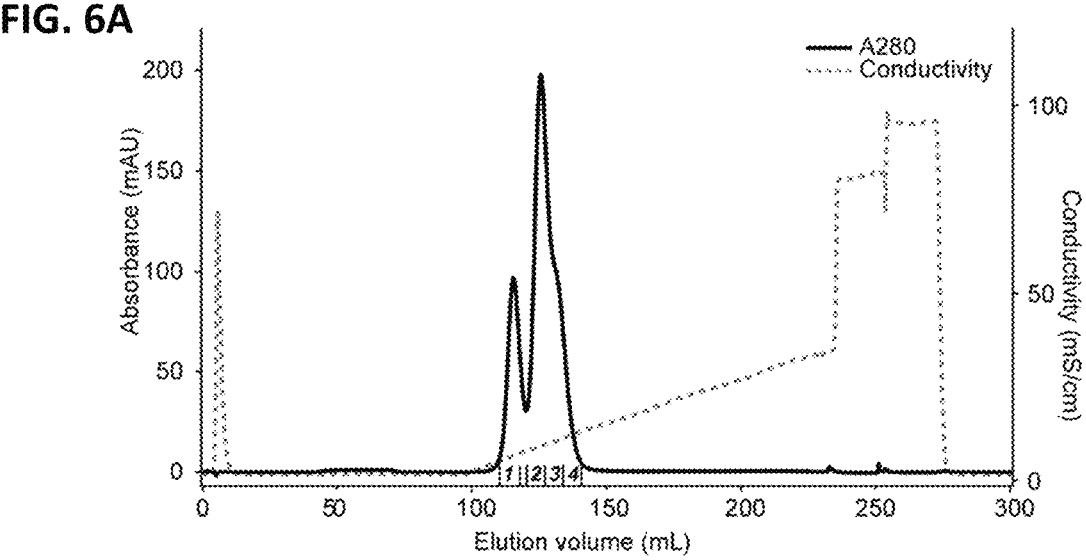
Figure 6B:
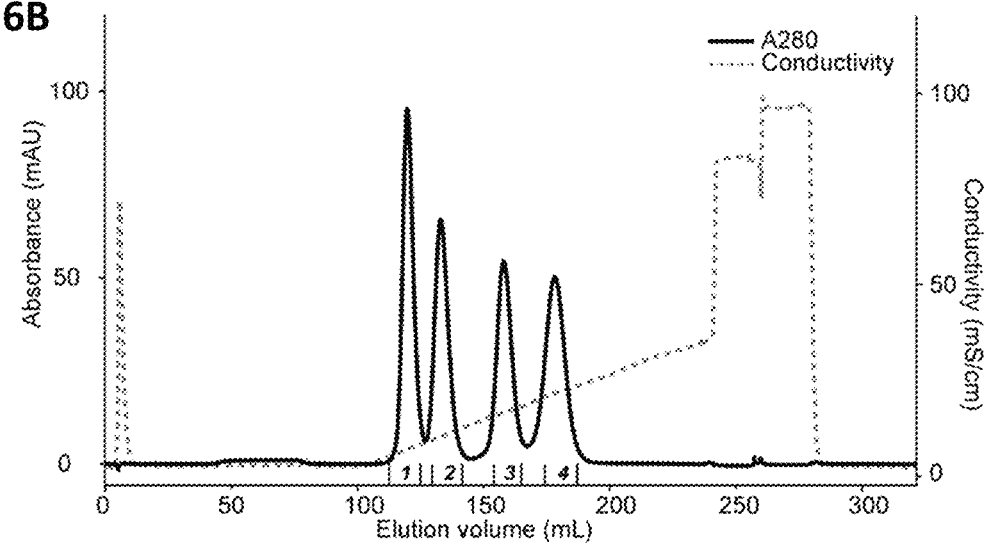
Figure 6C:
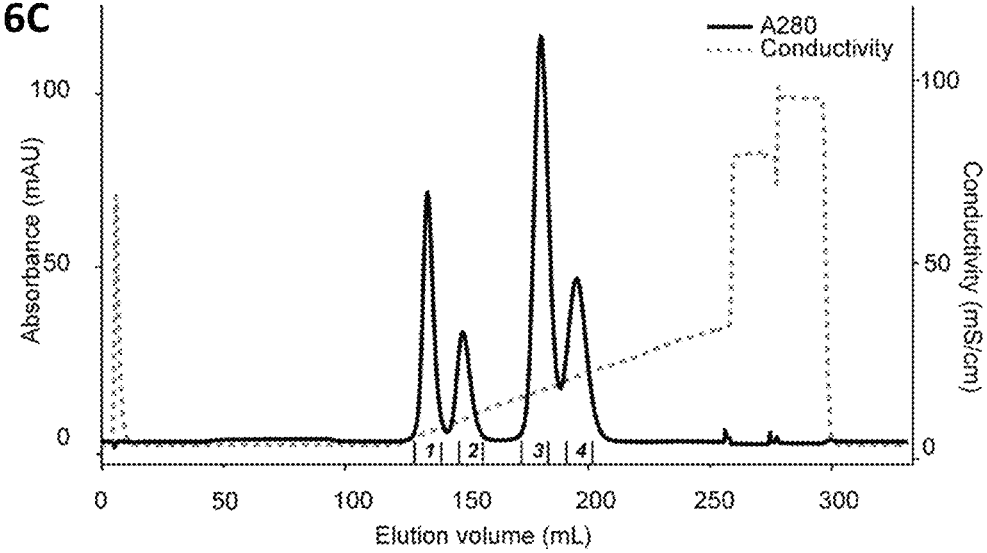
Figure 6D:
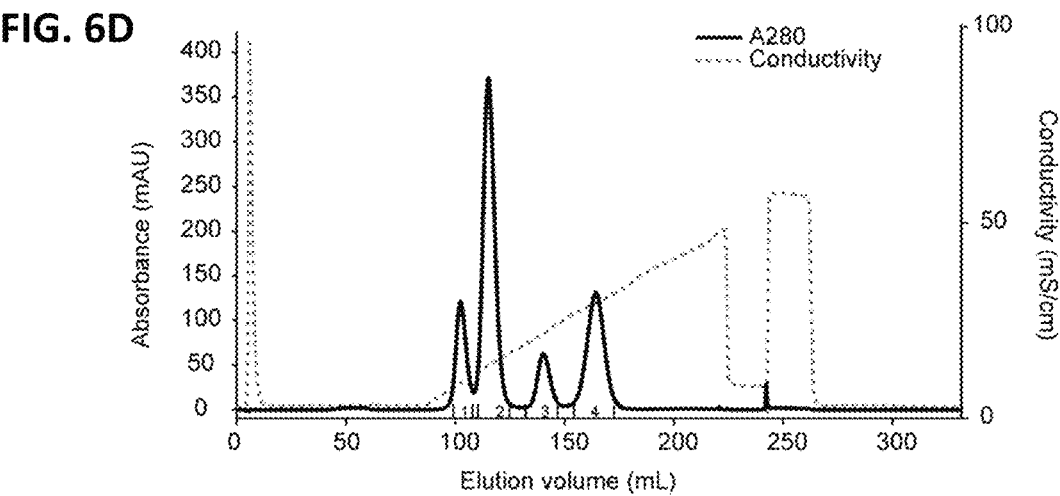
Figure 6E:
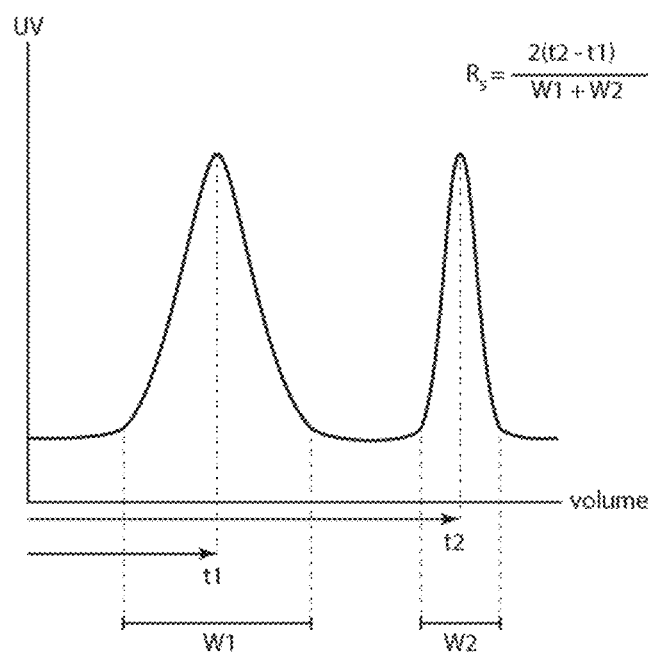

The resolution of adjacent peaks was calculated using the Peak Integrate function of Unicorn software version 6.32 (GE Healthcare). The Peak Window was manually selected and peaks were manually assigned between minima by visual inspection of the profile. The resolution was calculated using resolution algorithm (Ret2-Ret1)/((Width2+Width1)/2), using a vertical drop line. Alternatively, the resolution was calculated with the Peak Integrate function of Unicorn software version 6.32 (GE Healthcare), using a skim function with a skim ratio of 10, as indicated in the respective Examples. For simplicity, the preferred method uses a vertical drop line. FIG. 6E summarizes the principle of the resolution calculation. The amount of protein in each peak was estimated by integrating the chromatogram, correcting for the extinction coefficients of each antibody as calculated based upon the primary amino acid sequence of the antibodies.

Figure 1E:
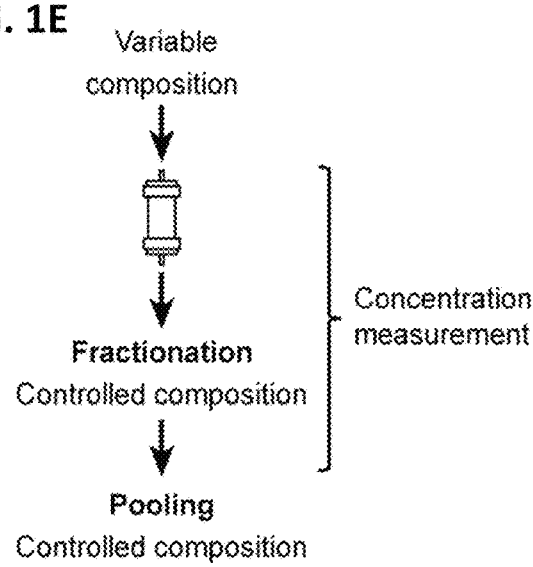

Example 7: Use of Charge Modulated Antibodies, Separation of an Antibody Mixture by Gradient Elution on a Preparative Cation Exchange Column and Recovery to Yield an Antibody Mixture of Pre-Defined Composition This example describes a procedure to take a mixture of variable composition, perform a chromatography step that provides resolution between the individual components of the polyclonal mixture, and fractionate the eluted antibodies such that they can be pooled using a concentration measurement of the fractions to yield a mixture of pre-determined composition (FIG. 1E).

The design of charge modulated variants of human antibodies IgG1-1014-005, IgG1-1021-511, and IgG1-2F8 and the production thereof was described in Example 2. In brief, mutations were introduced at framework amino acid positions at which the natural germline repertoire displays charge variation, to minimize the impact on potential immunogenicity. In specific cases, the peptide context in which a charged amino acid occurs in the germline was transferred, as illustrated for light chain variants with neutral mutations at position 4.

Each of seven light chain vectors was combined with each of seven heavy chain vectors in a pairwise fashion to generate 49 unique combinations for IgG1-1014-005, IgG1-1021-511 and IgG1-2F8. The sequences are summarized in FIG. 2. The antibodies were produced by transfecting the heavy and light chain DNA sequences as described in Example 3, and the antibody titers were determined as described in Example 4. FIG. 3 shows that most of the charge variants were well tolerated with respect to production levels with the exception of heavy chain mutation Q6E in antibody IgG1-1014-005, which had a detrimental effect on the expression of all variants containing this mutation.

Figure 4A:
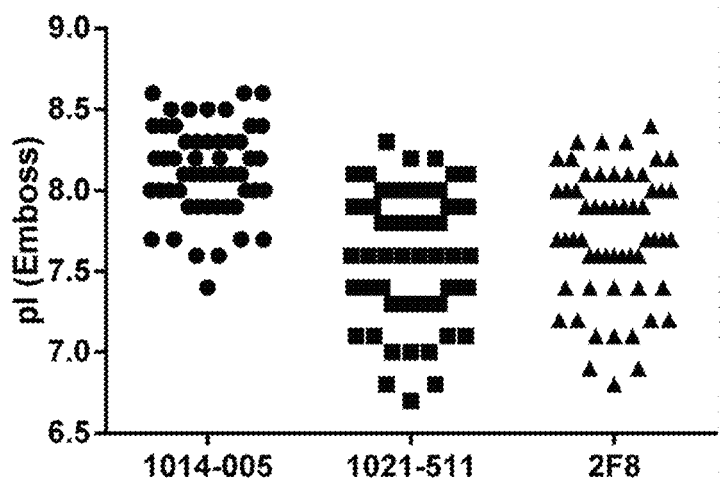
Figure 4B:
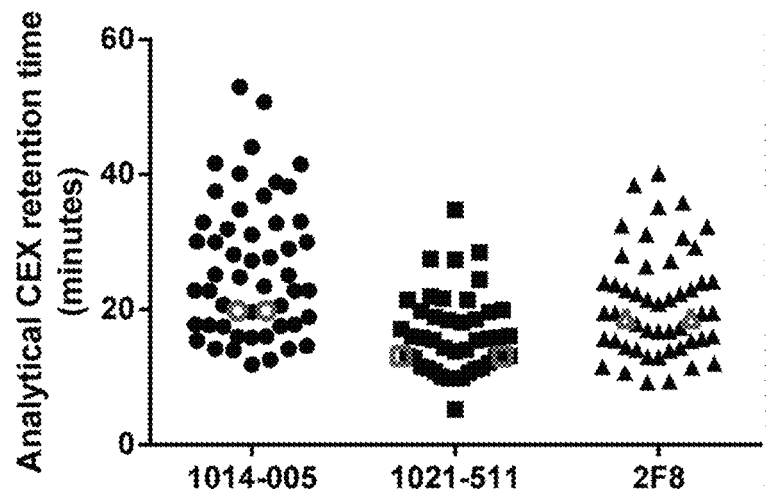
Figure 4C:
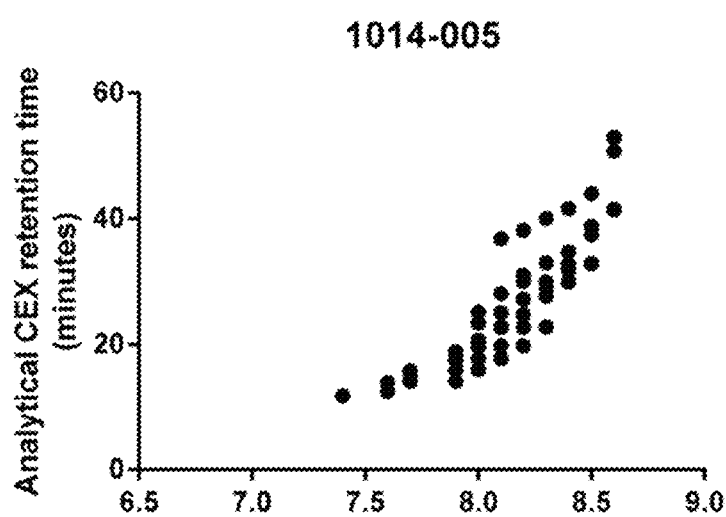
Figure 4D:
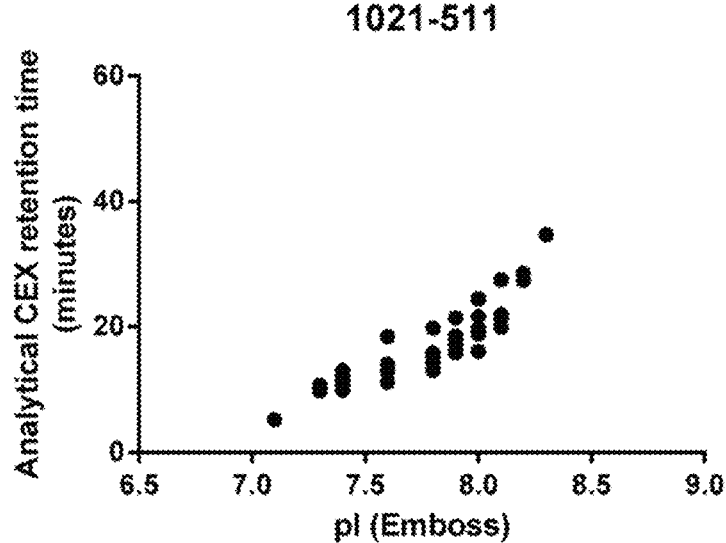
Figure 4E:
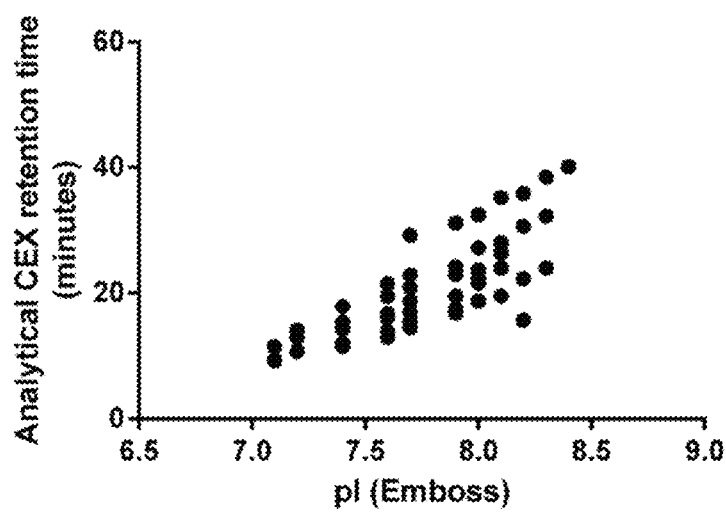

The antibody charge variants were analyzed for their theoretical isoelectric points using the pepstats module of EMBOSS (Jemboss version 1.5; Carver, T and Bleasby A. Bioinformatics. 2003 Sep. 22; 19 (14): 1837-43) using the concatenated sequences of the heavy and light chains. A range of isoelectric points could be sampled by combining the possible heavy and light chain variants (FIG. 4A).

The antibody charge variants were purified as described in Example 5 and analyzed by analytical cation exchange chromatography as described in Example 8, as a model system to describe the diversity of the charge properties of the antibody variants. A broad diversity of retention times were sampled for each of IgG1-1014-005, IgG1-1021-511 and IgG1-2F8 (FIG. 4B-E), showing that the mutations are sufficient to impact the behavior of the antibody variants in a cation exchange chromatography assay.

To imitate an upstream process for producing mixtures of antibodies in a single co-production event, antibody supernatants were separately produced and mixed. In the first instance, antibody supernatants were mixed such that highest and lowest concentration antibodies were within 2-fold of each other in order to assess the separation behavior of the mixtures on a preparative cation exchange resin. The antibody supernatants were separately produced as described in Example 3, the immunoglobulin titers were determined as described in Example 4 and the supernatants were mixed using the antibody titers to yield a mixture of approximately 10 mg immunoglobulin in a total volume of approximately 150 mL. Input mixtures of antibody variants IgG1-1014-005-HCLC, IgG1-2F8-HCLC, IgG1-1021-511-HCLC and IgG1-1014-153 were generated as a control antibody mixture without charge-modulation. Alternatively, the charge variants IgG1-2F8-HB3LC, IgG1-1014-005-HB3LB1 and IgG1-1021-511-HA3LB2 were selected with IgG1-1014-153 for inclusion in the input mixture to improve the separation behavior by cation exchange chromatography. These charge variants contained the following mutants as compared with the HCLC variants. IgG1-2F8-HB3LC: E6Q, A24K, E97G; IgG1-1014-005-HB3LB1: E17A, Q75A, S93R (HC) and E95Q (LC); IgG1-1021-511-HA3LB2: K48Q, Q90E, A96D (HC) and E48K (LC) (FIG. 2), The cell culture supernatant mixtures were purified by protein A affinity chromatography as described in Example 5. The mixtures of antibodies were captured and purified from bulk contaminants (FIG. 5).

The two protein A-purified input antibody mixtures were analyzed for their behavior on a preparative cation exchange chromatography column. The mixtures were buffer exchanged into Loading Buffer (20 mM $NaHPO_4$, pH 6.75) by dialysis and loaded onto 5 mL Capto S ImpAct columns (GE Healthcare) in separate experiments as described in Example 6. The antibodies were eluted using a linear gradient from 0% to 38% (v/v) of Elution Buffer (20 mM $NaHPO_4$, 1M NaCl pH 6.75) across 30 column volumes, collecting the eluate in 2 mL fractions. The antibodies in the charge-modulated antibody mixture were well separated, whereas the antibodies in the non-charge modulated mixture were not well separated (FIG. 6A,B). The resolution of the peaks from the separation of the charge-modulated mixture was calculated as described in Example 6, using a vertical drop line. The non-charge modulated antibodies were not well separated, and only a two peaks can be observed, from the separation of the four antibodies, hence only a single resolution could be calculated (Table 1).

Figure 7A:
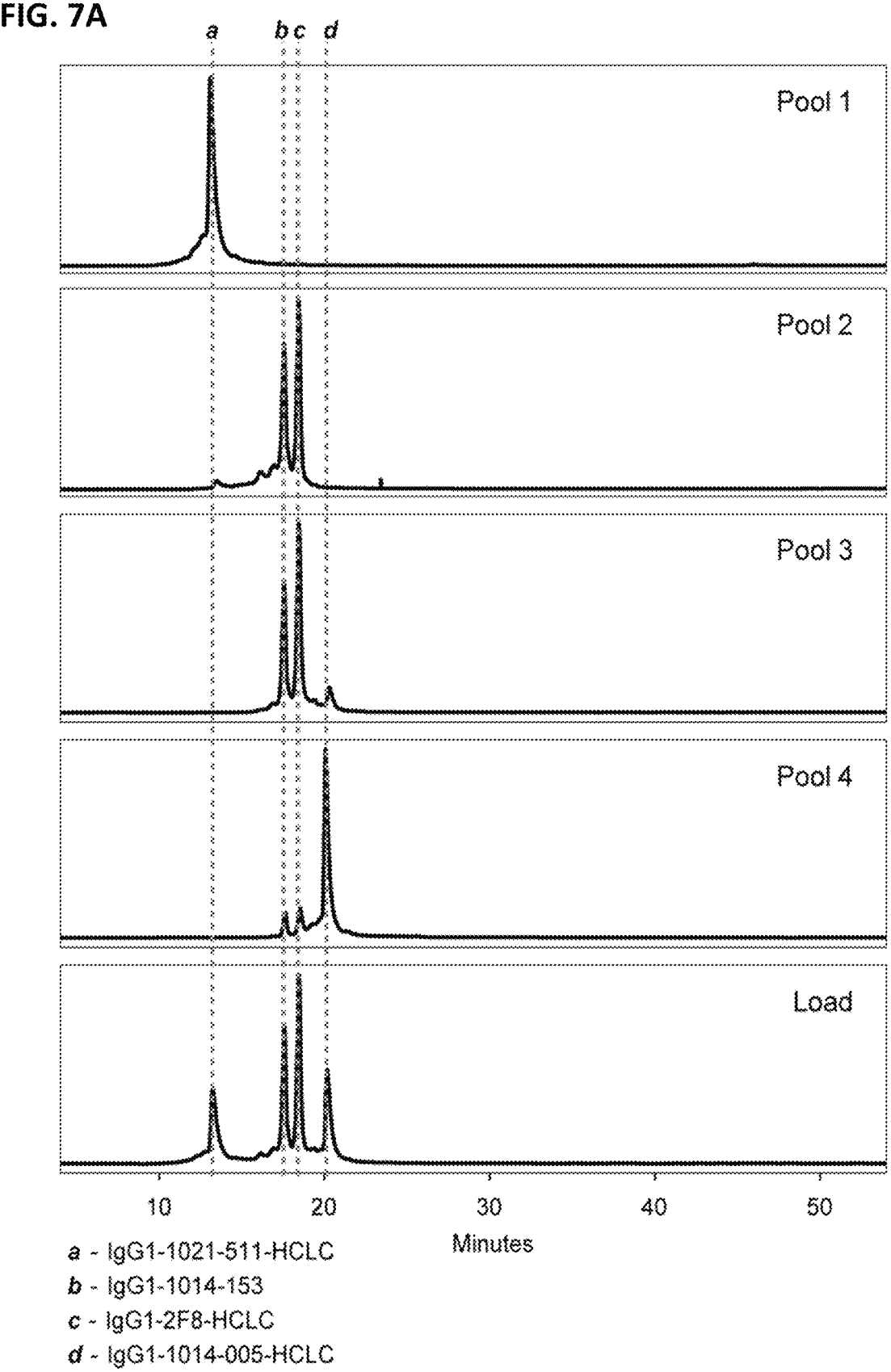
Figure 7B:
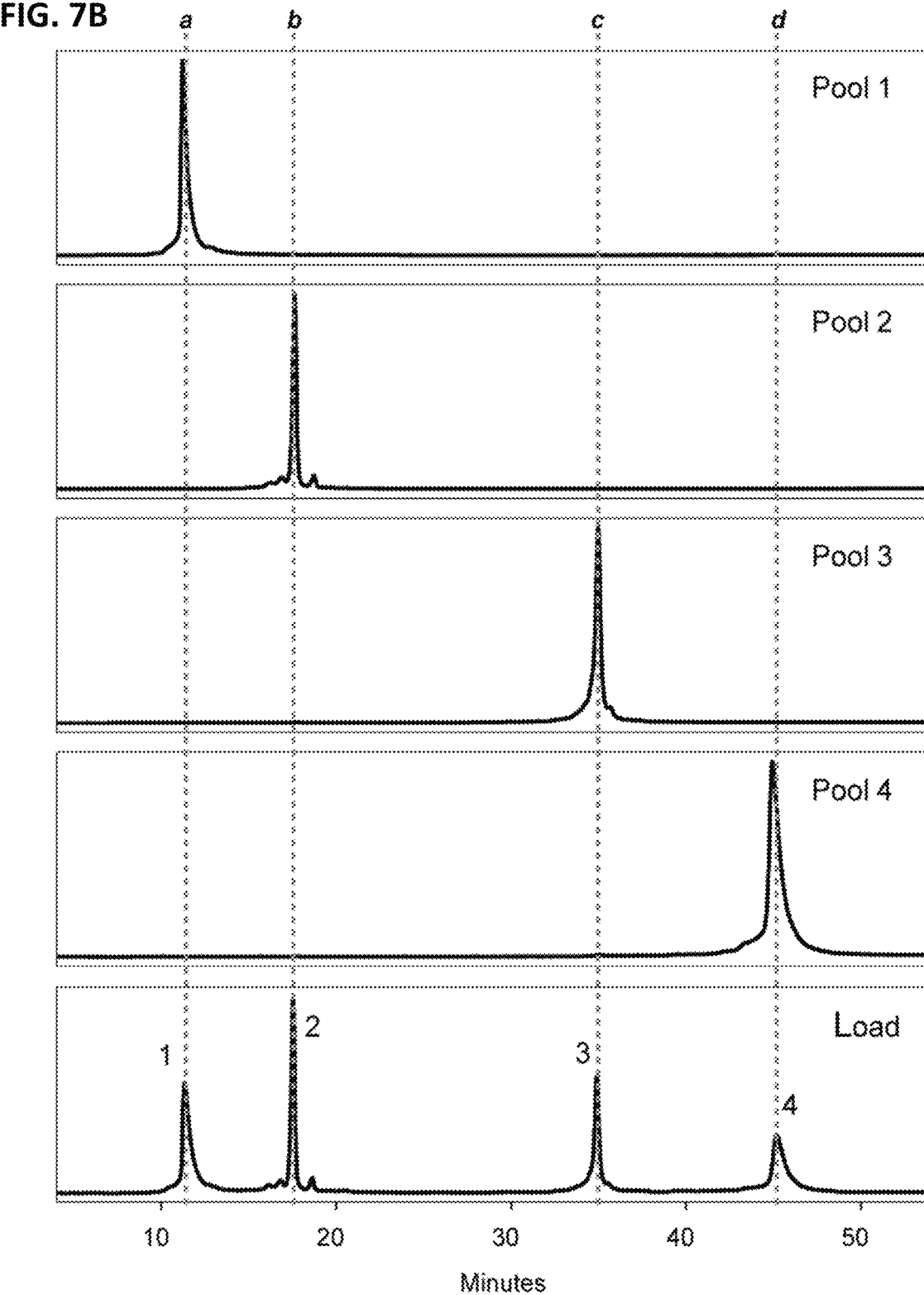
Figure 7C:
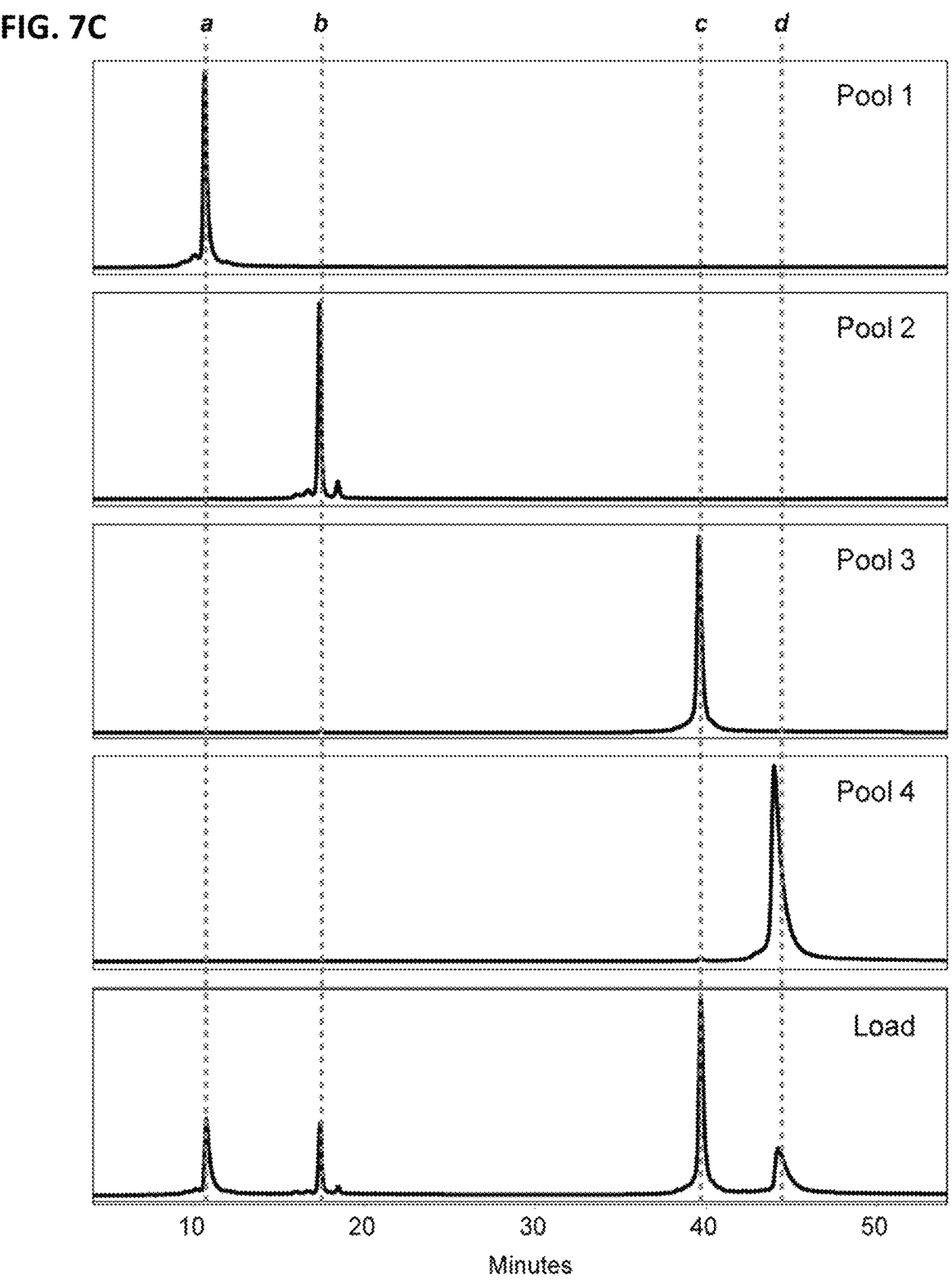
Figure 7D:
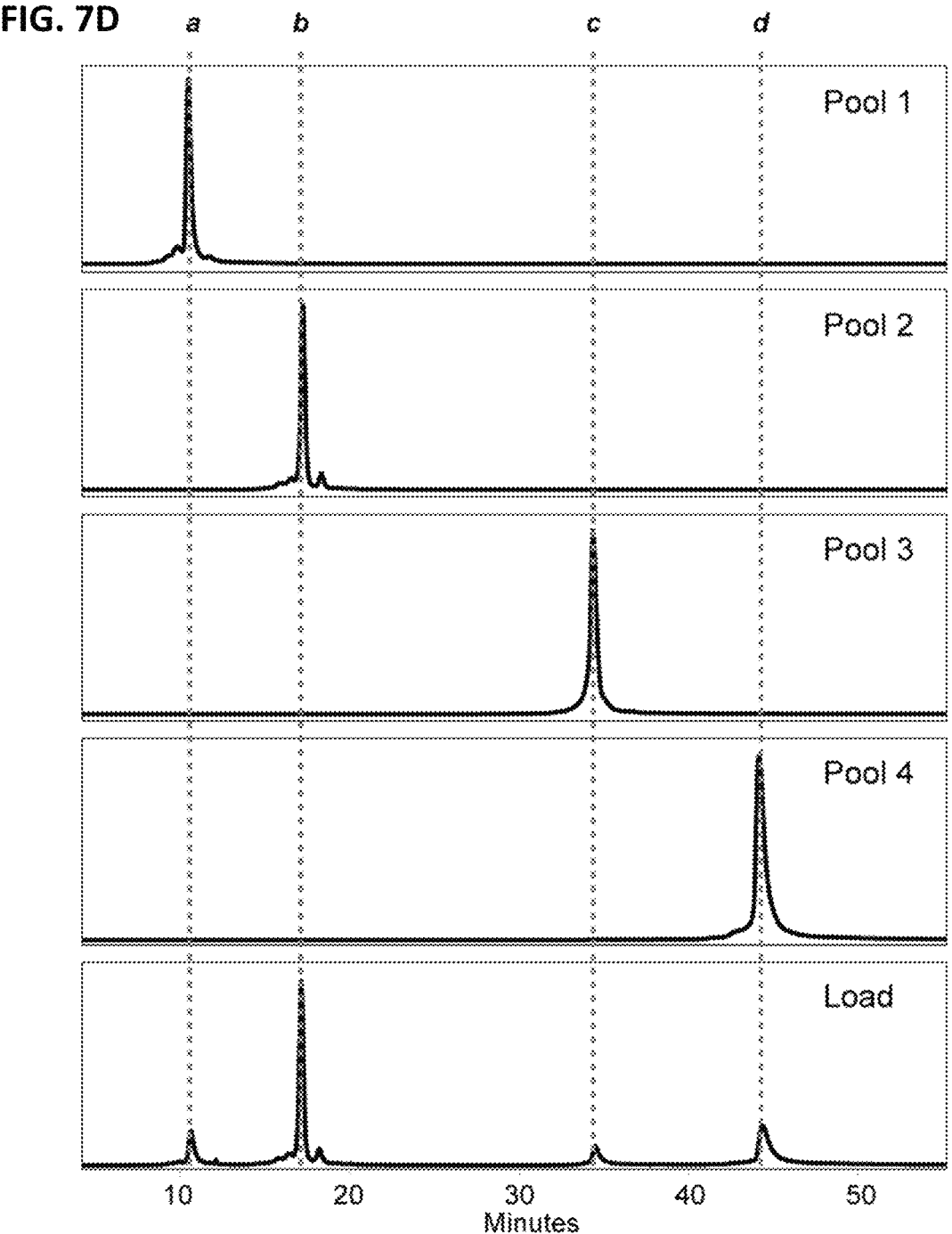

The fractions from the preparative cation exchange experiment, together with the load fraction, were analyzed by analytical cation exchange chromatography to find their identity and relative purity. Fractions were pooled based upon inspection of chromatogram with detection at 280 nm, concentrated using a Sartorius stedim biotech Vivaspin 6, 10000 MWCO PES (product No VS060L). The composition of the pooled fractions was confirmed using analytical cation exchange chromatography, as described in Example 8. The pooled fractions from separation of the charge-modulated antibody mixture were essentially pure, showing that the antibody species were resolved (FIG. 7B). In contrast, fractions from the non-charge modulated variants were not substantially pure, confirming that the species were not well resolved by preparative cation exchange chromatography (FIG. 7A).

The example shows a method for determining the separability an antibody mixture by chromatography: the non-charge modified variants were not separated by chromatography since the peaks could not be resolved and fractions did not contain predominantly (>80%) pure proteins. The example further shows that the amino acid sequence of the antibodies can be modified to obtain separability by chromatography. For example, introducing basic residues or removing acidic residues from IgG1-2F8-HCLC to yield IgG1-2F8-HB3LC via the E6Q, A24K and E97G point mutations (FIG. 2A) causes an increase in the retention time of IgG1-2F8-HB3LC compared with IgG1-2F8-HCLC in the preparative cation exchange experiment (FIG. 6). The combination of amino acid changes allowed the mixture of antibodies to be resolved by preparative cation exchange chromatography (FIG. 6B, Table 1).

An alternative charge-modulated antibody mixture was prepared in order to show that preparative cation exchange chromatography could be used to separate an input mixture of antibodies such that the mixture could be recovered in a predetermined ratio. The antibody supernatants containing recombinantly expressed IgG1-2F8-HB3LB3 (with HC mutants E6Q, A24K, E97G and LC mutants E68Q, E80G and T90K compared with IgG1-2F8-HCLC), IgG1-1014-005-HB3LB1, IgG1-1021-511-HA3LB2 and IgG1-1014-153 were separately produced as described in Example 3, the immunoglobulin titers were determined as described in Example 4 and the supernatants were mixed using the antibody titers to yield a final amount of 21 mg of an input mixture with recombinant antibodies in the ratio 5:3:2:1. Alternatively, the antibody supernatants containing recombinantly expressed IgG1-2F8-HB3LC, IgG1-1014-005-HB3LB1, IgG1-1021-511-HA3LB2 and IgG1-1014-153 were separately produced as described in Example 3, the immunoglobulin titers were determined as described in Example 4 and the supernatants were mixed using the antibody titers to yield a final amount of 24 mg of an input mixture with recombinant antibodies in the ratio 1:3:2:5. These mixtures were intended to mimic co-production processes with release specifications of 1:1:1:1, but where the upstream process was not under sufficient control to provide the desire composition and hence, a chromatography step was required to normalize the ratio. The antibody mixtures were purified by protein A affinity chromatography as described in Example 5. The mixtures of antibodies were captured and purified from bulk contaminants (FIG. 5).

The protein A-purified input antibody mixture was separated on a preparative cation exchange chromatography column. The mixture was buffer exchanged into Loading Buffer (20 mM NaHPO$_4$, pH 6.75) by dialysis and loaded onto a 5 mL Capto S ImpAct column (GE Healthcare) as described in Example 6. The antibodies were eluted using a linear gradient from 0% to 38% (v/v) of Elution Buffer (20 mM NaHPO$_4$, 1M NaCl pH 6.75) across 30 column volumes, collecting the eluate in 2 mL fractions. The chromatograms show four resolved peaks (FIGS. 6C and D). The resolution of the peaks from the separation of the charge-modulated mixture was calculated as described in Example 6, showing the antibodies to be resolved with a resolution >0.3 (Table 1).

The fractions from the preparative cation exchange experiment, together with the load fraction, were analyzed by analytical cation exchange chromatography to find their identity and relative purity. Fractions were pooled based upon inspection of chromatogram with detection at 280 nm, concentrated using a Sartorius stedim biotech Vivaspin 6, 10000 MWCO PES (product No VS060L) and the composition of the fractions was confirmed using analytical cation exchange chromatography, as described in Example 8. The pooled fractions from separation of the charge-modulated antibody mixtures were sufficiently pure to provide full control of relative composition of the components of the mixtures (FIG. 7C-F). The peaks were individually pooled, analyzed for their concentration using a Nanodrop ND-1000 spectrophotometer (Isogen Life Science, Maarssen, The Netherlands) and extinction coefficients calculated from the primary amino acid sequence of the pure antibodies. The fractions were re-mixed using the concentration measurement of the pooled fractions to yield mixtures with approximately equal mass concentrations of the antibodies. The composition of the mixtures was analyzed using analytical cation exchange chromatography, as described in Example 8, to yield an antibody mixture of approximately pre-defined 1:1:1:1 composition (FIG. 7E, F; Table 2). Purity analysis of the intermediate pools would not be required before pooling for an established process where the purity of each pool had been shown to be consistently similar during robustness testing experiments.

TABLE 1

Quantitation of preparative cation exchange chromatograms of antibody mixtures, analyzed for the integrated peak area and resolution relative to the previous peak.

| Antibody mixture | Antibody code | Calculated relative mass (%) | Resolution |
|---|---|---|---|
| IgG1-1021-511-HCLC, | IgG1-1021-511-HCLC | ND | |
| IgG1-1014-153, | IgG1-1014-153 | ND | 0.50 |
| IgG1-2F8-HCLC, | IgG1-2F8-HCLC | ND | ND |
| IgG1-1014-005-HCLC | IgG1-1014-005-HCLC | ND | ND |
| IgG1-1021-511-HA3LB2, | IgG1-1021-511-HA3LB2 | 27.7 | |
| IgG1-1014-153, | IgG1-1014-153 | 24.3 | 0.78 |
| IgG1-2F8-HB3LC, | IgG1-2F8-HB3LC | 22.9 | 1.26 |
| IgG1-1014-005-HB3LB1* | IgG1-1014-005-HB3LB1 | 25.1 | 0.86 |
| IgG1-1021-511-HA3LB2, | IgG1-1021-511-HA3LB2 | 20.2 | |
| IgG1-1014-153, | IgG1-1014-153 | 11.6 | 0.82 |
| IgG1-2F8-HB3LB3, | IgG1-2F8-HB3LB3 | 46.5 | 1.77 |
| IgG1-1014-005-HB3LB1 | IgG1-1014-005-HB3LB1 | 21.7 | 0.74 |
| IgG1-1021-511-HA3LB2, | IgG1-1021-511-HA3LB2 | 14.5 | |
| IgG1-1014-153, | IgG1-1014-153 | 50.8 | 0.64 |
| IgG1-2F8-HB3LC, | IgG1-2F8-HB3LC | 9.6 | 1.20 |
| IgG1-1014-005-HB3LB1** | IgG1-1014-005-HB3LB1 | 25.0 | 0.99 |

ND-not determined.
IgG1-2F8-HB3LC, IgG1-1014-005-HB3LB1, IgG1-1021-511-HA3LB2 and IgG1-1014-153 concentrations in input mixture
*within 2-fold of each other,
**in the ratio 1:3:2:5.

TABLE 2

Quantitation of the analytical cation exchange chromatography profiles of input and normalized antibody mixtures.

| Antibody mixture | Antibody code | Relative Area input mixture (%) | Relative Area End Product (%) |
|---|---|---|---|
| IgG1-1021-511-HA3LB2, | IgG1-1021-511-HA3LB2 | 20.9 | 22.7 |
| IgG1-1014-153, | IgG1-1014-153 | 11.9 | 25.7 |
| IgG1-2F8-HB3LB3, | IgG1-2F8-HB3LB3 | 46.6 | 28.3 |
| IgG1-1014-005-HB3LB1 | IgG1-1014-005-HB3LB1 | 20.5 | 23.4 |
| IgG1-1021-511-HA3LB2, | IgG1-1021-511-HA3LB2 | 13.1 | 23.9 |
| IgG1-1014-153, | IgG1-1014-153 | 54.2 | 26.3 |
| IgG1-2F8-HB3LC, | IgG1-2F8-HB3LC | 8.8 | 26.1 |
| IgG1-1014-005-HB3LB1 | IgG1-1014-005-HB3LB1 | 23.5 | 23.7 |

Example 8: Analysis of Purified Antibodies and Antibody Mixtures Using Analytical Cation Exchange Chromatography High Pressure Liquid Chromatography (HPLC)-analytical cation exchange chromatography (CIEX) was used to compare retention times of different antibodies and charge-modulated antibody mutants and to quantify relative amounts of the antibodies in the antibody input and output mixtures. Stock solutions of sodium phosphate buffer pH 7.0 were prepared from $Na_2HPO_4:2H_2O$ and $NaH_2PO_4$ (anhydrous) in MilliQ water. Antibody samples at 2 mg/mL in mobile Phase A (10 mM phosphate buffer, pH 7.0) were injected onto the HPLC. Alternatively, the products of the small-scale purifications described in Example 5 were directly injected onto the HPLC. The differently charged IgG molecules were separated using a ProPac WCX-10 4 mm×250 mm analytical column with a flow rate of 1 mL/min. 25 µL of sample was injected and elution was performed with a gradient of Mobile Phase A (10 mM phosphate buffer, pH 7.0) to Mobile Phase B (10 mM phosphate buffer, pH 7.0, 0.25 M NaCl) with detection at 280 nm. Empower 3 software (Waters) was used to analyze chromatograms and report the retention time and total peak area of a particular antibody, and this was further corrected with extinction coefficients, calculated from the primary amino acid sequences of the antibodies, to determine the relative abundance of each component in the input and output mixtures and chromatography fractions. Chromatograms of the individual antibodies were used as reference to identify their position in the end-product and to define the integration boundaries of the antibodies.

Example 9: Use of Charge Modulated Antibodies, Separation of an Antibody Mixture by Sequential Step Elutions on a Preparative Cation Exchange Column and Recovery to Yield an Antibody Mixture of Pre-Defined Composition This example describes a procedure to take a mixture of variable composition, perform a chromatography step that provides resolution between the individual components of the polyclonal mixture, and fractionate the eluted antibodies such that they can be pooled using a concentration measurement of the fractions to yield a mixture of pre-determined composition (FIG. 1E).

Mixtures of five recombinantly-produced antibodies with equal mass ratio were generated either as charge-modulated or non-charge-modulated antibodies to assess their separability by preparative cation exchange chromatography. The non-charge modulated mixture comprised IgG1-7D8, IgG1-224, IgG1-CD37-37-3, IgG1-CD19-21D4-K409R and IgG1-CD52-Campath (Example 1). Alternatively, an E345K point mutation into IgG1-CD19-21D4-E345K and IgG1-CD52-Campath-E345K as described in Example 1 to yield a charge-modulated mixture of IgG1-7D8, IgG1-224, IgG1-CD37-37-3, IgG1-CD19-21D4-E345K and IgG1-CD52-Campath-E345K. The antibodies mixtures were prepared by recombinantly expressing the individual antibodies using a transient production or CHO-K1 based expression system as described in Example 3. The individually purified by Protein A affinity chromatography as described in Example 5. The concentrations of the individual antibodies were measured using a Nanodrop ND-1000 spectrophotometer (Isogen Life Science, Maarssen, The Netherlands) and extinction coefficients calculated from the primary amino acid sequence of the pure antibodies. The antibody mixtures were prepared in PBS buffer (12.6 mM $NaH_2PO_4$, 140 mM NaCl, pH 7.4 buffer, B.Braun or Thermo Fisher) by mixing the antibodies in an equal mass ratio using the concentrations.

Figure 8A:
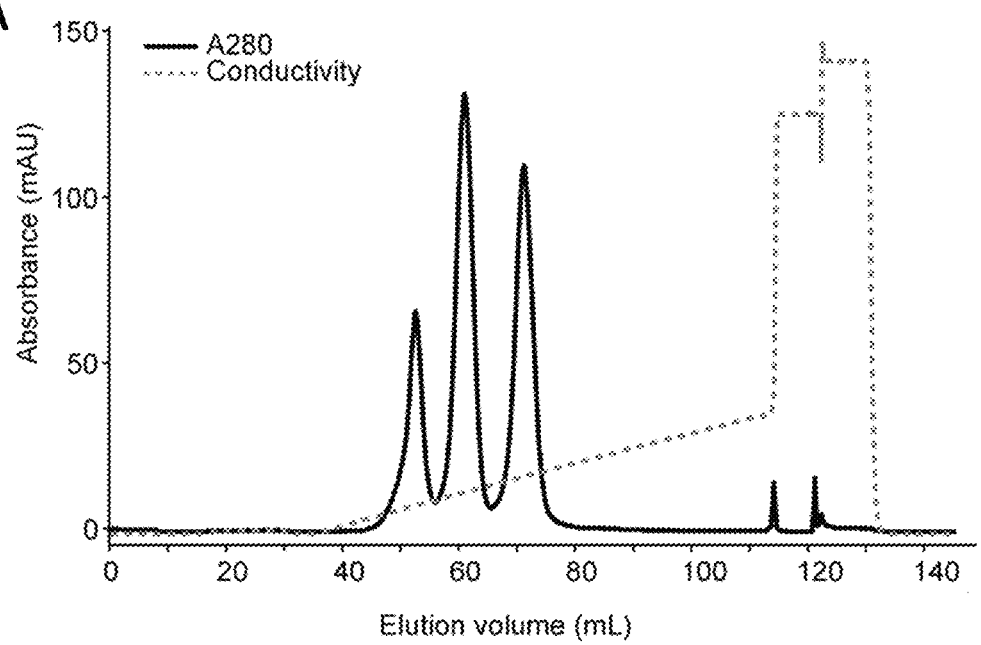
Figure 8B:
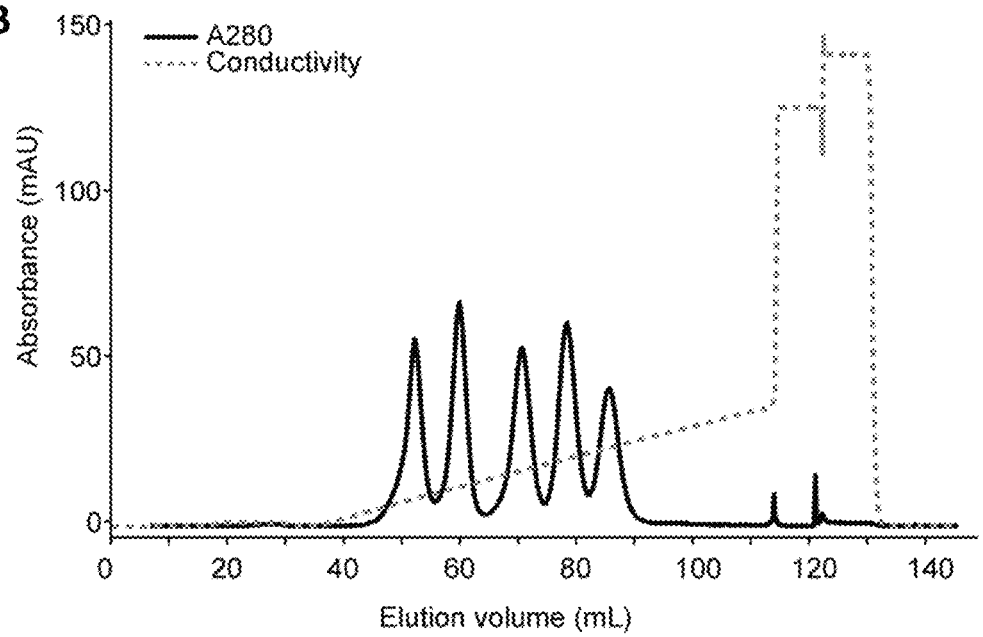
Figure 8C:
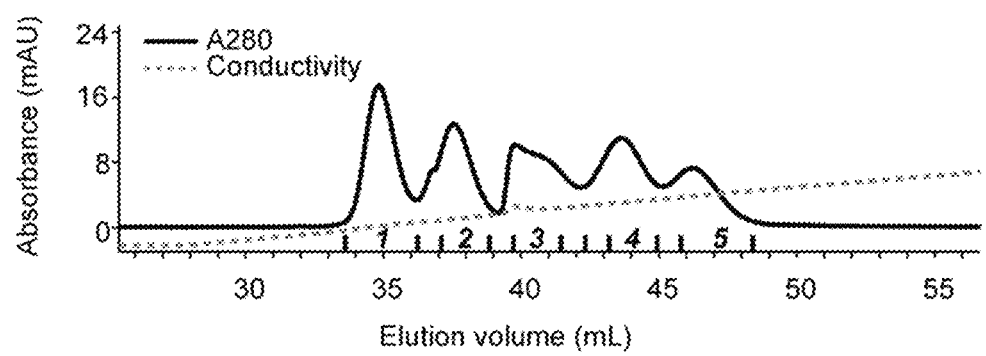
Figure 8D:
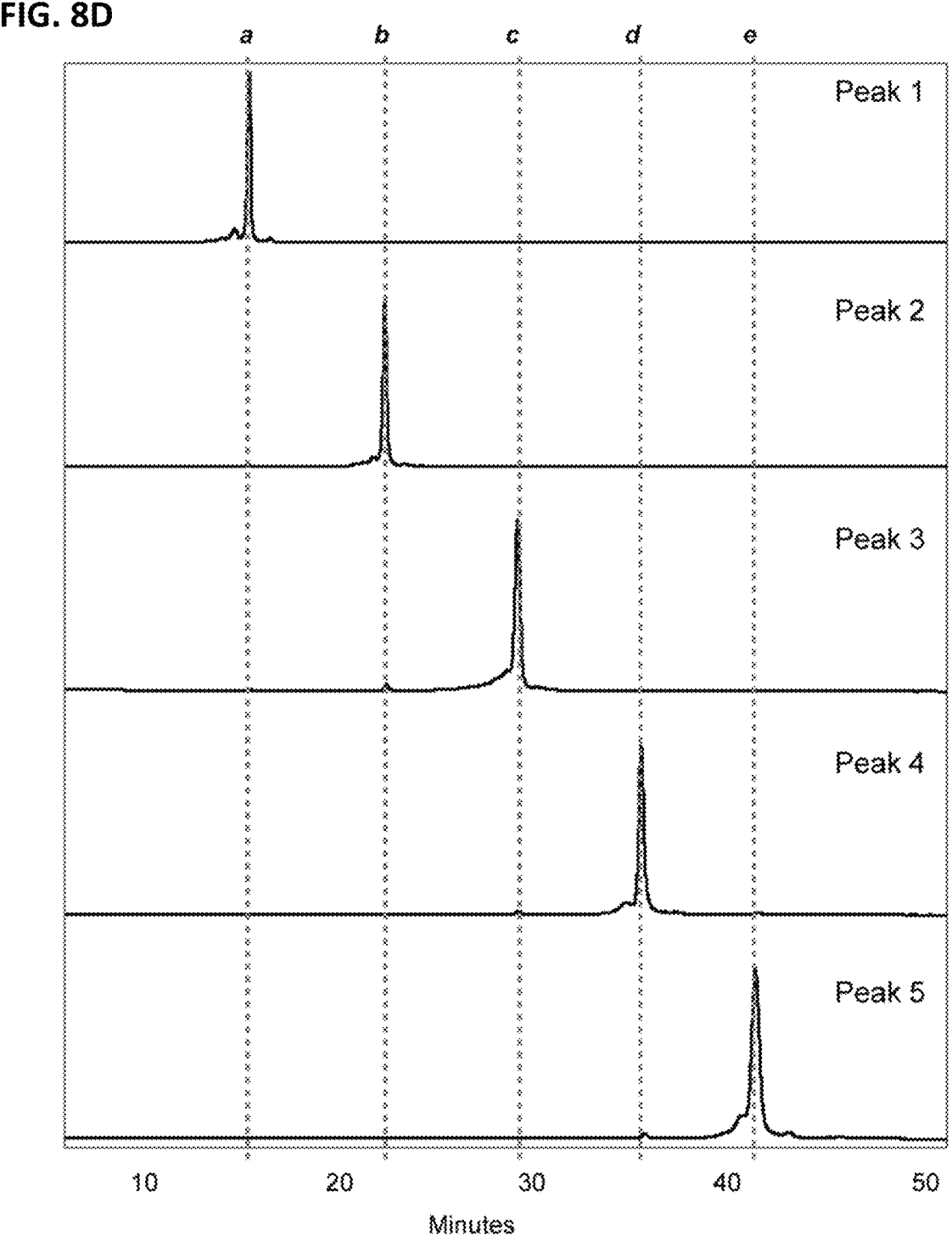

The charge-modulated and non-charge-modulated mixtures were analyzed for their behavior on a preparative cation exchange chromatography column. The mixtures were diluted 20-fold into Loading Buffer (20 mM $NaHPO_4$, pH 6.5) and loaded onto 5 mL Capto S ImpAct columns (GE Healthcare) in separate experiments as described in Example 6. The antibodies were eluted using a linear 40 column volume gradient from 0% to 25% (v/v) Elution Buffer (20 mM $NaHPO_4$, 1000 mM NaCl pH 6.5) using a load of 1 g/L resin. Alternatively, the antibodies were eluted using a linear 40 column volume gradient from 0% to 75% (v/v) Elution Buffer (20 mM $NaHPO_4$, 1000 mM NaCl pH 6.5) using a load of 0.2 g/L resin. FIG. 8A shows that the five non-charge-modulated antibodies were not resolved in the chromatography experiment since the charge properties of the antibodies are not sufficiently different to enable separation. The K409R mutation does not significantly affect the elution behavior of the IgG1-CD19-21D4 antibody since it is not on the surface of the antibody and does result a change in net charge. FIG. 8B shows that the separation of the 5 charge-modulated antibodies gives rise to five distinct peaks. The identity of each of the 5 main peaks was assessed by pooling the peaks and analyzing using analytical cation exchange chromatography with the purified proteins as reference standards, as described in Example 8. Each peak in the preparative chromatogram corresponds to a single antibody (FIGS. 8 C, D) and the peaks assigned in order of increasing retention time are IgG1-7D8, IgG1-224, IgG1-CD37-37-3, IgG1-CD19-21D4-E345K and IgG1-CD52-Campath-E345K, respectively. Comparison of FIGS. 8A and 8B show that the introduction of the E345K point mutation results in antibodies that elute with an increased retention time that allows the chromatography peaks of the antibodies to be resolved. Hence, these data show that the charge-modulated antibody mixture does contain a difference that enables separation of the monoclonal antibodies by chromatography.

Cost-effective manufacturing benefits from a high load of antibodies on the chromatography resin to reduce the volume of resin required to purify a given mass of an antibody mixture. The variation of the chromatographic properties of the charge-modulated antibodies with increasing load was studied to control for peak broadening with increasing antibody load. A mixture of equal masses of IgG1-7D8, IgG1-224, IgG1-CD37-37-3, IgG1-CD19-21D4-E345K and IgG1-CD52-Campath-E345K was prepared. The individual antibodies were recombinantly expressed from CHO-K1 cell as described in Example 3. The individually purified by Protein A affinity chromatography as described in Example 5. The concentrations of the individual antibodies were measured using a Nanodrop ND-1000 spectrophotometer (Isogen Life Science, Maarssen, The Netherlands) and extinction coefficients calculated from the primary amino acid sequence of the pure antibodies. The antibody mixtures were prepared in PBS buffer (12.6 mM $NaH_2PO_4$, 140 mM NaCl, pH 7.4 buffer, B.Braun or Thermo Fisher) by mixing the antibodies in an equal mass ratio using the concentrations. The loading study was performed on a preparative cation exchange chromatography column. The mixture were diluted 20-fold into Loading Buffer (20 mM $NaHPO_4$, pH 6.5) and loaded onto 5 mL Capto S ImpAct columns (GE Healthcare) in separate experiments as described in Example 6. The antibodies were eluted using a linear 40 column volume gradient from 0% to 25% (v/v) Elution Buffer (20 mM $NaHPO_4$, 1000 mM NaCl pH 6.5) using final total loads amounts of 0.2, 0.5, 1.0, 2.0, 5.0, 10, 20, or 50 g/L.

Figure 8E:
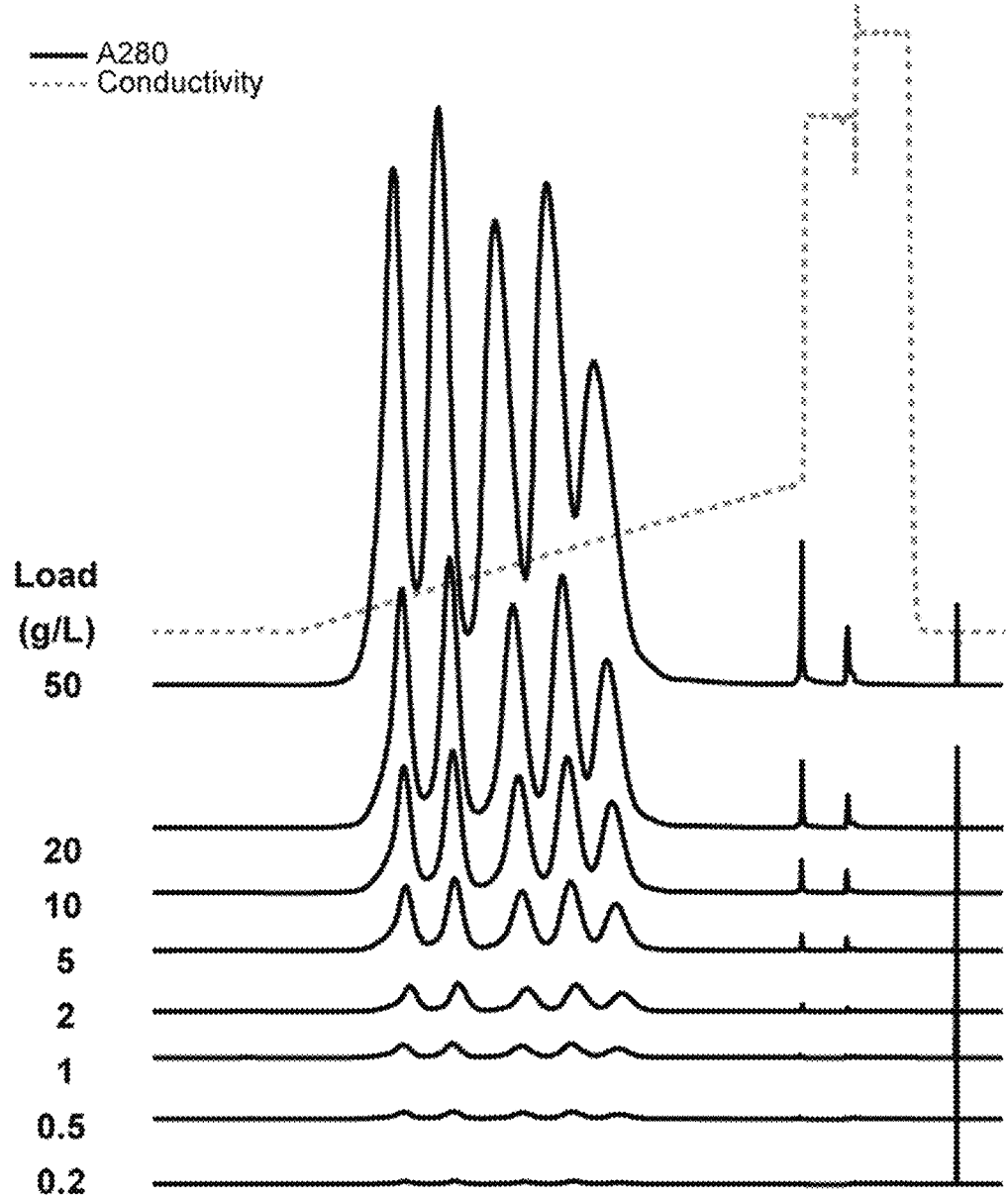

Five distinct peaks were detected for all antibody loads (FIG. 8E). The resolution was quantified as described in Example 6, using a vertical drop line. Some degree of broadening was detected at the highest column loads, but the peaks were resolved (resolution >0.3) in all cases (Table 3), showing that the separation can be performed at a load that is relevant for manufacturing applications.

Antibody mixtures were generated to mimic a process, comprising a co-production processes and a capture purification step, with release specification of 1:1:1:1:1, but where the upstream process was not under sufficient control to provide the desire composition and hence an additional chromatography step was required to normalize the ratio of the antibodies. Three non-normalized mixtures of IgG1-7D8, IgG1-224, IgG1-CD37-37-3, IgG1-CD19-21D4-E345K and IgG1-CD52-Campath-E345K and a 1:1:1:1:1 mixture were prepared. The individual antibodies were recombinantly expressed from CHO-K1 cell as described in Example 3. The individually purified by Protein A affinity chromatography as described in Example 5. The concentrations of the individual antibodies were measured using a Nanodrop ND-1000 spectrophotometer (Isogen Life Science, Maarssen, The Netherlands) and extinction coefficients calculated from the primary amino acid sequence of the pure antibodies. The antibody mixtures were prepared in PBS buffer (12.6 mM $NaH_2PO_4$, 140 mM NaCl, pH 7.4 buffer, B.Braun or Thermo Fisher) by mixing the individually purified antibodies in mass ratios of 1:1:1:1:1 or 0.30:0.50:1.0:0.38:0.38 or 1.0:0.25:0.38:1.0:0.50 or 0.50:1.0:0.40:1.0:0.83.

The gradient-based separation scheme was converted to sequential step elutions, as an alternative that could simplify the manufacturing process. In final chromatography scheme, the mixtures were diluted 20-fold in Loading Buffer (20 mM $NaHPO_4$, pH 6.5). The separation was performed according to Example 6, except that the antibodies were eluted with 5 sequential step elution steps of 8 column volume containing Loading buffer mixed with 19.5%, 29.4%, 38.6%, 44.6% and 61.2% (v/v) Elution Buffer (20 mM $NaHPO_4$, 250 mM NaCl pH 6.5). 30 mL fractions were collected, with the fractionation commencing at the start of each step of the elution.

Figure 9A:
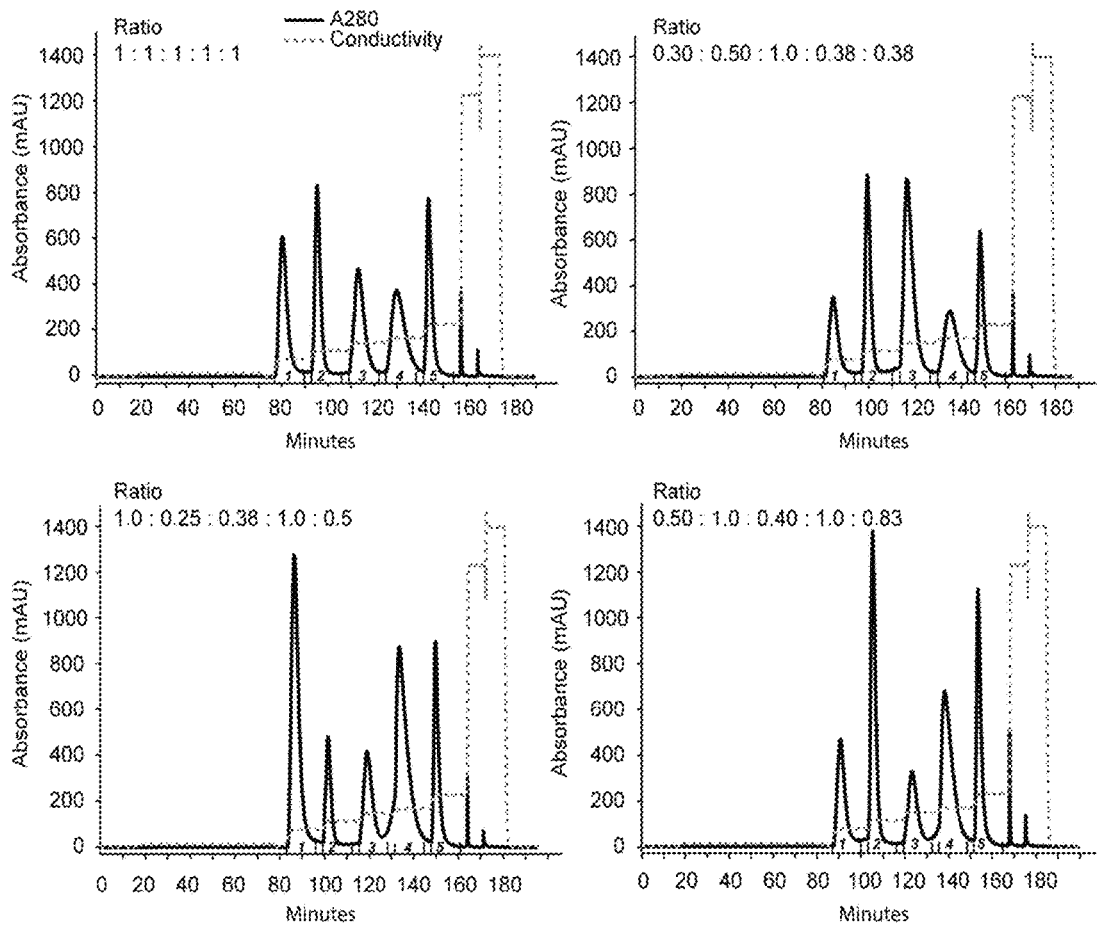
Figure 9B:
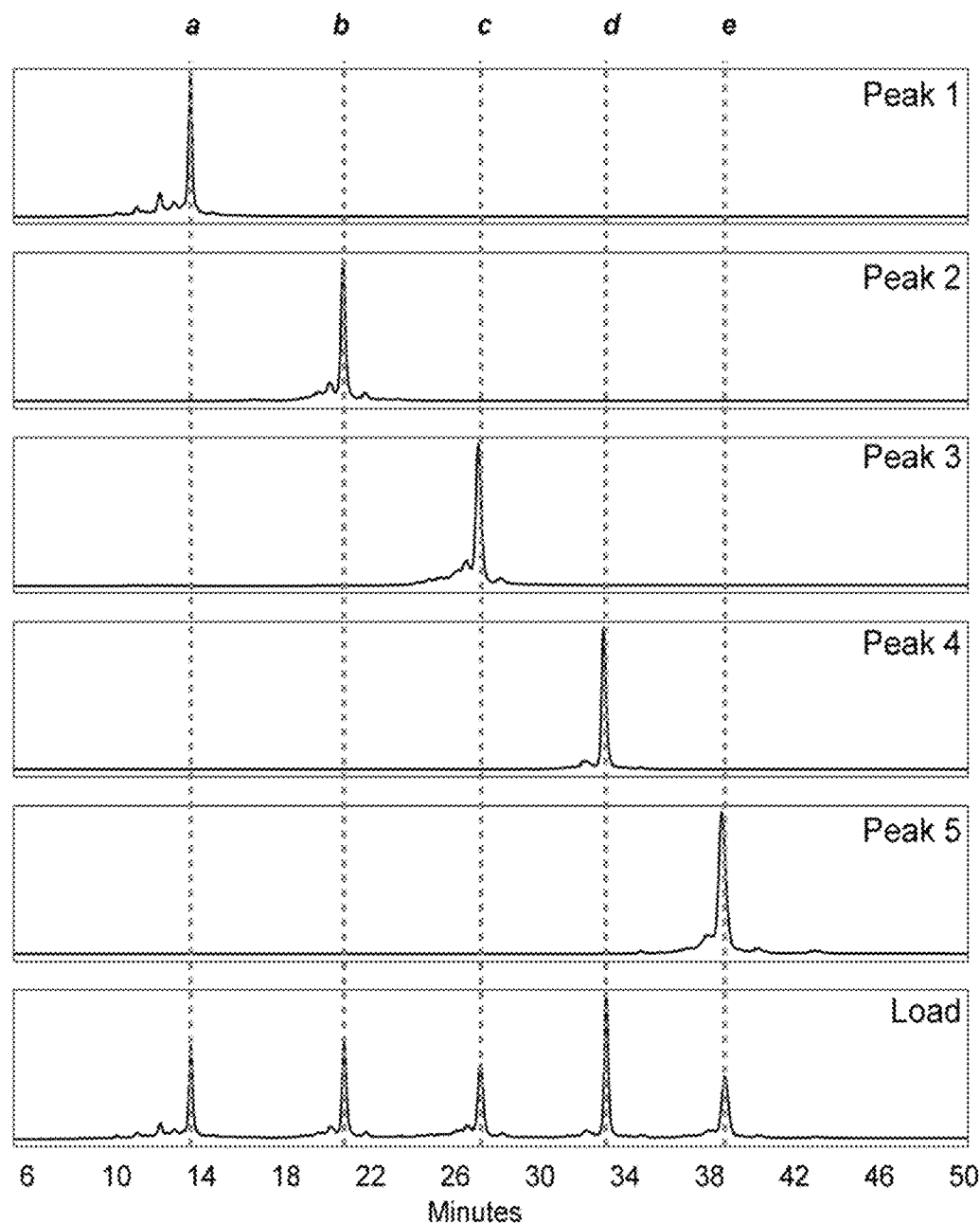
Figure 9C:
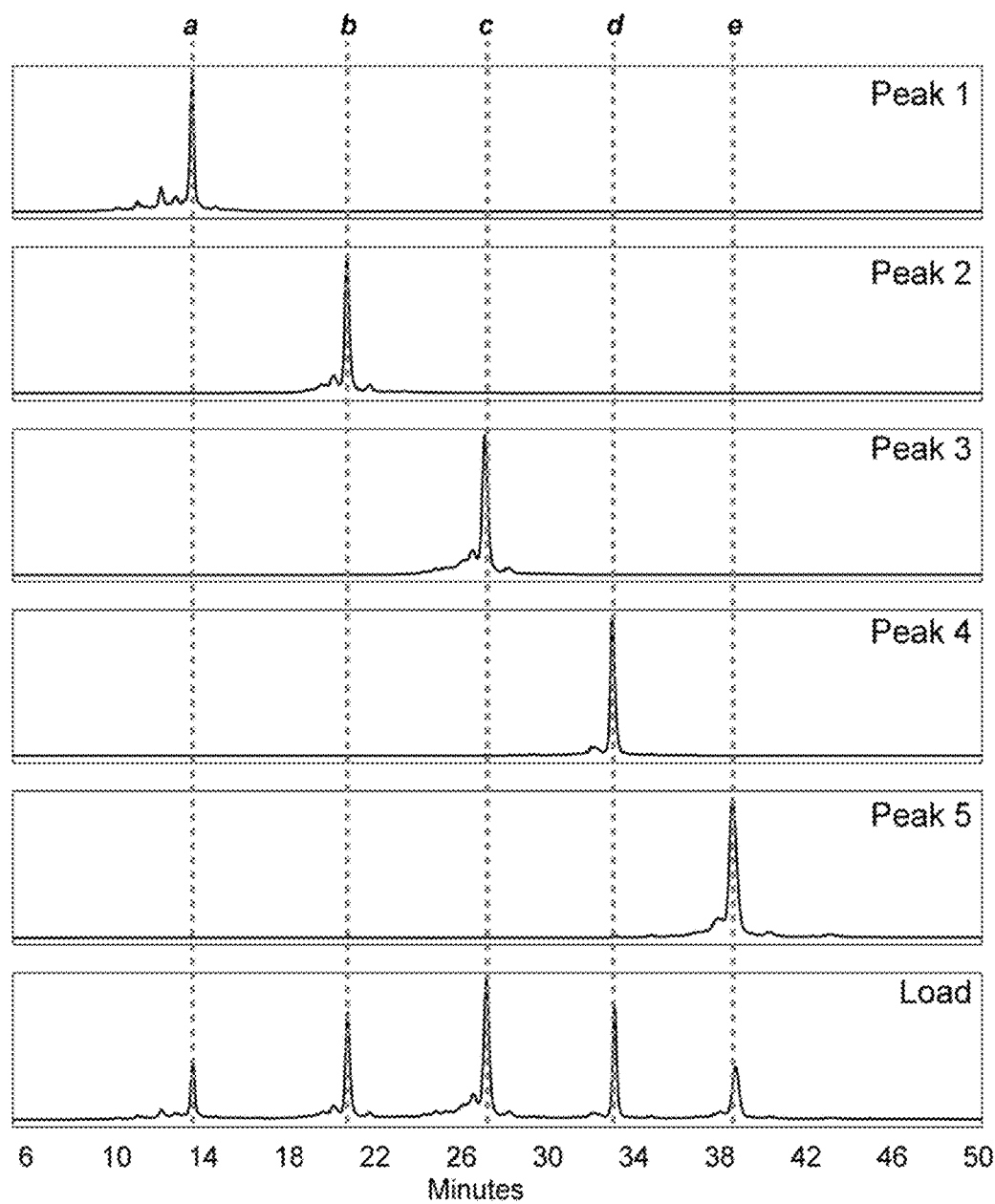
Figure 9D:
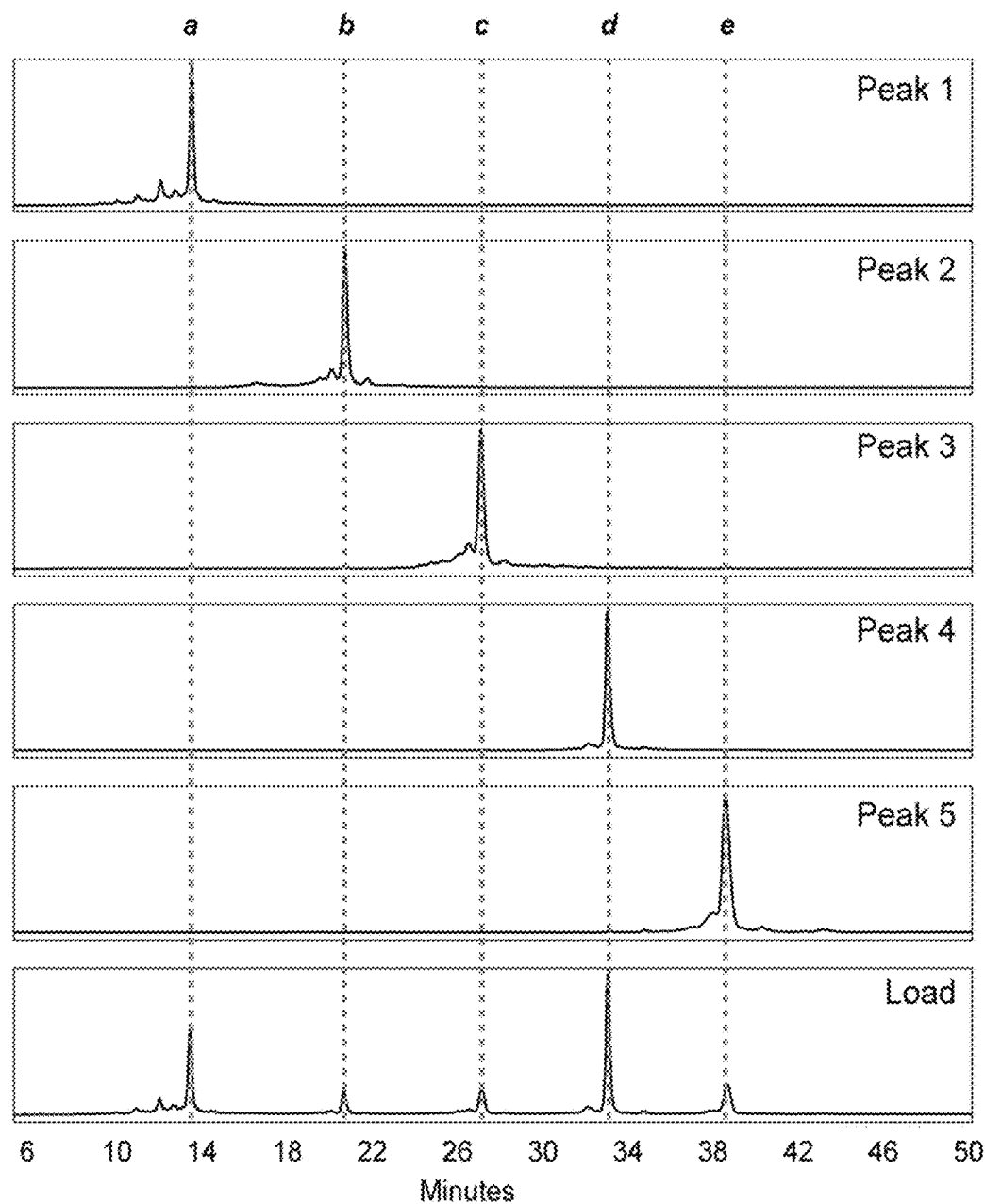
Figure 9E:
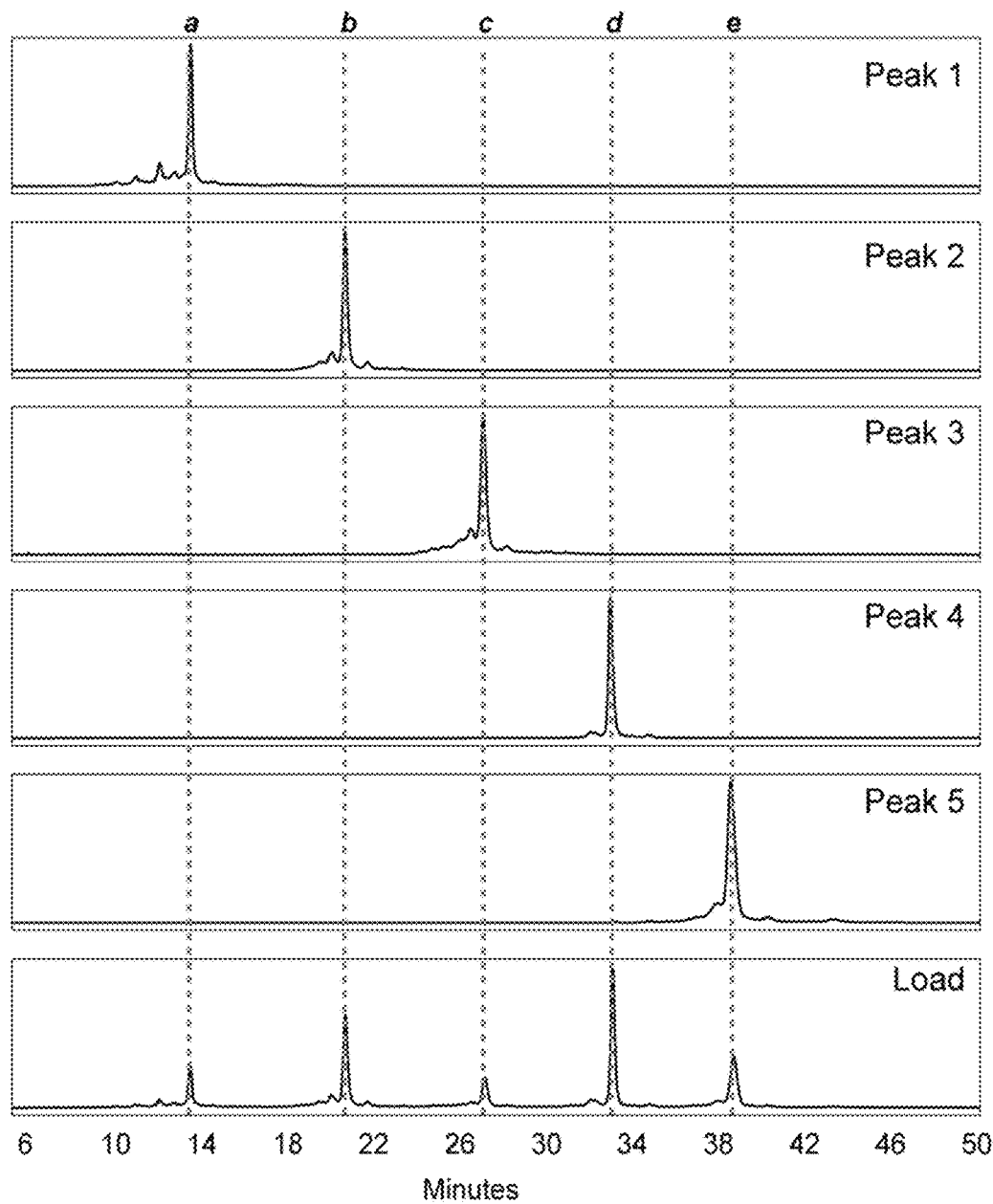

This elution and fractionation scheme was challenged with the different compositions of charge-modulated antibody mixtures, with the total loads of each antibody summarized in Table 4. FIG. 9A shows that each of the mixtures was separated into 5 peaks that were individually fractionated. The concentration was derived from the integral of the chromatogram, using the pooling function of the Unicorn software version 6.32 (GE Healthcare) according to the manufacturer's guidelines. Alternatively, the concentration of the fractions was analyzed by measured the absorbance at 280 nm measured using a Nanodrop ND-1000 spectrophotometer (Isogen Life Science, Maarssen, The Netherlands) and extinction coefficients calculated from the primary amino acid sequence of the pure antibodies. The composition of the load samples and each individual fraction was confirmed using analytical cation exchange chromatography (Example 8). The analysis of the chromatograms shows a good correlation between the amount of each antibody that was loaded and the amount that was inferred from the integration of the chromatogram (Table 4). Each fraction was analyzed by analytical cation exchange chromatography and the data confirmed that each fraction contained highly pure (>98%) antibody (FIG. 9 B-E). Analytical cation exchange analysis on the fractions would not necessarily be required before pooling of the fractions in an optimized process since process design and/or robustness testing could show that the purity of the fractions was under control. An approximately equimolar output mixture of the antibodies was prepared by mixing fractions using the concentration of each antibody fractions, inferred from the integral of the chromatogram, to calculate the volume required to generate an approximately equal mass concentration of the antibodies. Alternatively, an approximately equimolar output mixture of the antibodies was prepared by mixing fractions using the concentration of each antibody fractions, inferred from measuring the concentration of the isolated fractions, to calculate the volume required to generate an approximately equal mass concentration of the antibodies. The composition of the end products was analyzed using analytical cation exchange chromatography as described in Example 8. In both cases the pooling gave rise to an antibody product that complied with predetermined composition, with a tolerance (Table 5). This example shows that the composition of an antibody load of variable composition can be controlled using chromatography at relevant loads and using a series of step elutions.

TABLE 3

Quantitation of preparative cation exchange chromatograms of antibody mixtures, analyzed for the integrated peak area and resolution, using a vertical drop line, relative to the previous peak.

| Antibody load | Antibody code | Calculated relative mass (%) | Resolution |
|---|---|---|---|
| 0.2 | IgG1-7D8, | 21.3 | |
| | IgG1-224, | 20.6 | 0.83 |
| | IgG1-CD37-37-3, | 18.8 | 1.32 |
| | IgG1-CD19-21D4-E345K | 22.7 | 0.98 |
| | IgG1-CD52-Campath-E345K | 16.7 | 1.07 |
| 0.5 | IgG1-7D8, | 19.6 | |
| | IgG1-224, | 20.3 | 0.72 |
| | IgG1-CD37-37-3, | 20.5 | 1.24 |
| | IgG1-CD19-21D4-E345K | 21.4 | 0.91 |
| | IgG1-CD52-Campath-E345K | 18.2 | 0.93 |
| 1.0 | IgG1-7D8, | 19.5 | |
| | IgG1-224, | 20.2 | 0.69 |
| | IgG1-CD37-37-3, | 20.2 | 1.19 |
| | IgG1-CD19-21D4-E345K | 21.3 | 0.90 |
| | IgG1-CD52-Campath-E345K | 18.8 | 0.88 |
| 2.0 | IgG1-7D8, | 19.5 | |
| | IgG1-224, | 20.0 | 0.73 |
| | IgG1-CD37-37-3, | 20.0 | 1.14 |
| | IgG1-CD19-21D4-E345K | 21.3 | 0.88 |
| | IgG1-CD52-Campath-E345K | 19.2 | 0.79 |

TABLE 3-continued

Quantitation of preparative cation exchange chromatograms of antibody mixtures, analyzed for the integrated peak area and resolution, using a vertical drop line, relative to the previous peak.

| Antibody load | Antibody code | Calculated relative mass (%) | Resolution |
|---|---|---|---|
| 5.0 | IgG1-7D8, | 19.2 | |
| | IgG1-224, | 19.8 | 0.73 |
| | IgG1-CD37-37-3, | 19.9 | 1.13 |
| | IgG1-CD19-21D4-E345K | 21.2 | 0.88 |
| | IgG1-CD52-Campath-E345K | 19.8 | 0.71 |
| 10.0 | IgG1-7D8, | 19.2 | |
| | IgG1-224, | 19.7 | 0.69 |
| | IgG1-CD37-37-3, | 19.9 | 1.12 |
| | IgG1-CD19-21D4-E345K | 21.2 | 0.89 |
| | IgG1-CD52-Campath-E345K | 19.9 | 0.51 |
| 20.0 | IgG1-7D8, | 19.0 | |
| | IgG1-224, | 19.7 | 0.60 |
| | IgG1-CD37-37-3, | 19.9 | 1.10 |
| | IgG1-CD19-21D4-E345K | 21.2 | 0.91 |
| | IgG1-CD52-Campath-E345K | 20.3 | 0.41 |
| 50.0 | IgG1-7D8, | 18.5 | |
| | IgG1-224, | 19.9 | 0.57 |
| | IgG1-CD37-37-3, | 19.7 | 1.04 |
| | IgG1-CD19-21D4-E345K | 21.2 | 0.96 |
| | IgG1-CD52-Campath-E345K | 20.7 | 0.40 |

TABLE 4

Quantitation of preparative cation exchange chromatograms of antibody mixtures of different compositions, analyzed for the integrated peak area.

| Initial ratio of monoclonal antibodies | Antibody code | Loaded mass | Calculated relative mass (%) |
|---|---|---|---|
| 1:1:1:1:1 | IgG1-7D8, | 20 | 19.7 |
| | IgG1-224, | 20 | 19.3 |
| | IgG1-CD37-37-3, | 20 | 19.3 |
| | IgG1-CD19-21D4-E345K | 20 | 20.0 |
| | IgG1-CD52-Campath-E345K | 20 | 18.8 |
| 0.30:0.50:1.0:0.38:0.38 | IgG1-7D8, | 12 | 12.3 |
| | IgG1-224, | 20 | 20.5 |
| | IgG1-CD37-37-3, | 40 | 33.0 |
| | IgG1-CD19-21D4-E345K | 15 | 15.4 |
| | IgG1-CD52-Campath-E345K | 15 | 15.3 |
| 1.0:0.25:0.38:1.0:0.50 | IgG1-7D8, | 40 | 38.6 |
| | IgG1-224, | 10 | 11.5 |
| | IgG1-CD37-37-3, | 15 | 16.1 |
| | IgG1-CD19-21D4-E345K | 40 | 40.0 |
| | IgG1-CD52-Campath-E345K | 20 | 20.1 |
| 0.50:1.0:0.40:1.0:0.83 | IgG1-7D8, | 15 | 15.8 |
| | IgG1-224, | 30 | 28.4 |
| | IgG1-CD37-37-3, | 12 | 12.9 |
| | IgG1-CD19-21D4-E345K | 30 | 31.3 |
| | IgG1-CD52-Campath-E345K | 25 | 24.6 |

TABLE 5

Quantitation of the analytical cation exchange chromatography profiles of input and normalized antibody mixtures.

| | | | Analytical cation exchange quantitation (%) | |
|---|---|---|---|---|
| Mass Ratio | Antibody code | Load (mg) | End product. In-line concentration measurement | End product. Concentration measurement of fractions |
| 1:1:1:1:1 | IgG1-7D8, | 20.6 | ND | ND |
| | IgG1-224, | 20.2 | ND | ND |
| | IgG1-CD37-37-3, | 20.3 | ND | ND |
| | IgG1-CD19-21D4-E345K | 19.2 | ND | ND |
| | IgG1-CD52-Campath-E345K | 19.7 | ND | ND |
| 0.30:0.50:1.0:0.38:0.38 | IgG1-7D8, | 13.4 | 20.2 | 21.0 |
| | IgG1-224, | 21.6 | 21.1 | 20.8 |
| | IgG1-CD37-37-3, | 34.2 | 21.3 | 22.0 |
| | IgG1-CD19-21D4-E345K | 14.9 | 18.1 | 18.1 |
| | IgG1-CD52-Campath-E345K | 16.1 | 19.3 | 18.1 |
| 1.0:0.25:0.38:1.0:0.50 | IgG1-7D8, | 32.0 | 21.8 | 23.4 |
| | IgG1-224, | 9.9 | 19.6 | 18.0 |
| | IgG1-CD37-37-3, | 12.4 | 20.2 | 18.7 |
| | IgG1-CD19-21D4-E345K | 30.3 | 18.0 | 20.3 |
| | IgG1-CD52-Campath-E345K | 15.4 | 20.4 | 19.6 |
| 0.50:1.0:0.40:1.0:0.83 | IgG1-7D8, | 13.9 | 20.8 | 19.0 |
| | IgG1-224, | 25.7 | 21.6 | 23.4 |
| | IgG1-CD37-37-3, | 11.8 | 20.0 | 18.0 |
| | IgG1-CD19-21D4-E345K | 26.5 | 16.4 | 21.7 |
| | IgG1-CD52-Campath-E345K | 22.1 | 21.2 | 17.9 |

ND - not determined.

Example 10: KappaSelect Separations of Modified 1561-2F8-F405L Variants Using Purified Proteins or Cell Culture Supernatant Four 1 mL KappaSelect (GE Healthcare) columns were joined in tandem. The columns were pre-equilibrated with Phosphate Buffered Saline (PBS; 12.6 mM sodium phosphate, 140 mM sodium chloride, PH 7.4, B.Braun or Thermo Fisher). Antibody cell culture supernatants were filtered over 0.2 μm dead-end filters and the IgG1 expression level was quantified using Bio-Layer Interferometry as described in Example 4. Between 40 mL and 80 mL of cell culture supernatants containing between 10 mg and 30 mg of unpurified IgG1-2F8-F405L variants was loaded onto the KappaSelect columns. Alternatively, 16 mg purified IgG-2F8-F405L was diluted to a total volume of 80 mL with PBS (B.Braun) and loaded onto the columns. The columns were washed with PBS, and eluted sequentially with 0.1 M Glycine HCl pH 3.0 and 0.1 M Glycine HCl pH 2.0. The eluted fractions were neutralized with a few drops of 2M Tris HCl pH 9.0, dialyzed into PBS (B.Braun) using 10 kDa molecular-weight cutoff Slide-A-Lyzer carriages (ThermoFisher) of the appropriate size. The column was cleaned using 6 M guanidine HCl. The flow-through fractions were combined with the PBS wash and analyzed by SDS-PAGE, as described in Example 13.

Example 11: CaptureSelect® KappaXL Separations of Modified IgG1-7D8-K409R Variants from Cell Culture Supernatant or Purified Immunoglobulin Solutions A column containing approximately 1 ml of packed resin was packed manually from homogeneous CaptureSelect® KappaXL (ThermoFisher) slurry into a 6.6 mm bore HiT column (Omnifit), according to manufacturer's instructions. The column was pre-equilibrated with Phosphate Buffered Saline (PBS; 12.6 mM sodium phosphate, 140 mM sodium chloride, pH 7.4, ThermoFisher). Antibody cell culture supernatants were filtered over 0.2 μm dead-end filters and the IgG1 expression level was quantified using Bio-Layer Interferometry as described in Example 4. 10 ml of the supernatant, containing 1-10 mg unpurified IgG1-7D8-K409R variants, was loaded onto the CaptureSelect® KappaXL column. The column was washed sequentially with approximately five column volumes of PBS and three column volumes of 0.1 M Citrate NaOH pH 5.0. Bound material was eluted with 0.1 M Citrate NaOH pH 3.5. Fractions of 1 mL were neutralized with a few drops of 2 M Tris HCl pH 9.0. The column was washed with 6M Guanidine HCl. The flow-through was pooled with the PBS wash. Fractions that contained significant absorption at 280 nm peak from either the pH 5.0 wash or the pH 3.5 elution were pooled. The load, pooled flow-through and pooled fractions were analyzed using Bio-Layer Interferometry and CE-SDS, as described in Examples 4 and 14.

Example 12: Protein L Separations of Modified IgG1-2F8-F405L Variants with Modified Kappa Light Chain Variable Domains A 5 mL HiTrap Protein L Column (GE Healthcare) was pre-equilibrated with Phosphate Buffered Saline (PBS; 12.6 mM sodium phosphate, 140 mM sodium chloride, pH 7.4). Antibody cell culture supernatants containing IgG-2F8-F405L-R18P, IgG-2F8-F405L-T20S-T22S, IgG-2F8-F405L-R24S or IgG-2F8-F405L-K107L were filtered over 0.2 μm dead-end filters and the IgG1 expression level was quantified using Bio-Layer Interferometry as described in Example 4. 10 ml of the supernatant was loaded onto the HiTrap Protein L column. Alternatively, antibody culture supernatants were purified by Protein A chromatography, as described in Example 5. Between 0.8 mg and 2.8 mg of purified IgG-2F8-F405L, IgG-2F8-F405L-S9L or IgG-2F8-F405L-S12P were mixed to a total volume of 10 mL in PBS and loaded onto the HiTrap Protein L column. The column was washed with PBS and specifically bound material was eluted sequentially with 0.1 M glycine-HCl pH 3.5, 3.0 and 2.5 and neutralized with a few drops of 2M Tris pH 9.0. The column was washed using 15 mM sodium hydroxide. The material in the flow-through was analyzed using Bio-Layer Interferometry and CE-SDS, as described in Examples 4 and 14.

Example 13: Analysis of Samples of Chromatography Flow-Through Fractions Using Sodium Dodecyl Sulfate-Polyacrylamide Gel Electrophoresis (SDS-PAGE)

Samples were mixed with equal amounts of NuPAGE LDS Sample Buffer (Invitrogen) and heated at 70° C. for 10 minutes. SDS-PAGE was performed under non-reducing conditions on 4-12% NuPAGE Bis-Tris gels (Invitrogen) using a modified Laemmli method (Laemmli 1970 Nature 227 (5259): 680-5), with 1× NuPAGE MOPS SDS Running Buffer (Invitrogen). The SDS-PAGE gels were stained with Coomassie and digitally imaged using an OptiGo imaging system (Isogen Life Sciences). SeeBlue Plus2 Pre-stained Standard was used as a molecular weight standard (Invitrogen).

Example 14: Analysis of Samples of Chromatography Fractions Using Capillary Electrophoresis-Sodium Dodecyl Sulfate (CE-SDS)

Samples were filtered over 0.2 μm dead-end filters before analysis. Sample concentrations were adjusted by diluting in PBS such that the concentration was not greater than 250 μg/mL, using the Bio-Layer Interferometry concentration measurement described in Example 4 or based upon the absorption at 280 nm. CE-SDS was performed using a LabChip GXII (Caliper Life Sciences, MA) on a HT Protein Express LabChip (Caliper Life Sciences, MA) under non-reducing conditions according to manufacturer's instructions. Data were analysed using LabChipGX software V3.1 (Caliper Life Sciences, MA).

Example 15: Identification of Knock-Out Mutations for the CaptureSelect® LC-Kappa (Hu) Affinity Matrix As described by the manufacturer, the CaptureSelect® LC-kappa (Hu) affinity matrices, KappaSelect and CaptureSelect® KappaXL (GE-Healthcare, BAC), both contain a 13 kDa Llama antibody fragment recognizing a unique epitope on the constant part of the human kappa L chain (CL). Furthermore, according to the manufacturer, the fragment is cross-reactive with non-human primate species and non-cross-reactive with mouse, rabbit, bovine and rat L chains or with human lambda L chains.

Sequence alignment of the kappa CL domain of these different species revealed several amino acid residues that were conserved in human and primate kappa sequences, but different in the other sequences. Of these, residues exposed in the complex of light and heavy chain were selected for analysis and human kappa L chains were designed containing the mouse (mm) CL domain or single point-mutations corresponding with their mouse-specific counterparts (FIG. 10). An additional point-mutation (F135L) was introduced into the mmCL domain to facilitate efficient pairing with human H-chains.

Figure 12A:
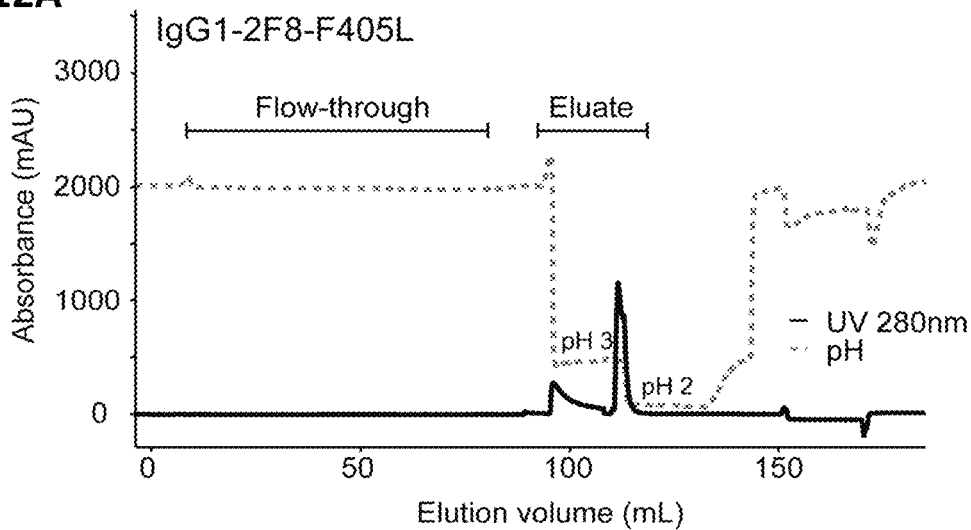
Figure 12B:
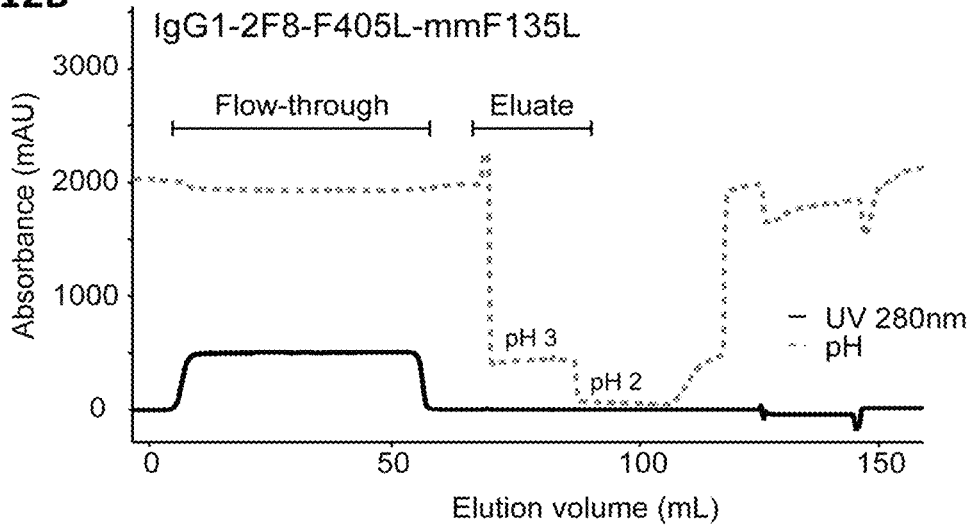
Figure 12C:
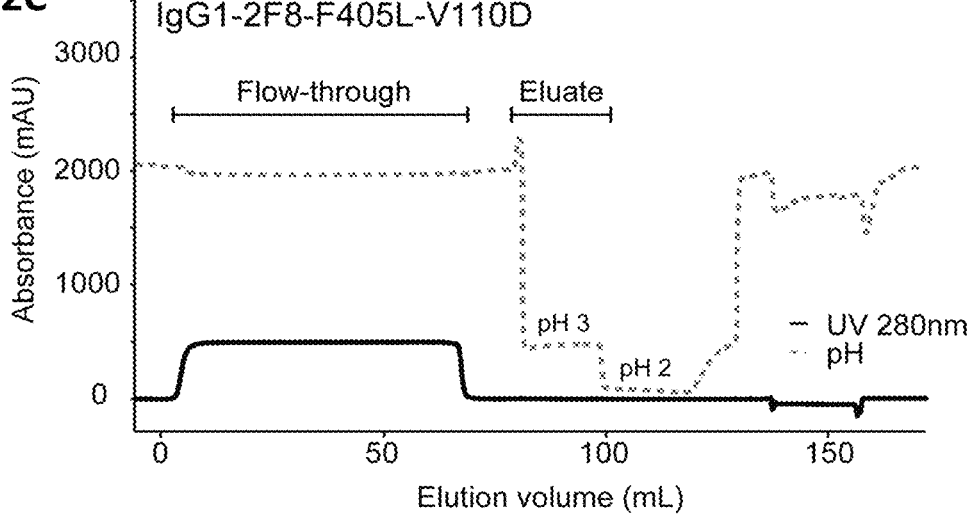
Figure 12D:
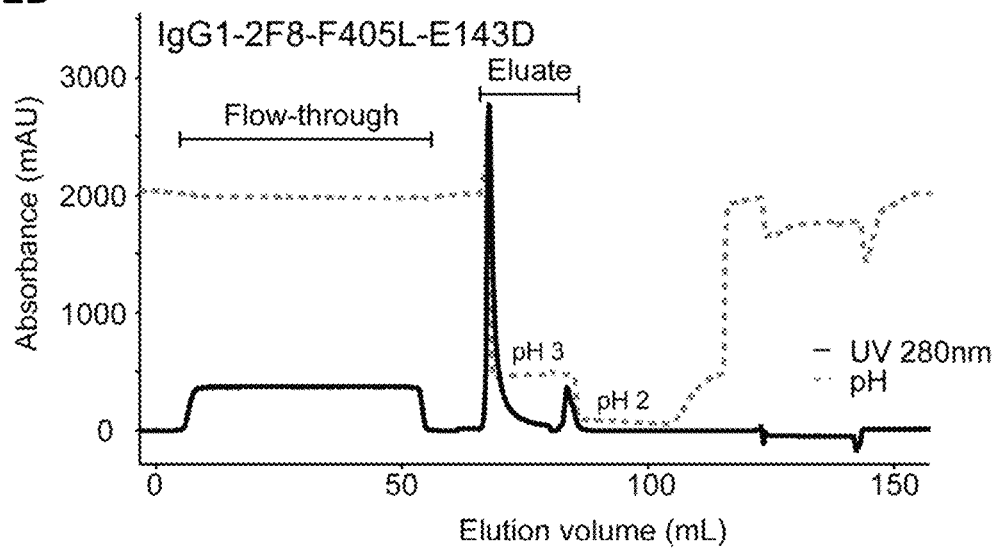
Figure 12E:
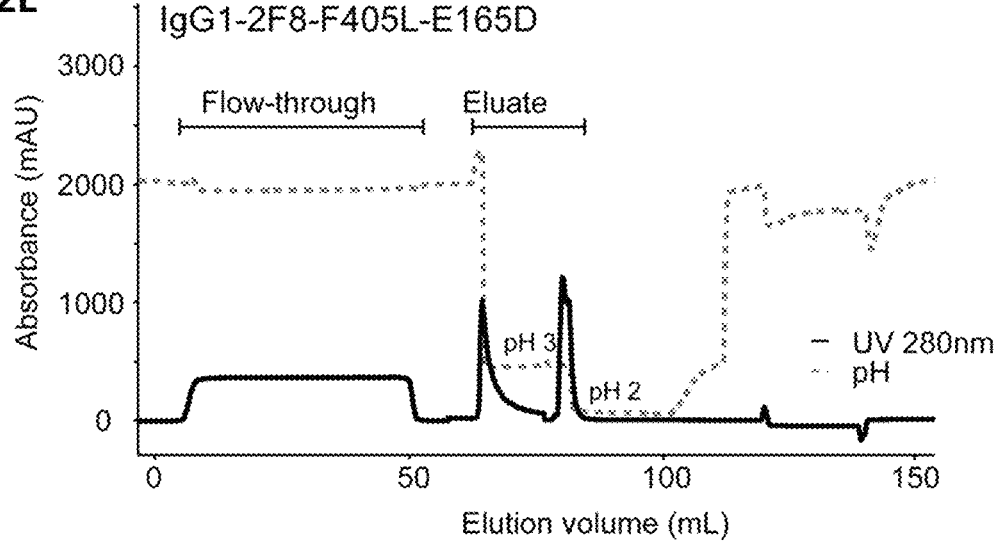
Figure 12F:
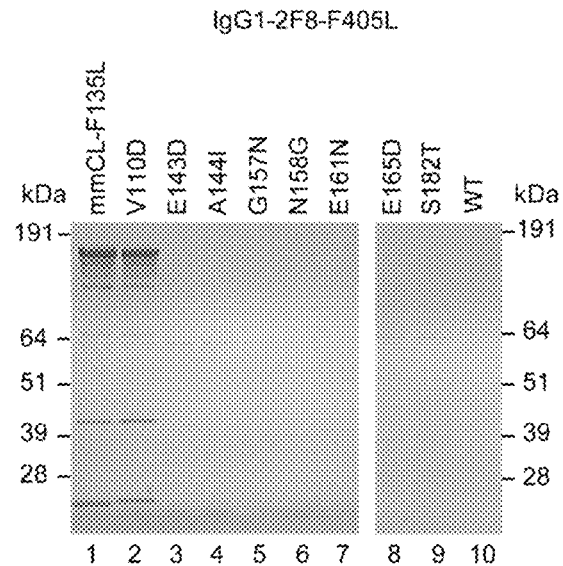
Figure 13A:
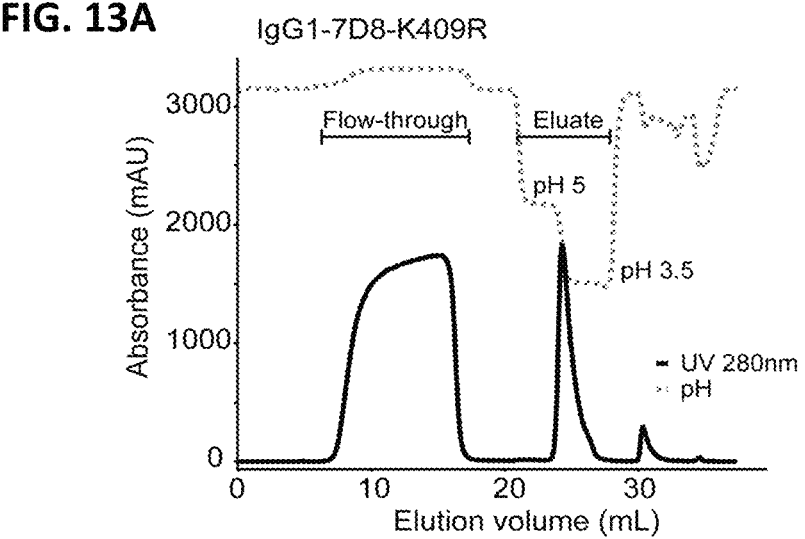
Figure 13B:
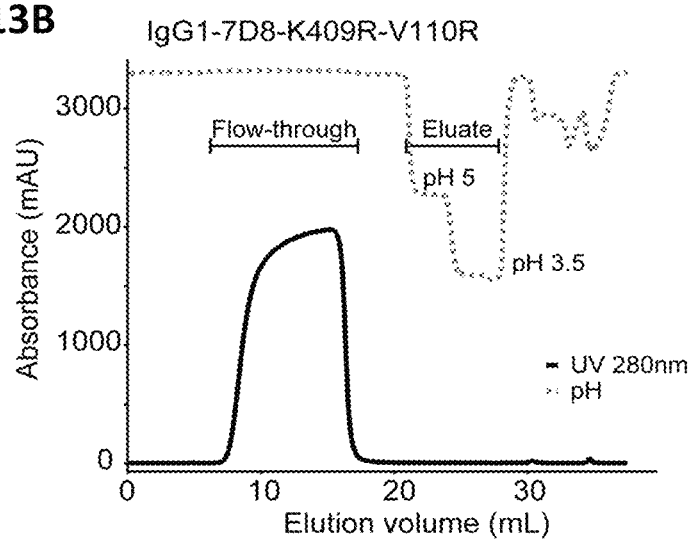
Figure 13C:
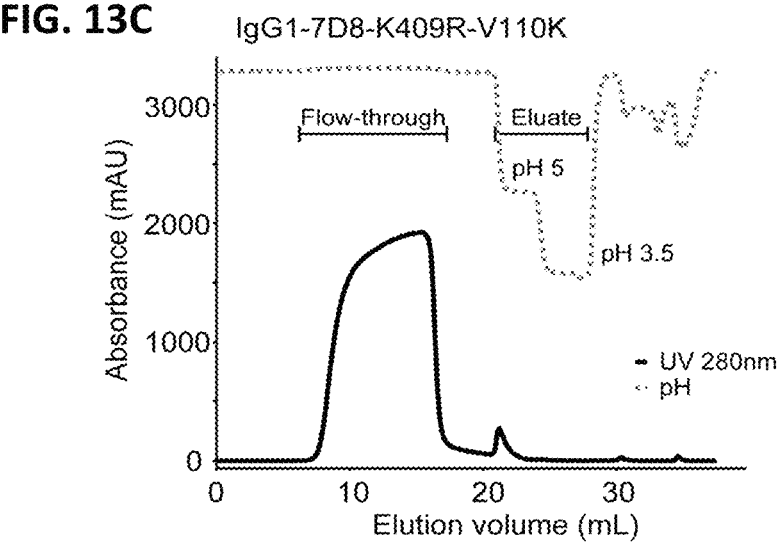
Figure 13D:
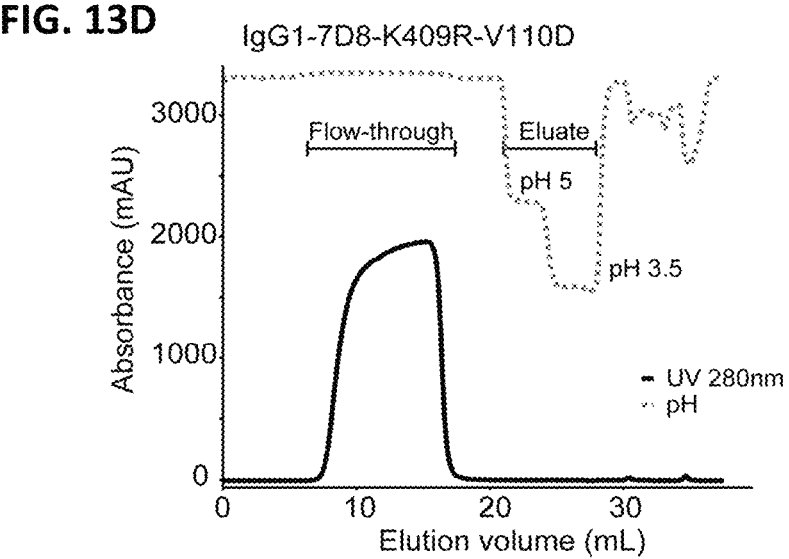
Figure 13E:
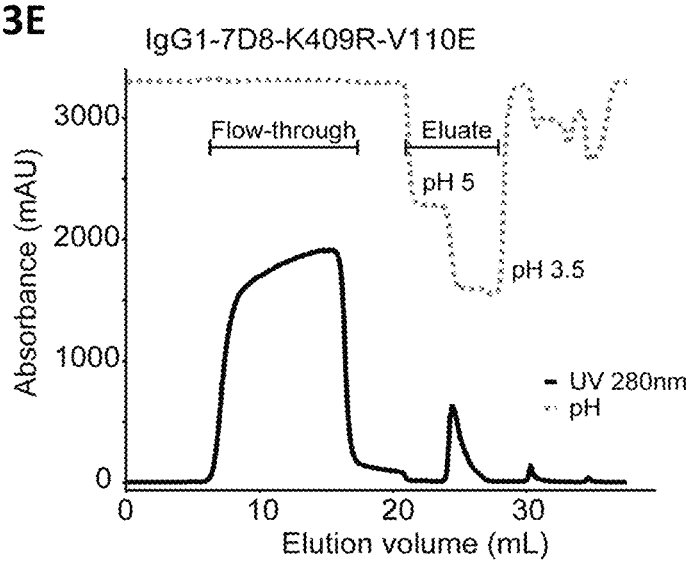
Figure 13F:
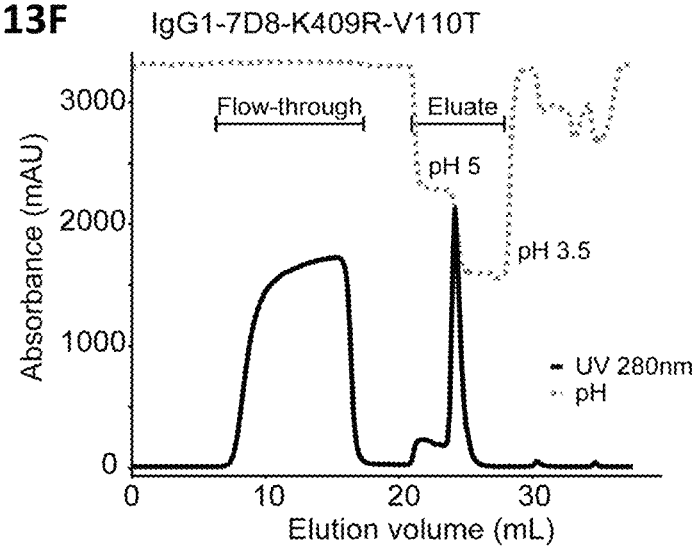

Nine kappa L-chain mutants were expressed (Table 6) in combination with the appropriate H-chains and assessed for their ability to bind to KappaSelect resin (as described in Example 10). Purified IgG1-2F8-F405L was used as a positive control for affinity purifications using KappaSelect resin (FIG. 12). As expected, the IgG1-2F8-F405L containing the mmCL (F135L) L-chain, could not be purified by KappaSelect resins (FIG. 12B). With the exception of V110D, all mutants could still be purified, suggesting that V110 in the kappa LC is directly or indirectly part of the KappaSelect binding site (FIG. 12). IgG1-2F8-F405L-E143D predominantly elutes at a higher pH than the other mutants, which is indicative of a weaker interaction with the column resin (FIG. 12D). The effects of the single point mutations on binding to the KappaSelect resin are summarized in Table 7, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

The tolerability of the CaptureSelect® KappaXL affinity matrix for substitutions in residue V110 of the kappa L-chain was further assessed by purifying (as described in Example 11) individually expressed kappa L-chain mutants, in combination with the appropriate H-chain, that contained substitutions at position V110 to all natural amino acids (except C). As expected, IgG1-7D8-K409R bound to the resin since an elution peak at 280 nm is detected during the pH 3.5 elution. The V110D substitution abrogated binding to the KappaSelect resin also prevented binding to CaptureSelect® KappaXL binding, suggesting that both matrices bind to the same or similar epitopes. V110R was the only other mutation that showed no detectable interaction with the resin under these conditions (FIGS. 13 and 14). Other IgG1-7D8-K409R variants show a reduced affinity for the resin. For example IgG1-7D8-K409R-V110E is detected in the pH 3.5 eluate and flow-through fractions, IgG1-7D8-K409R-V110K is detected in the pH 5.0 wash and flow-through fractions, and IgG1-7D8-K409R-V110T elutes during both the pH 5.0 wash and pH 3.5 elution (FIGS. 13 and 14). The effects of the single point mutations on binding to the CaptureSelect® KappaXL resin are summarized in Table 8, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

TABLE 6

| IgG1-2F8-F405L and IgG1-7D8-K409R Kappa L-chain variants | | |
|---|---|---|
| IgG1-2F8-F405L-mmCL(F135L) | IgG1-2F8-F405L-G157N | IgG1-2F8-F405L-S182T |
| IgG1-2F8-F405L-V110D | IgG1-2F8-F405L-N158G | IgG1-2F8-F405L-A193T |
| IgG1-2F8-F405L-E143D | IgG1-2F8-F405L-E161N | IgG1-2F8-F405L-T206V |
| IgG1-2F8-F405L-A144I | IgG1-2F8-F405L-E165D | |
| IgG1-2F8-F405L-S9L | IgG1-2F8-F405L-S12P | IgG1-2F8-F405L-R18P |
| IgG1-2F8-F405L-T20S-T22S | IgG1-2F8-F405L-R24S | IgG1-2F8-F405L-K107L |
| IgG1-7D8-K409R-V110A | IgG1-7D8-K409R-V110D | IgG1-7D8-K409R-V110E |
| IgG1-7D8-K409R-V110F | IgG1-7D8-K409R-V110G | IgG1-7D8-K409R-V110H |
| IgG1-7D8-K409R-V110I | IgG1-7D8-K409R-V110K | IgG1-7D8-K409R-V110L |
| IgG1-7D8-K409R-V110M | IgG1-7D8-K409R-V110N | IgG1-7D8-K409R-V110P |
| IgG1-7D8-K409R-V110Q | IgG1-7D8-K409R-V110R | IgG1-7D8-K409R-V110S |
| IgG1-7D8-K409R-V110T | IgG1-7D8-K409R-V110W | IgG1-7D8-K409R-V110Y |

TABLE 7

Binding behavior IgG1-2F8-F405L and Variants to KappaSelect resin

| IgG1-2F8-F405L variant | Affinity |
|---|---|
| IgG1-2F8-F405L | +++ |
| IgG1-2F8-F405L-V110D | − |
| IgG1-2F8-F405L-E143D | ++ |
| IgG1-2F8-F405L-A144I | +++ |
| IgG1-2F8-F405L-G157N | +++ |
| IgG1-2F8-F405L-N158G | +++ |
| IgG1-2F8-F405L-E161N | +++ |
| IgG1-2F8-F405L-E165D | +++ |
| IgG1-2F8-F405L-S182T | +++ |

TABLE 8

Binding behavior IgG1-7D8-K409R and Variants to CaptureSelect ® KappaXL resin

| IgG1-7D8-K409R variant | Affinity |
|---|---|
| IgG1-7D8-K409R | +++ |
| IgG1-7D8-K409R-V110A | +++ |
| IgG1-7D8-K409R-V110D | − |
| IgG1-7D8-K409R-V110E | + |
| IgG1-7D8-K409R-V110F | ++ |
| IgG1-7D8-K409R-V110G | +++ |
| IgG1-7D8-K409R-V110H | + |
| IgG1-7D8-K409R-V110I | ++ |
| IgG1-7D8-K409R-V110K | + |
| IgG1-7D8-K409R-V110L | +++ |
| IgG1-7D8-K409R-V110M | +++ |
| IgG1-7D8-K409R-V110N | + |
| IgG1-7D8-K409R-V110P | + |
| IgG1-7D8-K409R-V110Q | + |
| IgG1-7D8-K409R-V110R | − |
| IgG1-7D8-K409R-V110S | ++ |
| IgG1-7D8-K409R-V110T | ++ |
| IgG1-7D8-K409R-V110W | + |
| IgG1-7D8-K409R-V110Y | ++ |

Example 16: Identification of Knock-Out Mutations for the Protein L Affinity Matrix Protein L has also been described to bind to the variable portion of kappa subtypes I, III and IV but not to kappa subtype II or most lambda subtypes (Nilson et al. J Biol Chem. 1992; 267 (4): 2234-9). Furthermore, the epitope of protein L on human and murine kappa lights chains has been identified by X-ray crystallography (Graille et al. Structure. 2001 9 (8): 679-87; Graille et al. Biol Chem. 2002 277 (49): 47500-6). Analysis of these crystal structures identifies 17 residues as being important contact residues in both structures (FIG. 11). Of these, 7 residues were selected based upon analysis of the structures and sequence alignments and were mutated to residues commonly found at the equivalent position in either the kappa subtype II or most lambda subtype I sequences using single or double point mutations (FIG. 11, Table 6).

These kappa L-chain mutants were expressed in combination with the appropriate H-chains and assessed for their ability to bind to Protein L resin (as described in Example 12). The purified IgG1-2F8-F405L positive control and most of the mutated proteins were bound by the resin. In contrast, IgG1-2F8-S12P does not bind to the resin under these conditions (FIG. 15). The effects of the point mutations on binding to the HiTrap Protein L column are summarized in Table 9, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

TABLE 9

Binding behavior IgG1-2F8-F405L and Variants to Protein L resin

| IgG1-2F8-F405L variant | Affinity |
|---|---|
| IgG1-2F8-F405L | +++ |
| IgG1-2F8-F405L-S9L | +++ |
| IgG1-2F8-F405L-S12P | − |
| IgG1-2F8-F405L-R18P | +++ |
| IgG1-2F8-F405L-T20S-T22S | +++ |
| IgG1-2F8-F405L-R24S | +++ |
| IgG1-2F8-F405L-K107L | +++ |

Example 17: Binding Specificity of IgG1 Variants to HiTrap Protein L

A 5 mL HiTrap Protein L column (GE Healthcare) was pre-equilibrated with Phosphate Buffered Saline (PBS; 12.6 mM sodium phosphate, 140 mM sodium chloride, pH 7.4). Antibody culture supernatants were purified by Protein A chromatography, as described in Example 5. Approximately 250 μg of purified IgG1-2F8-V110D, IgG1-7D8-S12P or IgG1-HepC were mixed with PBS to a total volume of 5 mL and loaded onto the HiTrap Protein L column in separate experiments. The column was washed with PBS followed by 0.02 M sodium citrate-NaOH, pH 5.0 and specifically bound material was eluted with 0.1 M glycine-HCl pH 3.0. The column was cleaned using 0.015 M NaOH.

Example 18 Binding specificity of IgG1 Variants to HiTrap KappaSelect A 5 mL HiTrap KappaSelect column (GE Healthcare) was pre-equilibrated with Phosphate Buffered Saline (PBS; 12.6 mM sodium phosphate, 140 mM sodium chloride, pH 7.4). Antibody culture supernatants were purified by Protein A chromatography, as described in Example 5. Approximately 500 μg of purified IgG1-2F8-V110D, IgG1-7D8-S12P or IgG1-HepC were mixed with PBS to a total volume of 5 mL and loaded onto the HiTrap KappaSelect column in separate experiments. The column was washed with PBS and 0.1 M glycine-HCl pH 3.0. Specifically bound material was eluted with 0.1 M glycine-HCl pH 2.5. The column was cleaned using 6 M Guanidine HCl.

Example 19: Binding Specificity of IgG1 Variants to HiTrap LambdaFabSelect

A 1 mL HiTrap LambdaFabSelect column (GE Healthcare) was pre-equilibrated with Phosphate Buffered Saline (PBS; 12.6 mM sodium phosphate, 140 mM sodium chloride, pH 7.4). Antibody culture supernatants were purified by Protein A chromatography, as described in Example 5. Approximately 500 μg of purified IgG1-2F8-V110D, IgG1-7D8-S12P or IgG1-HepC were mixed with PBS to a total volume of 5 mL and loaded onto the HiTrap LambdaFab-Select column in separate experiments. The column was washed with PBS and specifically bound material was eluted with 0.1 M glycine-HCl pH 2.0, followed by 0.5 M acetic acid. The column was cleaned using 0.025 M NaOH.

Example 20: Specificity of Antibody Variants for Affinity Chromatography Resins

As described by the manufacturer, the CaptureSelect® LC-lambda (Hu) affinity matrix, LambdaFabSelect (GE-Healthcare), contains a 13 kDa Llama antibody fragment recognizing a unique epitope on the constant part of the human kappa L chain. KappaSelect binds to an epitope on the constant part of the human kappa L chain and the V110D mutation prevents the interaction with the resin (Example 15), whereas Protein L binds to subtypes of kappa light chains, and introducing an S12P mutation into an antibody with a kappa light chain prevented interaction with the resin (Example 16). IgG1-HepC with a lambda L chain and IgG1-2F8 and IgG1-7D8 with a kappa L chain were selected as components of a recombinant antibody mixture. The V110D and S12P point mutations were introduced into the IgG1-2F8-V110D and IgG1-7D8-S12P as described in Example 1 and the specificities of the individually produced and purified antibodies were tested for binding to Protein L, KappaSelect and LambdaFabSelect as described in Examples 17, 18 and 19, respectively. FIG. 16 shows that IgG1-2F8-V110D, IgG1-7D8-S12P and IgG1-HepC each specifically bind to Protein L, KappaSelect and Lambda-FabSelect resins, respectively.

Example 21: Binding Capacity Determination of HiTrap KappaSelect

A 1 mL KappaSelect (GE Healthcare) column was pre-equilibrated with Phosphate Buffered Saline (PBS; 12.6 mM sodium phosphate, 140 mM sodium chloride, pH 7.4, B.Braun or Thermo Fisher). 75 mg of purified IgG1-7D8-K409R in PBS in a total volume of approximately 40 mL was loaded onto the KappaSelect column (GE Healthcare) using a flow rate of 0.25, 0.5 or 1 mL/minute. The column was washed with PBS, specifically bound protein was eluted with 0.1 M Glycine HCl pH 2.5 and the column was cleaned using 6 M guanidine HCl. The flow-through was pooled, sterile filtered and analyzed for protein concentration by absorption at 280 nm using a Nanodrop ND-1000 spectrophotometer (Isogen Life Science, Maarssen, The Netherlands). Analysis of the protein concentrations in the flow-through allowed the capacity of the column to be inferred to be between 37 and 41 mg, based upon the difference in protein amounts between the load and flow-through material. The binding capacity was essentially independent of the flow-rate confirming that that the column was saturated. FIG. 17 shows the chromatograms for the binding capacity determination experiments.

Example 22: Control of the Composition of a Recombinant Antibody Mixture of IgG1 Variants Using KappaSelect Affinity Chromatography This example describes a procedure to take a mixture of variable composition and perform chromatography using affinity chromatography resins with specificity for the different components so that excess antibodies are depleted to yield a mixture of pre-determined composition (FIG. 1C).

Figure 5A:
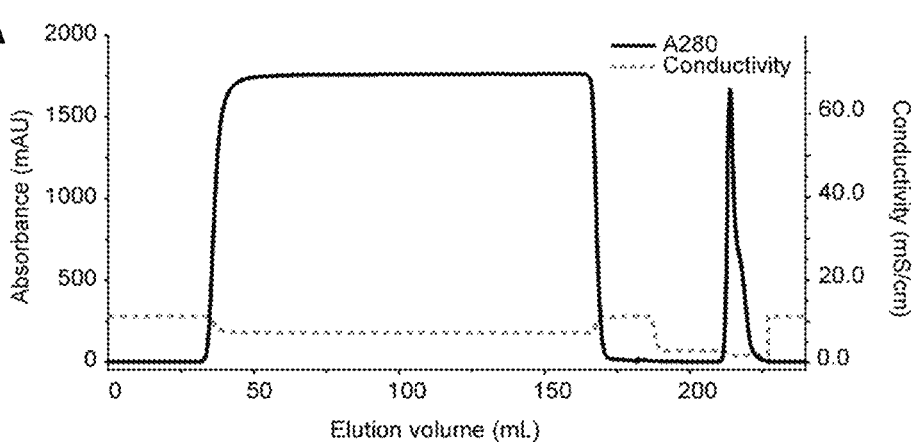
Figure 5B:
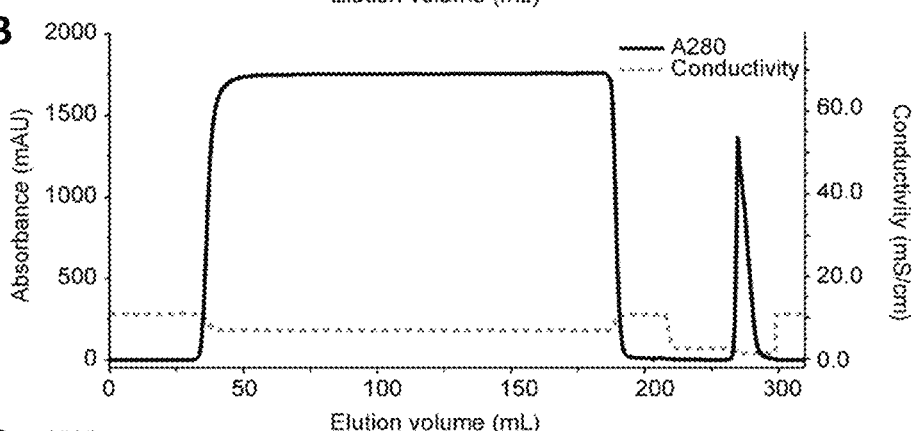
Figure 5C:
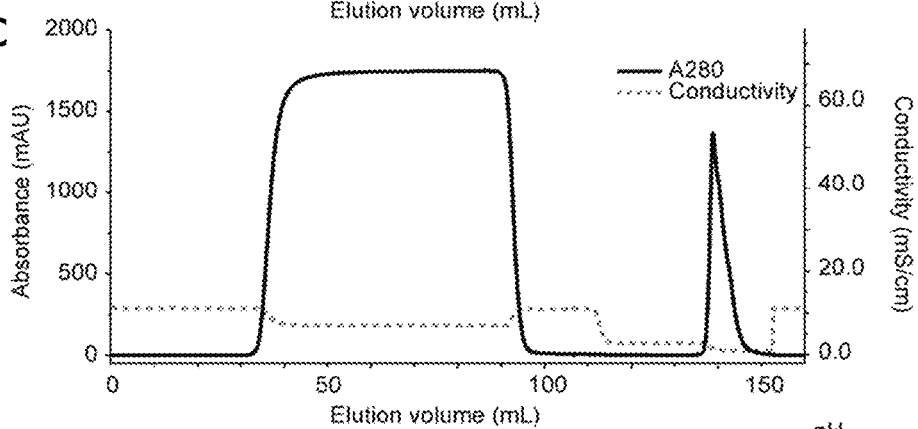
Figure 5D:
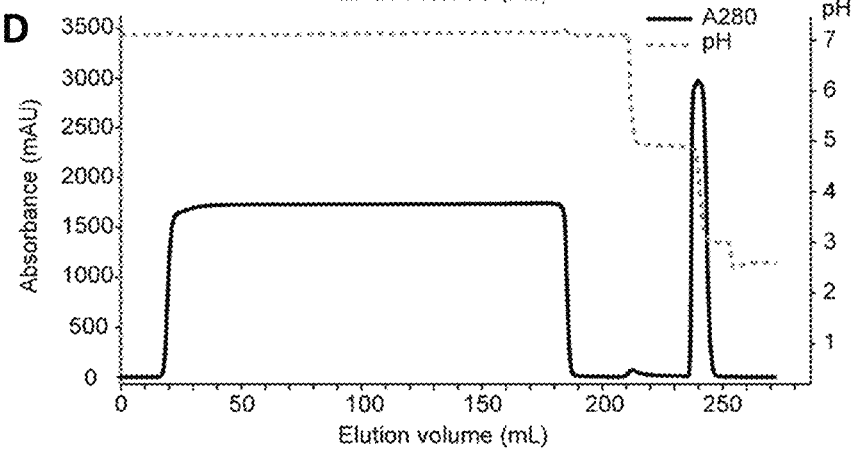
Figure 5E:
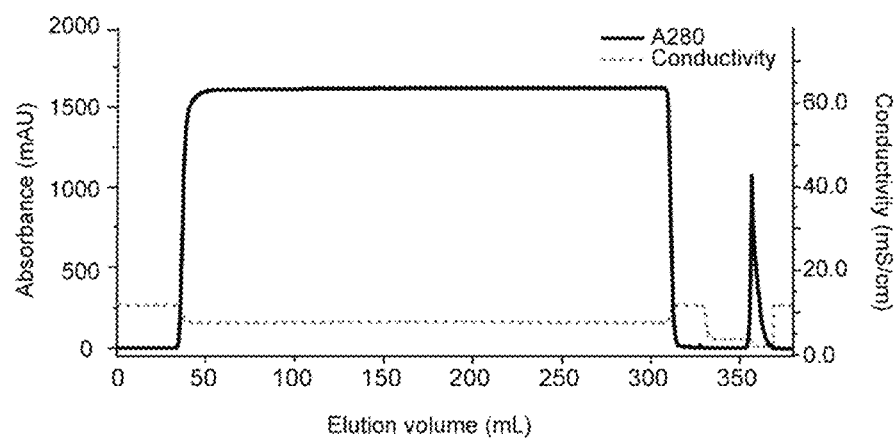

IgG1-2F8-V110D, IgG1-7D8-S12P or IgG1-HepC were recombinantly produced as described in Example 3 and the antibody titers were calculated as described in Example 4. The culture supernatants were mixed to yield a theoretical ratio antibody concentrations of 1:2.4:1 according to the biolayer interferometry measurements, to simulate an upstream process for co-production of a mixture of antibodies. This ratio was selected to mimic an upstream co-production process that targeted a 1:1:1 mass ratio of the three antibodies, but where the IgG1-7D8-S12P was overproduced, such that the composition of the mixture was not under control and required a chromatography separation to achieve the desired ratio. The mixture was purified by Protein A affinity chromatography as described in Example 5. FIG. 5D shows the chromatogram for the protein A purification of the antibody mixture. The mixture was analyzed for protein concentration by absorption at 280 nm using a Nanodrop ND-1000 spectrophotometer (Isogen Life Science, Maarssen, The Netherlands), with an extinction coefficient of the average of the three antibodies, calculated using the primary amino acid sequence of the antibodies. The composition was analyzed using analytical cation exchange chromatography as described in Example 8. FIG. 19 shows that purified IgG1-2F8-V110D, IgG1-7D8-S12P and IgG1-HepC are resolved by analytical cation exchange chromatography. The analytical cation exchange chromatogram (FIG. 19), the concentration measurement and the volume allowed the mass amounts of the three components of the mixture to be estimated (Table 10). The IgG1-7D8-S12P was in a suitable excess that it could be removed by a 1 mL KappaSelect column, based upon the binding capacity determination for IgG1-7D8-K409R in Example 21, which assumed that the capacity for the IgG1-7D8 variants was similar since the mutations were not in the same domains as the epitopes of the KappaSelect resin. This experimental setup was to mimic a process where the size of the column or the number of cycles was adjusted such that the column capacity was suitable to specifically remove the excess of the antibody from the mixture.

A 1 mL KappaSelect (GE Healthcare) column was pre-equilibrated with Phosphate Buffered Saline (PBS; 12.6 mM sodium phosphate, 140 mM sodium chloride, pH 7.4, B.Braun or Thermo Fisher). 116.9 mg recombinant antibody mixture in a total volume of 56.7 mL in PBS was loaded onto the KappaSelect column using a 50 mL superloop (GE Healthcare). The column was washed with PBS, bound materials were eluted with 0.1 M Glycine HCl pH 2.5 and the column was cleaned using 6 M guanidine HCl. The flow-through fractions were pooled, dialyzed into PBS using 10 kDa molecular-weight cutoff Slide-A-Lyzer carriages (ThermoFisher) of the appropriate size and the pooled fractions were sterile filtered. The concentration of the pool was measured by absorption at 280 nm using a Nanodrop ND-1000 spectrophotometer, with an extinction coefficient of the average of the three antibodies, calculated using the primary amino acid sequence of the antibodies (Isogen Life Science, Maarssen, The Netherlands). The composition was analyzed using analytical cation exchange chromatography as described in Example 8 as shown in FIG. 19. Quantification of the composition of the antibody mixture shows that the chromatography gave rise to an antibody product that complied with predetermined 1:1:1, to within a tolerance (Table 10), showing that the composition of an antibody load of variable composition can be controlled using chromatography.

TABLE 10

Quantitation of the analytical cation exchange chromatography profiles of input and normalized antibody mixtures.

| Mass Ratio | Antibody code | Input | | Output with controlled composition | |
|---|---|---|---|---|---|
| | | Analytical CIEX quantitation (%) | Mass amount (mg) | Analytical CIEX quantitation (%) | Mass amount (mg) |
| 1:2.4:1: | IgG1-2F8-V110D | 23.2 | 27.1 | 31.5 | 22.3 |
| | IgG1-7D8-S12P | 53.2 | 62.2 | 34.9 | 24.7 |
| | IgG1-HepC | 23.6 | 27.6 | 33.6 | 23.7 |
| | Total | | 116.9 | | 70.6 |

Example 23: Use of Charge Modulated Antibodies, Separation of an Antibody Mixture by Sequential Step Elutions on a Preparative Cation Exchange Column and Recovery to Yield an Antibody Mixture of Pre-Defined Composition This example describes a procedure to take a mixture of variable composition, perform an analytical assay to determine the composition and perform a chromatography step where the design space has been sufficiently pre-analyzed such that waste fractions containing excess antibodies can be extracted to yield a mixture of pre-determined composition (FIG. 1D).

Mixtures of IgG1-7D8, IgG1-224, IgG1-CD37-37-3, IgG1-CD19-21D4-E345K and IgG1-CD52-Campath-E345K (Example 1) were prepared by recombinantly expressing the individual antibodies using a transient production or CHO-K1 based expression system as described in Example 3 and individually purified by Protein A affinity chromatography as described in Example 5. The concentrations of the individual antibodies were measured using a Nanodrop ND-1000 spectrophotometer (Isogen Life Science, Maarssen, The Netherlands) and extinction coefficients calculated from the primary amino acid sequence of the pure antibodies. The antibody mixtures were prepared in PBS buffer (12.6 mM $NaH_2PO_4$, 140 mM NaCl, pH 7.4 buffer, B.Braun or Thermo Fisher) by mixing the antibodies in an equal mass ratio at a final concentration of 15.6 mg/mL.

An elution scheme in which each of the antibodies can be individually eluted by sequential step elutions is described in Example 9. Each of the 5 steps in the elution scheme was converted into two steps in which the first had a variable ionic strength, whereas the second was the same as that used in Example 9. The first step was designed to elute a broad peak that contained a single antibody specificity and that was similar in height and width for each of the five antibodies. The second step was designed to elute all of the remaining protein and provide baseline separation before elution of the next protein.

The antibody mixtures were diluted 20-fold in Loading Buffer (20 mM $NaHPO_4$, pH 6.5). During the screening of the salt concentration, the separation was performed according to Example 6 with a load of 10 g/L resin, except that the antibodies were eluted with 10 sequential step elution steps of alternating 10 and 7 column volumes containing Loading Buffer mixed with 13%, 19.5%, 20.7%, 29.4%, 31.5%, 39.5%, 39.5%, 44.6%, 47%, 61.2%; 13.5%, 19.5%, 21.2%, 29.4%, 32%, 39.5%, 39.6%, 44.6%, 47.5%, 61.2%; 14%, 19.5%, 21.7%, 29.4%, 32.5%, 39.5%, 39.8%, 44.6%, 48%, 61.2%; 14.5%, 19.5%, 22.2%, 29.4%, 33%, 39.5%, 40%, 44.6%, 48.5%, 61.2% or 15%, 19.5%, 22.7%, 29.4%, 33.5%, 39.5%, 40.2%, 44.6%, 49%, 61.2% (v/v) Elution Buffer (20 mM NaHPO$_4$, 250 mM NaCl pH 6.5) in separate experiments. The final conditions used Loading Buffer mixed with 14%, 19.5%, 21.7%, 29.4%, 32.5%, 39.5%, 39.8%, 44.6%, 48% and 61.2% v/v) Elution Buffer (20 mM NaHPO$_4$, 250 mM NaCl pH 6.5) to elute the antibodies. FIG. 20A shows the variation of peak shape varies with ionic strength for each of the five antibodies, with higher % buffer B corresponding to increased peak heights, and FIG. 20B shows the elution scheme that was selected based upon the chromatogram.

To study the design space, different ratios of the five antibodies were applied to the column in separate experiments. For each ratio, the volume of eluted protein that was depleted from the mixture was systematically varied, as described below. The output mixtures pools were analyzed by analytical cation exchange chromatography to understand the relationship between the amount of each protein in the pool and the volume of the depleted fractions. In this example, the design space of three proteins (IgG1-7D8, IgG1-CD37-37-3 and IgG1-CD52-Campath-E345K; peaks 1 3 and 5) was studied, whereas two proteins (IgG1-224 and IgG1-CD19-21D4-E345K; peaks 2 and 4) were not depleted so that they could be used as controls in the analytical cation exchange experiments.

Five mixtures of IgG1-7D8, IgG1-224, IgG1-CD37-37-3, IgG1-CD19-21D4-E345K and IgG1-CD52-Campath-E345K with different ratios of the antibodies were prepared in PBS buffer (12.6 mM NaH$_2$PO$_4$, 140 mM NaCl, pH 7.4 buffer, B.Braun or Thermo Fisher) at final concentrations between 2.6 mg/ml and 3.0 mg/ml. The mixtures had respectively mass ratios of 1.5:1:1.5:1:1.5, 2.5:1:2.5:1:2.5, 1.5:1:1:1.5:1.5, 2:1:1:2:2, 2.5:1:1:2.5:2.5.

Each mixture was diluted 20-fold in Loading Buffer (20 mM NaHPO$_4$, pH 6.5). The separation was performed according to Example 6 with a load of 10 g/L resin, except that the antibodies were eluted with 10 sequential step elution steps of alternating 10 and 7 column volumes of Loading Buffer mixed with 14%, 19.5%, 21.7%, 29.4%, 32.5%, 39.5%, 39.8%, 44.6%, 48% and 61.2% v/v) Elution Buffer (20 mM NaHPO$_4$, 250 mM NaCl pH 6.5). The end product protein mixtures were eluted into a single output vessel with the exception of a designated pre-determined waste volume, which was eluted into a separate vessel by switching the respective outlet valve, beginning two column volumes after the start of the elution of IgG1-7D8, IgG1-CD37-37-3 and IgG1-CD52-Campath-E345K; peaks 1 3 and 5 (FIG. 20C). Each mixture was purified in a design space experiment that comprises 5 different chromatography experiments that were essentially the same except that the waste volume was set to 0 mL, 10 mL, 20 mL, 30 ml or 40 mL, respectively (1.5:1:1.5:1:1.5 and 2.5:1:2.5:1:2.5 mixtures), or 0 mL, 12.5 mL, 25 ml, 37.5 ml or 50 mL, respectively (1.5:1:1:1.5:1.5, 2:1:1:2:2, 2.5:1:1:2.5:2.5). FIG. 20C shows an exemplary chromatogram during the design space experiments.

The end product pools collected during the design space experiments were analyzed by analytical cation exchange chromatography as described in Example 8. A set of analytical cation exchange chromatograms for one design space experiment (2.5:1:2.5:1:2.5 mixture) is shown in FIG. 20D, showing the effect of depleting increasing volumes during the first elution step of IgG1-7D8, IgG1-CD37-37-3 and IgG1-CD52-Campath-E345K.

The areas of each of the 5 peaks in each analytical cation exchange chromatogram were converted into concentrations by correcting for the specific extinction coefficients of the individual proteins and normalized against the concentration of IgG1-224 (peak 2; 1.5:1:1:1.5:1.5, 2:1:1:2:2 and 2.5:1:1: 2.5:2.5 mixtures) or IgG1-224 and IgG1-CD19-21D4-E345K (peaks 2 and 4; 1.5:1:1.5:1:1.5 and 2.5:1:2.5:1:2.5 mixtures). For each set of experiments corresponding to a single antibody mixture with different waste volumes, the masses of each protein were normalized against the amount of protein from the purification in which no waste volume was removed to calculate the fraction of retained protein (Table 11; FIG. 20E-F). In this example, the data for IgG1-7D8, IgG1-CD37-37-3 and IgG1-CD52-Campath-E345K, normalized for the load amount of each protein, were fitted assuming a linear correlation between the mass of the protein in the pool and the volume of the waste fraction. This is a simplified model of the chromatographic behavior since it assumes no complexity in the peak shape and no change in the peak share with the column load. The R$^2$ correlation coefficients were 0.97, 0.95 and 0.93 respectively for the three proteins (FIG. 20E). Finally, all of the data, normalized for the load amount of each protein, were simultaneously fitted as a simple model to describe the relative depletion of all five proteins with increasing waste volume (FIG. 20F). This model assumes that the elution behavior of all proteins is identical under these conditions. The model was applied to four antibody different mixtures of IgG1-7D8, IgG1-224, IgG1-CD37-37-3, IgG1-CD19-21D4-E345K and IgG1-CD52-Campath-E345K with different antibody compositions, with release specifications of 20%+/−2% for each component. First, the mixtures were prepared by mixing the individually protein A purified components in PBS buffer (12.6 mM NaH$_2$PO$_4$, 140 mM NaCl, pH 7.4 buffer, B.Braun or Thermo Fisher) to mimic an upstream process with insufficient control of the composition followed by a capture chromatography step. Next, the mixtures were analyzed by analytical cation exchange chromatography as described in Example 8. The areas of each of the 5 peaks in the analytical action exchange chromatograms were converted into mass concentrations by correcting for the specific extinction coefficients of the individual proteins, and the amounts of each protein to be loaded onto the preparative cation exchange column were inferred by assuming a total protein load of 10 g/L resin. The waste volumes for each protein were calculated according to the following equation:

$$V=(m_{min}-m)/mk$$

where V=waste volume to yield an equi-mass mixture, m=mass of protein on column, m$_{min}$=mass of limiting protein on column, k=first order approximation of depletion rate FIG. 20F (−0.0178 mL-1).

Next, preparative cation exchange chromatography was preformed to recover an equi-mass mixture of the five antibodies. The separation was performed according to Example 6 with a load of 10 g/L resin, except that the antibodies were eluted with 10 sequential step elution steps of alternating 10 and 7 column volumes containing Loading Buffer mixed with 14%, 19.5%, 21.7%, 29.4%, 32.5%, 39.5%, 39.8%, 44.6%, 48% and 61.2% v/v) Elution Buffer (20 mM NaHPO$_4$, 250 mM NaCl pH 6.5). The end product protein mixtures were eluted into a single output vessel with the exception of designated pre-determined waste volumes that began two column volumes after the start of the elution, which were eluted into a separate vessel, for each of the four non-limiting antibodies. Finally, the end product protein mixtures were analyzed by analytical cation exchange chromatography according to Example 8. The preparative cation exchange chromatograms of the four mixtures and the analytical cation exchange chromatograms of the input material and end products are summarized in FIGS. 20G-N. The waste volumes and results are summarized in Table 12.

The results show that whereas input mixtures A-C were out of specifications (20%+/−2% for each component), the output mixtures we within specifications, showing that the approach could be used to control the composition of a polyclonal mixture.

Input mixture D was out of specification, but was not brought into specification by applying the method. This mixture had the largest excess of IgG1-CD52-Campath-E345K, which was least well described by the design space experiments as demonstrated by a lower correlation coefficient (FIG. 20E), and large excess of IgG1-224, which was not varied in the design space experiments. The method could be improved for more challenging mixtures by refining the model to better describe the relationship between the output amount of each antibody and the waste volume. An improved model could be established for example by applying a different model for each component in the mixture, by using more data points in the model, by applying interpolation between experimental points instead of relying on first-order approximation, or by using a more complex model, such as fitting Gaussian peak shapes.

TABLE 11

Quantitation of the depletion rate of individual antibody components from the input mixtures as a function of the depleted volume during preparative cation exchange chromatography of a 2.5:1:1:2.5:2.5 mixture of IgG1-7D8, IgG1-224, IgG1-CD37-37-3, IgG1-CD19-21D4-E345K and IgG1-CD52-Campath-E345K. Analytical cation exchange chromatography peak areas were normalized for each tested antibody (Area_rel) relative to the area observed for undepleted IgG1-224 as an internal control (Area_ref), while correcting for their respective extinction coefficients (ext. coeff .; ε). The fraction of protein retained (prot_ret) was then normalized relative to the amount present in the input mixture measured at 0.0 mL depleted volume. The depletion rate k was then determined as the first-order derivative (slope) of fraction protein retained (prot_ret) over the depleted volume (depleted V).

| depleted V(mL) | IgG1-7D8 Area (uV * sec) | IgG1-224 Area (uV * sec) | IgG1-CD37-37-3 Area (uV * sec) | IgG1-CD19-21D4-E345K Area (uV * sec) | IgG1-CD52-Campath-E345K Area (uV * sec) |
|---|---|---|---|---|---|
| 0.0 | 607497 | 206432 | 233547 | 600592 | 467760 |
| 12.5 | 658064 | 260614 | 269351 | 770532 | 392771 |
| 25.0 | 470623 | 275221 | 191529 | 791904 | 192960 |
| 37.5 | 259813 | 359182 | 102702 | 1043105 | 149374 |
| 50.0 | 139631 | 386318 | 62461 | 1116451 | 135682 |
| ext. coeff. | 1.528 | 1.495 | 1.529 | 1.569 | 1.317 |

Calculation of relative area: Area_rel = (Area_sample/Area_ref) * (ε_ref/ε_sample)

| depleted V(mL) | Area_rel (fraction) | Area_rel (fraction) | Area_rel (fraction) | Area_rel (fraction) | Area_rel (fraction) |
|---|---|---|---|---|---|
| 0.0 | 2.88 | 1.00 | 1.11 | 2.77 | 2.57 |
| 12.5 | 2.47 | 1.00 | 1.01 | 2.82 | 1.71 |
| 25.0 | 1.67 | 1.00 | 0.68 | 2.74 | 0.80 |
| 37.5 | 0.71 | 1.00 | 0.28 | 2.77 | 0.47 |
| 50.0 | 0.35 | 1.00 | 0.16 | 2.75 | 0.40 |

Calculation of fraction protein retained: prot_ret = Area_rel (V)/Area_rel (V = 0.0)

| depleted V(mL) | prot_ret (fraction) | prot_ret (fraction) | prot_ret (fraction) | prot_ret (fraction) | prot_ret (fraction) |
|---|---|---|---|---|---|
| 0.0 | 1.00 | 1.00 | 1.00 | 1.00 | 1.00 |
| 12.5 | 0.86 | 1.00 | 0.91 | 1.02 | 0.67 |
| 25.0 | 0.58 | 1.00 | 0.62 | 0.99 | 0.31 |
| 37.5 | 0.25 | 1.00 | 0.25 | 1.00 | 0.18 |
| 50.0 | 0.12 | 1.00 | 0.14 | 0.99 | 0.15 |

Calculation of depletion rate k (1/mL): k = d(prot ret)/dV (slope of first order approximation)

| | IgG1-7D8 | IgG1-224 | IgG1-CD37-37-3 | IgG1-CD19-21D4-E345K | IgG1-CD52-Campath-E345K |
|---|---|---|---|---|---|
| k(1/mL) | −0.0189 | 0.0000 | −0.0190 | −0.0003 | −0.0174 |

TABLE 12

Quantitation of the analytical cation exchange chromatography profiles of input and output antibody mixtures, normalized for the specific extinction coefficients of the individual components, and the preparative chromatography waste volumes.

| Antibody mixture | Antibody | Input area (%) | Waste volume (mL) | Output area (%) |
|---|---|---|---|---|
| A | IgG1-7D8, | 24.4 | 20.0 | 21.5 |
|   | IgG1-224, | 15.9 | 0.0 | 20.0 |
|   | IgG1-CD37-37-3, | 18.7 | 8.6 | 21.7 |
|   | IgG1-CD19-21D4-E345K | 19.2 | 9.8 | 18.6 |
|   | IgG1-CD52-Campath-E345K | 21.9 | 15.8 | 18.2 |
| B | IgG1-7D8, | 25.4 | 23.4 | 20.8 |
|   | IgG1-224, | 19.8 | 13.8 | 19.5 |
|   | IgG1-CD37-37-3, | 24.6 | 22.3 | 21.2 |
|   | IgG1-CD19-21D4-E345K | 15.1 | 0.3 | 19.0 |
|   | IgG1-CD52-Campath-E345K | 15.0 | 0.0 | 19.5 |
| C | IgG1-7D8, | 32.6 | 34.1 | 18.2 |
|   | IgG1-224, | 19.7 | 18.9 | 19.6 |
|   | IgG1-CD37-37-3, | 13.2 | 0.0 | 21.7 |
|   | IgG1-CD19-21D4-E345K | 17.3 | 13.5 | 19.3 |
|   | IgG1-CD52-Campath-E345K | 17.2 | 13.4 | 21.2 |
| D | IgG1-7D8, | 17.8 | 13.2 | 25.2 |
|   | IgG1-224, | 22.6 | 22.7 | 17.7 |
|   | IgG1-CD37-37-3, | 13.7 | 0.0 | 22.5 |
|   | IgG1-CD19-21D4-E345K | 17.7 | 12.9 | 20.9 |
|   | IgG1-CD52-Campath-E345K | 28.2 | 29.5 | 13.7 |

Example 24: Control of the Composition of a Recombinant Antibody Mixture of IgG1 Variants Using Affinity Chromatography This example describes a procedure to take a mixture of variable composition and perform chromatography using affinity chromatography resins with specificity for the different components that are eluted to yield a mixture of pre-determined composition (FIG. 1B).

IgG1-2F8-V110D, IgG1-7D8-S12P or IgG1-HepC were recombinantly produced as described in Example 3 and the antibody titers were calculated as described in Example 4. These proteins were selected or engineered to bind specifically to Protein L (GE Healthcare), KappaSelect (GE Healthcare), or LambdaFabSelect (GE Healthcare) resins, respectively, as described in Examples 15, 16 and 20. The culture supernatants were mixed to yield theoretical antibody concentration ratio of approximately 1:1:1 or 1:1.5:2 and a total amount of approximately 185 mg or 275 mg, respectively, according to the biolayer interferometry measurements, to simulate an upstream process for co-production of a mixture of antibodies.

Figure 21A:
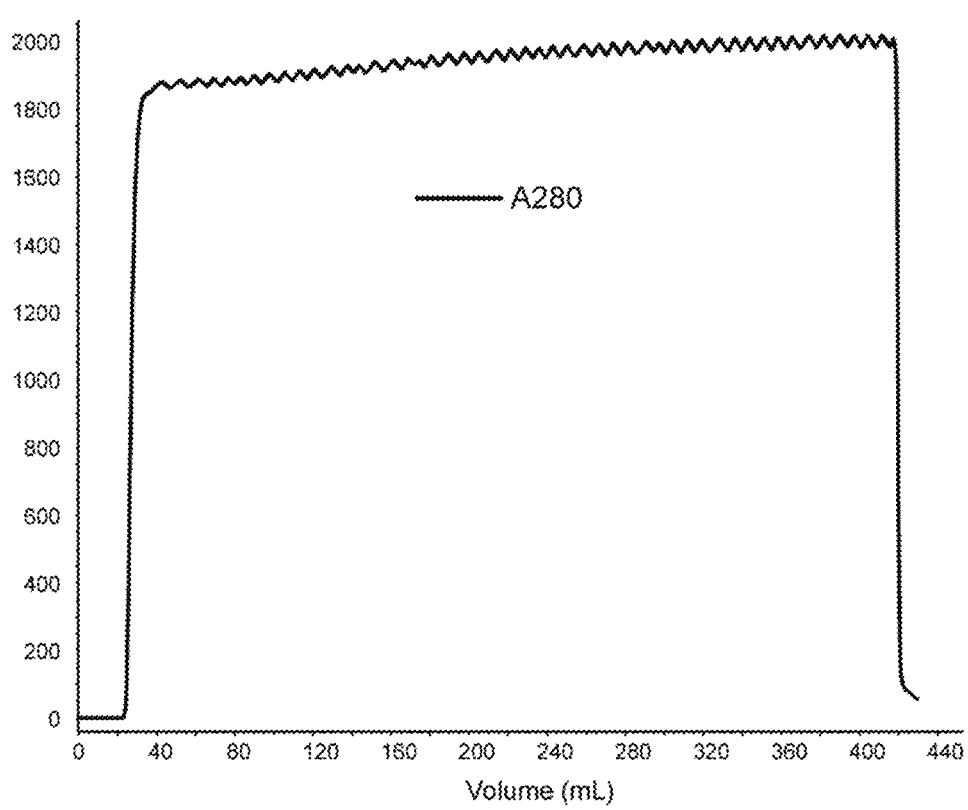
Figure 21B:
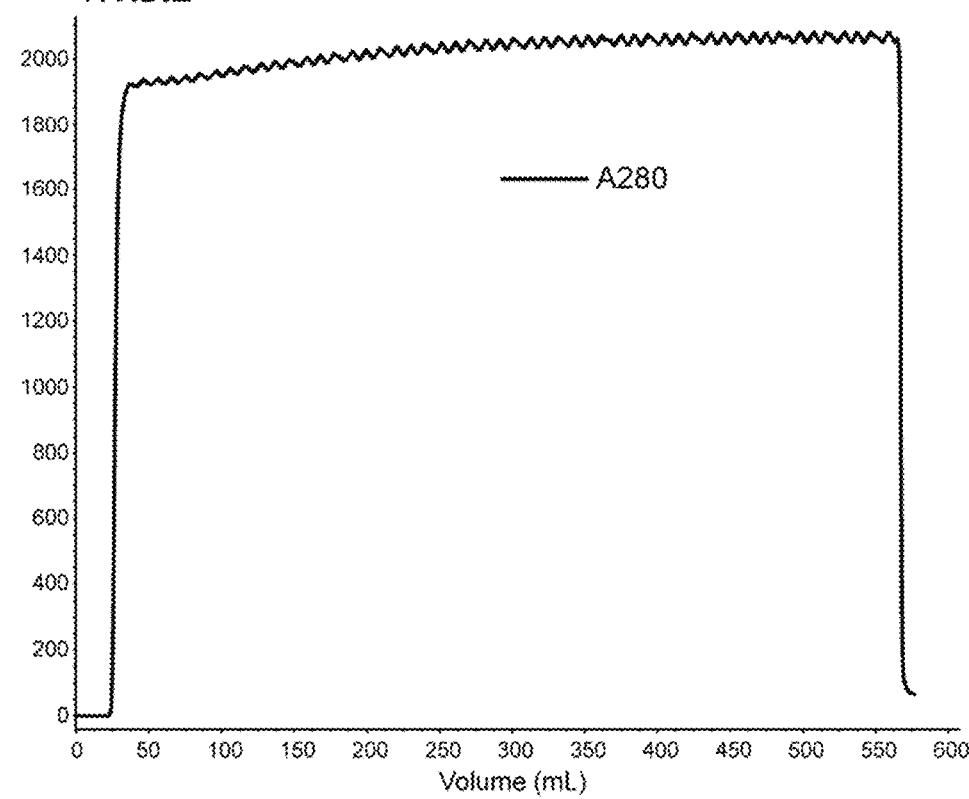

1 mL HiTrap® KappaSelect (GE Healthcare), LambdaFabSelect (GE Healthcare) and Protein L (GE Healthcare) columns that were joined in tandem were pre-equilibrated with Phosphate Buffered Saline (PBS; 12.6 mM sodium phosphate, 140 mM sodium chloride, pH 7.4, B.Braun or Thermo Fisher). Supernatant containing approximately 180 mg or 270 mg of the 1:1:1 or 1:1.5:2 mixtures of IgG1-2F8-V110D, IgG1-7D8-S12P and IgG1-HepC were loaded onto the columns at a flow rate of 0.5 mL/minute and washed with PBS (FIG. 21A-B).

Figure 21C:
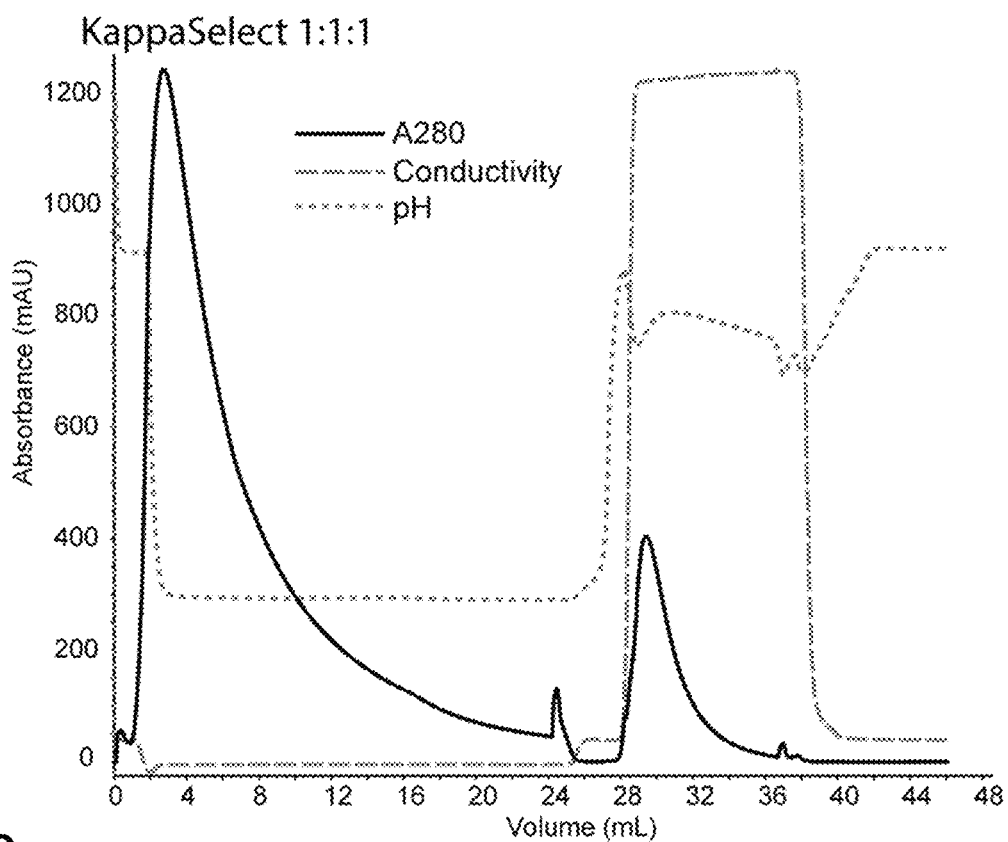
Figure 21D:
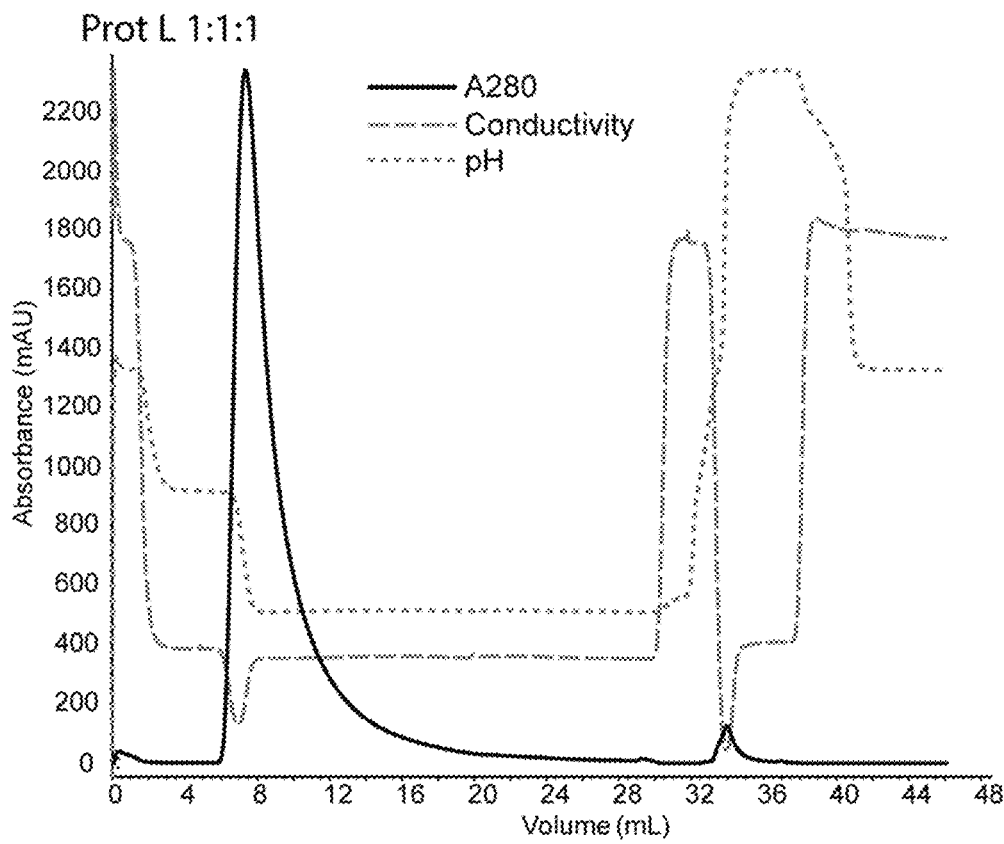
Figure 21E:
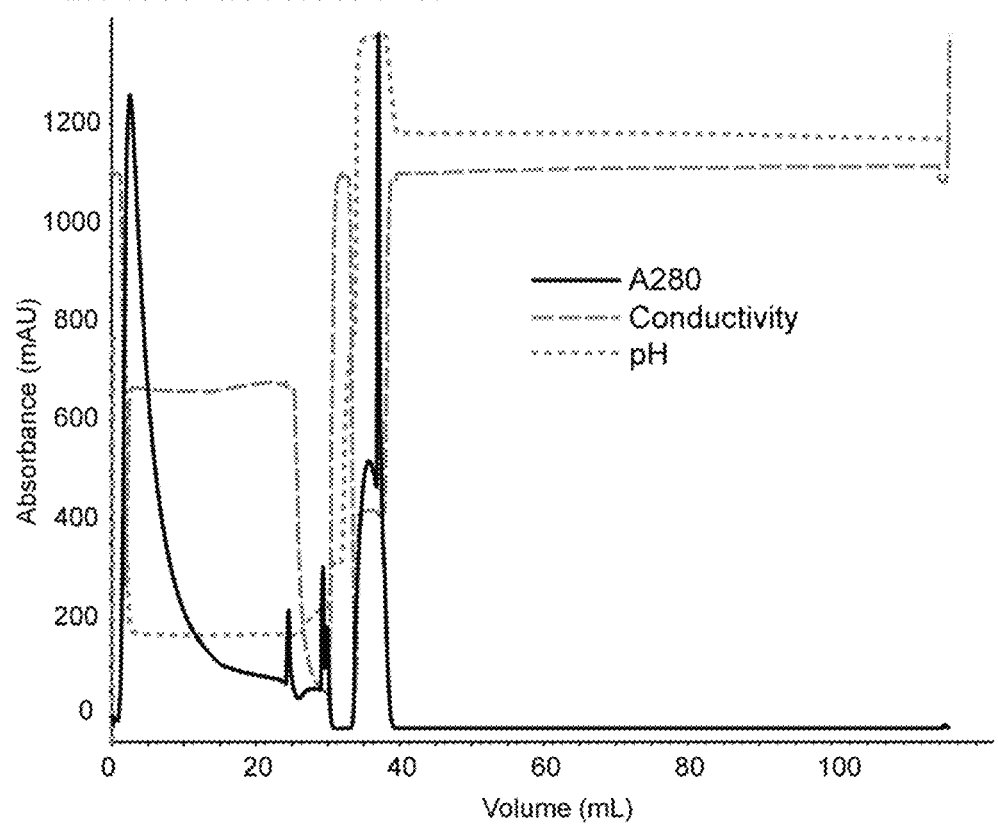

The columns were eluted individually since there were differences in the elution and cleaning buffers between the columns. The HiTrap KappaSelect column was eluted with 0.1 M glycine-HCl pH 3.0. Specifically bound material was eluted with 0.1 M glycine-HCl pH 2.5. The column was cleaned using 6 M Guanidine HCl. The HiTrap Protein L column was washed with 0.02 M sodium citrate-NaOH, pH 5.0 and specifically bound material was eluted with 0.1 M glycine-HCl pH 3.0. The column was cleaned using 0.015 M NaOH. The HiTrap LambdaFabSelect column (GE Healthcare) was eluted with 0.1 M glycine-HCl pH 2.0, followed by 0.5 M acetic acid. The column was cleaned using 0.025 M NaOH. Exemplary chromatograms are shown in FIGS. 21C-E. The eluted fractions with significant absorption at 280 nM in each case were pooled, dialyzed into PBS using 30 kDa molecular-weight cutoff Slide-A-Lyzer carriages (ThermoFisher) of the appropriate size and the pooled fractions were sterile filtered.

Figure 21F:
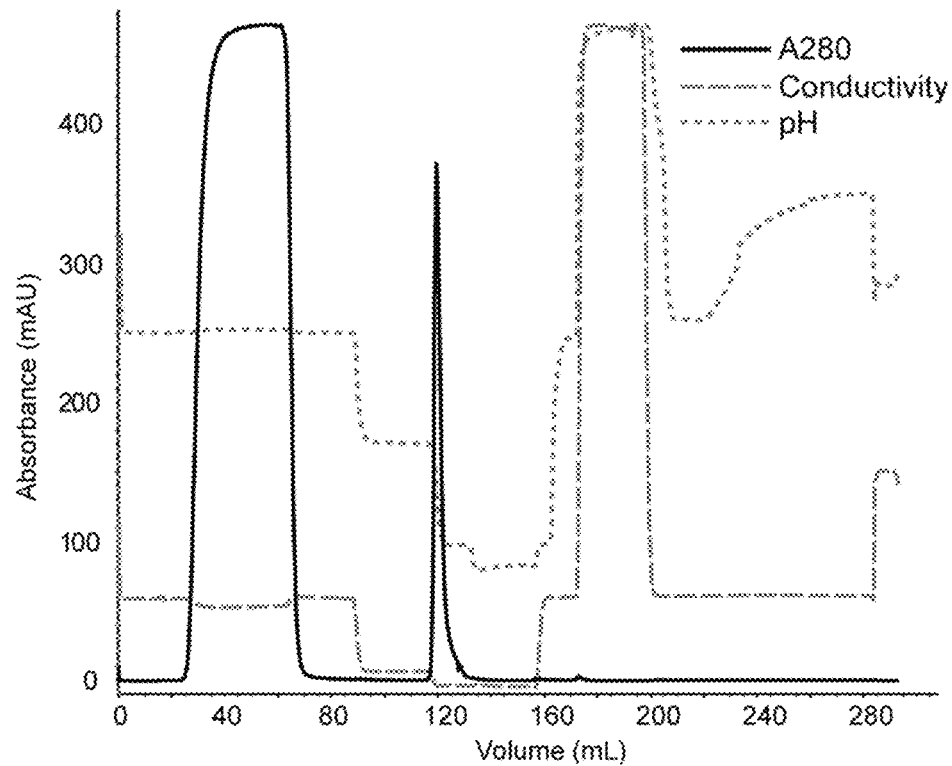

Alternatively, approximately 5 mg of the supernatant containing 1:1:1 or 1:1.5:2 mixtures of IgG1-2F8-V110D, IgG1-7D8-S12P and IgG1-HepC were purified by Protein A affinity chromatography as described in Example 5. FIG. 21F shows an exemplary chromatogram for the protein A purification of the antibody mixture.

Figure 21G:
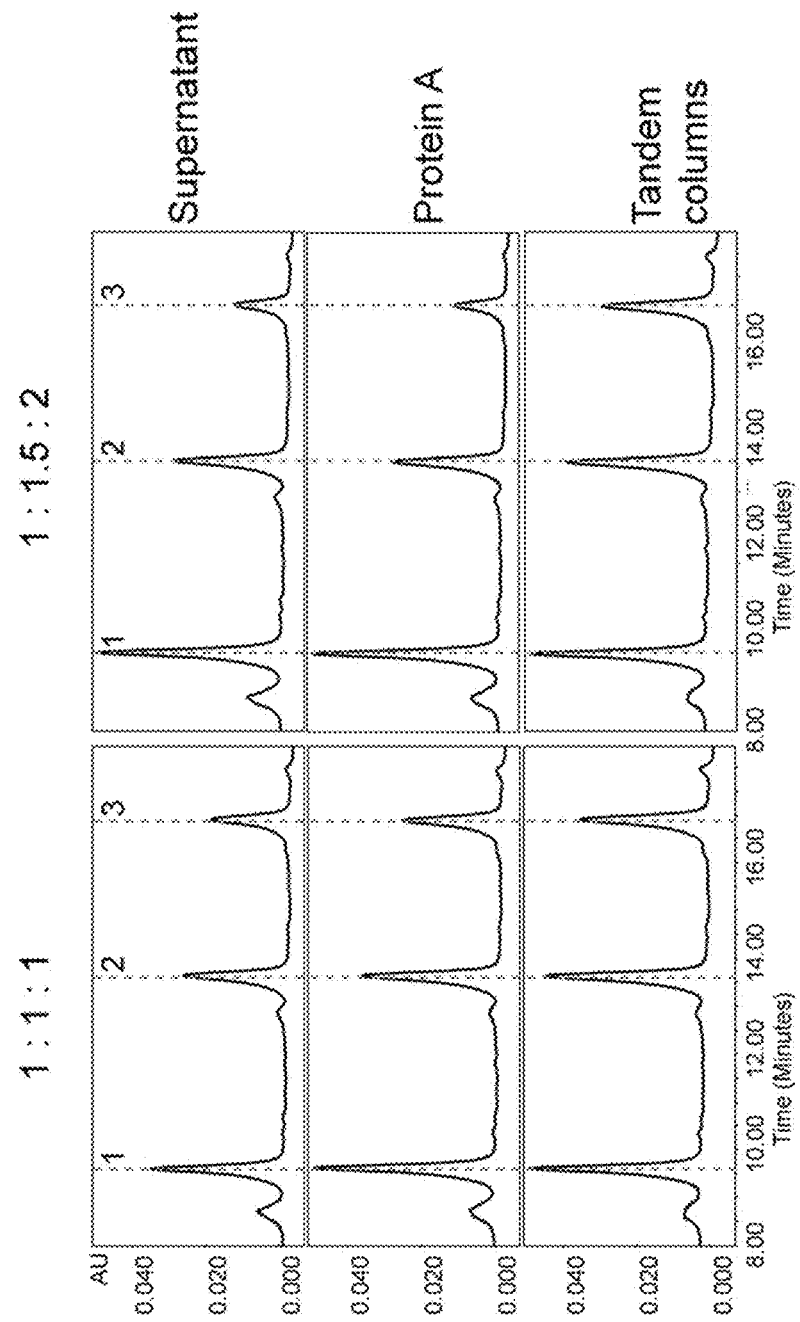

The composition of the output mixtures from the different purification experiments was analyzed using analytical cation exchange chromatography as described in Example 8, together with the sterile filtered cell culture supernatant mixtures that were loaded onto the analytical cation exchange columns and analyzed by a method analogous to that described in Example 8. The chromatograms are shown in FIG. 21G and quantified in Table 13. The data show that whereas the ratios of the input mixtures are significantly different and the protein A purification step does not significantly alter the composition of the mixtures, the tandem purification of Protein L, KappaSelect and LambdaFabSelect produce an output mixture of similar composition for both mixtures, showing that this approach can be used to control the composition of a polyclonal antibody mixture. The output ratio could be adjusted by adjusting the relative amounts of resin in three orthogonal affinity columns, based upon the experimentally determined dynamic binding capacities of the resins under relevant loading conditions. If light-chain specific affinity resins are used, an orthogonal step could be required to remove co-purified free light chain or light chain dimers.

TABLE 13

Quantitation of the analytical cation exchange chromatography profiles of input and normalized antibody mixtures.

| | | Analytical cation exchange quantitation (%) | | |
|---|---|---|---|---|
| Ratio | Antibody code | Supernatant input mixture | Protein A-purified mixture | Output mixture with controlled composition |
| 1:1:1 | IgG1-2F8-V110D | 30.6 | 30.2 | 35.6 |
|   | IgG1-7D8-S12P | 34.5 | 34.7 | 35.9 |
|   | IgG1-HepC | 34.9 | 35.1 | 28.4 |
| 1:1.5:2 | IgG1-2F8-V110D | 19.7 | 18.9 | 32.7 |
|   | IgG1-7D8-S12P | 34.7 | 34.8 | 35.5 |
|   | IgG1-HepC | 45.6 | 46.3 | 31.8 |

The invention claimed is:

1. A method for producing an output mixture of two or more different antibodies having a difference in their amino acid sequences, which difference enables separation of the antibodies by chromatography, wherein the difference in the amino acid sequence of said two or more different antibodies results in a difference in (i) the charge properties of the two or more antibodies so that the two or more antibodies interact differently with a chromatography resin, (ii) the hydrophobic properties of the two or more antibodies so that the two or more antibodies interact differently with a chromatography resin, or (iii) affinity for a chromatography resin, and wherein the two or more different antibodies are present in said output mixture at, or essentially at, a desired or predetermined concentration ratio; and the method comprises the steps of:

(a) providing an input mixture wherein the two or more different antibodies are not present at, or essentially at, the desired or predetermined concentration ratio;

(b) separating the two or more antibodies by said chromatography; and (c) recovering the two or more antibodies in the amounts required to provide the output mixture.

2. The method according to claim 1, further comprising processing said output mixture to produce a drug substance, wherein the two or more different antibodies are present at, or essentially at, the desired or predetermined concentration ratio.

3. The method according to claim 1, wherein each of the two or more antibodies in the input mixture is also found in the output mixture.

4. The method according to claim 1, wherein (i) step (c) comprises recovering the two or more antibodies in the same pool or fraction or (ii) step (c) comprises recovering the two or more antibodies in multiple pools or fractions, and combining said multiple pools or fractions or parts of said multiple pools or fractions, thereby obtaining the output mixture.

5. The method according to claim 1, wherein the chromatography in step (b) produces an eluate and a flow-through and the output mixture is produced by:
   i) collecting the eluate and discarding the flow-through; or
   ii) discarding the eluate and collecting the flow-through.

6. The method according to claim 5, wherein step (b) comprises adjusting the conditions of the chromatography step so that the total binding capacity for a given antibody under these conditions is adequate to retain the amount of each antibody which is required in order to provide the output mixture.

7. The method according to claim 1, wherein
   (a) the least abundant of said two or more different antibodies is present in an amount which is at least 1% (w/w), 2% (w/w), 3% (w/w), 4% (w/w), 5% (w/w), 6% (w/w), 7% (w/w), 8% (w/w), 9% (w/w) or 10% (w/w) of the amount of the most abundant of the said two or more different antibodies; and/or
   (b) the two or more antibodies are present in such amounts that the ratio (w/w) between the amounts of any two antibodies is between 1:5 and 5:1.

8. The method according to claim 1, wherein at least one of said two or more antibodies is an antibody binding an antigen expressed on the surface of a tumor and/or an antigen associated with or expressed during an immune or autoimmune disease, an inflammatory disease, a cardiovascular disease, a disease in the central nervous system (CNS) or a musculo-skeletal disease.

9. The method according to claim 1, wherein the chromatography resin is selected from the group consisting of: affinity resin, ion exchange resin, hydrophobic interaction resin and mixed mode resin.

10. The method according to claim 1, wherein the method comprises the separation of the two or more antibodies and depletion of excess of one or more of the antibodies to recover the predetermined ratio of the two or more different antibodies.

11. The method according to claim 1, wherein the two or more different antibodies of the output mixture are recovered in a single pool in step (c).

12. The method according to claim 1, wherein the two or more antibodies are separated in step (b) into different fractions and wherein the fractions which contain one of the antibodies at a purity of at least 80% are subsequently pooled at the predetermined concentration ratio of the different antibodies to recover the output mixture.

13. The method according to claim 1, comprising
   i) separating in step (b) the two or more antibodies into different fractions, and selecting for each antibody one or more fractions containing that antibody at a purity of at least 80%; and
   ii) providing said output mixture by pooling volumes of the selected fractions, the size of the volumes being adjusted to provide the predetermined concentration ratio of said two or more antibodies.

14. The method according to claim 1, comprising a further step of determining the concentration of the antibodies in each fraction prior to the pooling of the antibodies.

15. The method according to claim 1, wherein the separation of the two or more antibodies is done by (a) a single chromatography step using a single chromatography resin or (b) use of a mixture of chromatography resins at a predetermined ratio.

16. The method according to claim 1, wherein the composition of the input mixture is measured using an analytical assay prior to step (b).

17. The method according to claim 1, wherein the method comprises an initial step of determining the separability of the two or more antibodies by chromatography, and if the different antibodies are inseparable, then modifying the amino acid sequence of one or more of the antibodies to obtain separability by chromatography.

18. The method according to claim 17, wherein the modification comprises a modification in the constant domain of one or more of the antibodies, a modification in the variable domain of one or more of the antibodies, and/or a modification in the framework sequence of the light chain variable region and/or of the heavy chain variable region.

19. The method according to claim 17, wherein the modifications do not alter the functional characteristics of the one or more modified antibodies.

20. The method according to claim 19, wherein the functional characteristics which are unaltered are selected from the group consisting of: the antibody binding affinity, effector functions, avidity and clustering.

21. The method according to claim 17, wherein
   (a) the modification comprises one or more amino acid substitutions in the heavy chain variable region and/or in the light chain variable region of one or more of the antibodies, wherein the substitution is at a position selected from the group consisting of: 1, 6, 17, 24, 48, 75, 90, 93, 96, and 97 in the heavy chain variable region and/or from the group consisting of: 1, 4, 47, 48, 51, 68, 74, 80, 90, 93, and 95 in the light chain variable region, wherein the numbering is according to the IMGT numbering of IgG1 variable regions,
   (b) modifying the one or more antibodies comprises introducing at least one amino acid substitution in a kappa light chain constant region of one or more of the antibodies, wherein the substitution eliminates binding to an affinity resin and wherein the substitution is selected from the group comprising V110D, V110R, V110E, V110H, V110K, V110N, V110P, V110Q, V110W and E143D using the EU numbering system and wherein the chromatography uses the affinity resin for which the substitution eliminates binding,
   (c) modifying the one or more antibodies comprises introducing at least one amino acid substitution which is an S12P substitution in the light chain variable region when using IMGT for numbering, wherein the substitution eliminates binding to an affinity resin and wherein the chromatography uses the affinity resin for which the substitution eliminates binding,
   (d) modifying the one or more antibodies comprises introducing at least one amino acid substitution in said one or more of the antibodies, wherein the substitution is in the CH1 domain and comprises an S157T and/or a T164S mutation using the EU numbering system, wherein the substitution eliminates binding to an affinity resin, and wherein the chromatography uses the affinity resin for which the substitution eliminates binding, and/or
   (e) modifying the one or more antibodies comprises introducing at least one amino acid substitution in the heavy chain constant region of said one or more antibodies, wherein the substitution is selected from the group comprising M252A, S254M, E380A, E380M, E382A, E382L, S426M, M428G, M428T, M428V, H433D, N434A, N434G, N434S, and M428A using the EU numbering system, wherein the substitution eliminates binding to an affinity resin, and wherein the chromatography uses the affinity resin for which the substitution eliminates binding.

22. The method according to claim 21, wherein the one or more substitutions introduce an amino acid which has a different charge than the wild type amino acid at the corresponding position.

23. The method according to claim 22, wherein the one or more amino acid substitutions comprises an E345K substitution in the heavy chain constant region using the EU numbering system.

24. The method of claim 21, wherein
   (i) the affinity reagent in subpart (b) for which binding is eliminated is a resin which binds to the kappa light chain such as a KappaSelect or KappaXL resin,
   (ii) the affinity resin in subpart (c) is Protein L resin,
   (iii) the affinity resin in subpart (d) is an IgG-CH1 affinity resin, and/or
   (iv) affinity resin in subpart (e) is Protein G resin.

25. The method according to claim 1, wherein two or more antibodies are determined to be separable
   (a) if the resolution (Rs) is Rs≥20.3 as determined in one or more chromatography assays selected from the group consisting of: hydrophobic interaction chromatography assay, cation exchange chromatography assay, and a mixed mode chromatography assay; using an ionic strength gradient with Rs≥0.3 according to the equation Rs=2 (t2−t1)/(W1+W2) where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline, or
   (b) as determined in an affinity chromatography assay if baseline separation is achieved between antibodies in the unbound fractions that do not bind to the column and fractions eluting from the column, or if the resolution (Rs) is Rs≥0.3 as determined in an affinity chromatography assay using a pH gradient with Rs≥0.3 according to the equation Rs=2 (t2−t1)/(W1+W2) where t1=retention time of a given antibody, t2=retention time of the sequentially-eluting antibody, and W1 and W2 are the corresponding peak widths of the antibodies at the bases of the peaks obtained by extrapolating the relatively straight sides of the main peaks to the baseline.

26. The method according to claim 1, wherein the two or more different antibodies are:
   (a) expressed in and provided from different production host cells,
   (b) expressed in and provided from different production host cells co-cultured in a single vessel, or
   (c) co-expressed in a single production host cell.

27. The method according to claim 1, wherein the two or more different antibodies are selected from the group comprising IgG1, IgG2, IgG3 or IgG4 antibodies or a combination thereof.

28. The method according to claim 1, wherein the two or more different antibodies are full length antibodies.

29. The method according to claim 1, wherein the two or more different antibodies are humanized antibodies, chimeric antibodies, human antibodies or a combination of these.

30. The method according to claim 1, wherein at least one of said two or more different antibodies is a monoclonal antibody.

31. The method according to claim 1, wherein the method is for the production of an antibody batch for the treatment of a disease, for clinical trials, for toxicology studies or for determining batch-to-batch consistency.

32. The method according to claim 1, wherein at least one of the two or more different antibodies is specific for a target on a tumor cell.

33. The method according to claim 8, wherein the tumor is a metastatic solid tumor.

34. The method according to claim 8, wherein the tumor is a hematologic tumor.

35. The method of claim 8, wherein the target on a tumor cell is erbB1, erbB2, erbB3, erbB4, MUC-1, CD19, CD20, CD4, CD38, CD138, CXCR5, c-Met, HERV-envelop protein, periostin, Bigh3, SPARC, BCR, CD79, CD37, EGFrvIII, U-CAM, AXL, Tissue Factor, CD74, EpCAM, or MRP3.

36. The method of claim 32, wherein the target on an effector cell is CD1, CD3, CD4, CD8, FcgammaRIII, CD25, CD89, CD32, CD32a, FCεRI, CD40, or FcgammaRI.

* * * * *

UNITED STATES PATENT AND TRADEMARK OFFICE
CERTIFICATE OF CORRECTION

PATENT NO. : 12,247,065 B2
APPLICATION NO. : 17/253286
DATED : March 11, 2025
INVENTOR(S) : Richard Hibbert et al.

It is certified that error appears in the above-identified patent and that said Letters Patent is hereby corrected as shown below:

In the Claims

At Column 135, Claim number 25, Line number 19, delete "(a) if the resolution (Rs) is Rs$\geq$20.3 as determined in one" and insert --(a) if the resolution (Rs) is Rs$\geq$0.3 as determined in one--

At Column 136, Claim number 32, Line number 29, delete "on a tumor cell." and insert --on a tumor cell and/or is specific for a target on an effector cell.--

At Column 136, Claim number 35, Line number 34, delete "The method of claim 8, wherein the target on a tumor" and insert --The method of claim 32, wherein the target on a tumor--

Signed and Sealed this
Twenty-ninth Day of April, 2025

Coke Morgan Stewart
*Acting Director of the United States Patent and Trademark Office*

SEQUENCE LISTING

<160> NUMBER OF SEQ ID NOS: 64

<210> SEQ ID NO 1
<211> LENGTH: 122
<212> TYPE: PRT
<213> ORGANISM: Homo Sapiens

<400> SEQUENCE: 1

Glu Val Gln Leu Val Glu Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Tyr Phe Tyr Gly Met Asp Val Trp
            100                 105                 110

Gly Gln Gly Thr Thr Val Thr Val Ser Ser
        115                 120

<210> SEQ ID NO 2
<211> LENGTH: 122
<212> TYPE: PRT
<213> ORGANISM: Homo Sapiens

<400> SEQUENCE: 2

Glu Val Gln Leu Val Glu Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Glu Asp Thr Ala Ile Tyr Tyr Cys
                85                  90                  95

Ala Arg Gln Arg Gly Asp Tyr Tyr Tyr Phe Tyr Gly Met Asp Val Trp
            100                 105                 110

Gly Gln Gly Thr Thr Val Thr Val Ser Ser
        115                 120

<210> SEQ ID NO 3
<211> LENGTH: 122
<212> TYPE: PRT
<213> ORGANISM: Homo Sapiens

<400> SEQUENCE: 3

Glu Val Gln Leu Val Glu Ser Gly Ala Glu Val Lys Lys Pro Gly Glu
1               5                   10                  15

Ser Leu Lys Ile Ser Cys Ala Ala Ser Gly Tyr Ser Phe His Phe Tyr
            20                  25                  30

Trp Ile Gly Trp Val Arg Gln Met Pro Gly Lys Gly Leu Glu Trp Met
            35                  40                  45

Gly Ser Ile Tyr Pro Gly Asp Ser Asp Thr Arg Tyr Arg Pro Ser Phe
        50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Glu Asp Thr Ala Ile Tyr Tyr Cys
                85                  90                  95

Ala Arg Gln Arg Gly Asp Tyr Tyr Tyr Phe Tyr Gly Met Asp Val Trp
                100                 105                 110

Gly Gln Gly Thr Thr Val Thr Val Ser Ser
            115                 120

<210> SEQ ID NO 4
<211> LENGTH: 122
<212> TYPE: PRT
<213> ORGANISM: Homo Sapiens

<400> SEQUENCE: 4

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
            35                  40                  45

Gly Ser Ile Tyr Pro Gly Asp Ser Asp Thr Arg Tyr Arg Pro Ser Phe
        50                  55                  60

Gln Gly Arg Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Tyr Phe Tyr Gly Met Asp Val Trp
                100                 105                 110

Gly Gln Gly Thr Thr Val Thr Val Ser Ser
            115                 120

<210> SEQ ID NO 5
<211> LENGTH: 122
<212> TYPE: PRT
<213> ORGANISM: Homo Sapiens

<400> SEQUENCE: 5

Glu Val Gln Leu Val Gln Ser Gly Ala Glu Val Lys Lys Pro Gly Ala
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
            35                  40                  45

Gly Ser Ile Tyr Pro Gly Asp Ser Asp Thr Arg Tyr Arg Pro Ser Phe
        50                  55                  60

Gln Gly Arg Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Tyr Phe Tyr Gly Met Asp Val Trp
                100                 105                 110

Gly Gln Gly Thr Thr Val Thr Val Ser Ser
            115                 120

<210> SEQ ID NO 6
<211> LENGTH: 122
<212> TYPE: PRT
<213> ORGANISM: Homo Sapiens

<400> SEQUENCE: 6

Glu Val Gln Leu Val Gln Ser Gly Ala Glu Val Lys Lys Pro Gly Ala
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Arg Val Thr Ile Ser Ala Asp Lys Ser Ile Ser Thr Ala Tyr
65                  70                  75                  80

Leu Gln Trp Thr Arg Leu Lys Ala Ser Asp Thr Ala Ile Tyr Tyr Cys
                85                  90                  95

Ala Arg Gln Arg Gly Asp Tyr Tyr Phe Tyr Gly Met Asp Val Trp
            100                 105                 110

Gly Gln Gly Thr Thr Val Thr Val Ser Ser
            115                 120

<210> SEQ ID NO 7
<211> LENGTH: 122
<212> TYPE: PRT
<213> ORGANISM: Homo Sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Phe Tyr Gly Met Asp Val Trp
            100                 105                 110

Gly Gln Gly Thr Thr Val Thr Val Ser Ser
            115                 120

<210> SEQ ID NO 8
<211> LENGTH: 122
<212> TYPE: PRT
<213> ORGANISM: Homo Sapiens

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Phe Tyr Gly Met Asp Val Trp
            100                 105                 110

Gly Gln Gly Thr Thr Val Thr Val Ser Ser
            115                 120

<210> SEQ ID NO 9
<211> LENGTH: 107
<212> TYPE: PRT
<213> ORGANISM: Homo Sapiens

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Homo Sapiens

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Asp Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 11
<211> LENGTH: 107
<212> TYPE: PRT
<213> ORGANISM: Homo Sapiens

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Asp Gln Val Pro Gln Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 12
<211> LENGTH: 107
<212> TYPE: PRT
<213> ORGANISM: Homo Sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Homo Sapiens

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Lys Ile Ser Arg Leu Gln

```
                65                  70                  75                  80
Pro Glu Asp Phe Ala Val Tyr Tyr Cys Gln Gln Tyr Gly Ser Ser Leu
                    85                  90                  95

Thr Phe Gly Gly Gly Thr Lys Val Glu Ile Lys
                100                 105

<210> SEQ ID NO 14
<211> LENGTH: 107
<212> TYPE: PRT
<213> ORGANISM: Homo Sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Lys Val Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Lys Ile Ser Arg Leu Gln
65                  70                  75                  80

Pro Glu Asp Phe Ala Val Tyr Tyr Cys Gln Gln Tyr Gly Ser Ser Leu
                    85                  90                  95

Thr Phe Gly Gly Gly Thr Lys Val Glu Ile Lys
                100                 105

<210> SEQ ID NO 15
<211> LENGTH: 107
<212> TYPE: PRT
<213> ORGANISM: Homo Sapiens

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Val Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                    85                  90                  95

Thr Phe Gly Gly Gly Thr Lys Val Glu Ile Lys
                100                 105

<210> SEQ ID NO 16
<211> LENGTH: 124
<212> TYPE: PRT
<213> ORGANISM: Homo Sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

Ala Met Asn Trp Val Arg Gln Ala Pro Gly Lys Gly Leu Glu Trp Val
            35                  40                  45

Ser Gly Ile Ser Gly Ser Gly Gly His Thr Tyr His Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Asp Glu Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120

<210> SEQ ID NO 17
<211> LENGTH: 124
<212> TYPE: PRT
<213> ORGANISM: Homo Sapiens

<400> SEQUENCE: 17

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Gln Gly Leu Glu Trp Val
            35                  40                  45

Ser Gly Ile Ser Gly Ser Gly Gly His Thr Tyr His Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Asp Glu Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120

<210> SEQ ID NO 18
<211> LENGTH: 124
<212> TYPE: PRT
<213> ORGANISM: Homo Sapiens

<400> SEQUENCE: 18

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Gln Gly Leu Glu Trp Val
            35                  40                  45

Ser Gly Ile Ser Gly Ser Gly Gly His Thr Tyr His Ala Asp Ser Val
        50                  55                  60

Lys Gly Arg Phe Thr Ile Ser Arg Asp Asn Ser Lys Asn Thr Leu Tyr
 65                  70                  75                  80

Leu Glu Met Asn Ser Leu Arg Asp Glu Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120

<210> SEQ ID NO 19
<211> LENGTH: 124
<212> TYPE: PRT
<213> ORGANISM: Homo Sapiens

<400> SEQUENCE: 19

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Asp Ile Leu Thr Gly Tyr Tyr Asn Leu Leu Asp
            100                 105                 110

Tyr Trp Gly Gln Gly Thr Leu Val Thr Val Ser Ser
            115                 120

<210> SEQ ID NO 20
<211> LENGTH: 124
<212> TYPE: PRT
<213> ORGANISM: Homo Sapiens

<400> SEQUENCE: 20

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Asp Arg Tyr Asp Ile Leu Thr Gly Tyr Tyr Asn Leu Leu Asp
            100                 105                 110

Tyr Trp Gly Gln Gly Thr Leu Val Thr Val Ser Ser
            115                 120

<210> SEQ ID NO 21
<211> LENGTH: 124
<212> TYPE: PRT
<213> ORGANISM: Homo Sapiens

<400> SEQUENCE: 21

Glu Val Gln Leu Leu Gln Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Gly Ile Ser Gly Ser Gly Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120

<210> SEQ ID NO 22
<211> LENGTH: 124
<212> TYPE: PRT
<213> ORGANISM: Homo Sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Gly Ile Ser Gly Ser Gly Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120

<210> SEQ ID NO 23
<211> LENGTH: 124
<212> TYPE: PRT
<213> ORGANISM: Homo Sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Gly Ile Ser Gly Ser Gly Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Asp Ile Leu Thr Gly Tyr Tyr Asn Leu Leu Asp
            100                 105                 110

Tyr Trp Gly Gln Gly Thr Leu Val Thr Val Ser Ser
            115                 120

<210> SEQ ID NO 24
<211> LENGTH: 107
<212> TYPE: PRT
<213> ORGANISM: Homo Sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Glu Ala Pro Lys Ser Leu Ile
        35                  40                  45

Tyr Ala Ala Ser Ser Leu Gln Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
            100                 105

<210> SEQ ID NO 25
<211> LENGTH: 107
<212> TYPE: PRT
<213> ORGANISM: Homo Sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Glu Ala Pro Lys Ser Leu Ile
        35                  40                  45

Tyr Ala Ala Ser Ser Leu Gln Ser Gly Val Pro Asp Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
            100                 105

<210> SEQ ID NO 26
<211> LENGTH: 107
<212> TYPE: PRT
<213> ORGANISM: Homo Sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Glu Ala Pro Lys Ser Leu Ile

```
                35                  40                  45
Tyr Ala Ala Ser Ser Leu Gln Ser Gly Val Pro Asp Arg Phe Ser Gly
 50                  55                  60

Ser Glu Ser Gly Thr Asp Phe Thr Leu Thr Ile Ser Ser Leu Glu Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Ala Lys Val Glu Ile Lys
            100                 105

<210> SEQ ID NO 27
<211> LENGTH: 107
<212> TYPE: PRT
<213> ORGANISM: Homo Sapiens

<400> SEQUENCE: 27

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Ala Lys Val Glu Ile Lys
            100                 105

<210> SEQ ID NO 28
<211> LENGTH: 107
<212> TYPE: PRT
<213> ORGANISM: Homo Sapiens

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Ala Lys Val Glu Ile Lys
            100                 105

<210> SEQ ID NO 29
<211> LENGTH: 107
<212> TYPE: PRT
<213> ORGANISM: Homo Sapiens

<400> SEQUENCE: 29
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
            100                 105

<210> SEQ ID NO 30
<211> LENGTH: 107
<212> TYPE: PRT
<213> ORGANISM: Homo Sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
            100                 105

<210> SEQ ID NO 31
<211> LENGTH: 125
<212> TYPE: PRT
<213> ORGANISM: Homo Sapiens

<400> SEQUENCE: 31

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Gly Ile Thr Met Val Arg Gly Val Met Lys Asp Tyr Phe
            100                 105                 110
```

```
Asp Tyr Trp Gly Gln Gly Thr Leu Val Thr Val Ser Ser
        115                 120                 125

<210> SEQ ID NO 32
<211> LENGTH: 125
<212> TYPE: PRT
<213> ORGANISM: Homo Sapiens

<400> SEQUENCE: 32

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 33
<211> LENGTH: 125
<212> TYPE: PRT
<213> ORGANISM: Homo Sapiens

<400> SEQUENCE: 33

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Gln Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 34
<211> LENGTH: 125
<212> TYPE: PRT
<213> ORGANISM: Homo Sapiens

<400> SEQUENCE: 34

Glu Val Gln Leu Val Gln Ser Gly Gly Gly Val Val Gln Pro Gly Arg
1               5                   10                  15
```

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
            115                 120                 125

<210> SEQ ID NO 35
<211> LENGTH: 125
<212> TYPE: PRT
<213> ORGANISM: Homo Sapiens

<400> SEQUENCE: 35

Glu Val Gln Leu Val Gln Ser Gly Gly Gly Val Val Gln Pro Gly Arg
 1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
            85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
            115                 120                 125

<210> SEQ ID NO 36
<211> LENGTH: 125
<212> TYPE: PRT
<213> ORGANISM: Homo Sapiens

<400> SEQUENCE: 36

Glu Val Gln Leu Val Gln Ser Gly Gly Gly Val Val Gln Pro Gly Arg
 1               5                   10                  15

Ser Leu Arg Leu Ser Cys Lys Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
            85                  90                  95

```
Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 37
<211> LENGTH: 125
<212> TYPE: PRT
<213> ORGANISM: Homo Sapiens

<400> SEQUENCE: 37

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Homo Sapiens

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 39
<211> LENGTH: 107
<212> TYPE: PRT
<213> ORGANISM: Homo Sapiens

<400> SEQUENCE: 39

Asp Ile Gln Met Thr Gln Ser Pro Ser Ser Leu Ser Ala Ser Val Gly
```

-continued

```
                1               5                  10                  15
Asp Arg Val Thr Ile Thr Cys Arg Ala Ser Gln Asp Ile Ser Ser Ala
                20                  25                  30

Leu Val Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
            50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105
```

<210> SEQ ID NO 40
<211> LENGTH: 107
<212> TYPE: PRT
<213> ORGANISM: Homo Sapiens

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
                20                  25                  30

Leu Val Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
            50                  55                  60

Ser Glu Ser Gly Thr Asp Phe Thr Leu Thr Ile Ser Ser Leu Glu Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105
```

<210> SEQ ID NO 41
<211> LENGTH: 107
<212> TYPE: PRT
<213> ORGANISM: Homo Sapiens

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
                20                  25                  30

Leu Val Trp Tyr Gln Gln Lys Pro Gly Lys Ala Pro Glu Leu Leu Ile
                35                  40                  45

Tyr Asp Ala Ser Ser Leu Glu Ser Gly Val Pro Ser Arg Phe Ser Gly
            50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105
```

```
<210> SEQ ID NO 42
<211> LENGTH: 107
<212> TYPE: PRT
<213> ORGANISM: Homo Sapiens

<400> SEQUENCE: 42

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 43
<211> LENGTH: 107
<212> TYPE: PRT
<213> ORGANISM: Homo Sapiens

<400> SEQUENCE: 43

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Lys Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Homo Sapiens

<400> SEQUENCE: 44

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Lys Ile Ser Ser Leu Gln Pro
65                  70                  75                  80
```

```
Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 45
<211> LENGTH: 107
<212> TYPE: PRT
<213> ORGANISM: Homo Sapiens

<400> SEQUENCE: 45

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 46
<211> LENGTH: 330
<212> TYPE: PRT
<213> ORGANISM: Homo Sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 47
<211> LENGTH: 107
<212> TYPE: PRT
<213> ORGANISM: Homo Sapiens

<400> SEQUENCE: 47

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 48
<211> LENGTH: 105
<212> TYPE: PRT
<213> ORGANISM: Homo Sapiens

<400> SEQUENCE: 48

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

-continued

His Arg Ser Tyr Ser Cys Gln Val Thr His Glu Gly Ser Thr Val Glu
            85                  90                  95

Lys Thr Val Ala Pro Thr Glu Cys Ser
            100                 105

<210> SEQ ID NO 49
<211> LENGTH: 122
<212> TYPE: PRT
<213> ORGANISM: Homo Sapiens

<400> SEQUENCE: 49

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 50
<211> LENGTH: 107
<212> TYPE: PRT
<213> ORGANISM: Homo Sapiens

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 51
<211> LENGTH: 121
<212> TYPE: PRT
<213> ORGANISM: Homo Sapiens

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Val Ile His Trp Val Arg Gln Ala Pro Gly Lys Gly Leu Glu Trp Val
            35                  40                  45

Thr Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Met Tyr Tyr Cys
                85                  90                  95

Ala Arg Gly Gly Ile Thr Gly Thr Thr Gly Val Phe Asp Tyr Trp Gly
            100                 105                 110

Gln Gly Thr Leu Val Thr Val Ser Ser
        115                 120

<210> SEQ ID NO 52
<211> LENGTH: 107
<212> TYPE: PRT
<213> ORGANISM: Homo Sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Tyr Gly Thr Asp Phe Ser Leu Thr Ile Ser Ser Leu Gln Pro
65                  70                  75                  80

Glu Asp Phe Ala Ile Tyr Tyr Cys Gln Gln Tyr Lys Ser Tyr Pro Ile
                85                  90                  95

Thr Phe Gly Gln Gly Thr Arg Leu Glu Ile Lys
            100                 105

<210> SEQ ID NO 53
<211> LENGTH: 115
<212> TYPE: PRT
<213> ORGANISM: Homo Sapiens

<400> SEQUENCE: 53

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 54
<211> LENGTH: 107
<212> TYPE: PRT
<213> ORGANISM: Homo Sapiens

<400> SEQUENCE: 54

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105

<210> SEQ ID NO 55
<211> LENGTH: 121
<212> TYPE: PRT
<213> ORGANISM: Homo Sapiens

<400> SEQUENCE: 55

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Asp Phe Trp Gly
            100                 105                 110

Gln Gly Thr Leu Val Thr Val Ser Ser
        115                 120

<210> SEQ ID NO 56
<211> LENGTH: 107
<212> TYPE: PRT
<213> ORGANISM: Homo Sapiens

<400> SEQUENCE: 56

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile

```
                35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Phe Asn Ser Tyr Pro Tyr
                 85                  90                  95
Thr Phe Gly Gln Gly Thr Lys Leu Glu Ile Lys
                100                 105
```

<210> SEQ ID NO 57
<211> LENGTH: 121
<212> TYPE: PRT
<213> ORGANISM: Homo Sapiens

<400> SEQUENCE: 57

```
Gln Val Gln Leu Gln Glu Ser Gly Pro Gly Leu Val Arg Pro Ser Gln
 1               5                  10                  15
Thr Leu Ser Leu Thr Cys Thr Val Ser Gly Phe Thr Phe Thr Asp Phe
                 20                  25                  30
Tyr Met Asn Trp Val Arg Gln Pro Pro Gly Arg Gly Leu Glu Trp Ile
                 35                  40                  45
Gly Phe Ile Arg Asp Lys Ala Lys Gly Tyr Thr Thr Glu Tyr Asn Pro
 50                  55                  60
Ser Val Lys Gly Arg Val Thr Met Leu Val Asp Thr Ser Lys Asn Gln
 65                  70                  75                  80
Phe Ser Leu Arg Leu Ser Ser Val Thr Ala Ala Asp Thr Ala Val Tyr
                 85                  90                  95
Tyr Cys Ala Arg Glu Gly His Thr Ala Ala Pro Phe Asp Tyr Trp Gly
                100                 105                 110
Gln Gly Ser Leu Val Thr Val Ser Ser
            115                 120
```

<210> SEQ ID NO 58
<211> LENGTH: 107
<212> TYPE: PRT
<213> ORGANISM: Homo Sapiens

<400> SEQUENCE: 58

```
Asp Ile Gln Met Thr Gln Ser Pro Ser Ser Leu Ser Ala Ser Val Gly
 1               5                  10                  15
Asp Arg Val Thr Ile Thr Cys Lys Ala Ser Gln Asn Ile Asp Lys Tyr
                 20                  25                  30
Leu Asn Trp Tyr Gln Gln Lys Pro Gly Lys Ala Pro Lys Leu Leu Ile
                 35                  40                  45
Tyr Asn Thr Asn Asn Leu Gln Thr Gly Val Pro Ser Arg Phe Ser Gly
 50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Leu Gln His Ile Ser Arg Pro Arg
                 85                  90                  95
Thr Phe Gly Gln Gly Thr Lys Val Glu Ile Lys
                100                 105
```

<210> SEQ ID NO 59
<211> LENGTH: 117
<212> TYPE: PRT

<213> ORGANISM: Homo Sapiens

<400> SEQUENCE: 59

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Phe Trp Thr Trp Ile Arg Gln Ser Pro Gly Lys Gly Leu Glu Trp Ile
        35                  40                  45

Gly Glu Ser Asn Tyr Ala Gly Ser Thr Arg Tyr Asn Pro Ser Leu Lys
    50                  55                  60

Ser Arg Val Thr Ile Ser Val Asp Thr Ser Gln Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Trp Ala Val Asp Gly Met Asp Val Trp Gly Gln Gly Thr Thr
            100                 105                 110

Val Thr Val Ser Ser
        115

<210> SEQ ID NO 60
<211> LENGTH: 109
<212> TYPE: PRT
<213> ORGANISM: Homo Sapiens

<400> SEQUENCE: 60

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Glu Arg Phe Ser Gly Ser
    50                  55                  60

Arg Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Ser
                85                  90                  95

Trp Val Phe Gly Gly Gly Thr Lys Leu Thr Val Leu Gly
            100                 105

<210> SEQ ID NO 61
<211> LENGTH: 329
<212> TYPE: PRT
<213> ORGANISM: Homo Sapiens

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 62
<211> LENGTH: 251
<212> TYPE: PRT
<213> ORGANISM: Staphylococcus aureus

<400> SEQUENCE: 62

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Lys
        35                  40                  45

Lys Leu Asn Glu Ser Gln Ala Pro Lys Ala Asp Asn Asn Phe Asn Lys
    50                  55                  60

Glu Gln Gln Asn Ala Phe Tyr Glu Ile Leu Asn Met Pro Asn Leu Asn
65                  70                  75                  80

Glu Glu Gln Arg Asn Gly Phe Ile Gln Ser Leu Lys Asp Asp Pro Ser
                85                  90                  95

Gln Ser Ala Asn Leu Leu Ser Glu Ala Lys Lys Leu Asn Glu Ser Gln
            100                 105                 110

Ala Pro Lys Ala Asp Asn Lys Phe Asn Lys Glu Gln Gln Asn Ala Phe

```
            115                 120                 125
Glu Ile Leu His Leu Pro Asn Leu Asn Glu Glu Gln Arg Asn Gly Phe
            130                 135                 140

Ile Gln Ser Leu Lys Asp Asp Pro Ser Gln Ser Ala Asn Leu Leu Ala
145                 150                 155                 160

Glu Ala Lys Lys Leu Asn Asp Ala Gln Ala Pro Lys Ala Asp Asn Lys
                165                 170                 175

Phe Asn Lys Glu Gln Gln Asn Ala Phe Tyr Glu Ile Leu His Leu Pro
            180                 185                 190

Asn Leu Thr Glu Glu Gln Arg Asn Gly Phe Ile Gln Ser Leu Lys Asp
            195                 200                 205

Asp Pro Ser Val Ser Lys Glu Ile Leu Ala Glu Ala Lys Lys Leu Asn
210                 215                 220

Asp Ala Gln Ala Pro Lys Glu Asp Asn Asn Lys Pro Gly Lys Glu
225                 230                 235                 240

Asp Gly Asn Lys Pro Gly Lys Glu Asp Gly Asn
                245                 250

<210> SEQ ID NO 63
<211> LENGTH: 384
<212> TYPE: PRT
<213> ORGANISM: Streptococcus sp. group

<400> SEQUENCE: 63

Val Asp Ser Pro Ile Glu Asp Thr Pro Ile Ile Arg Asn Gly Gly Glu
1               5                   10                  15

Leu Thr Asn Leu Leu Gly Asn Ser Glu Thr Thr Leu Ala Leu Arg Asn
                20                  25                  30

Glu Glu Ser Ala Thr Ala Asp Leu Thr Ala Ala Val Ala Asp Thr
            35                  40                  45

Val Ala Ala Ala Ala Glu Asn Ala Gly Ala Ala Ala Trp Glu Ala
        50                  55                  60

Ala Ala Ala Ala Asp Ala Leu Ala Lys Ala Lys Ala Asp Ala Leu Lys
65                  70                  75                  80

Glu Phe Asn Lys Tyr Gly Val Ser Asp Tyr Tyr Lys Asn Leu Ile Asn
                85                  90                  95

Asn Ala Lys Thr Val Glu Gly Ile Lys Asp Leu Gln Ala Gln Val Val
                100                 105                 110

Glu Ser Ala Lys Lys Ala Arg Ile Ser Glu Ala Thr Asp Gly Leu Ser
            115                 120                 125

Asp Phe Leu Lys Ser Gln Thr Pro Ala Glu Asp Thr Val Lys Ser Ile
            130                 135                 140

Glu Leu Ala Glu Ala Lys Val Leu Ala Asn Arg Glu Leu Asp Lys Tyr
145                 150                 155                 160

Gly Val Ser Asp Tyr His Lys Asn Leu Ile Asn Asn Ala Lys Thr Val
                165                 170                 175

Glu Gly Val Lys Glu Leu Ile Asp Glu Ile Leu Ala Ala Leu Pro Lys
            180                 185                 190

Thr Asp Thr Tyr Lys Leu Ile Leu Asn Gly Lys Thr Leu Lys Gly Glu
            195                 200                 205

Thr Thr Thr Glu Ala Val Asp Ala Ala Thr Ala Glu Lys Val Phe Lys
        210                 215                 220

Gln Tyr Ala Asn Asp Asn Gly Val Asp Gly Glu Trp Thr Tyr Asp Asp
225                 230                 235                 240
```

```
Ala Thr Lys Thr Phe Thr Val Thr Glu Lys Pro Glu Val Ile Asp Ala
            245                 250                 255

Ser Glu Leu Thr Pro Ala Val Thr Tyr Lys Leu Val Ile Asn Gly
        260                 265                 270

Lys Thr Leu Lys Gly Glu Thr Thr Lys Ala Val Asp Ala Glu Thr
        275                 280                 285

Ala Glu Lys Ala Phe Lys Gln Tyr Ala Asn Asp Asn Gly Val Asp Gly
        290                 295                 300

Val Trp Thr Tyr Asp Asp Ala Thr Lys Thr Phe Thr Val Thr Glu Met
305                 310                 315                 320

Val Thr Glu Val Pro Gly Asp Ala Pro Thr Glu Pro Glu Lys Pro Glu
                325                 330                 335

Ala Ser Ile Pro Leu Val Pro Leu Thr Pro Ala Thr Pro Ile Ala Lys
                340                 345                 350

Asp Asp Ala Lys Lys Asp Asp Thr Lys Lys Glu Asp Pro Glu Ala Lys
                355                 360                 365

Lys Asp Asp Ala Lys Lys Ala Gly Thr Leu Pro Thr Thr Gly Glu Gly
                370                 375                 380

<210> SEQ ID NO 64
<211> LENGTH: 938
<212> TYPE: PRT
<213> ORGANISM: Finegoldia magna

<400> SEQUENCE: 64

Ala Glu Glu Asp Asn Thr Asp Asn Asn Leu Ser Met Asp Glu Ile Ser
1               5                   10                  15

Asp Ala Tyr Phe Asp Tyr His Gly Asp Val Ser Asp Ser Val Asp Pro
                20                  25                  30

Val Glu Glu Glu Ile Asp Glu Ala Leu Ala Lys Ala Leu Ala Glu Ala
            35                  40                  45

Lys Glu Thr Ala Lys Lys His Ile Asp Ser Leu Asn His Leu Ser Glu
    50                  55                  60

Thr Ala Lys Lys Leu Ala Lys Asn Asp Ile Asp Ser Ala Thr Thr Ile
65                  70                  75                  80

Asn Ala Ile Asn Asp Ile Val Ala Arg Ala Asp Val Met Glu Arg Lys
                85                  90                  95

Thr Ala Glu Lys Glu Glu Ala Glu Lys Leu Ala Ala Lys Glu Thr
            100                 105                 110

Ala Lys Lys His Ile Asp Glu Leu Lys His Leu Ala Asp Lys Thr Lys
        115                 120                 125

Glu Leu Ala Lys Arg Asp Ile Asp Ser Ala Thr Thr Ile Asn Ala Ile
    130                 135                 140

Asn Asp Ile Val Ala Arg Ala Asp Val Met Glu Arg Lys Thr Ala Glu
145                 150                 155                 160

Lys Glu Glu Ala Glu Lys Leu Ala Ala Lys Glu Thr Ala Lys Lys
                165                 170                 175

His Ile Asp Glu Leu Lys His Leu Ala Asp Lys Thr Lys Glu Leu Ala
            180                 185                 190

Lys Arg Asp Ile Asp Ser Ala Thr Thr Ile Asp Ala Ile Asn Asp Ile
        195                 200                 205

Val Ala Arg Ala Asp Val Met Glu Arg Lys Leu Ser Glu Lys Glu Thr
        210                 215                 220

Pro Glu Pro Glu Glu Glu Val Thr Ile Lys Ala Asn Leu Ile Phe Ala
225                 230                 235                 240
```

```
Asp Gly Ser Thr Gln Asn Ala Glu Phe Lys Gly Thr Phe Ala Lys Ala
                245                 250                 255

Val Ser Asp Ala Tyr Ala Tyr Ala Asp Ala Leu Lys Lys Asp Asn Gly
            260                 265                 270

Glu Tyr Thr Val Asp Val Ala Asp Lys Gly Leu Thr Leu Asn Ile Lys
        275                 280                 285

Phe Ala Gly Lys Lys Glu Lys Pro Glu Glu Pro Lys Glu Glu Val Thr
    290                 295                 300

Ile Lys Val Asn Leu Ile Phe Ala Asp Gly Lys Thr Gln Thr Ala Glu
305                 310                 315                 320

Phe Lys Gly Thr Phe Glu Glu Ala Thr Ala Lys Ala Tyr Ala Tyr Ala
                325                 330                 335

Asp Leu Leu Ala Lys Glu Asn Gly Glu Tyr Thr Ala Asp Leu Glu Asp
            340                 345                 350

Gly Gly Asn Thr Ile Asn Ile Lys Phe Ala Gly Lys Glu Thr Pro Glu
        355                 360                 365

Thr Pro Glu Glu Pro Lys Glu Glu Val Thr Ile Lys Val Asn Leu Ile
    370                 375                 380

Phe Ala Asp Gly Lys Ile Gln Thr Ala Glu Phe Lys Gly Thr Phe Glu
385                 390                 395                 400

Glu Ala Thr Ala Lys Ala Tyr Ala Tyr Ala Asn Leu Leu Ala Lys Glu
                405                 410                 415

Asn Gly Glu Tyr Thr Ala Asp Leu Glu Asp Gly Gly Asn Thr Ile Asn
            420                 425                 430

Ile Lys Phe Ala Gly Lys Glu Thr Pro Glu Thr Pro Glu Glu Pro Lys
        435                 440                 445

Glu Glu Val Thr Ile Lys Val Asn Leu Ile Phe Ala Asp Gly Lys Thr
    450                 455                 460

Gln Thr Ala Glu Phe Lys Gly Thr Phe Glu Glu Ala Thr Ala Glu Ala
465                 470                 475                 480

Tyr Arg Tyr Ala Asp Leu Leu Ala Lys Val Asn Gly Glu Tyr Thr Ala
                485                 490                 495

Asp Leu Glu Asp Gly Gly Tyr Thr Ile Asn Ile Lys Phe Ala Gly Lys
            500                 505                 510

Glu Gln Pro Gly Glu Asn Pro Gly Ile Thr Ile Asp Glu Trp Leu Leu
        515                 520                 525

Lys Asn Ala Lys Glu Glu Ala Ile Lys Glu Leu Lys Glu Ala Gly Ile
    530                 535                 540

Thr Ser Asp Leu Tyr Phe Ser Leu Ile Asn Lys Ala Lys Thr Val Glu
545                 550                 555                 560

Gly Val Glu Ala Leu Lys Asn Glu Ile Leu Lys Ala His Ala Gly Glu
                565                 570                 575

Glu Thr Pro Glu Leu Lys Asp Gly Tyr Ala Thr Tyr Glu Glu Ala Glu
            580                 585                 590

Ala Ala Ala Lys Glu Ala Leu Lys Asn Asp Asp Val Asn Asn Ala Tyr
        595                 600                 605

Glu Ile Val Gln Gly Ala Asp Gly Arg Tyr Tyr Val Leu Lys Ile
    610                 615                 620

Glu Val Ala Asp Glu Glu Pro Gly Glu Asp Thr Pro Glu Val Gln
625                 630                 635                 640

Glu Gly Tyr Ala Thr Tyr Glu Glu Ala Glu Ala Ala Lys Glu Ala
                645                 650                 655
```

-continued

```
Leu Lys Glu Asp Lys Val Asn Asn Ala Tyr Glu Val Val Gln Gly Ala
            660             665                 670

Asp Gly Arg Tyr Tyr Tyr Val Leu Lys Ile Glu Asp Lys Glu Asp Glu
            675             680                 685

Gln Pro Gly Glu Glu Pro Gly Glu Asn Pro Gly Ile Thr Ile Asp Glu
    690             695                 700

Trp Leu Leu Lys Asn Ala Lys Glu Asp Ala Ile Lys Glu Leu Lys Glu
705             710                 715                 720

Ala Gly Ile Ser Ser Asp Ile Tyr Phe Asp Ala Ile Asn Lys Ala Lys
                725             730                 735

Thr Val Glu Gly Val Glu Ala Leu Lys Asn Glu Ile Leu Lys Ala His
            740             745                 750

Ala Glu Lys Pro Gly Glu Asn Pro Gly Ile Thr Ile Asp Glu Trp Leu
            755             760                 765

Leu Lys Asn Ala Lys Glu Ala Ala Ile Lys Glu Leu Lys Glu Ala Gly
    770             775                 780

Ile Thr Ala Glu Tyr Leu Phe Asn Leu Ile Asn Lys Ala Lys Thr Val
785             790                 795                 800

Glu Gly Val Glu Ser Leu Lys Asn Glu Ile Leu Lys Ala His Ala Glu
            805             810                 815

Lys Pro Gly Glu Asn Pro Gly Ile Thr Ile Asp Glu Trp Leu Leu Lys
            820             825                 830

Asn Ala Lys Glu Asp Ala Ile Lys Glu Leu Lys Glu Ala Gly Ile Thr
            835             840                 845

Ser Asp Ile Tyr Phe Asp Ala Ile Asn Lys Ala Lys Thr Ile Glu Gly
850             855                 860

Val Glu Ala Leu Lys Asn Glu Ile Leu Lys Ala His Lys Lys Asp Glu
865             870                 875                 880

Glu Pro Gly Lys Lys Pro Gly Glu Asp Lys Lys Pro Glu Asp Lys Lys
            885             890                 895

Pro Gly Glu Asp Lys Lys Pro Glu Asp Lys Lys Pro Gly Asp Lys Lys
            900             905                 910

Pro Glu Asp Lys Lys Pro Gly Lys Thr Asp Lys Asp Ser Pro Asn Lys
            915             920                 925

Lys Lys Lys Ala Lys Leu Pro Lys Ala Gly
930             935
```